US011427829B2

(12) United States Patent
Bower et al.

(10) Patent No.: US 11,427,829 B2
(45) **Date of Patent: *Aug. 30, 2022**

(54) FUNGAL GENOME MODIFICATION SYSTEMS AND METHODS OF USE

(71) Applicant: Danisco US Inc., Palo Alto, CA (US)

(72) Inventors: Benjamin S. Bower, Palo Alto, CA (US); Jimmy Chan, Palo Alto, CA (US); Jing Ge, Palo Alto, CA (US); Xiaogang Gu, Palo Alto, CA (US); Susan Mampusti Madrid, Palo Alto, CA (US); Danfeng Song, Palo Alto, CA (US); Mingmin Song, Palo Alto, CA (US); Michael Ward, Palo Alto, CA (US)

(73) Assignee: DANISCO US INC, Palo Alto, CA (US)

( * ) Notice: Subject to any disclaimer, the term of this patent is extended or adjusted under 35 U.S.C. 154(b) by 750 days.

This patent is subject to a terminal disclaimer.

(21) Appl. No.: 15/536,836

(22) PCT Filed: Dec. 15, 2015

(86) PCT No.: PCT/US2015/065693

§ 371 (c)(1),
(2) Date: Jun. 16, 2017

(87) PCT Pub. No.: WO2016/100272

PCT Pub. Date: Jun. 23, 2016

(65) Prior Publication Data

US 2018/0002710 A1 Jan. 4, 2018

(30) Foreign Application Priority Data

Dec. 16, 2014 (WO) ................ PCT/CN2014/093914
Dec. 16, 2014 (WO) ................ PCT/CN2014/093916
Dec. 16, 2014 (WO) ................ PCT/CN2014/093918

(51) Int. Cl.

*C12N 15/00* (2006.01)
*C12N 15/80* (2006.01)
*C12N 9/22* (2006.01)
*C12N 15/11* (2006.01)

(52) U.S. Cl.

CPC ............... *C12N 15/80* (2013.01); *C12N 9/22* (2013.01); *C12N 15/11* (2013.01); *C12N 2310/20* (2017.05)

(58) Field of Classification Search

CPC .......... C12N 15/80; C12N 9/22; C12N 15/11; C12N 2310/20

See application file for complete search history.

(56) References Cited

U.S. PATENT DOCUMENTS

| | | | | |
|---|---|---|---|---|
| 8,697,359 | B1 | 4/2014 | Zhang et al. | |
| 2017/0159094 | A1* | 6/2017 | Natunen | C12Y 204/99 |
| 2017/0226533 | A1* | 8/2017 | Frisch | C12N 15/905 |
| 2019/0194692 | A1* | 6/2019 | Meijrink | C12P 1/02 |

FOREIGN PATENT DOCUMENTS

| | | | | |
|---|---|---|---|---|
| WO | 2013141680 | A1 | | 9/2013 |
| WO | 2014191521 | A2 | | 12/2014 |
| WO | 2015054507 | A1 | | 4/2015 |
| WO | WO-2015054507 | A1 | * | 4/2015 |

OTHER PUBLICATIONS

DiCarlo et al., Nucleic Acids Research, 2013, vol. 41, pp. 4336-4343. (Year: 2013).*
Arazoe et al., FEMS Microbiol. Lett., 352, 2, 221-229 (Year: 2014).*
DeBoer eet al., Fug. Genet. and Biol., 47, 10, 839-846 (Year: 2010).*
Nodvig et al. (PloS ONE 2015 vol. 10 No. 7: pp. 1-12, published Jul. 15, 2015) (Year: 2015).*
Zhang etal (Curr Microbiol 2011 vol. 62: pp. 1342-1346). (Year: 2011).*
Liu et al (Cell Discovery 2015 vol. 1: pp. 1-11; published online May 12, 2015). (Year: 2015).*
Liang Liu et al., CRISPR-Cas system: a powerful tool for genome editing, Plant Molecular Biology, 2014, pp. 209-218, vol. 85.
Chandler Julie M et al, "Protein profiling of the dimorphic, pathogenic fungus, *Penicillium marneffei*", Proteome Science, Biomed Central, London, GB,No. 1, Jun. 4, 2008 (Jun. 4, 2008), p. 17.
Giedrius Gasiunas et al., Cas9-crRNA ribonucleoprotein complex mediates specific DNA cleavage for adaptive immunity in bacteria, Proc. Nal. Acad. Sci. USA, 2012, E2579-86, vol. 109.
Martin Jinek et al., A Programmable Dual-RNA-Guided DNA Endonuclease in Adaptive Bacterial Immunity, Science, Aug. 17, 2012, pp. 816-821, vol. 337.
Le Cong et al., Multiplex Genome Engineering Using CRISPR/Cas Systems, Science, Feb. 15, 2013, pp. 819-823, vol. 339. Cas9, Science, Feb. 15, 2013, pp. 823-826, vol. 339.
Fuller Kevin K et al., "Development of the CRISPR/Cas9 System for Targeted Gene Disruption in Aspergillus fumigatus ", Eukaryotic Cell Nov. 2015,vol. 14, No. 11, Nov. 2015 (Nov. 2015), p. 1073-1080.
Rui Liu, Ling Chen, Yanping Jiang, Zhihuazhou, Gen Zou, "Efficient genome editing in filamentous fungus *Trichoderma reesei* using the CRISPR/Cas9 system", Cell Discovery,vol. 1, May 12, 2015 (May 12, 2015), p. 1-11.
Christina S. Nødvig et al., "A CRISPR-Cas9 System for Genetic Engineering of Filamentous Fungi", PLOS ONE, vol. 10, No. 7, Jul. 15, 2015 (Jul. 15, 2015), p. e0133085.

(Continued)

*Primary Examiner* — Catherine S Hibbert

(57) ABSTRACT

Compositions and methods are provided for genome modification at a target site in the genome of a filamentous fungal cell. The methods and compositions are drawn to a guide polynucleotide/Cas endonuclease system for modifying or altering the target site. Aspects in which the filamentous fungal cell being modified has a defective non-homologous end joining pathway are also provided.

16 Claims, 12 Drawing Sheets

Specification includes a Sequence Listing.

(56) References Cited

OTHER PUBLICATIONS

Prashant Mali et al., RNA Guided Human Genome Engineering via P. Mali et al., "RNA-Guided Human Genome Engineering via Cas9", Science, vol. 339, No. 6121, Jan. 3, 2013 (Jan. 3, 2013), p. 823-826.
Takayuki Arazoe et al., "Tailor-made CRISPR/Cas system for highly efficient targeted gene replacement in the rice blast fungus", Biotechnology and Bioengineering, vol. 112, No. 12, Dec. 14, 2015 (Dec. 14, 2015), p. 2543-2549.
Chi Zhang et al., "Highly efficient CRISPR mutagenesis by microhomology-mediated end joining in Aspergillus fumigatus", Fungal Genetics and Biology,vol. 86, Dec. 14, 2015 (Dec. 14, 2015), p. 47-57.
De Boer P et al., "Highly efficient gene targeting in Penicillium chrysogenum using the bi-partite approach in DELTAlig4 or DELTAku70 mutants", Oct. 1, 2010 (Oct. 1, 2010), vol. 47, No. 10, p. 839-846.
Takayuki Arazoe et al., "Site-specific DNA double-strand break generated by I-Scel endonuclease enhances ectopic homologous recombination in Pyricularia oryzae", FEMS Microbiology Letters,vol. 352, No. 2, Feb. 26, 2014 (Feb. 26, 2014), p. 221-229.
J. E. Dicarlo et al., "Genome engineering in *Saccharomyces cerevisiae* using CRISPR-Cas systems", Nucleic Acids Research,vol. 41, No. 7, Mar. 4, 2013 (Mar. 4, 2013), p. 4336-4343.
Yoshizui Ishino et al., Nucleotide Sequence of the iap Gene, Responsible for Alkaline Phosphatase Isozyme Conversion in *Escherichia coli*, and Identification of the Gene Product, Journal of Bacteriology, Dec. 1987, pp. 5429-5433.
Atsuo Nakata et al., Unusual Nucleotide Arrangement with Repeated Sequences in the *Escherichia coli* K-12 Chromosome, Journal of Bacteriology, Jun. 1989, pp. 3553-3556, vol. 171, No. 6.
Peter M. A. Groenen et al., Nature of DNA polymorphis in the direct repeat cluster of *Mycobacterium tuberculosis* application for strain differentiation by a novel typing method, Molecular Microbiology, 1993, pp. 1057-1065, vol. 10, No. 5.
Nancy Hoe et al., Rapid Molecular Genetic Subtyping of Serotype M1 Group A *Streptococcus* Strains, Emerging Infectious Diseases, Mar.-Apr. 1999, pp. 254-263, vol. 5, No. 2.
Bernd Masepohl et al., Long tandemly repeated repetitive (LTRR) sequences in the filamentous cyanobacterium *Anabaena* sp. PCC7120, Biochimica et Biophysica Acta, 1996, pp. 26-30.
F. J. M. Mojica et al., Long stretches of short tandem repeats are present in the largest replicons of the Archaea Haloferax mediterranei and Haloferax volcanii and could be involved in replicon partitioning, Molecular Microbiology, 1995, pp. 85-93, vol. 17, No. 1.
Norah Rudin et al., Genetic and Physical Analysis of Double-Strand Break Repair and Recombination in *Saccharomyces cerevisiae*, Genetics, Jul. 1989, pp. 519-534, vol. 122.
Fatima Smih et al., Double-strand breaks at the target locus stimulate gene targeting in embryonic stem cells, Nucleic Acids Research, 1995, pp. 5012-5019, vol. 23, No. 24.
Patrick D. Hsu et al., Development and Applications of CRISPR-Cas9 for Genome Engineering, Cell, Jun. 5, 2014, pp. 1262-1278, vol. 157.
Bernd Zetsche et al., Cpf1 Is a Single RNA-Guided Endonuclease of a Class 2 CRISPR-Cas System, Cell, Oct. 22, 2015, pp. 759-771, vol. 163.
Jean-Yves Bleuyard et al., Recent advances in understanding of the DNA double-strand break repair machinery of plants, DNA Repair, 2006, pp. 1-12, vol. 5.
Ralph Siebert et al., Efficient Repair of Genomic Double-Strand Breaks by Homologous Recombination between Directly Repeated Sequences in the Plant Genome, The Plant Cell, May 2002, pp. 1121-1131, vol. 14.
Michael Pacher et al., Two Unlinked Double-Strand Breaks Can Induce Reciprocal Exchanges in Plant Genomes via Homologous Recombination and Nonhomologous End Joining, Genetics, 2007, pp. 21-29, vol. 175.
Sander and Joung, Nature Biology 2013 pp. 1-9—Reference Not Included.
International Search Report—PCT/US2015/065693—dated Apr. 13, 2016.

* cited by examiner

T. reesei U6 gene SEQ ID NO:1

AAAAAACACTAGTAAGTACTTACTTATGTATTATTAACTACTTTAGCTAACTTCTGCAGTACTACCT
AAGAGGCTAGGGGTAGTTTTATAGCAGACTTATAGCTATTATTTTTATTTAGTAAAGTGCTTTTAAA
GTAAGGTCTTTTTTATAGCACTTTTTATTTATTATAATATATATTATATAATAATTTTAAGCCTGGAATA
GTAAAGAGGCTTATATAATAATTTATAGTAATAAAAGCTTAGCAGCTGTAATATAATTCCTAAAGAA
ACAGCATGAAATGGTATTATGTAAGAGCTATAGTCTAAAGGCACTCTGCTGGATAAAAATAGTGG

"TATA" Box
CTATAAGTCTGCTGCAAAACTACCCCCAACCTCGTAGG TATATAA GTACTGTTTGATGGTAGTCTA

Intron
Trans. Start
A-Box
B-Box
TC G CCTTCGGGCATT TGGTCAATTTA TAACGATACAG GTTCGTTTC GGCTTTTCCTCGGAACCC

CCAGAGGTCATCAGTTCGAATCGCTAACAG GTCA*ACAGAGAAGATTAGCATGGCCCCTGC*ACT

Terminator
*AAGGATGACACGC*TCACTCAAAGAGAAGCTAAACA TTTTTTTTCTCTT CCAAGTCGTGATGGTTA TCTTTTTGCTTAGAGAATCTATTCTTGTGGACGATTAGTATTGGTAAATCCCTGCTGCACATTGCGGC
GGATGGTCTCAACGGCATAATACCCCATTCGTGATGCAGCGGTGATCTTCAATATGTAGTGTAATACG
TTGCATACACCACCAGGTTCGGTGCCTCCTGTATGTACAGTACTGTAGTTCGACTCCTCCGCGCAGG
TGGAAACGATTCCCTAGTGGGCAGGTATTTTGGCGGGGTCAAGAA

FIG. 1

FUNGAL GENOME MODIFICATION SYSTEMS AND METHODS OF USE

CROSS-REFERENCE TO RELATED APPLICATIONS

The present application claims priority to PCT Patent Appln. Ser. Nos. PCT/CN2014/093914, PCT/CN2014/093916, and PCT/CN2014/093918, all filed Dec. 16, 2014, which are hereby incorporated by reference in their entireties.

SEQUENCE LISTING

The sequence listing submitted via EFS, in compliance with 37 C.F.R. § 1.52(e), is incorporated herein by reference. The sequence listing text file submitted via EFS contains the file "U.S. Ser. No. 15/536,836" filed on Jun. 16, 2017, which is 164.99 kilobytes in size.

BACKGROUND

Bacteria and archaea have evolved adaptive immune defenses termed clustered regularly interspaced short palindromic repeats (CRISPR)/CRISPR-associated (Cas) systems that can introduce double strand beaks in DNA in a sequence-specific manner. Cas systems perform their functions through the activity of a ribonucleoprotein complex that includes short RNA sequences (tracrRNA and crRNA) and an RNA dependent endonuclease (Cas endonuclease) that targets a specific DNA sequence (through homology to a portion of the crRNA, called the variable targeting domain) and generates double strand breaks in the target. CRISPR loci were first recognized in *E. coli* (Ishino et al. (1987) J. Bacterial. 169:5429-5433; Nakata et al. (1989) J. Bacterial. 171:3553-3556), with similar interspersed short sequence repeats being subsequently identified in a number of bacterial species, including but not limited to *Haloferax mediterranei, Streptococcus pyogenes, Anabaena*, and *Mycobacterium tuberculosis* (Groenen et al. (1993) Mol. Microbiol. 10:1057-1065; Hoe et al. (1999) Emerg. Infect. Dis. 5:254-263; Masepohl et al. (1996) Biochim. Biophys. Acta 1307:26-30; Mojica et al. (1995) Mol. Microbiol. 17:85-93).

It is well known that inducing cleavage at a specific target site in genomic DNA can be used to introduce modifications at or near that site. For example, homologous recombination for gene targeting has been shown to be enhanced when the targeted DNA site contains a double-strand break (see, e.g., Rudin et al., Genetics 122:519-534; Smih et al., Nucl. Acids Res. 23:5012-5019). Given the site-specific nature of Cas systems, genome modification/engineering technologies based on these systems have been described, including in mammalian cells (see, e.g., Hsu et al.; Cell vol. 157, p 1262-1278, 5 Jun. 2014 entitled "Development and Applications of CRISPR-Cas9 for Genome Engineering"). The power of the Cas-based genome engineering comes from the ability to target virtually any specific location within a complex genome by designing a recombinant crRNA (or equivalently functional polynucleotide) in which the DNA-targeting region (variable targeting domain) of the crRNA is homologous to the desired target site in the genome and combining it with a Cas endonuclease (through any convenient means) into a functional complex in a host cell.

Although Cas-based genome engineering technologies have been applied to a number of different host cell types, the efficient use of such systems in fungal cells has proven to be difficult. Thus, there still remains a need for developing efficient and effective Cas-based genome engineering methods and compositions for modifying/altering a genomic target site in a fungal cell.

BRIEF SUMMARY

Compositions and methods are provided employing a guide RNA/Cas endonuclease system for promoting homologous recombination of a donor DNA with a genomic locus in a fungal cell, e.g., a filamentous fungal cell.

Aspects of the present disclosure are drawn to methods for homologous recombination of a donor DNA with a genomic locus in a fungal cell. In some embodiments, the method includes: a) introducing into a population of fungal cells a Cas endonuclease, a guide RNA, and a donor DNA comprising a domain with homology to a genomic locus of the fungal cell, wherein the Cas endonuclease and guide RNA are capable of forming a complex that enables the Cas endonuclease to act at a target site in or near the genomic locus of the fungal cells; and b) identifying at least one fungal cell from the population in which homologous recombination of the donor DNA with the genomic locus has occurred, where the Cas endonuclease, the guide RNA, or both are introduced transiently into the population of fungal cells.

In one aspect, the present disclosure are drawn to a method for homologous recombination of a donor DNA with a genomic locus in a fungal cell, the method including: a) introducing into a fungal cell a Cas endonuclease, a guide RNA, and a donor DNA comprising a domain with homology to a genomic locus of the fungal cell, wherein the Cas endonuclease and guide RNA are capable of forming a complex that enables the Cas endonuclease to act at a target site in or near the genomic locus of the fungal cell; and b) identifying if homologous recombination of the donor DNA with the genomic locus has occurred in the fungal cell, where the Cas endonuclease, the guide RNA, or both are introduced transiently into the population of fungal cells.

We have found that, in some embodiments, inhibiting or inactivating the non-homologous end joining (NHEJ) mechanism at the target site (i.e., the site of Cas endonuclease activity) in the fungal cells enhances homologous recombination of the donor DNA at the genomic locus. Therefore, aspects of the present invention include performing the homologous recombination methods as described herein under conditions in which the non-homologous end joining (NHEJ) mechanism at the target site in the fungal cells is not activated, non-functional, or reduced.

Rendering non-functional (inactivating) or reducing the NHEJ pathway at the target site in the filamentous fungal cell can be achieved in any convenient manner and can be either a long term (or stable) phenotype of the host cell or a short term (or transient) phenotype of the host cell. For example, long term inactivation of the NHEJ pathway can be achieved by chromosomal genetic alteration of one or more genes involved the NHEJ pathway so that its activity is reduced or eliminated from the host cell (e.g., deletion of a gene in the NHEJ pathway). This results in the obtainment of a progeny cell having the desired genetic alteration (homologous recombination between the donor DNA and the genomic DNA at the desired location) that still has a non-functional/inactivated or reduced NHEJ pathway. Alternatively, blocking the function of or reducing the NHEJ pathway at the target site in the host cell can be done transiently. For example, transient inactivation of the NHEJ pathway can be achieved by introducing into the host cell a transient recombinant DNA construct that expresses an inhibitory RNA or a dominant negative protein whose expression inhibits the expression or the activity of one or more specific components of the NHEJ pathway.

After obtaining a progeny cell having the desired genetic alteration, the transient recombinant DNA construct can be eliminated from the progeny cell, e.g., by removing selection pressure for maintenance of the transient recombinant DNA construct. In this way, the desired progeny cell will have a normally functioning NHEJ pathway. Examples of NHEJ pathway components that can be rendered non-functional or have a reduction in activity include ku80, ku70, rad50, mre11, xrs2, lig4, xrs, or any desired combination thereof. In one particular embodiment, the fungal cell has an inactivation or reduction in the expression and/or activity of ku80. It is noted here that the term "non-functional" when in reference to a particular component of the NHEJ pathway encompasses cases in which the component is absent from the cell (e.g., by gene deletion) as well as cases in which the component is present but non-functional (e.g., a non-functional mutant protein).

Alternatively, one can employ a Cas endonuclease that has nicking endonuclease activity (i.e., cleaves only one strand of DNA at the target site; also referred to herein as Cas nickases) rather than double-strand break activity. Inducing nicks at the targets site does not activate the NHEJ pathway at the target site as would a double-strand break, but does improve homologous recombination between the genomic locus of interest (one that includes or is near to the target site for the Cas nickase) and the donor DNA. Examples of Cas nickases include Cas endonuclease variants as described below.

Several different types of CRISPR-Cas systems have been described and can be classified as Type I, Type II, and Type III CRISPR-Cas systems (see, e.g., the description in Liu and Fan, CRISPR-Cas system: a powerful tool for genome editing. Plant Mol Biol (2014) 85:209-218). In certain aspects, the CRISPR-Cas system is a Type II CRISPR-Cas system employing a Cas9 endonuclease or variant thereof (including, e.g., a Cas nickase). The Cas9 endonuclease may be any convenient Cas9 endonuclease, including but not limited to Cas9 endonucleases, and functional fragments thereof, from the following bacterial species: *Streptococcus* sp. (e.g., *S. pyogenes, S. mutans*, and *S. thermophilus*), *Campylobacter* sp. (e.g., *C. jejuni*), *Neisseria* sp. (e.g., *N. meningitides*), *Francisella* sp. (e.g., *F. novicida*), and *Pasteurella* sp. (e.g., *P. multocida*). Numerous other species of Cas9 can be used. For example, functional Cas9 endonucleases or variants thereof containing an amino acid sequence that has at least 70% identity to any one of SEQ ID NOs:45 and 48 to 53 may be employed, e.g., at least 80% identity, at least 90% identity, at least 95% identity, at least 96% identity, at least 97% identity, at least 98% identity, at least 99% identity, and including up to 100% identity to any one of SEQ ID NOs:45 and 48 to 53.

In certain embodiments, introducing the Cas endonuclease and/or the guide RNA into the fungal cells includes introducing one or more DNA constructs comprising expressions cassettes for the Cas endonuclease, the guide RNA, or both into the fungal cells. The one or more DNA constructs, once in the fungal cells, express the Cas endonuclease and/or the guide RNA. In certain embodiments, the DNA construct is a circular DNA construct that includes: an expression cassette for the Cas endonuclease, an expression cassette for the guide RNA, and the donor DNA, where the Cas endonuclease can be either a double-strand break Cas endonuclease or a Cas nickase.

In certain embodiments, the introducing step includes directly introducing a Cas endonuclease polypeptide, a guide RNA, or both into the fungal cells. Any combination of direct introduction and using DNA constructs can be employed (e.g., introducing a DNA construct with an expression cassette for a Cas endonuclease into the fungal cell and directly introducing a guide RNA into the cell, either simultaneously or sequentially as desired).

In certain of the methods described herein, the Cas expression cassette in the DNA construct includes a Cas endonuclease encoding gene that is optimized for expression in the fungal cell. For example, a Cas endonuclease encoding gene that is optimized for expression in filamentous fungal cells includes a sequence that has at least 70% sequence identity to SEQ ID NO:44 (encoding Cas9 from *S. pyogenes*; SEQ ID NO:45).

In some instances, the Cas endonuclease is operably linked to one or more nuclear targeting signal (also referred to as a nuclear localization signal/sequence; NLS). SEQ ID NO:7 and SEQ ID NO:8 provide an example of a filamentous fungal cell optimized Cas9 gene with NLS sequences at the N- and C-termini and the encoded amino acid sequence, respectively. Many different NLSs are known in eukaryotes. They include monopartite, bipartite and tripartite types. Any convenient NLS can be used, the monopartite type being somewhat more convenient with examples including the SV40 NLS, a NLS derived from the *T. reesei* blr2 (blue light regulator 2) gene, or a combination of both.

In certain embodiments, the donor DNA comprises a polynucleotide sequence of interest, and wherein homologous recombination at the genomic locus results in the insertion of the polynucleotide sequence of interest in the genomic locus.

In some embodiments of the methods, the introducing step comprises introducing into the fungal cells a DNA construct comprising a sequence encoding a selectable marker or phenotypic marker as described herein. In certain embodiments, the DNA construct comprises both the sequence encoding the selectable marker and the donor DNA. In some embodiments, the DNA construct comprises a sequence encoding the Cas endonuclease, the sequence encoding the selectable marker, and the donor DNA. In some embodiments, the DNA construct comprises a sequence encoding the guide RNA, the sequence encoding the selectable marker, and the donor DNA. In particular embodiments, the DNA construct comprises a sequence encoding the Cas endonuclease, a sequence encoding the guide RNA, a sequence encoding a selectable marker, and the donor DNA. In certain embodiments, the DNA construct is a linear DNA construct. In certain embodiments, the DNA construct is a circular DNA construct.

Fungal cells that find use in the subject methods can be filamentous fungal cell species. In certain embodiments, the fungal cell is a Eumycotina or Pezizomycotina fungal cell. In some embodiments, the fungal cell is selected from *Trichoderma, Penicillium, Aspergillus, Humicola, Chrysosporium, Fusarium, Neurospora, Myceliophthora, Thermomyces, Hypocrea*, and *Emericella*. The filamentous fungi *Trichoderma reesei, P. chrysogenum, M. thermophila, Thermomyces lanuginosus, A. oryzae* and *A. niger* are of particular interest. Other fungal cells, including species of yeast, can also be employed.

The target site selected by a user of the disclosed methods can be located within a region of a gene of interest selected from the group consisting of an open reading frame, a promoter, a regulatory sequence, a terminator sequence, a regulatory element sequence, a splice site, a coding sequence, a polyubiquitination site, an intron site, and an intron enhancing motif. Examples of genes of interest include genes encoding acetyl esterases, aminopeptidases, amylases, arabinases, arabinofuranosidases, carboxypeptidases, catalases, cellulases, chitinases, cutinase, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, peroxidases, phenoloxidases, phytases, polygalacturonases, proteases, rhamno-galacturonases, ribonucleases, transferases, transport proteins, transglutaminases, xylanases, hexose oxidases, and combinations thereof. Target genes encoding regulatory proteins such as transcription factors, repressors, proteins that modifies other proteins such as kinases, proteins involved in post-translational modification (e.g., glycosylation) can be subjected to Cas mediated editing as well as genes involved in cell signaling, morphology, growth rate, and protein secretion. No limitation in this regard is intended.

In certain embodiments, the homologous recombination of the donor DNA with the genomic locus results in a modification of the DNA sequence at or near the target site, wherein the modification is selected from the group consisting of a deletion of one or more nucleotides, an insertion of one or more nucleotides, insertion of an expression cassette encoding a protein of interest, a substitution of one or more nucleotides, and any combination thereof. In some embodiments, the modification is originally present in the donor DNA. In certain embodiments, the protein of interest encoded by the expression cassette is an enzyme. In particular embodiments, the protein of interest is a hemicellulase, a peroxidase, a protease, a cellulase, a xylanase, a lipase, a phospholipase, an esterase, a cutinase, a pectinase, a keratinase, a reductase, an oxidase, a phenol oxidase, a lipoxygenase, a ligninase, a pullulanase, a tannase, a pentosanase, a mannanase, a beta-glucanase, an arabinosidase, a hyaluronidase, a chondroitinase, a laccase, an amylase, a glucoamylase, a variant thereof, a functional fragment thereof, or a hybrid or mixture of two or more thereof. In yet other particular embodiments, the protein of interest is a peptide hormone, a growth factor, a clotting factor, a chemokine, a cytokine, a lymphokine, an antibody, a receptor, an adhesion molecule, a microbial antigen, a variant thereof, a functional fragment thereof, or a hybrid or mixture of two or more thereof.

In some embodiments of the methods, the step of identifying a fungal cell having a genomic modification at or near the site of interest includes culturing the population of cells from step (a) under conditions to select for or screen for the homologous recombination or the modification. Such conditions include antibiotic selection conditions, conditions that select for or screen for auxotrophic cells, and the like. In some embodiments, the identifying step comprises culturing the population of cells from step (a) under conditions to screen for unstable transformants.

The method of any preceding claim, wherein the introducing step comprises introducing into the fungal cells a DNA construct comprising a sequence encoding a selectable marker and the donor DNA, and wherein the identifying step comprises culturing the population of cells from step (a) under conditions to screen for unstable transformants that have lost the selectable marker yet retained the donor DNA.

Other aspects of the present disclosure are drawn to recombinant fungal cells produced by the methods described above as well as those for use as parental host cells in performing the methods.

Thus, in certain embodiments, aspects of the present disclosure include recombinant fungal cells that including a first recombinant DNA construct comprising an expression cassette for a Cas endonuclease. In certain embodiments, the NHEJ pathway in the recombinant fungal cell is non-functional (inactivated) or reduced, e.g., where one or more components of the NHEJ pathway are inactivated, nonfunctional, or have reduced activity (e.g., ku80, ku70, rad50, mre11, xrs2, lig4, xrs, or combinations thereof). For example, the fungal cell can have an inactivated/reduced activity form of ku80. In certain other embodiments, the NHEJ pathway in the recombinant fungal cell is functional.

In certain embodiments, the Cas endonuclease expressed from the expression cassette is a Cas9 endonuclease or variant thereof. Alternatively, the Cas endonuclease expressed from the expression cassette is a Cas nickase.

As described above, in some cases the Cas endonuclease is a Cas9 endonuclease (or variant thereof). The Cas9 endonuclease may be any convenient Cas9 endonuclease including but not limited to Cas9 endonucleases, and functional fragments thereof, from the following bacterial species: *Streptococcus* sp. (e.g., *S. pyogenes, S. mutans*, and *S. thermophilus*), *Campylobacter* sp. (e.g., *C. jejuni*), *Neisseria* sp. (e.g., *N. meningitides*), *Francisella* sp. (e.g., *F. novicida*), and *Pasteurella* sp. (e.g., *P. multocida*). Numerous other species of Cas9 can be used. In certain of the fungal cells described herein, the first recombinant DNA construct includes a Cas endonuclease gene that is optimized for expression in the fungal cell. For example, a Cas endonuclease encoding gene that is optimized for expression in filamentous fungal cells includes a sequence that has at least 70% sequence identity to SEQ ID NO:44 (encoding Cas9 from *S. pyogenes*; SEQ ID NO:45). In some instances, the Cas endonuclease polypeptide is operably linked to one or more nuclear targeting signal (also referred to as a nuclear localization signal/sequence; NLS). Any convenient NLS can be used, with examples including the SV40 NLS (SEQ ID NO:46), a NLS derived from the *T. reesei* blr2 (blue light regulator 2) gene (SEQ ID NO:47), or a combination of both. In some embodiments, the recombinant DNA construct comprises a promoter operably linked to a filamentous fungal cell optimized polynucleotide sequence encoding a Cas9 endonuclease or variant thereof.

In certain aspects, the recombinant fungal cell described above further includes a second recombinant DNA construct capable of expressing a guide RNA, optionally through an expression cassette, where the guide RNA and Cas endonuclease are capable of forming a complex that enables the Cas endonuclease to act at a target site in the genome of the recombinant fungal cell, where by "act" is meant that the Cas endonuclease cleaves the DNA as expected (making either double-stranded cut or a nick). In some embodiments, the recombinant DNA construct or the expression cassette for the guide RNA comprises a DNA polymerase III dependent promoter functional in a Euascomycete or Pezizomycete, wherein the promoter is operably linked to the DNA encoding the guide RNA. In some embodiments, the promoter is derived from a *Trichoderma* U6 snRNA gene. In certain embodiments, the promoter comprises a nucleotide sequence with at least 60%, 65%, 70%, 75%, 80%, 85%, 90%, 95%, 96%, 97%, 98%, or 99% identity to SEQ ID NO: 40 or 41. In specific embodiments, the promoter comprises the sequence of SEQ ID NO: 40 or 41. In some embodiments, the recombinant DNA construct or the expression cassette for the guide RNA comprises a guide RNA-encoding DNA with an intron sequence from a *Trichoderma* U6 snRNA gene. In some embodiments, the intron sequence derived from *Trichoderma* U6 snRNA gene comprises a nucleotide sequence with at least 60%, 65%, 70%, 75%, 80%, 85%, 90%, 95%, 96%, 97%, 98%, or 99% identity to SEQ ID NO: 42. In specific embodiments, the intron sequence derived from *Trichoderma* U6 snRNA gene comprises the sequence of SEQ ID NO: 42.

In some instances, the recombinant fungal cell further includes a donor DNA that contains a polynucleotide of interest (which is intended by the user of the disclosed method to be inserted into the genome of the fungal cell at or near the target site in the genome via homologous recombination). Thus, in certain embodiments, the fungal cell has the polynucleotide of interest inserted at/near the target site. In some instances, the donor DNA comprises at least one of the following modifications in the domain with homology to the genomic locus of the fungal cell, as compared to the sequence of the genomic locus: a deletion of one or more nucleotides, an insertion of one or more nucleotides, insertion of an expression cassette encoding a protein of interest, a substitution of one or more nucleotides, and any combination thereof.

As noted above, we have shown that Cas-targeted homologous recombination is enhanced in cells in which the NHEJ pathway at the Cas target site is non-functional, reduced or inhibited. However, it is not required to have a non-functional, reduced or inhibited NHEJ pathway for a successful or even efficient Cas-targeted homologous recombination to occur.

In some embodiments, the recombinant fungal cell comprises a DNA construct comprising a sequence encoding a selectable marker or phenotypic marker as described herein. In certain embodiments, the DNA construct comprises both the sequence encoding the selectable marker and a donor DNA as described herein. In some embodiments, the DNA construct comprises a sequence encoding a Cas endonuclease as described herein, the sequence encoding the selectable marker, and the donor DNA. In some embodiments, the DNA construct comprises a sequence encoding a guide RNA as described herein, the sequence encoding the selectable marker, and the donor DNA. In particular embodiments, the DNA construct comprises a sequence encoding the Cas endonuclease, a sequence encoding the guide RNA, a sequence encoding a selectable marker, and the donor DNA. In certain embodiments, the DNA construct is a linear DNA construct. In certain embodiments, the DNA construct is a circular DNA construct. In certain embodiments, the DNA construct is at least partly integrated into or homologously recombined with the genome of the fungal cell. In particular embodiments, at least part or all of the donor DNA comprised in the DNA construct is integrated into or homologously recombined with the genome of the fungal cell, but the selectable marker-encoding sequence, the Cas endonuclease-encoding sequence, or the guide RNA-encoding sequence is not integrated into or homologously recombined with the genome of the fungal cell.

Fungal cells that find use in the subject methods include filamentous fungal cell species selected from *Trichoderma, Penicillium, Aspergillus, Humicola, Chrysosporium, Fusarium, Neurospora, Myceliophthora, Thermomyces, Hypocrea*, and *Emericella*. The filamentous fungi *Trichoderma reesei, P. chrysogenum, M. thermophila, Thermomyces lanuginosus, A. oryzae* and *A. niger* are of particular interest. Other fungal cells, including species of yeast, can also be employed.

The target site selected by a user of the disclosed methods can be located within a region of a gene of interest selected from the group consisting of: an open reading frame, a promoter, a regulatory sequence, a terminator sequence, a regulatory element sequence, a splice site, a coding sequence, a polyubiquitination site, an intron site, and an intron enhancing motif. Examples of genes of interest include genes encoding acetyl esterases, aminopeptidases, amylases, arabinases, arabinofuranosidases, carboxypeptidases, catalases, cellulases, chitinases, chymosin, cutinase, deoxyribonucleases, epimerases, esterases, α-galactosidases, β-galactosidases, α-glucanases, glucanlysases, endo-β-glucanases, glucoamylases, glucose oxidases, α-glucosidases, β-glucosidases, glucuronidases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, peroxidases, phenoloxidases, phytases, polygalacturonases, proteases, rhamno-galacturonases, ribonucleases, thaumatin, transferases, transport proteins, transglutaminases, xylanases, hexose oxidases, and combinations thereof. No limitation in this regard is intended.

Certain aspects of the present invention include recombinant polynucleotides that include a promoter sequence operably linked to a nucleotide sequence encoding a filamentous fungal cell optimized Cas9 endonuclease, where the filamentous fungal cell optimized Cas9 endonuclease is capable of binding to and creating a double strand break in a genomic target sequence in the filamentous fungal genome when complexed with a guide RNA. Examples of the filamentous fungal cell optimized Cas9 endonuclease gene include SEQ ID NO:44 and SEQ ID NO:7 and synonymous variants thereof that have improved expression in a filamentous fungal cell as compared to its parental native Cas9 encoding nucleotide sequence.

Additional recombinant polynucleotide sequences include those having a filamentous fungal cell-derived RNA polymerase III (pol III) driven promoter sequence in operable linkage to a heterologous gene. In some embodiments, the filamentous fungal cell-derived RNA pol III driven promoter sequence comprises a U6 gene promoter, e.g., SEQ ID NO:40, SEQ ID NO:41, or functional variants thereof. In some cases, the recombinant polynucleotide further includes an intron in the heterologous sequence derived from an RNA pol III transcribed gene (e.g., from the U6 gene, e.g., SEQ ID NO:42) and/or a transcriptional terminator from an RNA pol III transcribed gene (e.g., from the U6 gene, e.g., SEQ ID NO:43). In a particular embodiment, the heterologous sequence encodes a guide RNA.

Additional embodiments of the methods and compositions of the present disclosure are shown herein.

BRIEF DESCRIPTION OF THE DRAWINGS

The disclosure can be more fully understood from the following detailed description and the accompanying drawings, which form a part of this application.

FIG. 1 depicts the nucleotide sequence of a putative *T. reesei* U6 gene (SEQ ID NO:1). Elements of interest are indicated, including the TATA box (underlined), the transcriptional start site (downward arrow), the A-box (underlined), the Intron (forward arrow), the B-box (underlined;

within the Intron of the gene), the sequences that are identical to the human U6 gene (in bold italics), and the terminator (underlined).

Figure 2:
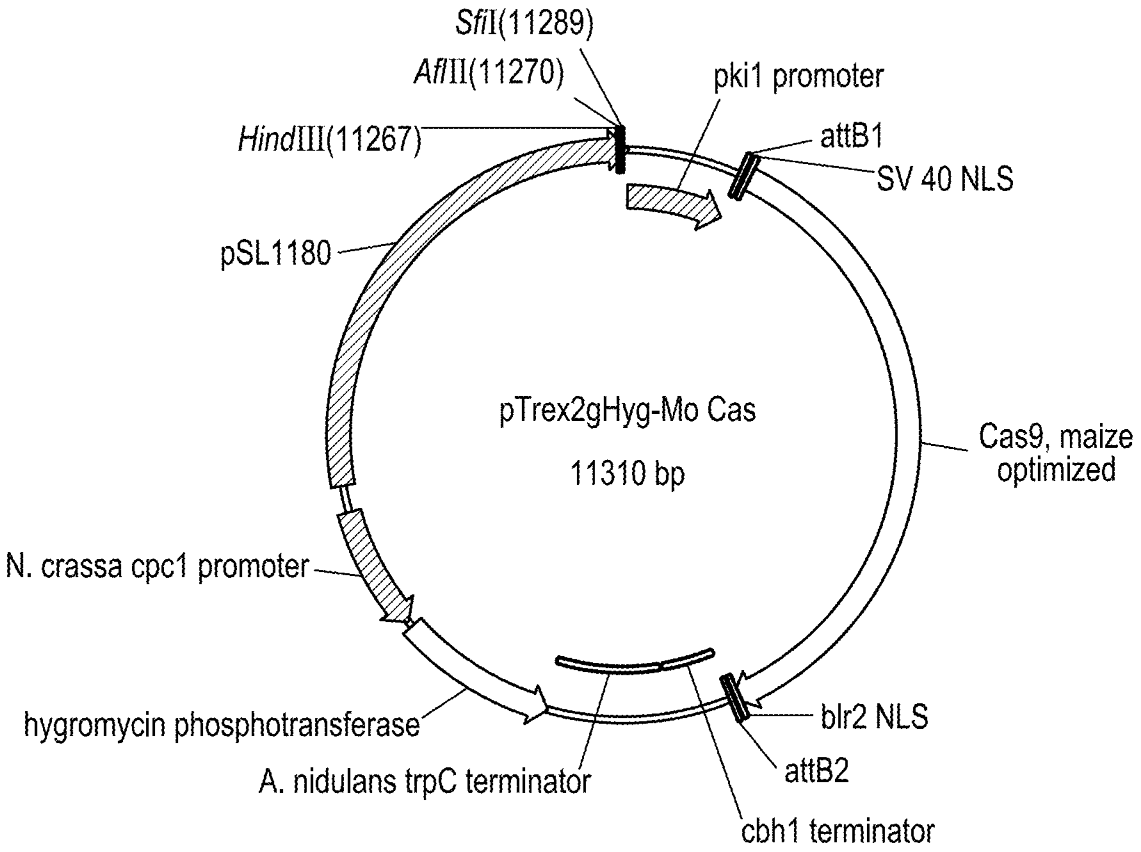

FIG. 2 shows a schematic of the pTrex2gHyg-Mo Cas plasmid.

Figure 3:
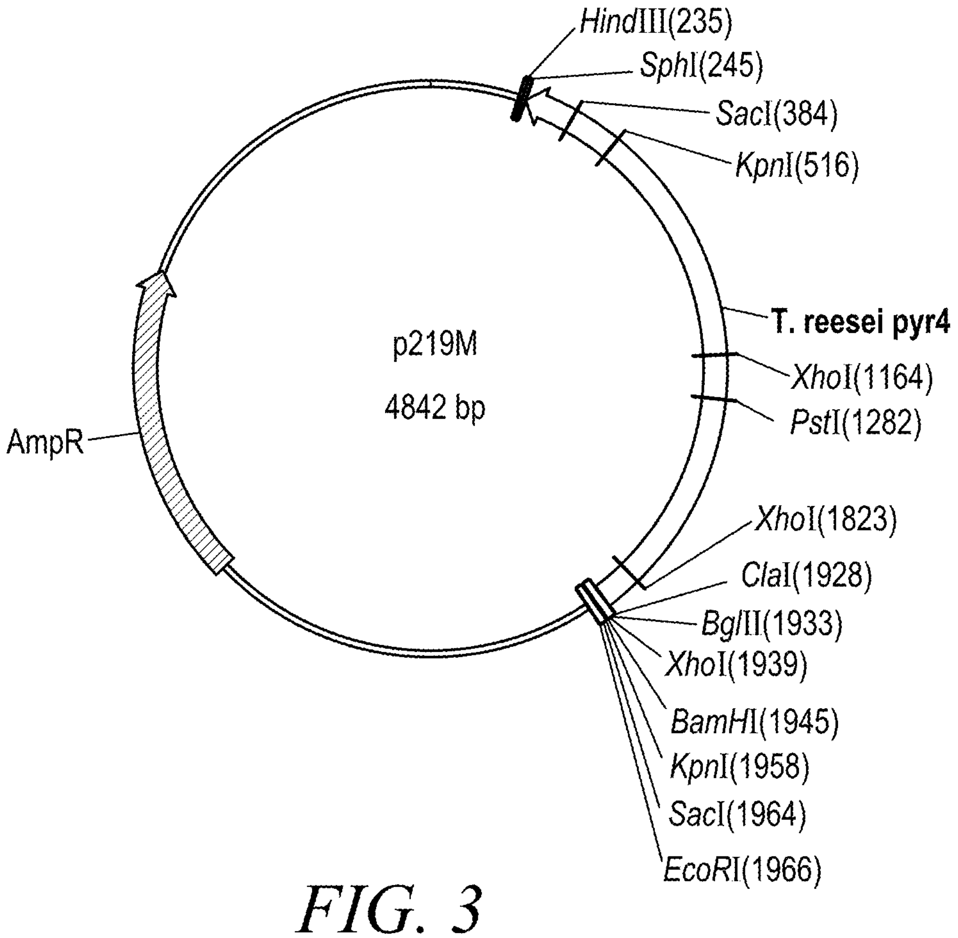

FIG. 3 shows a schematic of the p219M plasmid.

Figure 4:
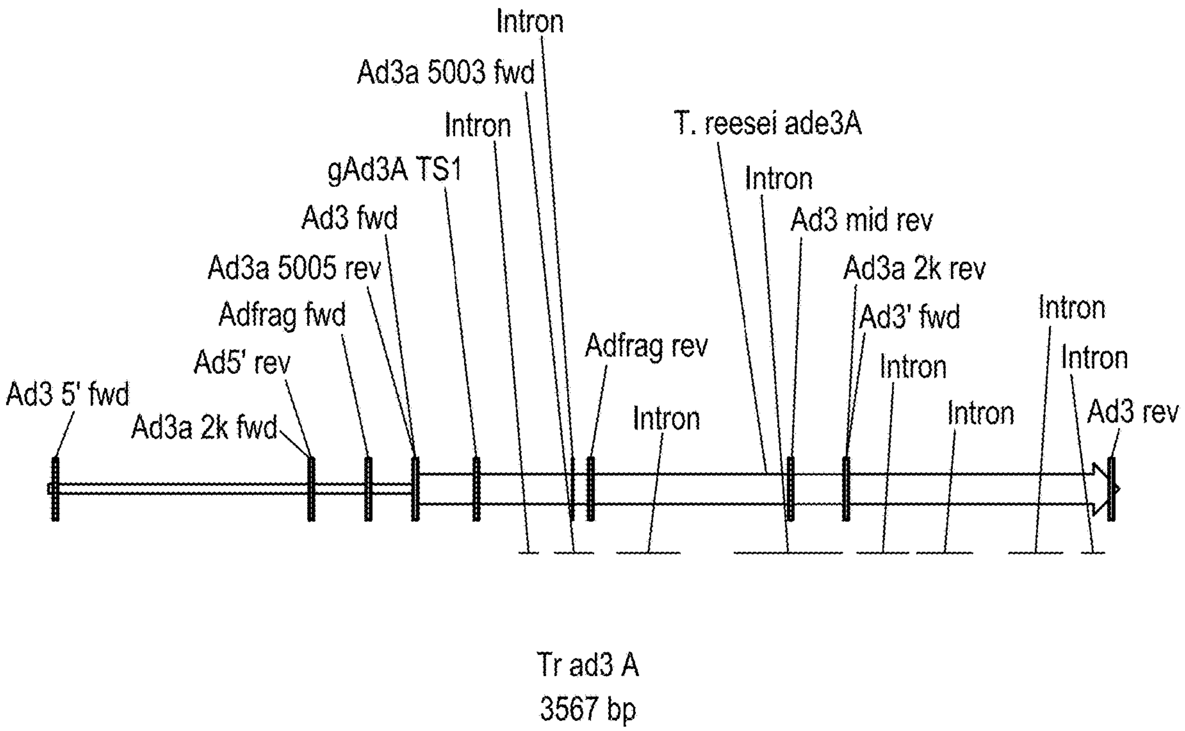

FIG. 4 shows a schematic of the *T. reesei* ad3A gene with PCR primer sites and intronic regions shown.

Figure 5:
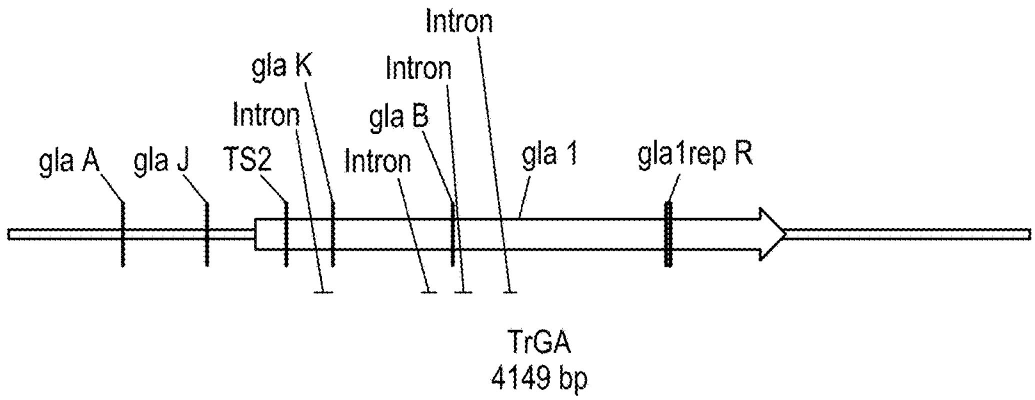

FIG. 5 shows a schematic of the *T. reesei* glucoamylase gene (TrGA) with PCR primer and intronic regions shown.

Figure 6:
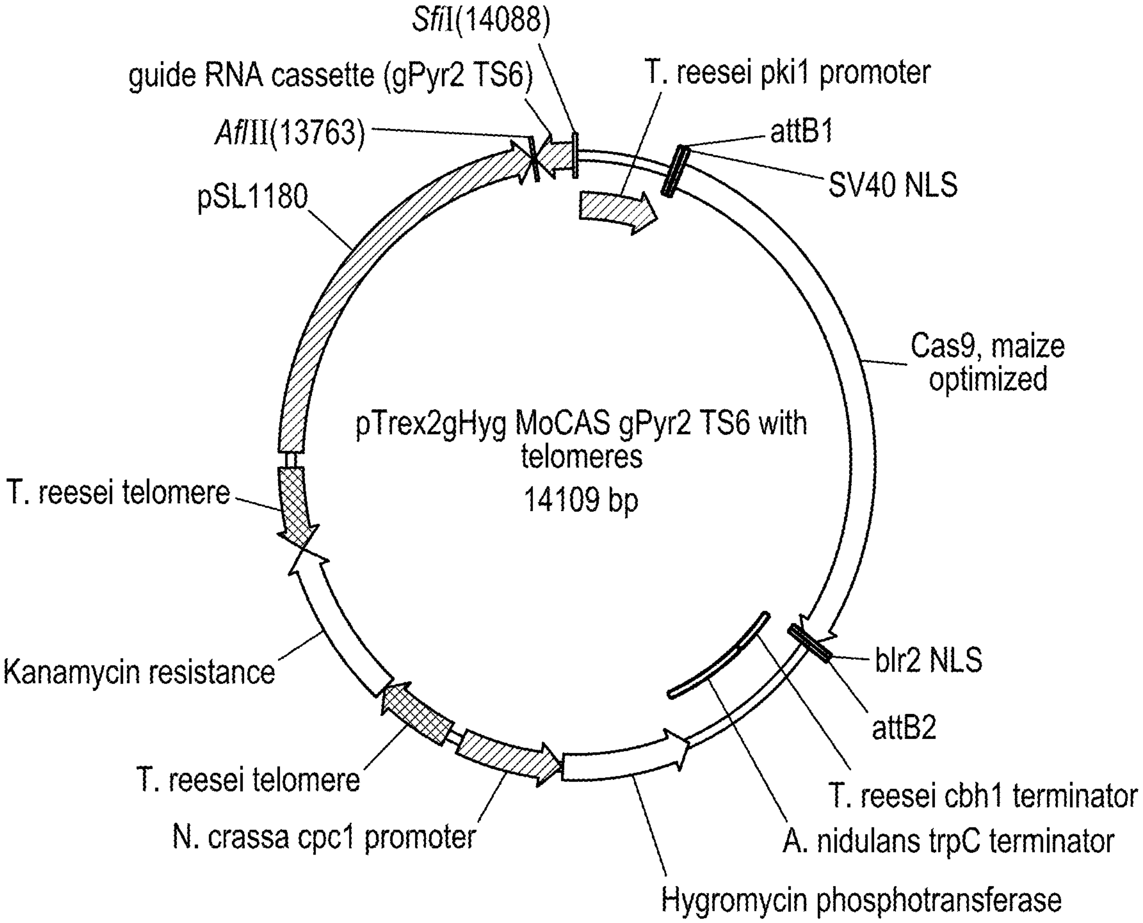

FIG. 6 shows a schematic of the pTrex2gHygMoCasgPyr2TS6 plasmid which includes telomere sequences.

Figure 7:
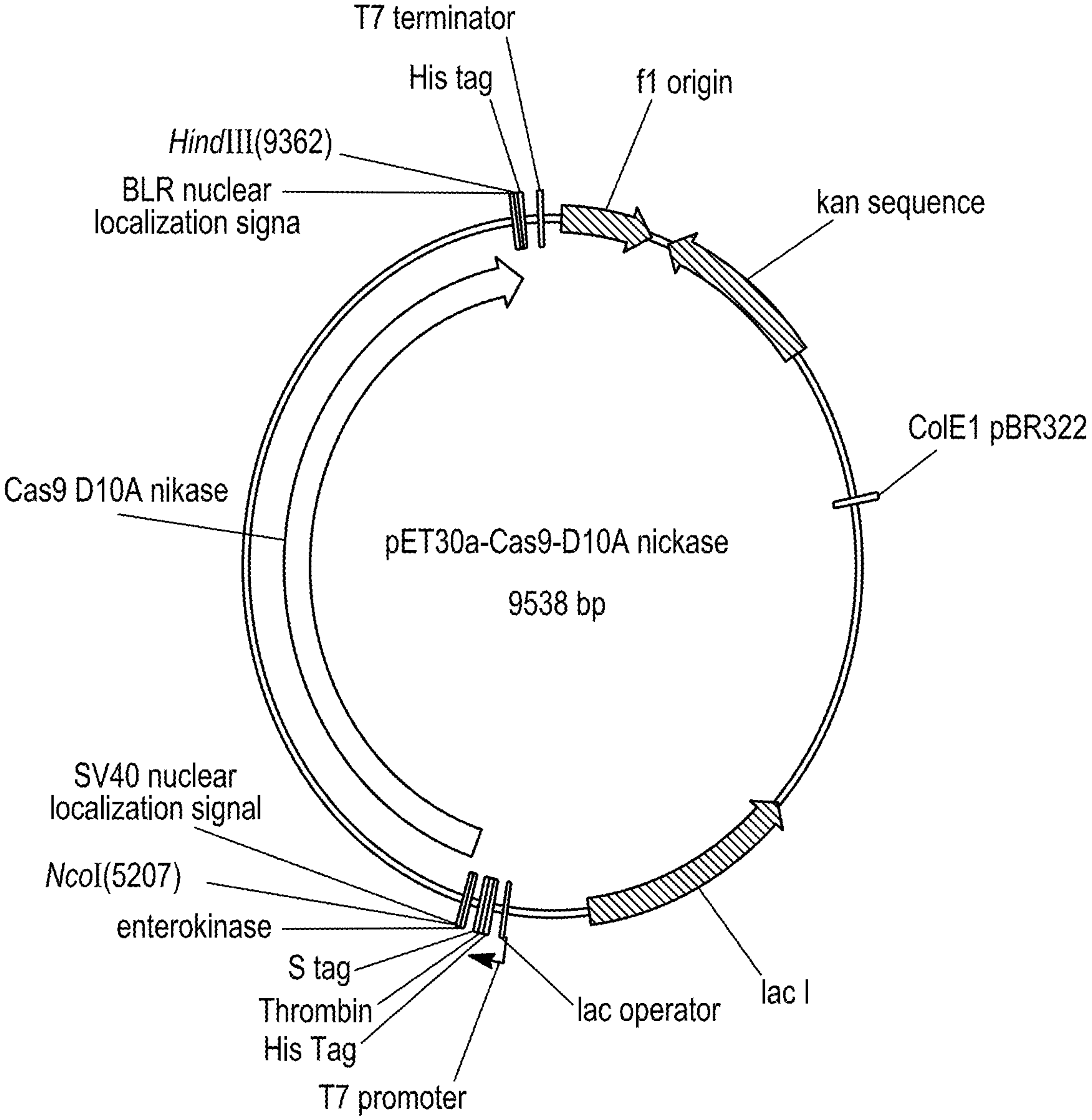

FIG. 7 shows a plasmid map of pET30a-Cas9-D10A nickase.

Figure 8A:
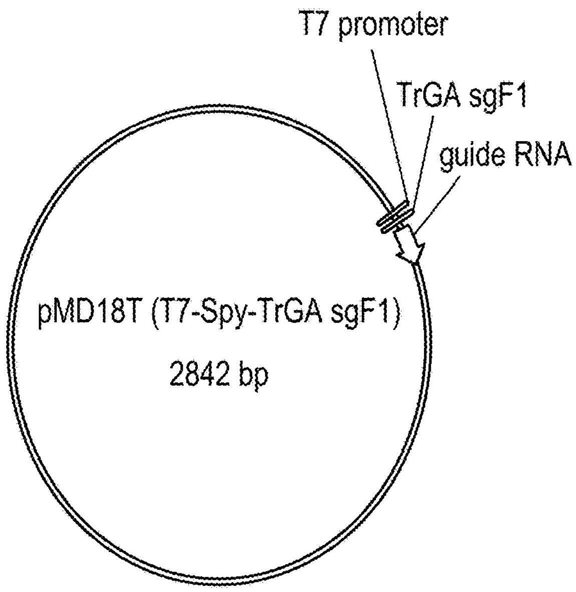
Figure 8B:
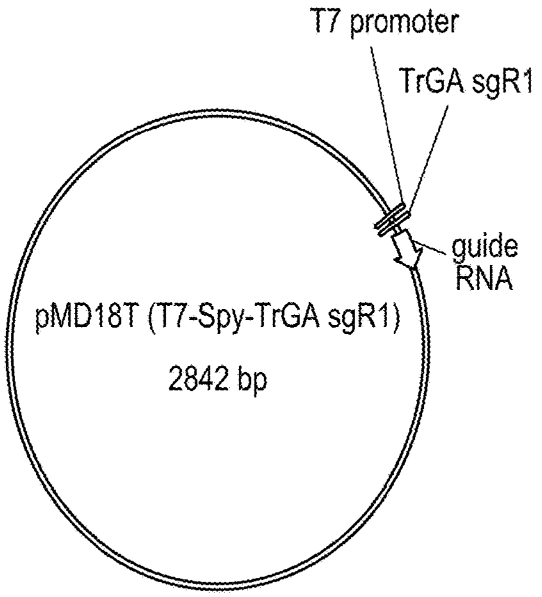

FIGS. 8A and 8B show plasmid maps of pMD18T (T7-Spy-TrGA_sgF1) (FIG. 8A) and pMD18T (T7-Spy-TrGA_sgR1) (FIG. 8B).

Figure 9:
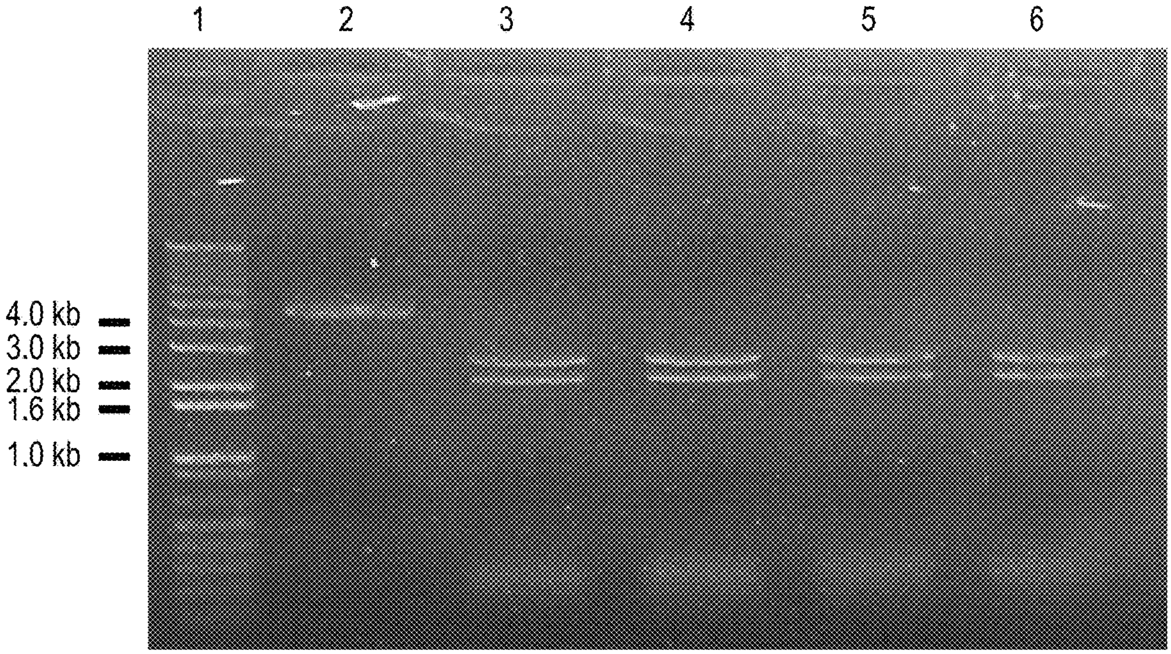

FIG. 9 is an agarose gel showing results of a SpyCas9 nuclease assay. Lane 1, DNA ladder; lane 2, control; lane 3 and 4, SpyCas9 assay in the presence of TrGA_sgR1; lane 5 and 6, SpyCas9 assay in the presence of TrGA_sgF1.

Figure 10:
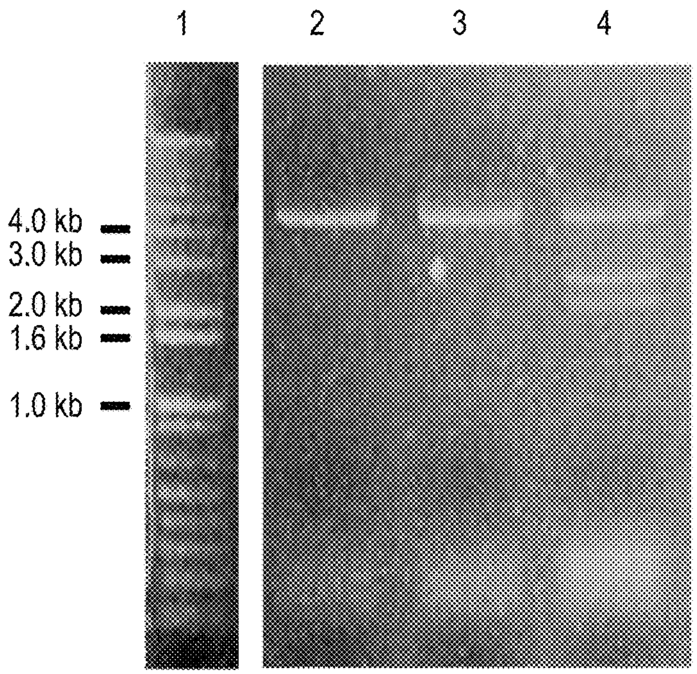

FIG. 10 is an agarose gel showing the results of SpyCas9 (D10A) assay. Lane 1, DNA ladder; lane 2, SpyCas9(D10A) with TrGA_sgF1 alone; lane 3, SpyCas9(D10A) with TrGA_sgR1 alone; lane 4, SpyCas9(D10A) with both RNAs.

Figure 11:
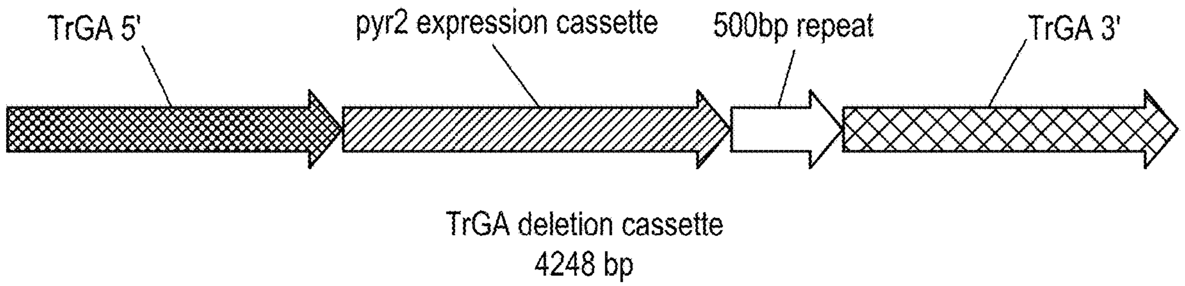

FIG. 11 is a Schematic diagram of TrGA deletion cassette.

Figure 12:
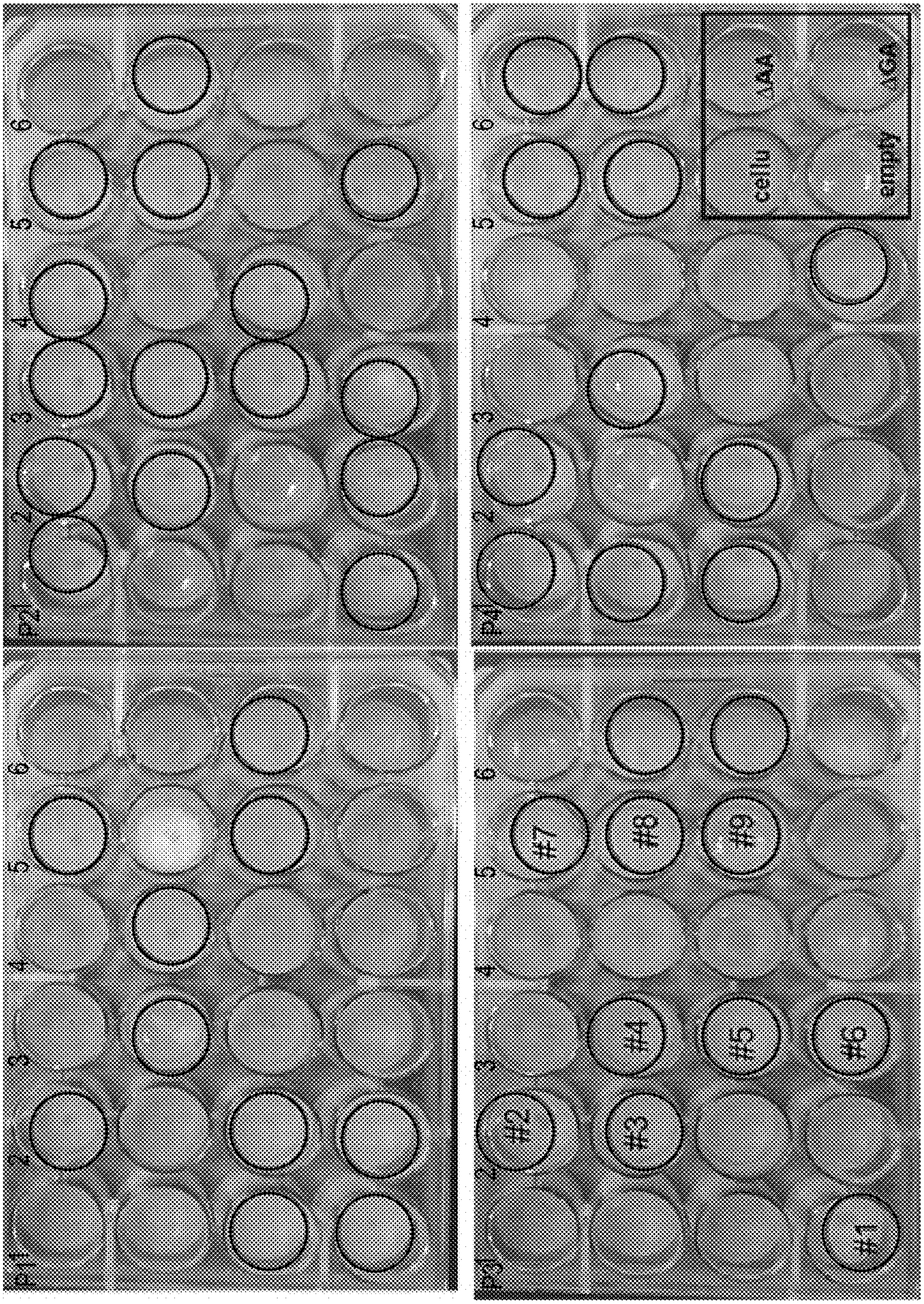

FIG. 12 shows 24-well plates with the morphology of transformants growing on Vogel's-starch agar. The transformants with the retarded growth phenotype are indicated by the circles. The morphology of 3 controls are shown in the square at the bottom right. "cellu"=quad-delete strain of *T. reesei* with additional deletions of the endoglucanase-3, endoglucanase-4, endoglucanase-5, endoglucanase-6, mannanase-1; "ΔAA"="cellu" strain of *T. reesei* with alpha-amylase gene deleted; "ΔGA"="cellu" strain of *T. reesei* with glucoamylase gene deleted; and "empty"=no cells (empty well). Selected clones #1 to #9 are indicated.

Figure 13A:
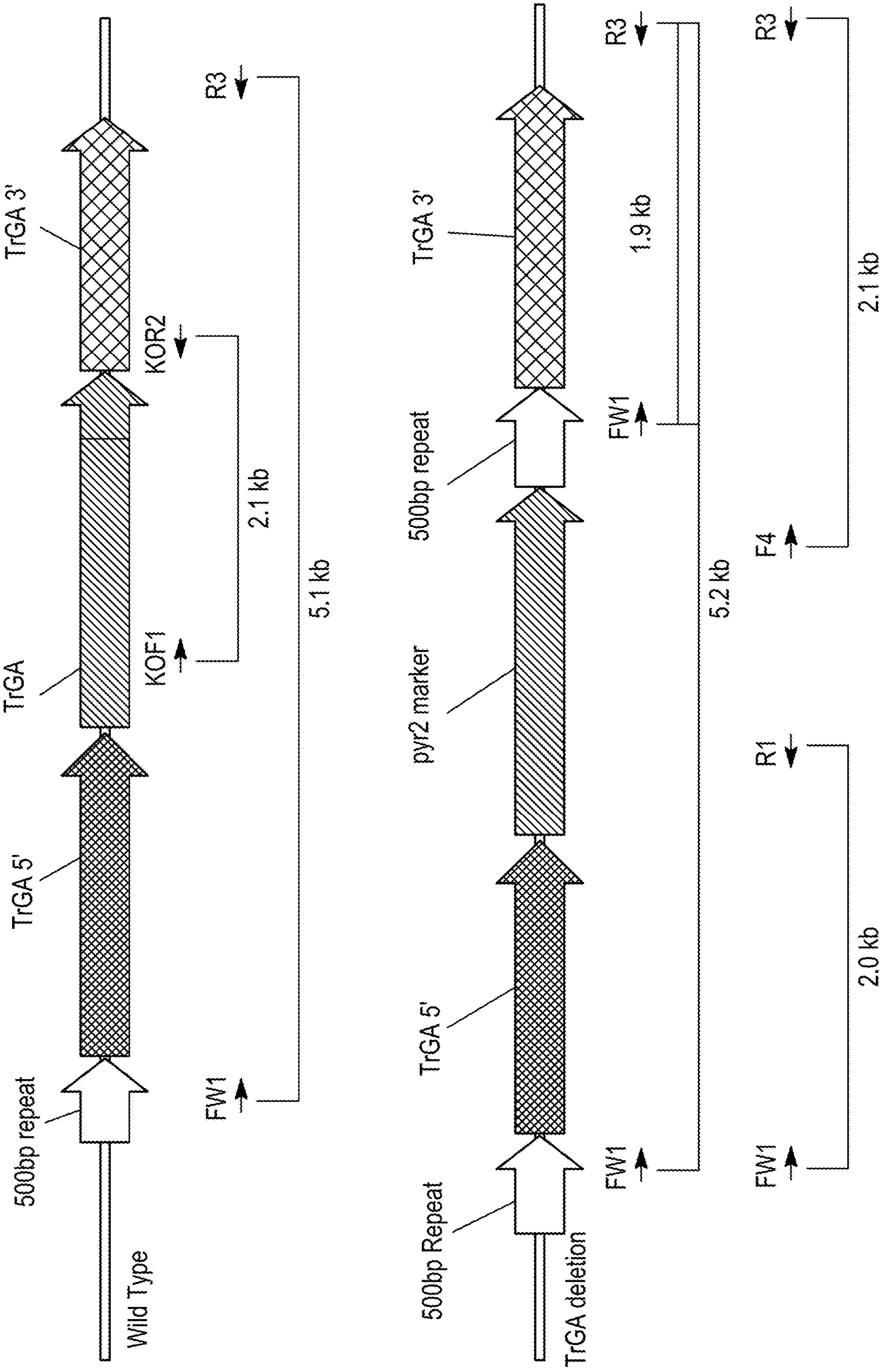
Figure 13B:
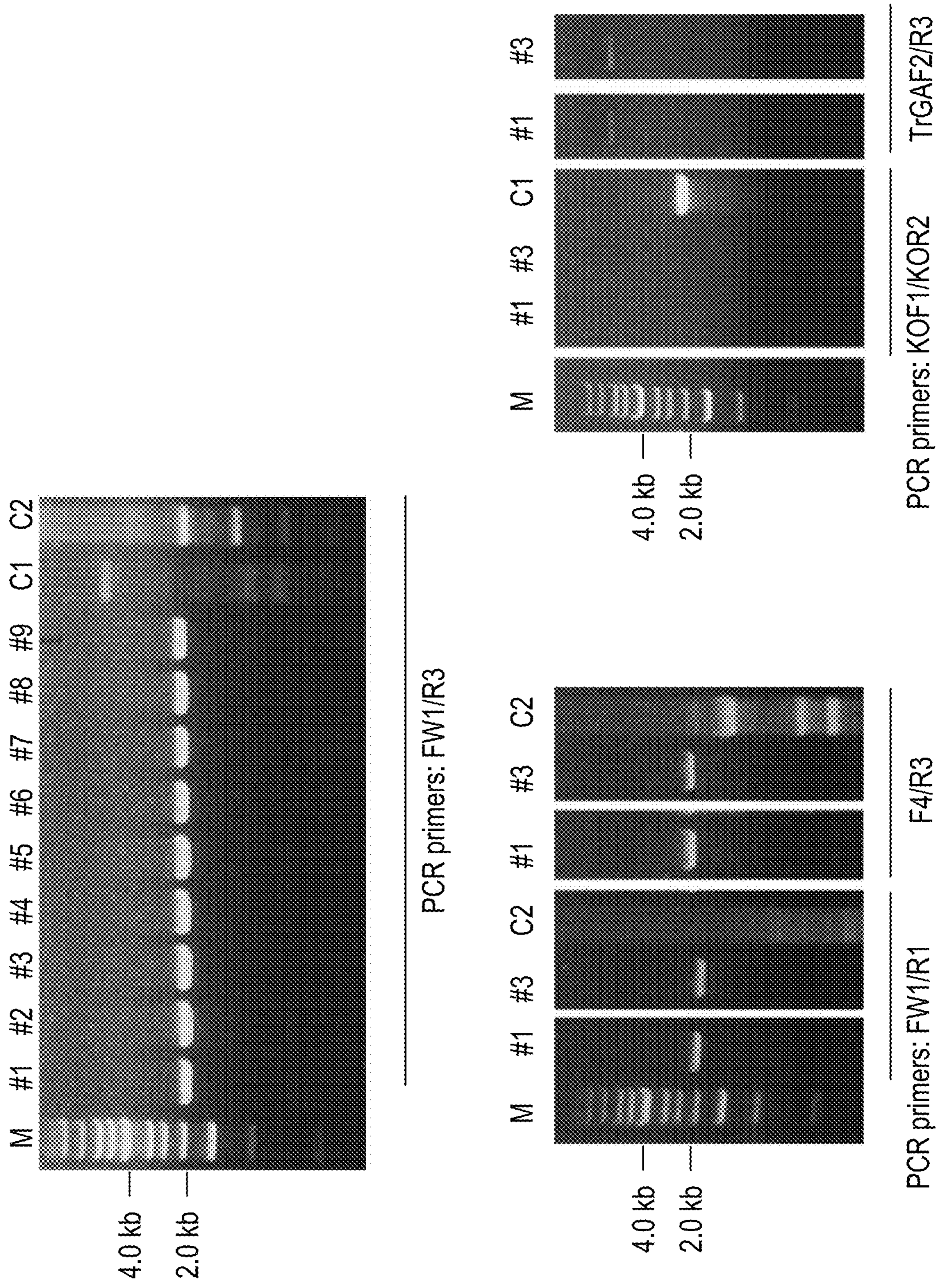

FIGS. 13A and 13B. Confirmation of TrGA deletion in *T. reesei*. (FIG. 13A) Schematic diagram showing the structure of TrGA locus in wild type and TrGA deletion strain, and the binding site of primers Fw1, R3, KOF1 (5'-gaacaatcttctttgcaatgttggtc-3') (SEQ ID NO:79), KOR2 (5'-ggcagactacaagtctactagtactac-3') (SEQ ID NO:58)., R1 (5'-gaggaagtcctgcttgtaggcaggc-3') (SEQ ID NO:80) and F4 (5'-cgacagagcagtcatatggggatacg-3') (SEQ ID NO:81). (FIG. 13B) Agarose gels showing results of PCRs. The PCR products were analyzed using 0.8% agarose gel, running at 140 volts for 30 min.

Figure 14:
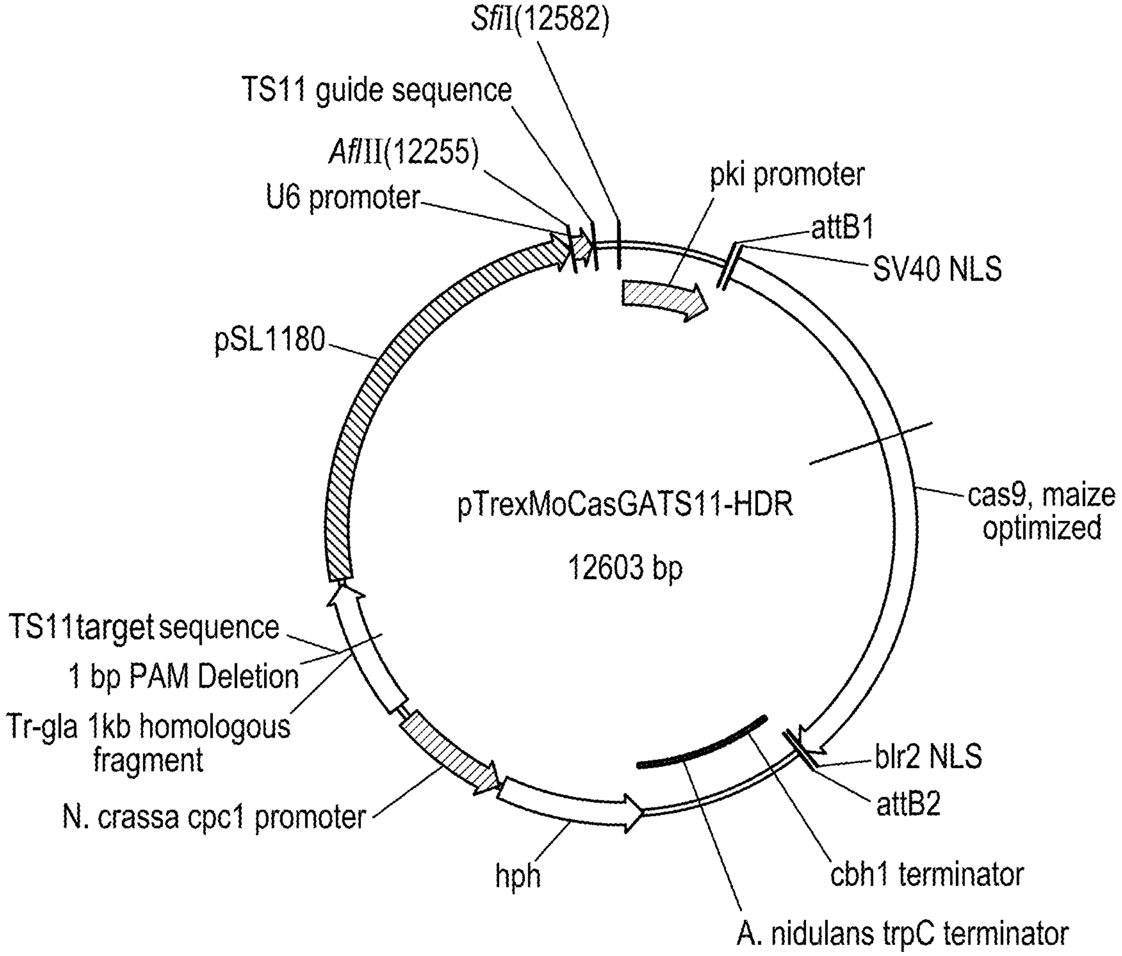

FIG. 14 shows a plasmid map of pTrexMoCasGATS11-HDR.

DETAILED DESCRIPTION

The present disclosure includes compositions and methods that find use in promoting homologous recombination of a donor DNA with a genomic locus in a fungal cell. The methods employ a functional guide RNA/Cas endonuclease complex which recognizes a desired target site and introduces a double strand break or nick at the site, which thereby promotes and/or enhances homologous recombination at or near the target site. In certain aspects, the non-homologous end joining (NHEJ) mechanism at the target site in the fungal cells is not activated, non-functional, or reduced, which we demonstrate herein improves the efficiency of the desired homologous recombination event.

Before the present compositions and methods are described in greater detail, it is to be understood that the present compositions and methods are not limited to particular embodiments described, and as such may, of course, vary. It is also to be understood that the terminology used herein is for the purpose of describing particular embodiments only, and is not intended to be limiting, since the scope of the present compositions and methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the present compositions and methods. The upper and lower limits of these smaller ranges may independently be included in the smaller ranges and are also encompassed within the present compositions and methods, subject to any specifically excluded limit in the stated range. Where the stated range includes one or both of the limits, ranges excluding either or both of those included limits are also included in the present compositions and methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. For example, in connection with a numerical value, the term "about" refers to a range of −10% to +10% of the numerical value, unless the term is otherwise specifically defined in context. In another example, the phrase a "pH value of about 6" refers to pH values of from 5.4 to 6.6, unless the pH value is specifically defined otherwise.

The headings provided herein are not limitations of the various aspects or embodiments of the present compositions and methods which can be had by reference to the specification as a whole. Accordingly, the terms defined immediately below are more fully defined by reference to the specification as a whole.

The present document is organized into a number of sections for ease of reading; however, the reader will appreciate that statements made in one section may apply to other sections. In this manner, the headings used for different sections of the disclosure should not be construed as limiting.

Unless defined otherwise, all technical and scientific terms used herein have the same meaning as commonly understood by one of ordinary skill in the art to which the present compositions and methods belongs. Although any methods and materials similar or equivalent to those described herein can also be used in the practice or testing of the present compositions and methods, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present compositions and methods are not entitled to antedate such publication by virtue of prior invention. Further, the dates of publication provided may be different from the actual publication dates which may need to be independently confirmed.

In accordance with this detailed description, the following abbreviations and definitions apply. Note that the singular forms "a," "an," and "the" include plural referents unless the context clearly dictates otherwise. Thus, for example, reference to "an enzyme" includes a plurality of such enzymes, and reference to "the dosage" includes reference to one or more dosages and equivalents thereof known to those skilled in the art, and so forth.

It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present compositions and methods described herein. Any recited method can be carried out in the order of events recited or in any other order which is logically possible.

Definitions

As used herein, a polypeptide referred to as a "Cas endonuclease" or having "Cas endonuclease activity" relates to a CRISPR associated (Cas) polypeptide encoded by a Cas gene where the Cas protein is capable of cutting a target DNA sequence when functionally coupled with one or more guide polynucleotides (see, e.g., U.S. Pat. No. 8,697,359 entitled "CRISPR-Cas systems and methods for altering expression of gene products"). Variants of Cas endonucleases that retain guide polynucleotide directed endonuclease activity are also included in this definition, including Cas variants that have nicking endonuclease activity, i.e., they introduce single strand nick at a double-stranded DNA target site (see definition below). (It is noted that wild-type Cas endonucleases identified to date introduce double-strand breaks at the target site.) A Cas endonuclease is guided by the guide polynucleotide to recognize and cleave a specific target site in double stranded DNA, e.g., at a target site in the genome of a cell. Several different types of CRISPR-Cas systems have been described and can be classified as Type I, Type II, and Type III CRISPR-Cas systems (see, e.g., the description in Liu and Fan, CRISPR-Cas system: a powerful tool for genome editing. Plant Mol Biol (2014) 85:209-218). In certain aspects, the CRISPR-Cas system is a Type II CRISPR-Cas system employing a Cas9 endonuclease or variant thereof (including, e.g., a Cas nickase). The Cas9 endonuclease may be any convenient Cas9 endonuclease, including but not limited to Cas9 endonucleases, and functional fragments thereof, from the following bacterial species: *Streptococcus* sp. (e.g., *S. pyogenes, S. mutans*, and *S. thermophilus*), *Campylobacter* sp. (e.g., *C. jejuni*), *Neisseria* sp. (e.g., *N. meningitides*), *Francisella* sp. (e.g., *F. novicida*), and *Pasteurella* sp. (e.g., *P. multocida*). Numerous other species of Cas9 can be used. For example, functional Cas9 endonucleases or variants thereof containing an amino acid sequence that has at least 70% identity to any one of SEQ ID NOs:45 and 48 to 53 may be employed, e.g., at least 80% identity, at least 90% identity, at least 95% identity, at least 96% identity, at least 97% identity, at least 98% identity, at least 99% identity, and including up to 100% identity to any one of SEQ ID NOs:45 and 48 to 53. In other embodiments, the Cas endonuclease or variant thereof is a Cpf1 endonuclease of the Type II CRISPR-Cas system. Cpf1 mediates robust DNA interference with features distinct from Cas9. Cpf1 lacks tracrRNA and utilizes a T-rich protospacer-adjacent motif. It cleaves DNA via a staggered DNA double-stranded break. See, e.g., Zetsche et al., Cell (2015) 163: 759-771.

As used herein, a "Cas nickase" is a Cas endonuclease that, when functionally coupled with one or more guide polynucleotides, is capable of introducing a single-strand nick into a target double stranded DNA sequence. Cas nickases can be generated recombinantly by inactivating one of the two nuclease domains in a parent Cas endonuclease (e.g., by site-directed mutagenesis). One non-limiting example of a Cas nickase is the Cas9 nickase described in Sander and Joung (Nature Biotechnology, 2013, 1-9) in which the RuvC domain is inactivated by a D10A mutation. As mentioned above, the general term "Cas endonuclease" encompasses both double-strand cutting and nicking Cas polypeptides. For example, if a guide RNA is described as being capable of directing a Cas endonuclease to a desired target site, it would do so for both a double-strand cutting Cas endonuclease and a nicking Cas polypeptide (as defined below).

As used herein, the term "guide polynucleotide" relates to a polynucleotide sequence that can form a complex with a Cas endonuclease and enables the Cas endonuclease to recognize and cleave a DNA target site. The guide polynucleotide can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA".

The guide polynucleotide can be a double molecule (also referred to as duplex guide polynucleotide) comprising a first nucleotide sequence domain (referred to as Variable Targeting domain or VT domain) that is complementary to a nucleotide sequence in a target DNA (also called the "protospacer" or "target site" below) and a second nucleotide sequence domain (referred to as Cas endonuclease recognition domain or CER domain) that interacts with a Cas endonuclease polypeptide. The CER domain of the double molecule guide polynucleotide comprises two separate molecules that are hybridized along a region of complementarity. The two separate molecules can be RNA, DNA, and/or RNA-DNA-combination sequences. In some embodiments, the first molecule of the duplex guide polynucleotide comprising a VT domain linked to a CER domain is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the crRNA naturally occurring in Bacteria and Archaea. In one embodiment, the size of the fragment of the crRNA naturally occurring in Bacteria and Archaea that is present in a crNucleotide disclosed herein can range from, but is not limited to, 2, 3, 4, 5, 6, 7, 8, 9, 10, 11, 12, 13, 14, 15, 16, 17, 18, 19, 20 or more nucleotides. In some embodiments the second molecule of the duplex guide polynucleotide comprising a CER domain is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides). In certain embodiments, the RNA that guides the RNA/Cas9 endonuclease complex is a duplexed RNA comprising a duplex crRNA-tracrRNA.

The guide polynucleotide can also be a single molecule comprising a first nucleotide sequence domain (referred to as Variable Targeting domain or VT domain) that is complementary to a nucleotide sequence in a target DNA and a second nucleotide domain (referred to as Cas endonuclease recognition domain or CER domain) that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. In some embodiments the single guide polynucleotide comprises a crNucleotide (comprising a VT domain linked to a CER domain) linked to a tracrNucleotide (comprising a CER domain), wherein the linkage is a nucleotide sequence comprising a RNA sequence, a DNA sequence, or a RNA-DNA combination sequence. The single guide polynucleotide being comprised of sequences from the crNucleotide and tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). In one embodiment of the disclosure, the single guide RNA comprises a crRNA or crRNA fragment and a tracrRNA or tracrRNA fragment of the type II CRISPR/Cas system that can form a complex with a type II Cas endonuclease, wherein the guide RNA/Cas endonuclease complex can direct the Cas endonuclease to a fungal cell genomic target site, enabling the Cas endonuclease to introduce a double strand break into the genomic target site.

One aspect of using a single guide polynucleotide versus a duplex guide polynucleotide is that only one expression cassette needs to be made to express the single guide polynucleotide in a target cell.

The term "variable targeting domain" or "VT domain" is used interchangeably herein and includes a nucleotide sequence that is complementary to one strand (nucleotide sequence) of a double strand DNA target site. The % complementation between the first nucleotide sequence domain (VT domain) and the target sequence is at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or is 100% complementary. The VT domain can be at least 12, 13, 14, 15, 16, 17, 18, 19, 20, 21, 22, 23, 24, 25, 26, 27, 28, 29 or 30 nucleotides in length. In some embodiments, the VT domain comprises a contiguous stretch of 12 to 30 nucleotides. The VT domain can be composed of a DNA sequence, a RNA sequence, a modified DNA sequence, a modified RNA sequence, or any combination thereof.

The term "Cas endonuclease recognition domain" or "CER domain" of a guide polynucleotide is used interchangeably herein and includes a nucleotide sequence (such as a second nucleotide sequence domain of a guide polynucleotide), that interacts with a Cas endonuclease polypeptide. The CER domain can be composed of a DNA sequence, a RNA sequence, a modified DNA sequence, a modified RNA sequence (see for example modifications described herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetraloop sequence, such as, but not limiting to a GAAA tetraloop sequence.

Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

As used herein, the term "guide polynucleotide/Cas endonuclease system" (and equivalents) includes a complex of a Cas endonuclease and a guide polynucleotide (single or double) that is capable of introducing a double strand break at a DNA target site. The Cas endonuclease unwinds the DNA duplex in close proximity of the DNA target site and cleaves both DNA strands upon recognition of a target sequence by a guide RNA, but only if the correct protospacer-adjacent motif (PAM) is appropriately oriented at the 3' end of the target sequence.

The terms "functional fragment", "fragment that is functionally equivalent", "functionally equivalent fragment", and the like, are used interchangeably and refer to a portion or subsequence of a parent polypeptide that retains the qualitative enzymatic activity of the parent polypeptide. For example, a functional fragment of a Cas endonuclease retains the ability to create a double-strand break with a guide polynucleotide. It is noted here that a functional fragment may have altered quantitative enzymatic activity as compared to the parent polypeptide.

The terms "functional variant", "variant that is functionally equivalent", "functionally equivalent variant", and the like are used interchangeably and refer to a variant of a parent polypeptide that retains the qualitative enzymatic activity of the parent polypeptide. For example, a functional variant of a Cas endonuclease retains the ability to create a double-strand break or a nick (depending on the variant in question) with a guide polynucleotide. It is noted here that a functional variant may have altered quantitative enzymatic activity as compared to the parent polypeptide.

Fragments and variants can be obtained via any convenient method, including site-directed mutagenesis and synthetic construction.

The term "genome" as it applies to a fungal cell cells encompasses not only chromosomal DNA found within the nucleus, but organelle DNA found within subcellular components (e.g., mitochondria) of the cell.

A "codon-modified gene" or "codon-preferred gene" or "codon-optimized gene" is a gene having its frequency of codon usage designed to mimic the frequency of preferred codon usage of the host cell. The nucleic acid changes made to codon-optimize a gene are "synonymous", meaning that they do not alter the amino acid sequence of the encoded polypeptide of the parent gene. However, both native and variant genes can be codon-optimized for a particular host cell, and as such no limitation in this regard is intended.

"Coding sequence" refers to a polynucleotide sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, 5' untranslated sequences, 3' untranslated sequences, introns, polyadenylation target sequences, RNA processing sites, effector binding sites, and stem-loop structures.

"Promoter" refers to a DNA sequence capable of controlling the expression of a coding sequence or functional RNA. The promoter sequence consists of proximal and more distal upstream elements, the latter elements often referred to as enhancers. An "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, and/or comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. As is well-known in the art, promoters can be categorized according to their strength and/or the conditions under which they are active, e.g., constitutive promoters, strong promoters, weak promoters, inducible/repressible promoters, tissue-specific/developmentally regulated promoters, cell-cycle dependent promoters, etc.

"RNA transcript" refers to the product resulting from RNA polymerase-catalyzed transcription of a DNA sequence. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. "Sense" RNA refers to RNA transcript that includes the mRNA and can be translated into protein within a cell or in vitro. "Antisense RNA" refers to an RNA transcript that is complementary to all or part of a target primary transcript or mRNA, and that, under certain conditions, blocks the expression of a target gene (see, e.g., U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated into a polypeptide but yet has an effect on cellular processes. The terms "complement" and "reverse complement" are used interchangeably herein with respect to mRNA transcripts, and are meant to define the antisense RNA of the message.

As used herein, "functionally attached" or "operably linked" means that a regulatory region or functional domain of a polypeptide or polynucleotide sequence having a known or desired activity, such as a promoter, enhancer region, terminator, signal sequence, epitope tag, etc., is attached to or linked to a target (e.g., a gene or polypeptide) in such a manner as to allow the regulatory region or functional domain to control the expression, secretion or function of that target according to its known or desired activity. For example, a promoter is operably linked with a coding sequence when it is capable of regulating the expression of that coding sequence (i.e., the coding sequence is under the transcriptional control of the promoter).

Standard recombinant DNA and molecular cloning techniques used herein are well known in the art.

"PCR" or "polymerase chain reaction" is a technique for the synthesis of specific DNA segments and consists of a series of repetitive denaturation, annealing, and extension cycles and is well known in the art.

The term "recombinant," when used in reference to a biological component or composition (e.g., a cell, nucleic acid, polypeptide/enzyme, vector, etc.) indicates that the biological component or composition is in a state that is not found in nature. In other words, the biological component or composition has been modified by human intervention from its natural state. For example, a recombinant cell encompass a cell that expresses one or more genes that are not found in its native parent (i.e., non-recombinant) cell, a cell that expresses one or more native genes in an amount that is different than its native parent cell, and/or a cell that expresses one or more native genes under different conditions than its native parent cell. Recombinant nucleic acids may differ from a native sequence by one or more nucleotides, be operably linked to heterologous sequences (e.g., a heterologous promoter, a sequence encoding a non-native or variant signal sequence, etc.), be devoid of intronic sequences, and/or be in an isolated form. Recombinant polypeptides/enzymes may differ from a native sequence by one or more amino acids, may be fused with heterologous sequences, may be truncated or have internal deletions of amino acids, may be expressed in a manner not found in a native cell (e.g., from a recombinant cell that over-expresses the polypeptide due to the presence in the cell of an expression vector encoding the polypeptide), and/or be in an isolated form. It is emphasized that in some embodiments, a recombinant polynucleotide or polypeptide/enzyme has a sequence that is identical to its wild-type counterpart but is in a non-native form (e.g., in an isolated or enriched form).

The terms “plasmid”, “vector” and “cassette” refer to an extra chromosomal element that carries a polynucleotide sequence of interest, e.g., a gene of interest to be expressed in a cell (an “expression vector” or “expression cassette”). Such elements are generally in the form of double-stranded DNA and may be autonomously replicating sequences, genome integrating sequences, phage, or nucleotide sequences, in linear or circular form, of a single- or double-stranded DNA or RNA, derived from any source, in which a number of nucleotide sequences have been joined or recombined into a unique construction which is capable of introducing a polynucleotide of interest into a cell. The polynucleotide sequence of interest may be a gene encoding a polypeptide or functional RNA that is to be expressed in the target cell. Expression cassettes/vectors generally contain a gene with operably linked elements that allow for expression of that gene in a host cell.

The term “expression”, as used herein, refers to the production of a functional end-product (e.g., an mRNA, guide RNA, or a protein) in either precursor or mature form.

“Introduced” in the context of inserting a polynucleotide or polypeptide into a cell (e.g., a recombinant DNA construct/expression construct) refers to any method for performing such a task, and includes any means of “transfection”, “transformation”, “transduction”, physical means, or the like, to achieve introduction of the desired biomolecule.

By “introduced transiently”, “transiently introduced”, “transient introduction”, “transiently express” and the like is meant that a biomolecule is introduced into a host cell (or a population of host cells) in a non-permanent manner. With respect to double stranded DNA, transient introduction includes situations in which the introduced DNA does not integrate into the chromosome of the host cell and thus is not transmitted to all daughter cells during growth as well as situations in which an introduced DNA molecule that may have integrated into the chromosome is removed at a desired time using any convenient method (e.g., employing a cre-lox system, by removing positive selective pressure for an episomal DNA construct, by promoting looping out of all or part of the integrated polynucleotide from the chromosome using a selection media, etc.). No limitation in this regard is intended. In general, introduction of RNA (e.g., a guide RNA, a messenger RNA, ribozyme, etc.) or a polypeptide (e.g., a Cas polypeptide) into host cells is considered transient in that these biomolecules are not replicated and indefinitely passed down to daughter cells during cell growth. With respect to the Cas/guide RNA complex, transient introduction covers situations when either of the components is introduced transiently, as both biomolecules are needed to exert targeted Cas endonuclease activity. Thus, transient introduction of a Cas/guide RNA complex includes embodiments where either one or both of the Cas endonuclease and the guide RNA are introduced transiently. For example, a host cell having a genome-integrated expression cassette for the Cas endonuclease (and thus not transiently introduced) into which a guide RNA is transiently introduced can be said to have a transiently introduced Cas/guide RNA complex (or system) because the functional complex is present in the host cell in a transient manner. In certain embodiments, the introducing step includes: (i) obtaining a parental fungal cell population that stably expresses the Cas endonuclease, and (ii) transiently introducing the guide RNA into the parental fungal cell population. Conversely, the introducing step can include: (i) obtaining a parental fungal cell population that stably expresses the guide RNA, and (ii) transiently introducing the Cas endonuclease into the parental fungal cell population.

“Mature” protein refers to a post-translationally processed polypeptide (i.e., one from which any pre- or propeptides present in the primary translation product have been removed). “Precursor” protein refers to the primary product of translation of mRNA (i.e., with pre- and propeptides still present). Pre- and propeptides may be but are not limited to intracellular localization signals.

“Stable transformation” refers to the transfer of a nucleic acid fragment into a genome of a host organism, including both nuclear and organellar genomes, resulting in genetically stable inheritance (the resulting host cell is sometimes referred to herein as a “stable transformant”). In contrast, “transient transformation” refers to the transfer of a nucleic acid fragment into the nucleus, or other DNA-containing organelle, of a host organism resulting in gene expression without integration or stable inheritance (sometimes referred to herein as “unstable transformation”, and the resulting host cell sometimes referred to herein as an “unstable transformant”). Host organisms containing the transformed nucleic acid fragments are referred to as “transgenic” organisms.

“Fungal cell”, “fungi”, “fungal host cell”, and the like, as used herein includes the phyla Ascomycota, Basidiomycota, Chytridiomycota, and Zygomycota (as defined by Hawksworth et al., In, Ainsworth and Bisby’s Dictionary of The Fungi, 8th edition, 1995, CAB International, University Press, Cambridge, UK) as well as the Oomycota (as cited in Hawksworth et al., supra) and all mitosporic fungi (Hawksworth et al., supra). In certain embodiments, the fungal host cell is a yeast cell, where by “yeast” is meant ascosporogenous yeast (Endomycetales), basidiosporogenous yeast, and yeast belonging to the Fungi Imperfecti (Blastomycetes). As such, a yeast host cell includes a *Candida, Hansenula, Kluyveromyces, Pichia, Saccharomyces, Schizosaccharomyces*, or *Yarrowia* cell. Species of yeast include, but are not limited to, the following: *Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, Kluyveromyces lactis*, and *Yarrowia lipolytica* cell.

The term “filamentous fungal cell” includes all filamentous forms of the subdivision Eumycotina or Pezizomycotina. Suitable cells of filamentous fungal genera include, but are not limited to, cells of *Acremonium, Aspergillus, Chrysosporium, Corynascus, Chaetomium, Fusarium, Gibberella, Humicola, Magnaporthe, Myceliophthora, Neurospora, Paecilomyces, Penicillium, Scytaldium, Talaromyces, Thermoascus, Thielavia, Tolypocladium, Hypocrea*, and *Trichoderma.*

Suitable cells of filamentous fungal species include, but are not limited to, cells of *Aspergillus awamori, Aspergillus fumigatus, Aspergillus foetidus, Aspergillus japonicus, Aspergillus nidulans, Aspergillus niger, Aspergillus oryzae, Chrysosporium lucknowense, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Hypocrea jecorina, Myceliophthora thermophila, Neurospora crassa, Neurospora intermedia, Penicillium purpurogenum, Penicillium canescens, Penicillium solitum, Penicillium funiculosum Phanerochaete chrysosporium, Talaromyces flavus, Thiela-*

*via terrestris, Trichoderma harzianum, Trichoderma koningii, Trichoderma longibrachiatum, Trichoderma reesei*, and *Trichoderma viride.*

The terms “target site”, “target sequence”, “genomic target site”, “genomic target sequence” (and equivalents) are used interchangeably herein and refer to a polynucleotide sequence in the genome of a fungal cell at which a Cas endonuclease cleavage is desired to promote a genome modification, e.g., homologous recombination with a donor DNA. The context in which this term is used, however, can slightly alter its meaning. For example, the target site for a Cas endonuclease is generally very specific and can often be defined to the exact nucleotide sequence/position, whereas in some cases the target site for a desired genome modification can be defined more broadly than merely the site at which DNA cleavage occurs, e.g., a genomic locus or region where homologous recombination is desired. Thus, in certain cases, the genome modification that occurs via the activity of Cas/guide RNA DNA cleavage is described as occurring “at or near” the target site. The target site can be an endogenous site in the fungal cell genome, or alternatively, the target site can be heterologous to the fungal cell and thereby not be naturally occurring in the genome, or the target site can be found in a heterologous genomic location compared to where it occurs in nature. In certain other cases, when the donor DNA comprises a domain with homology to a genomic locus of the fungal cells, the Cas endonuclease and guide RNA introduced to the fungal cells are capable of forming a complex that enables the Cas endonuclease to act at a target site in or near the genomic locus of the fungal cells. In some embodiments, the Cas endonuclease cut site (or target site) on the genomic DNA is in the homologous region between the donor DNA and the genomic locus, where homologous recombination can occur. In other embodiments, the cut site is near the homologous region between the donor DNA and the genomic locus which can be anywhere from 1 bp to about 10 kb away from the homologous region, e.g., 1 bp, 2 bp, 5 bp, 10 bp, 20 bp, 50 bp, 100 bp, 250 bp, 500 bp, 1 kb, 2 kb, 3 kb, 4 kb, 5 kb, 6 kb, 7 kb, 8 kb, 9 kb, or 10 kb away from the site of homologous region.

As used herein, “nucleic acid” means a polynucleotide and includes a single or a double-stranded polymer of deoxyribonucleotide or ribonucleotide bases. Nucleic acids may also include fragments and modified nucleotides. Thus, the terms “polynucleotide”, “nucleic acid sequence”, “nucleotide sequence” and “nucleic acid fragment” are used interchangeably to denote a polymer of RNA and/or DNA that is single- or double-stranded, optionally containing synthetic, non-natural, or altered nucleotide bases. Nucleotides (usually found in their 5'-monophosphate form) are referred to by their single letter designation as follows: “A” for adenosine or deoxyadenosine (for RNA or DNA, respectively), “C” for cytosine or deoxycytosine, “G” for guanosine or deoxyguanosine, “U” for uridine, “T” for deoxythymidine, “R” for purines (A or G), “Y” for pyrimidines (C or T), “K” for G or T, “H” for A or C or T, “I” for inosine, and “N” for any nucleotide.

The term “derived from” encompasses the terms “originated from,” “obtained from,” “obtainable from,” “isolated from,” and “created from,” and generally indicates that one specified material find its origin in another specified material or has features that can be described with reference to the another specified material.

As used herein, the term “hybridization conditions” refers to the conditions under which hybridization reactions are conducted. These conditions are typically classified by degree of “stringency” of the conditions under which hybridization is measured. The degree of stringency can be based, for example, on the melting temperature (Tm) of the nucleic acid binding complex or probe. For example, “maximum stringency” typically occurs at about Tm−5° C. (5° C. below the Tm of the probe); “high stringency” at about 5-10° C. below the Tm; “intermediate stringency” at about 10-20° C. below the Tm of the probe; and “low stringency” at about 20-25° C. below the Tm. Alternatively, or in addition, hybridization conditions can be based upon the salt or ionic strength conditions of hybridization, and/or upon one or more stringency washes, e.g.: 6×SSC=very low stringency; 3×SSC=low to medium stringency; 1×SSC=medium stringency; and 0.5×SSC=high stringency. Functionally, maximum stringency conditions may be used to identify nucleic acid sequences having strict identity or near-strict identity with the hybridization probe; while high stringency conditions are used to identify nucleic acid sequences having about 80% or more sequence identity with the probe. For applications requiring high selectivity, it is typically desirable to use relatively stringent conditions to form the hybrids (e.g., relatively low salt and/or high temperature conditions are used).

As used herein, the term “hybridization” refers to the process by which a strand of nucleic acid joins with a complementary strand through base pairing, as known in the art. More specifically, “hybridization” refers to the process by which one strand of nucleic acid forms a duplex with, i.e., base pairs with, a complementary strand, as occurs during blot hybridization techniques and PCR techniques. A nucleic acid sequence is considered to be “selectively hybridizable” to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, “maximum stringency” typically occurs at about Tm−5° C. (5° below the Tm of the probe); “high stringency” at about 5-10° C. below the Tm; “intermediate stringency” at about 10-20° C. below the Tm of the probe; and “low stringency” at about 20-25° C. below the Tm. Functionally, maximum stringency conditions may be used to identify sequences having strict identity or near-strict identity with the hybridization probe; while intermediate or low stringency hybridization can be used to identify or detect polynucleotide sequence homologs.

Intermediate and high stringency hybridization conditions are well known in the art. For example, intermediate stringency hybridizations may be carried out with an overnight incubation at 37° C. in a solution comprising 20% formamide, 5×SSC (150 mM NaCl, 15 mM trisodium citrate), 50 mM sodium phosphate (pH 7.6), 5×Denhardt’s solution, 10% dextran sulfate and 20 mg/mL denatured sheared salmon sperm DNA, followed by washing the filters in 1×SSC at about 37-50° C. High stringency hybridization conditions may be hybridization at 65° C. and 0.1×SSC (where 1×SSC=0.15 M NaCl, 0.015 M Na citrate, pH 7.0). Alternatively, high stringency hybridization conditions can be carried out at about 42° C. in 50% formamide, 5×SSC, 5×Denhardt’s solution, 0.5% SDS and 100 μg/mL denatured carrier DNA followed by washing two times in 2×SSC and 0.5% SDS at room temperature and two additional times in 0.1×SSC and 0.5% SDS at 42° C. And very high stringent hybridization conditions may be hybridization at 68° C. and 0.1×SSC. Those of skill in the art know how to adjust the temperature, ionic strength, etc. as necessary to accommodate factors such as probe length and the like.

The phrase "substantially similar" or "substantially identical," in the context of at least two nucleic acids or polypeptides, means that a polynucleotide or polypeptide comprises a sequence that has at least 90%, at least 91%, at least 92%, at least 93%, at least 94%, at least 95%, at least 96%, at least 97%, at least 98%, or even at least 99% identical to a parent or reference sequence, or does not include amino acid substitutions, insertions, deletions, or modifications made only to circumvent the present description without adding functionality.

"Sequence identity" or "identity" in the context of nucleic acid or polypeptide sequences refers to the nucleic acid bases or amino acid residues in two sequences that are the same when aligned for maximum correspondence over a specified comparison window.

The term "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90% or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, (1989) CABIOS 5:151-153; Higgins et al., (1992) Comput Appl Biosci 8:189-191) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

The "Clustal W method of alignment" corresponds to the alignment method labeled Clustal W (described by Higgins and Sharp, (1989) CABIOS 5:151-153; Higgins et al., (1992) Comput Appl Biosci 8:189-191) and found in the MegAlign™ v6.1 program of the LASERGENE bioinformatics computing suite (DNASTAR Inc., Madison, Wis.). Default parameters for multiple alignment (GAP PENALTY-10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

Unless otherwise stated, sequence identity/similarity values provided herein refer to the value obtained using GAP Version 10 (GCG, Accelrys, San Diego, Calif.) using the following parameters: % identity and % similarity for a nucleotide sequence using a gap creation penalty weight of 50 and a gap length extension penalty weight of 3, and the nwsgapdna.cmp scoring matrix; % identity and % similarity for an amino acid sequence using a GAP creation penalty weight of 8 and a gap length extension penalty of 2, and the BLOSUM62 scoring matrix (Henikoff and Henikoff, (1989) Proc. Natl. Acad. Sci. USA 89:10915). GAP uses the algorithm of Needleman and Wunsch, (1970) J Mol Biol 48:443-53, to find an alignment of two complete sequences that maximizes the number of matches and minimizes the number of gaps. GAP considers all possible alignments and gap positions and creates the alignment with the largest number of matched bases and the fewest gaps, using a gap creation penalty and a gap extension penalty in units of matched bases.

It is well understood by one skilled in the art that many levels of sequence identity are useful in identifying polypeptides from other species or modified naturally or synthetically wherein such polypeptides have the same or similar function or activity. Useful examples of percent identities include, but are not limited to, 50%, 55%, 60%, 65%, 70%, 75%, 80%, 85%, 90% or 95%, or any integer percentage from 50% to 100%. Indeed, any integer amino acid identity from 50% to 100% may be useful in describing the present disclosure, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

"Gene" includes a nucleic acid fragment that encodes and is capable to express a functional molecule such as, but not limited to, a specific polypeptide (e.g., an enzyme) or a functional RNA molecule (e.g., a guide RNA, an anti-sense RNA, ribozyme, etc.), and includes regulatory sequences preceding (5' non-coding sequences) and/or following (3' non-coding sequences) the coding sequence. "Native gene" refers to a gene as found in nature with its own regulatory sequences. A recombinant gene refers to a gene that is regulated by a different gene's regulatory sequences which could be from a different organism or the same organism.

A "mutated gene" is a gene that has been altered through human intervention. Such a "mutated gene" has a sequence that differs from the sequence of the corresponding non-mutated gene by at least one nucleotide addition, deletion, or substitution. In certain embodiments of the disclosure, the mutated gene comprises an alteration that results from a guide polynucleotide/Cas endonuclease system as disclosed herein. A mutated fungal cell is a fungal cell comprising a mutated gene.

As used herein, a "targeted mutation" is a mutation in a native gene that was made by altering a target sequence within the native gene using a method involving a double-strand-break-inducing agent that is capable of inducing a double-strand break in the DNA of the target sequence as disclosed herein or known in the art.

The term "donor DNA" or "donor nucleic acid sequence" or "donor polynucleotide" refers to a polynucleotide that contains a polynucleotide sequence of interest that is to be inserted at or near a target site or to replace a region at or near a target site, generally in conjunction with the activity of a Cas/guide polynucleotide complex (where the guide polynucleotide defines the target site, as detailed above). As such, the polynucleotide sequence of interest in the donor DNA may include a novel region to be inserted at or near the target site and/or a modified polynucleotide sequence when compared to the nucleotide sequence to be replaced/edited at or near the target site. In certain embodiments, the donor DNA construct further comprises a first and a second region of homology that flank the polynucleotide sequence of interest. The first and second regions of homology of the donor DNA share homology to a first and a second genomic region, respectively, present in or flanking the target site of the fungal cell genome. By "homology" is meant DNA sequences that are similar. For example, a "region of homology to a genomic region" that is found on the donor DNA is a region of DNA that has a similar sequence to a given "genomic region" in the fungal cell genome. A region of homology can be of any length that is sufficient to promote homologous recombination at the cleaved target site. For example, the region of homology can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800, 5-2900, 5-3000, 5-3100 or more bases in length such that the region of homology has sufficient homology to undergo homologous recombination with the corresponding genomic region. "Sufficient homology" indicates that two polynucleotide sequences have sufficient structural similarity to act as substrates for a homologous recombination reaction. The structural similarity includes overall length of each polynucleotide fragment, as well as the sequence similarity of the polynucleotides. Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

The amount of homology or sequence identity shared by a target and a donor polynucleotide can vary and includes total lengths and/or regions having unit integral values in the ranges of about 1-20 bp, 20-50 bp, 50-100 bp, 75-150 bp, 100-250 bp, 150-300 bp, 200-400 bp, 250-500 bp, 300-600 bp, 350-750 bp, 400-800 bp, 450-900 bp, 500-1000 bp, 600-1250 bp, 700-1500 bp, 800-1750 bp, 900-2000 bp, 1-2.5 kb, 1.5-3 kb, 2-4 kb, 2.5-5 kb, 3-6 kb, 3.5-7 kb, 4-8 kb, 5-10 kb, or up to and including the total length of the target site. These ranges include every integer within the range, for example, the range of 1-20 bp includes 1, 2, 3, 4, 5, 6, 7, 8, 9, 10, 11, 12, 13, 14, 15, 16, 17, 18, 19 and 20 bp. The amount of homology can also described by percent sequence identity over the full aligned length of the two polynucleotides which includes percent sequence identity of about at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. Sufficient homology includes any combination of polynucleotide length, global percent sequence identity, and optionally conserved regions of contiguous nucleotides or local percent sequence identity, for example sufficient homology can be described as a region of 75-150 bp having at least 80% sequence identity to a region of the target locus. Sufficient homology can also be described by the predicted ability of two polynucleotides to specifically hybridize under high stringency conditions, see, for example, Sambrook et al., (1989) Molecular Cloning: A Laboratory Manual, (Cold Spring Harbor Laboratory Press, NY); Current Protocols in Molecular Biology, Ausubel et al., Eds (1994) Current Protocols, (Greene Publishing Associates, Inc. and John Wiley & Sons, Inc); and, Tijssen (1993) Laboratory Techniques in Biochemistry and Molecular Biology—Hybridization with Nucleic Acid Probes, (Elsevier, New York).

As used herein, a "genomic region" is a segment of a chromosome in the genome of a fungal cell that is present on either side of the target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology.

As used herein, "homologous recombination" includes the exchange of DNA fragments between two DNA molecules at the sites of homology and is well described in the art.

A phenotypic marker is a screenable or selectable marker that includes visual markers and selectable markers whether it is a positive or negative selectable marker. Any phenotypic marker can be used. Specifically, a selectable or screenable marker comprises a DNA segment that allows one to identify, or select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

Examples of selectable markers include, but are not limited to, DNA segments that comprise restriction enzyme sites; DNA segments that encode products which provide resistance against otherwise toxic compounds and antibiotics, such as, chlorimuron ethyl, benomyl, Basta, and hygromycin phosphotransferase (HPT); DNA segments that encode products which are otherwise lacking in the recipient cell (e.g., tRNA genes, auxotrophic markers, dominant heterologous marker-amdS); DNA segments that encode products which can be readily identified (e.g., phenotypic markers such as β-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Methods for Modifying a Fungal Cell Genome

Methods are provided employing a guide RNA/Cas endonuclease system for promoting homologous recombination of a donor DNA with a genomic locus in a fungal cell, e.g., a filamentous fungal cell.

Aspects of the present disclosure include methods for homologous recombination of a DNA sequence with a genomic locus in the genome of a fungal cell by transiently introducing a Cas endonuclease/guide polynucleotide complex into the cell along with a donor DNA that includes a domain with homology to the genomic locus. The Cas endonuclease/guide polynucleotide complex is capable of acting at a desired target site in the genome of the fungal cell, where by "acting" is meant that the Cas endonuclease, guided by sequences in the guide polynucleotide (as defined above), cleaves either one or both strands of the DNA at the target site.

Introduction of the Cas endonuclease, guide polynucleotide, and the donor DNA can be done in any convenient manner, including transfection, transduction, transformation, electroporation, particle bombardment, cell fusion techniques, etc. Each of these components can be introduced simultaneously or sequentially as desired by the user. For example, a fungal cell can first be stably transfected with a Cas expression DNA construct followed by introduction of a guide polynucleotide into the stable transfectant (either directly or using a guide polynucleotide expressing DNA construct) with. This set up may even be advantageous as the user can generate a population of stable Cas transfectant fungal cells into which different guide polynucleotides can be introduced independently (in some cases, more than one guide polynucleotide can be introduced into the same cells should this be desired). In some embodiments, a Cas expressing fungal cell is obtained by the user, and thus the user does not need to introduce a recombinant DNA construct capable of expressing a Cas endonuclease into the cell, but rather only need introduce a guide polynucleotide into the Cas expressing cell.

In certain embodiments, a guide polynucleotide is introduced into the fungal cell by introducing a recombinant DNA construct that includes an expression cassette (or gene) encoding the guide polynucleotide. In some embodiments, the expression cassette is operably linked to a eukaryotic RNA pol III promoter. These promoters are of particular interest as transcription by RNA pol III does not lead to the addition of a 5' cap structure or polyadenylation that occurs upon transcription by RNA polymerase II from an RNA pol II dependent promoter. In certain embodiments, the RNA pol III promoter is a filamentous fungal cell U6 polymerase III promoter (e.g., SEQ ID NO:40 and functional variants thereof, e.g., SEQ ID NO:41; described in further detail below).

When a double-strand break is induced in the genomic DNA of a host cell (e.g., by the activity of a Cas endonuclease/guide RNA complex at a target site, the complex having double-strand endonuclease activity), the cell's DNA repair mechanism is activated to repair the break which, due to its error-prone nature, can produce mutations at double-strand break sites. The most common repair mechanism to bring the broken ends together is the nonhomologous end-joining (NHEJ) pathway (Bleuyard et al., (2006) DNA Repair 5:1-12). The structural integrity of chromosomes is typically preserved by the repair, but deletions, insertions, or other rearrangements are possible (Siebert and Puchta, (2002) Plant Cell 14:1121-31; Pacher et al., (2007) Genetics 175:21-9).

Surprisingly, we have found in filamentous fungi that non-homologous insertion of transformed DNA at the double-strand break is highly favored over simple end-joining between the two ends of the chromosomal DNA at a double-strand break. Therefore, in cases where the Cas endonuclease or guide RNA is provided by transformation with an expression cassette containing DNA construct or constructs, those DNA constructs, or fragments thereof, are inserted at the double-strand break at high frequency. This insertion occurs in the absence of homology between DNA sequences on the Cas endonuclease or guide RNA expression constructs and the sequences around the double-strand break. This process is also problematic when homologous recombination between a donor DNA and a genomic locus is desired, as insertion of the entire donor DNA is favored over homologous recombination. We have found that undesirable insertion of transformed DNA occurs even when it is in the form of a vector including telomere sequences that is expected to be maintained autonomously in the fungal cell.

DNA taken up by transformation may integrate in a stable fashion in the genome or it may be transiently maintained. Transient maintenance can be recognized by an unstable phenotype. For example, DNA uptake can be recognized by selection for a marker gene present on the transforming DNA. After transformation and selection, the transformants may be grown under non-selective conditions for several generations before transfer back to selective conditions. A stable transformant will be able to grow after transfer back to selective conditions whereas an unstable transformant will be unable to grow after transfer back to selective conditions due to loss of the transforming DNA. As shown in the Examples section below, we have demonstrated that it is possible to transiently express Cas endonuclease and/or guide RNA in fungal cells/unstable transformants.

In embodiments where unstable transformants are desired, a plasmid with telomere sequences to encourage autonomous replication can be used. Other types of plasmids that are designed for autonomous replication, such as those with autonomous replication sequences, centromere sequences or other sequences, can also be employed. Surprisingly, in *Trichoderma reesei* we have found that one can use plasmids with no known origin of replication, autonomous replication sequence, centromere or telomere sequences. By screening those transformants that show an unstable phenotype with respect to the selectable marker, efficient target site gene modification without vector DNA insertion is obtained (e.g., homologous recombination with a homologous region in a donor DNA).

Certain embodiments of the present disclosure include integrating a Cas endonuclease expression cassette and first selectable marker in the genome of a fungus, optionally flanked by repeats to allow subsequent removal (loop-out) of the expression cassette and first selectable marker, to produce a Cas endonuclease expressing host cell. These cells can be employed in numerous ways to obtain a genetic modification of interest, including homologous recombination with a donor DNA.

For example, a Cas endonuclease expressing host cell can be transformed with a DNA construct including a guide RNA expression cassette containing a second selectable marker (and optionally a separate donor DNA). Host cells that are selected for using the second selectable marker will express the guide RNA from this DNA construct, which enables Cas endonuclease activity and targeting to a defined target site of interest in the genome. Screening these host cells for transformants that show an unstable phenotype with respect to the second selectable marker will enable obtaining host cells with a modified site of interest (e.g., homologous recombination with the donor DNA) without DNA construct insertion.

As another example, a Cas endonuclease expressing host cell can be induced to uptake an in vitro synthesized guide RNA to enable Cas endonuclease activity and targeting to a defined site in the genome. In some cases, it will be desirable to induce uptake of both guide RNA and a separate DNA construct bearing a selectable marker gene to allow for selection of those cells that have taken up DNA and, at high frequency, are expected to have simultaneously taken up guide RNA. As above, screening those transformants that show an unstable phenotype with respect to the selectable marker for the genetic modification of interest (e.g., homologous recombination with a donor DNA) without vector DNA insertion is obtained.

As yet another example, a Cas endonuclease expressing host cell can be used to create a "helper strain" that can provide, in trans, the Cas endonuclease to a "target strain". In brief, a heterokaryon can be created between the helper strain and the target strain, e.g., by fusion of protoplasts from each strain or by anastomosis of hyphae depending on the species of filamentous fungus. Maintenance of the heterokaryon will depend on appropriate nutritional or other marker genes or mutations in each parental strain and growth on suitable selective medium such that the parental strains are unable to grow whereas the heterokaryon, due to complementation, is able to grow. Either at the time of heterokaryon formation or subsequently, a guide RNA is introduced by transfection (and optionally a donor DNA). The guide RNA may be directly introduced or introduced via a DNA construct having a Cas endonuclease expression cassette and a selectable marker gene. Cas endonuclease is expressed from the gene in the helper strain nucleus and is present in the cytoplasm of the heterokaryon. The Cas endonuclease associates with the guide RNA to create an active complex that is targeted to the desired target site(s) in the genome. Subsequently, spores are recovered from the heterokaryon and subjected to selection or screening to recover the target strain with a modification at or near the target site (e.g., homologous recombination with the donor DNA at a genomic locus). In cases in which an expression cassette is used to introduce the guide RNA, heterokaryons are chosen in which the guide RNA expression construct is not stably maintained.

As noted above, methods of the present disclosure include introducing a DNA construct into the cell (or donor DNA) that has DNA sequence homology with regions of the chromosomal DNA on each side of the target site of the Cas/guide RNA complex. The intent is for the DNA fragment (e.g., a linear DNA fragment) to integrate by homologous integration/recombination, repairing the cleavage in the DNA at the target site and, in most cases, introducing changes to genome at the desired locus (i.e., at or near the target site of the Cas/guide RNA complex). In many organisms, a double-strand break in the chromosomal DNA stimulates homologous integration of the linear DNA fragment at that site. Surprisingly, in filamentous fungi with a functioning NHEJ pathway we have found that, even when a donor fragment is introduced, insertion of DNA by non-homologous insertion at the double-strand break is highly favored over homologous recombination of the linear DNA fragment.

With respect to DNA repair in fungal cells, we have found that in the presence of a functioning NHEJ pathway, error-prone repair is highly favored over homologous recombination at a double strand break site. In other words, with respect to DNA repair of a double strand break in filamentous fungal cells, we have found that in the presence of a functioning NHEJ pathway, non-homologous insertion of DNA at the break is highly favored over (1) non-homologous end joining without DNA insertion and (2) homologous recombination at the double strand break site with a donor DNA. Therefore, in certain aspects of the present invention, the functioning of the non-homologous end joining (NHEJ) pathway at the target site in the fungal cell in the population is inhibited, not activated, non-functional, or reduced. This may be achieved in any convenient manner, some of which are described below.

In some embodiments, the functioning of the non-homologous end joining (NHEJ) pathway at the target site in the fungal cell is inhibited, not activated, non-functional, or reduced by altering the fungal host cell such that one or more components of the NHEJ pathway are non-functional or have reduced activity (e.g., deleted from the genome or mutated to be non-functional or less active). This alteration of the fungal cell can be achieved by any convenient means, including gene deletion, gene mutation, expression of a dominant-interfering recombinant protein, gene replacement, gene expression inhibition, e.g., using antisense RNA/RNAi methodology, and the like. In certain aspects, the one or more components of the NHEJ pathway are selected from the group consisting of ku80, ku70, rad50, mre11, xrs2, lig4, and xrs. As but one example, a fungal cell that finds use in aspects of the present invention includes a genetic modification that inhibits the expression and/or activity of ku80.

In additional embodiments, the functioning of the non-homologous end joining (NHEJ) pathway at the target site in the fungal cell is inhibited, not activated, non-functional, or reduced by using a Cas endonuclease that has DNA nicking activity, i.e., it cleaves only one strand of the DNA at the target site (also called Cas nickases). Unlike double-strand breaks in the DNA, nicks do not activate the NHEJ pathway but are sufficient to promote homologous recombination at or near the sire of cleavage with a donor DNA having one or more region of homology. Numerous Cas nickases, which are recombinant variants of wild-type Cas endonucleases, have been described in the art (see, e.g., definition above) and may be used in the disclosed methods.

In some instances, the donor DNA includes a first region and a second region that are homologous to corresponding first and second regions in the genome of the fungal cell, wherein the regions of homology generally include or surround the target site at which the genomic DNA is cleaved by the Cas endonuclease. These regions of homology promote homologous recombination with their corresponding genomic regions of homology resulting in exchange of DNA between the donor DNA and the genome. As such, the provided methods result in the integration of the polynucleotide of interest of the donor DNA at or near the cleavage site in the target site in the fungal cell genome, thereby altering the original target site, thereby producing an altered genomic target site.

The structural similarity between a given genomic region and the corresponding region of homology found on the donor DNA can be any degree of sequence identity that allows for homologous recombination to occur. For example, the amount of homology or sequence identity shared by the "region of homology" of the donor DNA and the "genomic region" of the fungal cell genome can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or even 100% sequence identity, such that the sequences undergo homologous recombination.

The region of homology on the donor DNA can have homology to any sequence flanking the target site. While in some embodiments the regions of homology share significant sequence homology to the genomic sequence immediately flanking the target site, it is recognized that the regions of homology can be designed to have sufficient homology to regions that may be further 5' or 3' to the target site. In still other embodiments, the regions of homology can also have homology with a fragment of the target site along with downstream genomic regions. In one embodiment, the first region of homology further comprises a first fragment of the target site and the second region of homology comprises a second fragment of the target site, wherein the first and second fragments are dissimilar.

As with the Cas endonuclease and the guide polynucleotide expression constructs, the donor DNA may be introduced by any convenient means (as discussed elsewhere herein).

In certain embodiments, the Cas endonuclease is a Cas9 endonuclease (see, e.g., WO 2013141680 entitled “RNA-directed DNA Cleavage by the Cas9-crRNA Complex”). Examples of Cas9 endonucleases include those from *Streptococcus* sp. (e.g., *S. pyogenes, S. mutans*, and *S. thermophilus*), *Campylobacter* sp. (e.g., *C. jejuni*), *Neisseria* sp. (e.g., *N. meningitides*), *Francisella* sp. (e.g., *F. novicida*), and *Pasteurella* sp. (e.g., *P. multocida*) (see, e.g., Cas9 endonucleases described in Fonfara et al., Nucleic Acids Res., 2013, pages 1-14: incorporated herein by reference). In some embodiments, the Cas endonuclease is encoded by an optimized Cas9 endonuclease gene, e.g., optimized for expression in a fungal cell (e.g., Cas9 encoding genes containing SEQ ID NO:44, e.g., SEQ ID NO:7, as described below).

In certain instances, the Cas endonuclease gene is operably linked to one or more polynucleotides encoding nuclear localization signals such that the Cas endonuclease/guide polynucleotide complex that is expressed in the cell is efficiently transported to the nucleus. Any convenient nuclear localization signal may be used, e.g., a polynucleotide encoding an SV40 nuclear localization signal present upstream of and in-frame with the Cas codon region and a polynucleotide encoding a nuclear localization signal derived from the *T. reesei* blr2 (blue light regulator 2) gene present downstream and in frame with the Cas codon region. Other nuclear localization signals can be employed.

In certain embodiments of the disclosure, the guide polynucleotide is a guide RNA that includes a crRNA region (or crRNA fragment) and a tracrRNA region (or tracrRNA fragment) of the type II CRISPR/Cas system that can form a complex with a type II Cas endonuclease. As indicated above, the guide RNA/Cas endonuclease complex can direct the Cas endonuclease to a fungal cell genomic target site, enabling the Cas endonuclease to introduce a double strand break into the genomic target site. In some cases, the RNA that guides the RNA/Cas9 endonuclease complex is a duplex that includes a crRNA and a separate tracrRNA. In other instances, the guide RNA is a single RNA molecule that includes both a crRNA region and a tracrRNA region (sometimes referred to herein as a fused guide RNA). One advantage of using a fused guide RNA versus a duplexed crRNA-tracrRNA is that only one expression cassette needs to be made to express the fused guide RNA.

Host cells employed in the methods disclosed herein may be any fungal host cells are from the phyla Ascomycota, Basidiomycota, Chytridiomycota, and Zygomycota (as defined by Hawksworth et al., In, Ainsworth and Bisby’s Dictionary of The Fungi, 8th edition, 1995, CAB International, University Press, Cambridge, UK) as well as the Oomycota (as cited in Hawksworth et al., supra) and all mitosporic fungi (Hawksworth et al., supra). In certain embodiments, the fungal host cells are yeast cells, e.g., *Candida, Hansenula, Kluyveromyces, Pichia, Saccharomyces, Schizosaccharomyces*, or *Yarrowia* cell. Species of yeast include, but are not limited to, the following: *Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, Kluyveromyces lactis*, and *Yarrowia lipolytica* cell. In additional embodiments, the fungal cells are filamentous fungal cells including but not limited to species of *Trichoderma, Penicillium, Aspergillus, Humicola, Chrysosporium, Fusarium, Neurospora, Myceliophthora, Hypocrea*, and *Emericella*. For example, the filamentous fungi *T. reesei* and *A. niger* find use in aspects of the disclosed methods.

Virtually any site in a fungal cell genome may be targeted using the disclosed methods, so long as the target site includes the required protospacer adjacent motif (PAM). In the case of the *S. pyogenes* Cas9, the PAM has the sequence NGG (5' to 3'; where N is A, G, C or T), and thus does not impose significant restrictions on the selection of a target site in the genome. Other known Cas9 endonucleases have different PAM sites (see, e.g., Cas9 endonuclease PAM sites described in Fonfara et al., Nucleic Acids Res., 2013, pages 1-14: incorporated herein by reference).

The length of the target site can vary, and includes, for example, target sites that are at least 12, 13, 14, 15, 16, 17, 18, 19, 20, 21, 22, 23, 24, 25, 26, 27, 28, 29, 30 or more nucleotides in length. It is further possible that the target site can be palindromic, that is, the sequence on one strand reads the same in the opposite direction on the complementary strand. The cleavage site can be within the target sequence or the cleavage site could be outside of the target sequence. In another variation, the cleavage could occur at nucleotide positions immediately opposite each other to produce a blunt end cut or, in other cases, the incisions could be staggered to produce single-stranded overhangs, also called “sticky ends”, which can be either 5' overhangs, or 3' overhangs.

In some cases, active variant target sequences in the genome of the fungal cell can also be used, meaning that the target site is not 100% identical to the relevant sequence in the guide polynucleotide (within the crRNA sequence of the guide polynucleotide). Such active variants can comprise at least 65%, 70%, 75%, 80%, 85%, 90%, 91%, 92%, 93%, 94%, 95%, 96%, 97%, 98%, 99% or more sequence identity to the given target site, wherein the active variant target sequences retain biological activity and hence are capable of being recognized and cleaved by a Cas endonuclease. Assays to measure the double-strand break of a target site by an endonuclease are known in the art and generally measure the overall activity and specificity of the agent on DNA substrates containing recognition sites.

Target sites of interest include those located within a region of a gene of interest. Non-limiting examples of regions within a gene of interest include an open reading frame, a promoter, a transcriptional regulatory element, a translational regulatory element, a transcriptional terminator sequence, an mRNA splice site, a protein coding sequence, an intron site, and an intron enhancing motif.

In certain embodiments, modification of the genome of the fungal cell results in a phenotypic effect that can be detected and, in many instances, is a desired outcome of the user. Non-limiting examples include acquisition of a selectable cell growth phenotype (e.g., resistance to or sensitivity to an antibiotic, gain or loss of an auxotrophic characteristic, increased or decreased rate of growth, etc.), expression of a detectable marker (e.g., fluorescent marker, cell-surface molecule, chromogenic enzyme, etc.), and the secretion of an enzyme the activity of which can be detected in culture supernatant.

When modification of the genome of the fungal cell results in a phenotypic effect, a donor DNA is often employed that includes a polynucleotide of interest that is (or encodes) a phenotypic marker. Any convenient phenotypic marker can be used, including any selectable or screenable marker that allows one to identify, or select for or against a fungal cell that contains it, often under particular culture conditions. Thus, in some aspects of the present invention, the identification of fungal cells having a desired genome modification incudes culturing the fungal population of cells that have received the Cas endonuclease and guide polynucleotide (and optionally a donor DNA) under conditions to select for or screen for cells having the modification at the target site. Any type of selection system may be employed, including assessing for the gain or loss of an enzymatic activity in the fungal cell (also referred to as a selectable marker), e.g., the acquisition of antibiotic resistance or gain/loss of an auxotrophic marker.

In some instances, the genomic modification in the fungal cells is detected directly using any convenient method, including sequencing, PCR, Southern blot, restriction enzyme analysis, and the like, including combinations of such methods.

In some embodiments, specific genes are targeted for modification using the disclosed methods, including genes encoding enzymes, e.g., acetyl esterases, aminopeptidases, amylases, arabinases, arabinofuranosidases, carboxypeptidases, catalases, cellulases, chitinases, cutinase, deoxyribonucleases, epimerases, esterases, α-galactosidases, β-galactosidases, α-glucanases, glucanlysases, endo-β-glucanases, glucoamylases, glucose oxidases, α-glucosidases, β-glucosidases, glucuronidases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, peroxidases, phenoloxidases, phytases, polygalacturonases, proteases, rhamno-galacturonases, ribonucleases, transferases, transport proteins, transglutaminases, xylanases, hexose oxidases, and combinations thereof.

There are numerous variations for implementing the methods described herein. For example, instead of having the Cas expression cassette present as an exogenous sequence in the fungal host cell, this cassette can be integrated into the genome of the fungal host cell. Generating this parental cell line would allow a user to simply introduce a desired guide RNA (e.g., as a guide RNA expression vector) which would then target the genomic site of interest as detailed elsewhere herein. In some of these embodiments, the integrated Cas gene can be designed to include polynucleotide repeats flanking it for subsequent loop-out/removal from the genome if needed.

Compositions of Fungal Cells

Aspects of the present invention include a transgenic fungal cell that finds use in carrying out the methods described above as well as the resulting fungal cell having a modified genome. Thus, embodiments of the present invention include a recombinant fungal cell produced by any aspect of the methods described herein as well as any parental fungal cell employed to produce them.

Certain embodiments of the present invention are drawn to a recombinant fungal cell comprising a Cas endonuclease, where the Cas endonuclease is expressed from a recombinant DNA construct in the cell (a first recombinant DNA construct). In some embodiments, the recombinant fungal cell has a non-functional or reduced-activity NHEJ pathway. The embodiments of the Cas endonuclease and the polynucleotide encoding it described in detail above find use in the fungal cell compositions in this section (a few of which are set forth below). This fungal cell finds use as a parent for generating a fungal cell with a desired genome modification of interest, where generating the genome modification includes introducing a guide polynucleotide (e.g., via an expression cassette) into the cell thus allowing the formation of a Cas/guide polynucleotide complex that drives the genetic modification (as described above). In certain aspects, one or more components of the NHEJ pathway are non-functional or have reduced activity in the recombinant fungal cells, e.g., ku80, ku70, rad50, mre11, xrs2, lig4, xrs, and combinations thereof. In one particular embodiment, the recombinant fungal cell has a genetic modification that inhibits the expression and/or activity of ku80. Any convenient genetic modification to achieve disruption of the NHEJ pathway component(s) may be employed, including but not limited to gene deletion, gene mutation, expression of a dominant-interfering recombinant protein, gene replacement, gene expression inhibition, e.g., using antisense RNA/RNAi methodology, and the like.

In certain aspects, the recombinant fungal cell further includes a second recombinant DNA construct capable of expressing a guide RNA, where the guide RNA and Cas endonuclease are capable of forming a complex that enables the Cas endonuclease to introduce a double strand break at a target site in the genome of the recombinant fungal cell. The embodiments of the guide polynucleotide and the polynucleotide encoding it described in detail above find use in the fungal cell compositions in this section (a few of which are set forth below). Expression of the guide RNA may be driven by a eukaryotic RNA pol III promoter, wherein certain embodiments the RNA pal Ill promoter is a filamentous fungal cell U6 gene promoter (e.g., SEQ ID NO:40 or SEQ ID NO:41 as described in further detail below) and functional variants thereof. The action of this complex can result in the modification of the genomic DNA sequence at the target site of the fungal cell (as described above), thus generating a fungal cell having a modification at (or near) the target site. The modification can include a deletion of one or more nucleotides, an insertion of one or more nucleotides, a substitution of one or more nucleotides, or any combination thereof. In some embodiments, the fungal cell further includes a donor DNA that has a polynucleotide of interest. The polynucleotide of interest in the donor DNA can be present in the genome at (or near) the target site (inserted into the genome, e.g., by homologous recombination), a process that is driven by the action of the Cas/guide polynucleotide complex at the target site.

In certain embodiment, the Cas endonuclease encoded by the recombinant polynucleotide is a Cas9 endonuclease. Any Cas9 endonuclease may be encoded, including but not limited to Cas9 endonucleases, and functional fragments thereof, from the following bacterial species: *Streptococcus* sp. (e.g., *S. pyogenes, S. mutans*, and *S. thermophilus*), *Campylobacter* sp. (e.g., *C. jejuni*), *Neisseria* sp. (e.g., *N. meningitides*), *Francisella* sp. (e.g., *F. novicida*), and *Pasteurella* sp. (e.g., *P. multocida*) (see, e.g., Cas9 endonucleases described in Fonfara et al., Nucleic Acids Res., 2013, pages 1-14: incorporated herein by reference). In some embodiments, the polynucleotide encoding the Cas endonuclease gene is one that has been optimized for expression in a filamentous fungal host cell, e.g., the polynucleotide shown in SEQ ID NO:44 (which is a filamentous fungal cell codon optimized version of the *S. pyogenes* Cas9 endonuclease) or SEQ ID NO:7 (which contains SEQ ID NO:44 and also includes N- and C-terminal NLS sequences). Additional codon-optimized Ca9 genes may be employed, including synonymous variants of SEQ ID NO:44 or SEQ ID NO:7. As described above, the Cas endonuclease can be operably linked to one or more nuclear localization signal, which function to enhance the cytoplasmic to nuclear transit of the Cas endonuclease to its site of action, i.e., in the nucleus of the cell. Any convenient nuclear localization signal may be employed, including the SV40 nuclear localization signal, a nuclear localization signal derived from the *T. reesei* blr2 (blue light regulator 2) gene, or a combination of both.

Any of a wide variety of filamentous fungal host cells find use in the present invention, including fungal host cells from the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., supra) and all mitosporic fungi (Hawksworth et al., supra). In certain embodiments, the fungal host cells are yeast cells, e.g., *Candida, Hansenula, Kluyveromyces, Pichia, Saccharomyces, Schizosaccharomyces*, or *Yarrowia* cell. Species of yeast include, but are not limited to, the following: *Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, Kluyveromyces lactis*, and *Yarrowia lipolytica* cell. In additional embodiments, the fungal cells are filamentous fungal cells including but not limited to species of *Trichoderma, Penicillium, Aspergillus, Humicola, Chrysosporium, Fusarium, Neurospora, Myceliophthora, Thermomyces, Hypocrea*, and *Emericella*. For example, the filamentous fungi *Trichoderma reesei, P. chrysogenum, M. thermophila, Thermomyces lanuginosus, A. oryzae* and *A. niger* find use in aspects of the disclosure.

As detailed above, the present invention is drawn generally to methods and compositions useful in modifying a target site of interest in the genome of a filamentous fungal cell. The particular target site of interest is determined by the user of such methods and composition and include sites that are located within a region of a gene of interest, including: a promoter, a regulatory sequence, a terminator sequence, a regulatory element sequence, a splice site, a coding sequence, a polyubiquitination site, an intron site, and an intron enhancing motif. In addition, any genes of interest can be selected by a user, including but not limited to: acetyl esterases, aminopeptidases, amylases, arabinases, arabinofuranosidases, carboxypeptidases, catalases, cellulases, chitinases, cutinase, deoxyribonucleases, epimerases, esterases, α-galactosidases, β-galactosidases, α-glucanases, glucanlysases, endo-β-glucanases, glucoamylases, glucose oxidases, α-glucosidases, β-glucosidases, glucuronidases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, peroxidases, phenoloxidases, phytases, polygalacturonases, proteases, rhamno-galacturonases, ribonucleases, transferases, transport proteins, transglutaminases, xylanases, hexose oxidases, and combinations thereof.

Recombinant Polynucleotides

Aspects of the present invention are drawn to recombinant polynucleotides that find use in the methods and compositions described herein.

Embodiments of the disclosure include a recombinant polynucleotide DNA construct having a promoter sequence operably linked to a fungal cell optimized nucleotide sequence encoding a Cas endonuclease. Embodiments of the disclosure include a recombinant polynucleotide DNA construct having a promoter sequence operably linked to a fungal cell optimized nucleotide sequence encoding a Cas endonuclease or a bacterial cell optimized nucleotide sequence encoding a Cas endonuclease. As described above, the Cas endonuclease encoded in the fungal cell optimized nucleotide sequence as well as the bacterial cell optimized nucleotide sequence are capable of acting at a target site in when complexed with a guide RNA. Any Cas endonuclease may be encoded by the optimized nucleotide sequences, including but not limited to a Cas9 endonuclease, e.g., Cas9 from *S. pyogenes*. In certain embodiments, the fungal cell optimized nucleotide sequence is optimized for expression in a filamentous fungal cell. For example, a filamentous fungal cell optimized sequence can encode a Cas9 endonuclease and contain the nucleotide sequence shown in SEQ ID NO:44 (100% identity) or encodes a Cas9 endonuclease and contains a nucleotide sequence that is at least 60%, 65%, 70%, 75%, 80%, 85%, 90%, 91%, 92%, 93%, 94%, 95%, 96%, 97%, 98%, 99% identical to SEQ ID NO:44. In certain embodiments, the bacterial cell optimized nucleotide sequence is optimized for expression in an *E. coli* cell. For example, an *E. coli* cell optimized sequence can encode a Cas9 endonuclease and contain the nucleotide sequence shown in SEQ ID NO:65 (100% identity) or encodes a Cas9 endonuclease and contains a nucleotide sequence that is at least 60%, 65%, 70%, 75%, 80%, 85%, 90%, 91%, 92%, 93%, 94%, 95%, 96%, 97%, 98%, 99% identical to SEQ ID NO:65.

Embodiments of the disclosure further relate to a *Trichoderma* sp. RNA polymerase III driven promoters. Transcription of a gene by RNA pol III from an RNA pol III directed promoter does not lead to the addition of a 5' cap structure or polyadenylation that occurs upon transcription by RNA polymerase II from an RNA pol II dependent promoter. As described in the Examples below, we have identified an RNA pol III driven promoter sequence in *T. reesei* that is associated with the U6 gene as well as the transcription terminator sequence. The full promoter sequence is set forth in SEQ ID NO:40 and the terminator sequence is set forth in SEQ ID NO:43. In addition, a shorter version of the U6 gene RNA pol III driven promoter was identified and is set forth in SEQ ID NO:41. Thus, aspects of the invention include a promoter that function as RNA pol III driven promoter and having a nucleotide sequence that is at least 60%, 65%, 70%, 75%, 80%, 85%, 90%, 91%, 92%, 93%, 94%, 95%, 96%, 97%, 98%, 99% or up to 100% identical to SEQ ID NO:40 or SEQ ID NO:41. This RNA pol III directed promoter sequence finds use in expressing any heterologous sequence of interest. Thus, aspects of the disclosure include recombinant polynucleotide sequences having a *T. reesei* derived RNA pol III driven promoter sequence operably linked to a heterologous sequence of interest. In certain embodiments, the heterologous sequence is one that encodes a guide polynucleotide, e.g., a tracrRNA, a crRNA, or a single guide RNA. Guide RNA encoding polynucleotides targeted to specific genomic sites of interest are described in detail in the Examples and include SEQ ID NOs:2 to 6. In certain embodiments, the recombinant polynucleotide further includes a transcriptional terminator sequence is operably linked to the heterologous sequence of interest (which is operably linked to the RNA pol III promoter), e.g., at a site downstream of the heterologous sequence of interest (where "downstream" refers to the direction of transcription, as is common in the art). The terminator sequence includes, in some embodiments, the polynucleotide sequence shown in SEQ ID NO:43 or functional variants thereof. Thus, in certain embodiments, the recombinant polynucleotide includes an RNA pol III promoter operably linked to a heterologous sequence of interest (e.g., a guide RNA) operably linked to a terminator.

Non-limiting examples or embodiments of compositions and methods disclosed herein are as follows:

1. A method for homologous recombination of a donor DNA with a genomic locus in a filamentous fungal cell, the method comprising:
 a) introducing into a population of fungal cells a Cas endonuclease, a guide RNA, and a donor DNA comprising a domain with homology to a genomic locus of the fungal cell, wherein the Cas endonuclease and guide RNA are capable of forming a complex that enables the Cas endonuclease to act at a target site in or near the genomic locus of the fungal cells; and
 b) identifying at least one fungal cell from the population in which homologous recombination of the donor DNA with the genomic locus has occurred,
 wherein the Cas endonuclease, the guide RNA, or both are introduced transiently into the population of fungal cells.
2. The method of embodiment 1, wherein the non-homologous end joining (NHEJ) mechanism at the target site in the fungal cells is not activated, non-functional, or reduced.
3. The method of embodiment 2, wherein the non-homologous end joining (NHEJ) pathway in the fungal cells comprises one or more non-functional or reduced-activity components.
4. The method of embodiment 3, wherein the one or more non-functional or reduced-activity components are selected from the group consisting of ku80, ku70, rad50, mre11, xrs2, lig4, xrs, and combinations thereof.
5. The method of embodiment 4, wherein the one or more non-functional or reduced-activity components is ku80.
6. The method of any preceding embodiment, wherein the Cas endonuclease is a Cas nickase.
7. The method of any one of embodiments 1-5, wherein the Cas endonuclease is a Cas9 endonuclease or variant thereof.
8. The method of embodiment 7, wherein the Cas9 endonuclease or variant thereof comprises a full length Cas9 or a functional fragment thereof from a species selected from the group consisting of: *Streptococcus* sp., *S. pyogenes, S. mutans, S. thermophilus, Campylobacter* sp., *C. jejuni, Neisseria* sp., *N. meningitides, Francisella* sp., *F. novicida*, and *Pasteurella* sp., *P. multocida.*
9. The method of embodiment 8, wherein the Cas9 endonuclease or variant thereof comprises an amino acid sequence that has at least 70% identity to any one of SEQ ID NOs:45 and 48 to 53.
10. The method of any preceding embodiment, wherein the donor DNA comprises a polynucleotide sequence of interest, and wherein homologous recombination at the genomic locus results in the insertion of the polynucleotide sequence of interest in the genomic locus.
11. The method of any preceding embodiment, wherein the introducing step comprises introducing a DNA construct comprising an expression cassette for the Cas endonuclease into the fungal cells.
12. The method of any preceding embodiment, wherein the introducing step comprises introducing a DNA construct comprising an expression cassette for the guide RNA into the fungal cells.
13. The method of any preceding embodiment or any one of embodiments 48-54, wherein the introducing step comprises introducing into the fungal cells a DNA construct comprising a sequence encoding a selectable marker.
14. The method of embodiment 13, wherein the DNA construct comprises both the sequence encoding the selectable marker and the donor DNA.
15. The method of any preceding embodiment, wherein the introducing step comprises introducing into the fungal cells a DNA construct comprising: a sequence encoding the Cas endonuclease, a sequence encoding the guide RNA, a sequence encoding a selectable marker, and the donor DNA.
16. The method of any one of embodiments 11 to 15, wherein the DNA construct is a linear DNA construct.
17. The method of any one of embodiments 11 to 15, wherein the DNA construct is a circular DNA construct.
18. The method of any one of embodiments 11 and 15-17, wherein the expression cassette for the Cas endonuclease or the sequence encoding the Cas endonuclease comprises a Cas coding sequence that is optimized for expression in the filamentous fungal cell.
19. The method of embodiment 18, wherein the Cas coding sequence is a Cas9 coding sequence comprising a polynucleotide sequence that is at least 70% identical to SEQ ID NO:44.
20. The method of any one of embodiments 1 to 10, 12 to 14, and 16-17, wherein the introducing step comprises directly introducing the Cas endonuclease into the fungal cells.
21. The method of any one of embodiments 1 to 11, 13 to 14, and 16 to 20, wherein the introducing step comprises directly introducing the guide RNA into the fungal cells.
22. The method of any preceding embodiment, wherein the Cas endonuclease is operably linked to a nuclear localization signal.
23. The method of any preceding embodiment, wherein the fungal cell is a Eumycotina or Pezizomycotina fungal cell.
24. The method of any preceding embodiment, wherein the fungal cell is selected from the group consisting of *Trichoderma, Penicillium, Aspergillus, Humicola, Chrysosporium, Fusarium, Myceliophthora, Neurospora, Hypocrea*, and *Emericella.*
25. The method of any preceding embodiment, wherein the target site is located within a region of a gene of interest selected from the group consisting of an open reading frame, a promoter, a regulatory sequence, a terminator sequence, a regulatory element sequence, a splice site, a coding sequence, a polyubiquitination site, an intron site, and an intron enhancing motif.
26. The method of any preceding embodiment, wherein the homologous recombination results in a modification of the DNA sequence at or near the target site, wherein the modication is selected from the group consisting of a deletion of one or more nucleotides, an insertion of one or more nucleotides, insertion of an expression cassette encoding a protein of interest, a substitution of one or more nucleotides, and any combination thereof.

27. The method of any preceding embodiment, wherein the identifying step comprises culturing the population of cells from step (a) under conditions to select for or screen for the homologous recombination or the modification.
28. The method of any preceding embodiment, wherein the identifying step comprises culturing the population of cells from step (a) under conditions to screen for unstable transformants.
29. The method of any preceding embodiment, wherein the introducing step comprises introducing into the fungal cells a DNA construct comprising a sequence encoding a selectable marker and the donor DNA, and wherein the identifying step comprises culturing the population of cells from step (a) under conditions to screen for unstable transformants that have lost the selectable marker yet retained the donor DNA.
30. A recombinant filamentous fungal cell produced by the method of any preceding embodiment.
31. A recombinant filamentous fungal cell comprising a first recombinant DNA construct comprising an expression cassette for a Cas endonuclease.
32. The recombinant fungal cell of embodiment 30 or 31, wherein the recombinant filamentous fungal cell comprises one or more non-functional or reduced activity component in the NHEJ pathway.
33. The recombinant fungal cell of embodiment 32, wherein the one or more components of the NHEJ pathway are selected from the group consisting of ku80, ku70, rad50, mre11, xrs2, lig4, and xrs.
34. The recombinant fungal cell of embodiment 33, wherein the fungal cell comprises a genetic modification that inhibits the expression and/or activity of ku80.
35. The recombinant fungal cell of embodiment 31, wherein the Cas endonuclease is a Cas nickase.
36. The recombinant fungal cell of any one of embodiments 30 to 35, further comprising a second recombinant DNA construct comprising an expression cassette for a guide RNA, wherein the guide RNA and Cas endonuclease are capable of forming a complex that enables the Cas endonuclease to act at a target site in the genome of the recombinant filamentous fungal cell.
37. The recombinant fungal cell of any one of embodiments 30 to 36 further comprising a donor DNA comprising a polynucleotide of interest.
38. The recombinant fungal cell of any one of embodiments 30 to 37, wherein the Cas endonuclease is a Cas9 endonuclease or variant thereof.
39. The recombinant fungal cell of embodiment 38, wherein the Cas9 endonuclease or variant thereof comprises an amino acid sequence that has at least 70% identity to any one of SEQ ID NOs:45 and 48 to 53.
40. The recombinant fungal cell of any one of embodiments 31 to 39, wherein the expression cassette for the Cas endonuclease comprises a polynucleotide sequence that is at least 70% identical to SEQ ID NO:44.
41. The recombinant fungal cell of any one of embodiments 31 to 40, wherein the expression cassette for the Cas endonuclease comprises a Cas endonuclease gene that is optimized for expression in the filamentous fungal cell.
42. The recombinant fungal cell of any one of embodiments 31 to 41, wherein the Cas endonuclease is operably linked to a nuclear localization signal.
43. The recombinant fungal cell of embodiment 42, wherein the nuclear localization signal is selected from the group consisting of SV40 nuclear localization signal (SEQ ID NO:46), a nuclear targeting signal derived from the *T. reesei* blr2 (blue light regulator 2) gene (SEQ ID NO:47), and a combination of both.
44. The recombinant fungal cell of any one of embodiments 30 to 43, wherein the fungal cell is a filamentous fungal cell selected from the group consisting of: *Trichoderma, Penicillium, Aspergillus, Humicola, Chrysosporium, Fusarium, Myceliophthora, Neurospora, Hypocrea*, and *Emericella*.
45. A recombinant DNA construct comprising a promoter operably linked to a filamentous fungal cell optimized polynucleotide sequence encoding a Cas9 endonuclease or variant thereof.
46. The recombinant DNA construct of embodiment 45, wherein the filamentous fungal cell optimized polynucleotide sequence is at least 70% identical to SEQ ID NO:44.
47. The method of embodiment 12, wherein the expression cassette for the guide RNA comprises a DNA polymerase Ill dependent promoter functional in a Euascomycete or Pezizomycete, and wherein the promoter is operably linked to the DNA encoding the guide RNA.
48. The method of embodiment 47, wherein the promoter is derived from a *Trichoderma* U6 snRNA gene.
49. The method of embodiment 48, wherein the promoter comprises a nucleotide sequence with at least 60%, 65%, 70%, 75%, 80%, 85%, 90%, 95%, 96%, 97%, 98%, or 99% identity to SEQ ID NO: 40 or 41.
50. The method of embodiment 49, wherein the promoter comprises the sequence of SEQ ID NO: 40 or 41.
51. The method of any one of embodiments 12 and 47-50, wherein the expression cassette for the guide RNA comprises a guide RNA-encoding DNA with an intron sequence from a *Trichoderma* U6 snRNA gene.
52. The method of embodiment 51, wherein the intron sequence derived from *Trichoderma* U6 snRNA gene comprises a nucleotide sequence with at least 60%, 65%, 70%, 75%, 80%, 85%, 90%, 95%, 96%, 97%, 98%, or 99% identity to SEQ ID NO: 42.
53. The method of embodiment 52, wherein the intron sequence derived from *Trichoderma* U6 snRNA gene comprises the sequence of SEQ ID NO: 42.

EXAMPLES

In the following Examples, unless otherwise stated, parts and percentages are by weight and degrees are Celsius. It should be understood that these Examples, while indicating embodiments of the disclosure, are given by way of illustration only. From the above discussion and these Examples, one skilled in the art can make various changes and modifications of the disclosure to adapt it to various usages and conditions. Such modifications are also intended to fall within the scope of the appended claims.

Section A: Introduction of Cas/Guide RNA by Expression Vectors

Example 1

Identification of *T. reesei* U6 snRNA Gene

An RNA polymerase III directed promoter is desired for production of guide RNA in *T. reesei* without the addition of a 5' cap structure or polyadenylation that would result from the use of a RNA polymerase II dependent promoter. However, no RNA polymerase III dependent promoter that is functional in *T. reesei* has been described. Known RNA polymerase III dependent promoters from other species were considered to be tested for their ability to function in *T. reesei* including the 5' upstream regions from the *Saccharomyces cerevisiae* snr52 gene, the human U6 snRNA gene, or the corn U6 snRNA gene.

More desirable was to identify a native *T. reesei* sequence that would function as an RNA polymerase III dependent promoter. The DNA sequence encoding the human U6 small nuclear RNA (snRNA; GenBank accession number M14486) was used to search the *T. reesei* v2 genome sequence (www.jgi.doe.gov) using the BLAST algorithm. A short region of *T. reesei* DNA sequence was identified with similarity to the human sequence. Examination of the surrounding DNA sequence and comparison with the U6 genes of yeasts, particularly Schizosaccharomyces pombe (Marck et al., 2006, Nucleic Acids Research 34:1816-1835), allowed a number of features of the *T. reesei* U6 gene to be putatively identified (SEQ ID NO:1, shown below). The start of the transcribed sequence and the terminator were identified as were an upstream TATA box. An intron apparently interrupts the transcribed region and possible A-box and B-box promoter elements can be recognized within the transcribed region, the latter within the intron. (see FIG. 1).

(SEQ ID NO: 1)

AAAAAACACTAGTAAGTACTTACTTATGTATTATTAACTACTTTAGCTAA

CTTCTGCAGTACTACCTAAGAGGCTAGGGGTAGTTTTATAGCAGACTTAT

AGCTATTATTTTTATTTAGTAAAGTGCTTTTAAAGTAAGGTCTTTTTTAT

AGCACTTTTTATTTATTATAATATATATTATATAATAATTTTAAGCCTGG

AATAGTAAAGAGGCTTATATAATAATTTATAGTAATAAAAGCTTAGCAGC

TGTAATATAATTCCTAAAGAAACAGCATGAAATGGTATTATGTAAGAGCT

ATAGTCTAAAGGCACTCTGCTGGATAAAAATAGTGGCTATAAGTCTGCTG

CAAAACTACCCCCAACCTCGTAGGTATATAAGTACTGTTTGATGGTAGTC

TATCGCCTTCGGGCATTTGGTCAATTTATAACGATACAGGTTCGTTTCGG

CTTTTCCTCGGAACCCCCAGAGGTCATCAGTTCGAATCGCTAACAGGTCA

ACAGAGAAGATTAGCATGGCCCCTGCACTAAGGATGACACGCTCACTCAA

AGAGAAGCTAAACATTTTTTTTCTCTTCCAAGTCGTGATGGTTATCTTTT

TGCTTAGAGAATCTATTCTTGTGGACGATTAGTATTGGTAAATCCCTGCT

GCACATTGCGGCGGATGGTCTCAACGGCATAATACCCCATTCGTGATGCA

GCGGTGATCTTCAATATGTAGTGTAATACGTTGCATACACCACCAGGTTC

GGTGCCTCCTGTATGTACAGTACTGTAGTTCGACTCCTCCGCGCAGGTGG

AAACGATTCCCTAGTGGGCAGGTATTTTGGCGGGGTCAAGAA

Example 2 sgRNA Sequences to Target *T. reesei* Genes

It has been shown that a single guide RNA (sgRNA) molecule can interact with the *Streptococcus pyogenes* Cas9 protein to target this endonuclease in vivo to a specific locus in a eukaryote genome. The sgRNA is a hybrid molecule designed as a fusion between the tracrRNA and crRNA observed naturally to be components of the *Streptococcus pyogenes* type II CRISPR-Cas system (Gasiunas et al. (2012) Proc. Natl. Acad. Sci. USA 109:E2579-86, Jinek et al. (2012) Science 337:816-21, Mali et al. (2013) Science 339:823-26, and Cong et al. (2013) Science 339:819-23). The first 20 nucleotides of the sgRNA are complementary to the target site in the genome. An additional sequence, protospacer adjacent motif (PAM) is also required to be present at the target site in the genome adjacent to the sgRNA-complementary region. In the case of the *S. pyogenes* Cas9 the PAM has the sequence NGG (where N is A, G, C or T).

The sequence of sgRNA used in these experiments is shown below where the 20 nucleotides designed to be complementary to the target site are shown as N residues (SEQ ID NO:2) (N=A, G, C, or U).

NNNNNNNNNNNNNNNNNNNNGUUUUAGAGCUAGAAAUAGCAAGUUAAAAU

AAGGCUAGUCCGUUAUCAACUUGAAAAAGUGGCACCGAGUCGGUGGUGC sgRNAs were designed to target different loci in the *T. reesei* genome. The sequence of an sgRNA (called gAd3A TS1) to target the *T. reesei* ad3A gene (Phosphoribosylamidoimidazole-succinocarboxamide synthase) at a site designated as target site 1 (TS1) is shown below (SEQ ID NO:3). The 20 nucleotide region that is complementary to the *T. reesei* genome sequence is shown in lower case.

guccucgagcaaaaggugccGUUUUAGAGCUAGAAAUAGCAAGUUAAAAU

AAGGCUAGUCCGUUAUCAACUUGAAAAAGUGGCACCGAGUCGGUGGUGC

The sequence of an sgRNA (called gTrGA TS2) to target the *T. reesei* gla1 (glucoamylase) gene at a site designated as target site 2 (TS2) is shown below (SEQ ID NO:4). The 20 nucleotide region that is complementary to the *T. reesei* genome sequence is shown in lower case.

guucagugcaauaggcgucuGUUUUAGAGCUAGAAAUAGCAAGUUAAAAU

AAGGCUAGUCCGUUAUCAACUUGAAAAAGUGGCACCGAGUCGGUGGUGC

The sequence of an sgRNA (called gTrGA TS11) to target the *T. reesei* gla1 (glucoamylase) gene at a site designated as target site 11 (TS11) is shown below (SEQ ID NO:5). The 20 nucleotide region that is complementary to the *T. reesei* genome sequence is shown in lower case.

gccaauggcgacggcagcacGUUUUAGAGCUAGAAAUAGCAAGUUAAA

AUAAGGCUAGUCCGUUAUCAACUUGAAAAAGUGGCACCGAGUCGGUGG

UGC

The sequence of an sgRNA (called gPyr2 TS6) to target the *T. reesei* pyr2 (orotate phosphoribosyltransferase) gene at a site designated as target site 6 (TS6) is shown below (SEQ ID NO:6). The 20 nucleotide region that is complementary to the *T. reesei* genome sequence is shown in lower case.

gcacagcgggaugcccuuguGUUUUAGAGCUAGAAAUAGCAAGUUAAA

AUAAGGCUAGUCCGUUAUCAACUUGAAAAAGUGGCACCGAGUCGGUGG

UGC

Example 3

Cas9 DNA and Protein Sequences for Expression in *T. reesei*

A codon optimized *Streptococcus pyogenes* Cas9-encoding gene, including NLS sequences, was designed, synthesized and tested for expression in *T. reesei* (SEQ ID NO:7). The encoded protein (SEQ ID NO:8) has an N-terminal SV40 nuclear localization signal (NLS; SEQ ID NO:46) and a C-terminal NLS derived from the *T. reesei* blr2 (blue light regulator 2) gene (SEQ ID NO:47; both are underlined in SEQ ID NO:8 below).

SEQ ID NO: 7

```
atggcaccgaagaagaagcgcaaggtgatggacaagaagtacagcatc
ggcctcgacatcggcaccaactcggtgggctgggccgtcatcacggac
gaatataaggtcccgtcgaagaagttcaaggtcctcggcaatacagac
cgccacagcatcaagaaaaacttgatcggcgccctcctgttcgatagc
ggcgagaccgcggaggcgaccaggctcaagaggaccgccaggagacgg
tacactaggcgcaagaacaggatctgctacctgcaggagatcttcagc
aacgagatggcgaaggtggacgactccttcttccaccgcctggaggaa
tcattcctggtggaggaggacaagaagcatgagcggcacccaatcttc
ggcaacatcgtcgacgaggtggcctaccacgagaagtacccgacaatc
taccacctccggaagaaactggtggacagcacagacaaggcggacctc
cggctcatctaccttgccctcgcgcatatgatcaagttccgcggccac
ttcctcatcgagggcgacctgaacccggacaactccgacgtggacaag
ctgttcatccagctcgtgcagacgtacaatcaactgttcgaggagaac
cccataaacgctagcggcgtggacgccaaggccatcctctcggccagg
ctctcgaaatcaagaaggctggagaaccttatcgcgcagttgccaggc
gaaaagaagaacggcctcttcggcaaccttattgcgctcagcctcggc
ctgacgccgaacttcaaatcaaacttcgacctcgcggaggacgccaag
ctccagctctcaaaggacacctacgacgacgacctcgacaacctcctg
gcccagataggagaccagtacgcggacctcttcctcgccgccaagaac
ctctccgacgctatcctgctcagcgacatccttcgggtcaacaccgaa
attaccaaggcaccgctgtccgccagcatgattaaacgctacgacgag
caccatcaggacctcacgctgctcaaggcactcgtccgccagcagctc
cccgagaagtacaaggagatcttcttcgaccaatcaaaaaacggctac
gcgggatatatcgacggcggtgccagccaggaagagttctacaagttc
atcaaaccaatcctggagaagatggacggcaccgaggagttgctggtc
aagctcaacagggaggacctcctcaggaagcagaggaccttcgacaac
ggctccatcccgcatcagatccacctgggcgaactgcatgccatcctg
cggcgccaggaggacttctacccgttcctgaaggataaccgggagaag
atcgagaagatcttgacgttccgcatcccatactacgtgggcccgctg
gctcgcggcaactcccggttcgcctggatgacccggaagtcggaggag
accatcacaccctggaactttgaggaggtggtcgataagggcgctagc
```

-continued

```
gctcagagcttcatcgagcgcatgaccaacttcgataaaaacctgccc
aatgaaaaagtcctccccaagcactcgctgctctacgagtacttcacc
gtgtacaacgagctcaccaaggtcaaatacgtcaccgagggcatgcgg
aagccggcgttcctgagcggcgagcagaagaaggcgatagtggacctc
ctcttcaagaccaacaggaaggtgaccgtgaagcaattaaaagaggac
tacttcaagaaaatagagtgcttcgactccgtggagatctcgggcgtg
gaggatcggttcaacgcctcactcggcacgtatcacgacctcctcaag
atcattaaagacaaggacttcctcgacaacgaggagaacgaggacatc
ctcgaggacatcgtcctcaccctgaccctgttcgaggaccgcgaaatg
atcgaggagaggctgaagacctacgcgcacctgttcgacgacaaggtc
atgaaacagctcaagaggcgccgctacactggttggggaaggctgtcc
cgcaagctcattaatggcatcagggacaagcagagcggcaagaccatc
ctggacttcctcaagtccgacgggttcgccaaccgcaacttcatgcag
ctcattcacgacgactcgctcacgttcaaggaagacatccagaaggca
caggtgagcgggcagggtgactccctccacgaacacatcgccaacctg
gccggctcgccggccattaaaaagggcatcctgcagacggtcaaggtc
gtcgacgagctcgtgaaggtgatgggccggcacaagcccgaaaatatc
gtcatagagatggccagggagaaccagaccacccaaaaagggcagaag
aactcgcgcgagcggatgaaacggatcgaggagggcattaaagagctc
gggtcccagatcctgaaggagcaccccgtggaaaatacccagctccag
aatgaaaagctctacctctactacctgcagaacggccgcgacatgtac
gtggaccaggagctggacattaatcggctatcggactacgacgtcgac
cacatcgtgccgcagtcgttcctcaaggacgatagcatcgacaacaag
gtgctcacccggtcggataaaaatcggggcaagagcgacaacgtgccc
agcgaggaggtcgtgaagaagatgaaaaactactggcgccagctcctc
aacgcgaaactgatcacccagcgcaagttcgacaacctgacgaaggcg
gaacgcggtggcttgagcgaactcgataaggcgggcttcataaaaagg
cagctggtcgagacgcgccagatcacgaagcatgtcgcccagatcctg
gacagccgcatgaatactaagtacgatgaaaacgacaagctgatccgg
gaggtgaaggtgatcacgctgaagtccaagctcgtgtcggacttccgc
aaggacttccagttctacaaggtccgcgagatcaacaactaccaccac
gcccacgacgcctacctgaatgcggtggtcgggaccgccctgatcaag
aagtacccgaagctggagtcggagttcgtgtacggcgactacaaggtc
tacgacgtgcgcaaaatgatcgccaagtccgagcaggagatcggcaag
gccacggcaaaatacttcttctactcgaacatcatgaacttcttcaag
accgagatcaccctcgcgaacggcgagatccgcaagcgcccgctcatc
gaaaccaacggcgagacgggcgagatcgtctgggataagggccgggat
ttcgcgacggtccgcaaggtgctctccatgccgcaagtcaatatcgtg
aaaaagacggaggtccagacgggcgggttcagcaaggagtccatcctc
ccgaagcgcaactccgacaagctcatcgcgaggaagaaggattgggac
ccgaaaaaatatggcggcttcgacagcccgaccgtcgcatacagcgtc
```

-continued

```
ctcgtcgtggcgaaggtggagaagggcaagtcaaagaagctcaagtcc
gtgaaggagctgctcgggatcacgattatggagcggtcctccttcgag
aagaacccgatcgacttcctagaggccaagggatataaggaggtcaag
aaggacctgattattaaactgccgaagtactcgctcttcgagctggaa
aacggccgcaagaggatgctcgcctccgcaggcgagttgcagaagggc
aacgagctcgccctcccgagcaaatacgtcaatttcctgtacctcgct
agccactatgaaaagctcaagggcagcccggaggacaacgagcagaag
cagctcttcgtggagcagcacaagcattacctggacgagatcatcgag
cagatcagcgagttctcgaagcgggtgatcctcgccgacgcgaacctg
gacaaggtgctgtcggcatataacaagcaccgcgacaaaccaatacgc
gagcaggccgaaaatatcatccacctcttcaccctcaccaacctcggc
gctccggcagccttcaagtacttcgacaccacgattgaccggaagcgg
tacacgagcacgaaggaggtgctcgatgcgacgctgatccaccagagc
atcacagggctctatgaaacacgcatcgacctgagccagctgggcgga
gacaagaagaagaagctcaagctctag
```

```
                                     SEQ ID NO: 8
MAPKKKRKVMDKKYSIGLDIGTNSVGWAVITDEYKVPSKKFKVLGNTD
RHSIKKNLIGALLFDSGETAEATRLKRTARRRYTRRKNRICYLQEIFS
NEMAKVDDSFFHRLEESFLVEEDKKHERHPIFGNIVDEVAYHEKYPTI
YHLRKKLVDSTDKADLRLIYLALAHMIKFRGHFLIEGDLNPDNSDVDK
LFIQLVQTYNQLFEENPINASGVDAKAILSARLSKSRRLENLIAQLPG
EKKNGLFGNLIALSLGLTPNFKSNFDLAEDAKLQLSKDTYDDDLDNLL
AQIGDQYADLFLAAKNLSDAILLSDILRVNTEITKAPLSASMIKRYDE
HHQDLTLLKALVRQQLPEKYKEIFFIDQSKNGYAGYIDGGASQEEFYK
FIKPILEKMDGTEELLVKLNREDLLRKQRTFDNGSIPHQIHLGELHAI
LRRQEDFYPFLKDNREKIEKILTFRIPYYVGPLARGNSRFAWMTRKSE
ETITPWNFEEVVDKGASAQSFIERMTNFDKNLPNEKVLPKHSLLYEYF
TVYNELTKVKYVTEGMRKPAFLSGEQKKAIVDLLFKTNRKVTVKQLKE
DYFKKIECFDSVEISGVEDRFNASLGTYHDLLKIIKDKDFLDNEENED
ILEDIVLTLTLFEDREMIEERLKTYAHLFDDKVMKQLKRRRYTGWGRL
SRKLINGIRDKQSGKTILDFLKSDGFANRNFMQLIHDDSLTFKEDIQK
AQVSGQGDSLHEHIANLAGSPAIKKGILQTVKVVDELVKVMGRHKPEN
IVIEMARENQTTQKGQKNSRERMKRIEEGIKELGSQILKEHPVENTQL
QNEKLYLYYLQNGRDMYVDQELDINRLSDYDVDHIVPQSFLKDDSIDN
KVLTRSDKNRGKSDNVPSEEVVKKMKNYWRQLLNAKLITQRKFDNLTK
AERGGLSELDKAGFIKRQLVETRQITKHVAQILDSRMNTKYDENDKLI
REVKVITLKSKLVSDFRKDFQFYKVREINNYHHAHDAYLNAVVGTALI
KKYPKLESEFVYGDYKVYDVRKMIAKSEQEIGKATAKYFFYSNIMNFF
KTEITLANGEIRKRPLIETNGETGEIVWDKGRDFATVRKVLSMPQVNI
VKKTEVQTGGFSKESILPKRNSDKLIARKKDWDPKKYGGFDSPTVAYS
VLVVAKVEKGKSKKLKSVKELLGITIMERSSFEKNPIDFLEAKGYKEV
```

-continued

```
KKDLIIKLPKYSLFELENGRKRMLASAGELQKGNELALPSKYVNFLYL
ASHYEKLKGSPEDNEQKQLFVEQHKHYLDEIIEQISEFSKRVILADAN
LDKVLSAYNKHRDKPIREQAENIIHLFTLTNLGAPAAFKYFDTTIDRK
RYTSTKEVLDATLIHQSITGLYETRIDLSQLGGDKKKKLKL
```

Example 4

Construction of Cas9 Expression Vectors

The synthetic DNA sequence encoding Cas9 shown above was inserted into pENTR/D-TOPO so that it would be between flanking attL1 and attL2 sites to enable transfer by Invitrogen™ Gateway® cloning technology (Thermo Fisher Scientific Inc., Grand Island, N.Y.) into suitable expression vectors. A Gateway compatible expression vector, pTrex2gHyg, was available that comprises the following features; the promoter region from the *T. reeesi* pki1 (pyruvate kinase) gene and terminator region from the *T. reesei* cbh1 (cellobiohydrolase I) gene separated by Gateway cloning sites, a bacterial hygromycin phosphotransferase gene functionally linked to the *Neurospora crassa* cpc1 (cross pathway control 1) promoter region and the *Aspergillus nidulans* trpC (trifunctional protein with glutamine amido transferase, indoleglycerolphosphate synthase and phosphoribosylanthranilate isomerase activity) terminator region, and bacterial vector sequences for selection and maintenance in *E. coli*. The cas9 gene was cloned into pTrex2gHyg using the Gateway cloning procedure to give pTrex2gHyg MoCas (see FIG. 2).

Example 5

Construction of sgRNA Expression Vectors

Synthetic DNA sequences were obtained that encode the gAd3A TS1 sgRNA flanked by different putative RNA polymerase III dependent promoters and terminators. Each of these synthetic DNA sequences also had restriction enzyme recognition sites (EcoRI and BamHI) at either end.

The following sequence encodes the gAd3A TS1 sgRNA (underlined) with the *Saccharomyces cerevisiae* snr52 promoter and *S. cerevisiae* sup4 terminator (denoted gAd3A TS1-1; SEQ ID NO:9):

```
gaattcggatccTCTTTGAAAAGATAATGTATGATTATGCTTTCACTC
ATATTTATACAGAAACTTGATGTTTTCTTTCGAGTATATACAAGGTGA
TTACATGTACGTTTGAAGTACAACTCTAGATTTTGTAGTGCCCTCTTG
GGCTAGCGGTAAAGGTGCGCATTTTTTCACACCCTACAATGTTCTGTT
CAAAAGATTTTGGTCAAACGCTGTAGAAGTGAAAGTTGGTGCGCATGT
TTCGGCGTTCGAAACTTCTCCGCAGTGAAAGATAAATGATCgtcctcg
agcaaaaggtgccGTTTTAGAGCTAGAAATAGCAAGTTAAAATAAGGC
TAGTCCGTTATCAACTTGAAAAAGTGGCACCGAGTCGGTGGTGCTTTT
TTTGTTTTTTATGTCTgaattcggatcc
```

The following sequence encodes the gAd3A TS1 sgRNA (underlined) with the *T. reesei* U6 promoter and terminator (denoted gAd3A TS1-2; SEQ ID NO:10):

gaattcggatccAAAAAACACTAGTAAGTACTTACTTATGTATTATTA
ACTACTTTAGCTAACTTCTGCAGTACTACCTAAGAGGCTAGGGGTAGT
TTTATAGCAGACTTATAGCTATTATTTTTATTTAGTAAAGTGCTTTTA
AAGTAAGGTCTTTTTTATAGCACTTTTTATTTATTATAATATATATTA
TATAATAATTTTAAGCCTGGAATAGTAAAGAGGCTTATATAATAATTT
ATAGTAATAAAAGCTTAGCAGCTGTAATATAATTCCTAAAGAAACAGC
ATGAAATGGTATTATGTAAGAGCTATAGTCTAAAGGCACTCTGCTGGA
TAAAAATAGTGGCTATAAGTCTGCTGCAAAACTACCCCCAACCTCGTA
GGTATATAAGTACTGTTTGATGGTAGTCTATCgtcctcgagcaaaagg
tgccGTTTTAGAGCTAGAAATAGCAAGTTAAAATAAGGCTAGTCCGTT
ATCAACTTGAAAAAGTGGCACCGAGTCGGTGGTGCTTTTTTTTCTCTT
gaattcggatcc The following sequence encodes the gAd3A TS1 sgRNA (underlined) with the *T. reesei* U6 promoter, terminator and an intron (in italics) (denoted gAd3A TS1-3; SEQ ID NO:11):

gaattcggatccAAAAAACACTAGTAAGTACTTACTTATGTATTATTA
ACTACTTTAGCTAACTTCTGCAGTACTACCTAAGAGGCTAGGGGTAGT
TTTATAGCAGACTTATAGCTATTATTTTTATTTAGTAAAGTGCTTTTA
AAGTAAGGTCTTTTTTATAGCACTTTTTATTTATTATAATATATATTA
TATAATAATTTTAAGCCTGGAATAGTAAAGAGGCTTATATAATAATTT
ATAGTAATAAAAGCTTAGCAGCTGTAATATAATTCCTAAAGAAACAGC
ATGAAATGGTATTATGTAAGAGCTATAGTCTAAAGGCACTCTGCTGGA
TAAAAATAGTGGCTATAAGTCTGCTGCAAAACTACCCCCAACCTCGTA
GGTATATAAGTACTGTTTGATGGTAGTCTATCgtcctcgagcaaaagg
tgccGTTTTAGA*GCTAGAGTTCGTTTCGGCTTTTCCTCGGAACCCCCA*
*GAGGTCATCAGTTCGAATCGCTAACAG*AATAGCAAGTTAAAATAAGGC
TAGTCCGTTATCAACTTGAAAAAGTGGCACCGAGTCGGTGGTGCTTTT
TTTTCTCTTgaattcggatcc Plasmid p219M (FIG. 3) is an *E. coli* vector containing the *T. reesei* pyr4 (orotidine monophosphate decarboxylase) gene including its native promoter and terminator. This vector was digested with EcoRI and BamHI and the ends were dephosphorylated. Each of the above synthetic DNA molecules was digested with EcoRI and BamHI and ligated with the cut p219M to create a series of vectors containing an sgRNA expression cassette and the pyr4 gene. Each vector was designated by the name of the sgRNA that it encoded (for example, p219M gAd3A TS1-1 incorporates the gAd3A expression cassette with the *S. cerevisiae* snr52 promoter and sup4 terminator).

Guide RNA expression cassettes with a shorter *T. reesei* U6 promoter region were obtained as synthetic DNA. An example is provided here that includes the sequence for an sgRNA targeting the *T. reesei* gla1 gene at TS11 (SEQ ID NO:12; intron sequence is underlined).

AATTCCTAAAGAAACAGCATGAAATGGTATTATGTAAGAGCTATAGTC
TAAAGGCACTCTGCTGGATAAAAATAGTGGCTATAAGTCTGCTGCAAA
ACTACCCCCAACCTCGTAGGTATATAAGTACTGTTTGATGGTAGTCTA
TCgccaatggcgacggcagcacGTTTTAGAGCTAGAGTTCGTTTCGGC
TTTTCCTCGGAACCCCCAGAGGTCATCAGTTCGAATCGCTAACAGAAT
AGCAAGTTAAAATAAGGCTAGTCCGTTATCAACTTGAAAAAGTGGCAC
CGAGTCGGTGGTGCTTTTTTTTCTCTT The above gRNA expression cassette was amplified by PCR using primers gRNA fwd aflII (5'-cgtcagcttaag AATTCCTAAAGAAACAGCATGAAATGG; SEQ ID NO:13) and gRNA rev sfiI (5'-cgtcagggccacgtgggc-cAAGAGAAAAAAAAGCACCACCGACTCGG; SEQ ID NO:14). These primers add an aflII to the 5' end and an sfiI site to the 3' end of the guide RNA expression cassette. The PCR product was purified using a Qiagen PCR Purification Kit according to the manufacturer's directions. The PCR product was then digested with SfiI and AflII and cleaned again on a Qiagen PCR Purification Kit. Plasmid pTrex2g/Hyg MoCas was digested with SfiI and AflII and dephosphorylated using the Roche Rapid alkaline phosphatase kit (Roche Diagnostics Corp., IN). The digested plasmid and PCR product were finally ligated using the Roche Rapid DNA ligase kit to create pTrex2g/Hyg MoCas gTrGA TS11B. Other sgRNA expression cassettes were inserted into pTrex2g/Hyg MoCas in a similar manner.

Example 6

Cas9-Mediated Gene Inactivation in *Trichoderma reesei*

A series of experiments are described below in which a *Trichoderma reesei* strain was either co-transformed with two separate expression vectors, one for production of Cas9 and one for production of gRNA, or was transformed with a single vector for expression of both Cas9 and gRNA. These experiments demonstrate that the 5' upstream region from the *T. reesei* U6 gene promoted gRNA transcription only when the U6 intron is also present within the gRNA transcribed region. The experiments also demonstrate that targeted gene inactivation can occur with high efficiency in *T. reesei* transformants.

Inactivation of the ad3A Gene

A strain of *Trichoderma reesei* derived from the publicly available strain RL-P37 in which the genes (cbh1, cbh2, egl1, and egl2) encoding the four major secreted cellulases were deleted was used. This strain also lacked a functional pyr4 gene. Biolistic transformation (as described in US20060003408A1) was used to co-transform with a mixture of equal amounts of pTrex2gHyg MoCas (FIG. 2) and either p219M gAd3A TS1-1, p219M gAd3A TS1-2, or p219M gAd3A TS1-3. Transformants were selected on agar plates with Vogel's minimal medium containing 2% glucose, 100 mg/L hygromycin B and 200 mg/L adenine. After selection on the first plates transformant colonies were picked to fresh plates of the same selective medium. During growth on the second plate it was possible to distinguish between stable and unstable hygromycin-resistant transformants. Stable transformants grew more rapidly, the colonies had a smooth outline and the mycelium was more dense. Unstable transformants grew slower, had less dense mycelium and colonies had a ragged irregular outline. After growth on the second plate transformants were transferred to Vogel's medium with glucose, without hygromycin and with 14 mg/L adenine to screen for those which exhibited a red/brown color indicating that they were adenine auxotrophs. Five stable and 23 unstable transformants were obtained with p219M gAd3A TS1-1 and all were adenine prototrophs. Eleven stable and 38 unstable transformants were obtained with p219M gAd3A TS1-2 and all 11 stable and 29 of the unstable transformants were adenine prototrophs. Nineteen stable and 2 unstable transformants were obtained with p219M gAd3A TS1-3 and all were adenine auxotrophs. Clearly, adenine auxotrophs were only obtained with gAd3A TS1-3 that utilizes the *T. reesei* U6 promoter, intron and terminator to control transcription of sgAd3A TS1. Adenine auxotrophy indicates targeted Cas9 cleavage at the native *T. reesei* ad3A locus. It can be concluded that Cas9-mediated gene inactivation is efficient because all transformants with gAd3A TS1-3 that were tested were adenine auxotrophs.

In order to determine the mutations at the ad3A locus in co-transformants with pTrex2gHyg MoCas and p219M gAd3A TS1-3, genomic DNA was extracted from 10 stable adenine auxotrophic transformants. This DNA was used as template for PCR using several different primer pairs designed to generate products that spanned the Cas9 target site or were upstream or downstream of the target site. PfuUltra II Fusion HS DNA polymerase (Agilent Technologies, Santa Clara, Calif.) was used for the PCR according to the manufacturer's directions. In each case, the extension time was that suggested by the manufacturer for the expected size of the PCR product as described below. The sizes of the PCR products were evaluated by agarose gel electrophoresis.

A PCR product of the expected size (872 bp) was obtained in all transformants using Ad3 5' fwd+Ad3 5' rev primers (5'-tgaacacagccaccgacatcagc [SEQ ID NO:15] and 5'-gctggtgagggtttgtgctattg [SEQ ID NO:16] respectively) that amplify a region on the 5' side of the TS1 target site.

A PCR product of the expected size (1214 bp) was obtained in all transformants using Ad3 5' fwd+Ad3a 5005 rev primers (5'-tgaacacagccaccgacatcagc [SEQ ID NO:15] and 5'-gattgcttgggaggaggacat [SEQ ID NO:17] respectively) that amplify a region on the 5' side of the TS1 target site.

A PCR product of the expected size (904 bp) was obtained in all transformants using Ad3 3' fwd+Ad3 3' rev primers (5'-cgaggccactgatgaagttgttc [SEQ ID NO:18] and 5'-cagttttccaaggctgccaacgc [SEQ ID NO:19] respectively) that amplify a region on the 3' side of the TS1 target site.

A PCR product of the expected size (757 bp) was obtained in all transformants using Ad3a 5003 fwd+Ad3mid rev primers (5'-ctgatcttgcaccctggaaatc [SEQ ID NO:20] and 5'-ctctctatcatttgccaccctcc [SEQ ID NO:21] respectively) that amplify a region on the 3' side of the TS1 target site.

The above PCR results demonstrated that the genomic DNA preparations were of a quality sufficient to obtain PCR products from either upstream or downstream of the Cas9 target site.

No PCR product could be obtained for any transformants using Adfrag fwd+Adfrag rev primers (5'-ctccattcaccctcaattctcc [SEQ ID NO:22] and 5'-gttcccttggcggtgcttggatc [SEQ ID NO:23] respectively) spanning the TS1 target site in ad3A. The expected size for this PCR product presuming no large size change caused by Cas9 activity was approximately 764 bp.

No PCR product could be obtained for any transformants using Adfrag fwd+Ad3 3' rev primers (5'-ctccattcaccctcaattctcc [SEQ ID NO:22] and 5'-cagttttccaaggctgccaacgc [SEQ ID NO:19] respectively) spanning the TS1 target site in ad3A. The expected size for this PCR product presuming no large size change caused by Cas9 activity was approximately 2504 bp.

No PCR product could be obtained for any transformants using Ad3a 2k fwd+Ad3a 2k rev primers (5'-caatagcacaaaccctcaccagc [SEQ ID NO:24] and 5'-gaacaacttcatcagtggcctcg [SEQ ID NO:25] respectively) spanning the TS1 target site in ad3A. The expected size for this PCR product presuming no large size change caused by Cas9 activity was approximately 1813 bp.

Five of the transformants also gave no PCR product using Adfrag fwd+Ad3 mid rev primers (5'-ctccattcaccctcaattctcc [SEQ ID NO:22] and 5'-ctctctatcatttgccaccctcc [SEQ ID NO:21] respectively) spanning the TS1 target site. The expected size for this PCR product presuming no large size change caused by Cas9 activity was approximately 1438 bp.

Based on published data, Cas9-mediated inactivation of genes typically involves error-prone repair of a double-strand break in the DNA at the target site. The end result is small deletions or insertions (indels) at the target site. The above results from PCR analysis were surprising in that it was not possible to obtain a PCR product of the expected size that spanned the target site suggesting that inactivation of ad3A was not due to small insertions or deletions (indels) at the target site. Instead, these data are consistent with the possibilities that inactivation of ad3A was caused by a chromosomal rearrangement or large insertion at the target site.

Inactivation of the Glucoamylase (GA) Gene

A strain of *Trichoderma reesei* derived from the publicly available strain RL-P37 in which the genes (cbh1, cbh2, egl1, and egl2) encoding the four major secreted cellulases were deleted was used. This strain also lacked a functional pyr4 gene. This strain was co-transformed using the biolistic method with a mixture of equal amounts of pTrex2gHyg MoCas and p219M gTrGA TS2. Transformants were selected on agar plates with Vogel's minimal medium containing 1% glucose, 100 ug/ml hygromycin B and 2 mg/ml uridine. After selection on the first plates transformant colonies were picked to fresh plates of the same selective medium. During growth on the second plate it was possible to distinguish between stable and unstable hygromycin-resistant transformants. Seventeen stable and 4 unstable transformants were obtained. These transformants were transferred to Vogel's agar plates without glucose and with 1% insoluble starch to screen for presence or absence of secreted glucoamylase. Colonies able to secrete glucoamylase grow well and sporulate. Colonies unable to secrete glucoamylase grow with very sparse mycelium and are clearly distinguishable. Fourteen of the 17 stable transformants were unable to secrete glucoamylase and all 4 of the unstable transformants did not secrete glucoamylase.

In order to determine the mutations at the gla1 (glucoamylase) locus in co-transformants with pTrex2gHyg MoCas and p219M gTrGA TS2 genomic DNA was extracted from 5 stable glucoamylase non-producing transformants. This DNA was used as template for PCR using different primer pairs designed to generate products that spanned the Cas9 target site or were upstream or downstream of the target site. PfuUltra II Fusion HS DNA polymerase (Agilent Technologies) was used for the PCR according to the manufacturer's directions. In each case, the extension time was that suggested by the manufacturer for the expected size of the PCR product as described below. The sizes of the PCR products were evaluated by agarose gel electrophoresis.

No PCR product could be obtained for any transformants using glaA+glaB primers (5'-ccgttagttgaagatccttgccg [SEQ ID NO:26] and 5'-gtcgaggatttgcttcatacctc [SEQ ID NO:27] respectively) spanning the TS2 target site in gla1. The expected size for this PCR product presuming no large size change caused by Cas9 activity was approximately 1371 bp.

A band of the expected size (364 bp) was obtained in all transformants using glaA+glaJ primers (5'-ccgttagttgaagatccttgccg [SEQ ID NO:26] and 5'-tgccgactttgtccagtgattcg [SEQ ID NO:30] respectively) that amplify a region on the 5' side of the TS2 target site.

A band of the expected size (520 bp) was obtained in 4 of the transformants using glaK+glaB primers (5'-ttacatgtggacgcgagatagcg [SEQ ID NO:31] and 5'-gtcgaggatttgcttcatacctc [SEQ ID NO:27] respectively) that amplify a region on the 3' side of the TS2 target site. One of the transformants gave no PCR product with this primer pair.

A separate experiment intended to demonstrate inactivation of the gla1 gene by targeted Cas9 action was performed using a strain of *T. reesei* derived from RL-P37 and having an inactive pyr4 gene. Protoplasts of this strain were transformed with pTrex2gHyg MoCas gTrGA TS11 using a polyethylene glycol-mediated procedure (as described below). Transformants were selected on agar plates of Vogel's minimal medium with 2% glucose, 2 mg/ml uridine, 1.1M sorbitol and 100 ug/ml hygromycin B. After selection on the first plates transformant colonies were picked to fresh plates of the same selective medium without sorbitol. During growth on the second plate it was possible to distinguish between stable and unstable hygromycin-resistant transformants. Transformants were transferred to Vogel's agar plates without glucose and with 1% insoluble starch to screen for presence or absence of secreted glucoamylase. Five stable transformants, designated B #1, B #2, B #4, B #5 and B #6, which did not secrete glucoamylase were selected for further analysis. Genomic DNA was extracted from each of these transformants.

PCR was performed using genomic DNA as template and primers gla1repF and gla1repR (5'-gtgtgtctaatgcctccaccac [SEQ ID NO:32] and 5'-gatcgtgctagcgctgctgttg [SEQ ID NO:23] respectively) that generate a product of 983 bp from the wild-type gla1 locus spanning the TS11 target site. The PCR conditions included gradually reducing the primer annealing temperature with each PCR cycle and a long extension time to determine if there had been a large insertion at the target site. The specific PCR conditions were as follows.

Step 1: 94 C for 1 minute

Step 2: 94 C for 25 seconds

Step 3: 63 C for 30 seconds (temperature reduced by 0.2 C per cycle)

Step 4: 70 C for 8 minutes

Steps 2-4 repeated 24 more times

Step 5: Hold at 4C

A clear PCR product of greater than 12 kb was obtained from two of the transformants (B #1 and B #6) suggesting an increase of greater than 11 kb in the DNA region spanning the target site. The other three transformants gave only non-specific PCR products that appeared as low intensity bands on agarose gel electrophoresis. Sequence analysis of the >12 kb PCR product from B #6 demonstrated that DNA derived from plasmid pTrex2gHyg MoCas gTrGA TS11 was inserted at the TS11 target site.

PCR was performed using genomic DNA samples B #2, B #4, and B #5 and primer pair 1553R and 1555F (5'-CCGTGATGGAGCCCGTCTTCT [SEQ ID NO:34] and 5'-CGCGGTGAGTTCAGGCTTTTTC [SEQ ID NO:35] respectively). Primer 1553R binds to the gla1 gene on the 3' side of target site 11. Primer 1555F binds near the start codon of the hygromycin phosphotransferase (hygB) gene on the plasmid pTrex2gHyg MoCas gTrGA TS11. The same PCR conditions were used as above. PCR products of 4.5 kb and 6.5 were obtained for transformants B #4 and B #5 respectively. PCR products should only be obtained if the plasmid with the hygB gene had inserted into the gla1 gene. Presumably, the inserted plasmid DNA in transformants B #4, and B #5 was so large that it was not possible to obtain a PCR product using primers gla1repF and gla1repR.

Taken together, the PCR data demonstrated that stable hygromycin-resistant transformants with glucoamylase inactivation have arisen through insertion of large segments of the Cas9 and guide RNA expression vector at the target site in the gla1 gene.

Inactivation of the pyr2 Gene

Transformants of *T. reesei* strains QM6a or RL-P37 were generated by PEG-mediated transformation of protoplasts with derivatives of plasmid pTrex2gHyg MoCas that included guide RNA expression cassettes targeting different positions within the *T. reesei* pyr2 gene. Inactivation of this gene confers uridine auxotrophy and resistance to 5-fluororotic acid (FDA). Transformants were initially selected on medium containing hygromycin B. Upon transfer to fresh agar plates containing hygromycin B they were scored as stable or unstable. Transformants were then transferred to agar plates of Vogel's minimal medium with 2 mg/ml uridine and 1.2 mg/ml FOA. The ability to grow in the presence of FOA is indicative of uridine auxotrophy due to Cas9-mediated inactivation of the pyr2 gene.

Genomic DNA was extracted from some of the FOA resistant hygromycin stable and unstable transformants for PCR analysis. The primers used for this analysis were pyr2F (5'-gtataagagcaggaggagggag [SEQ ID NO:36]) and pyr2R (5'-gaacgcctcaatcagtcagtcg [SEQ ID NO:37]) designed to amplify a region of the pyr2 locus spanning the target sites and approximately 0.8 kb in length.

Among the QM6a transformants shown to be FOA resistant 18 stable and 5 unstable hygromycin resistant transformants were tested using the PCR protocol with an extension time sufficient to amplify the region of the pyr2 locus presuming the size to be similar to that in a wild-type strain. None of the stable transformants gave a PCR product with this short extension time whereas 2 of the unstable transformants did give a PCR product. DNA sequence analysis of these two PCR products showed that one had a single nucleotide deletion and the other had a 111 nt deletion at the expected target site.

Among the RL-P37 transformants shown to be FOA resistant 4 stable and 2 unstable hygromycin resistant transformants were tested using the PCR protocol with a short extension time. None of the stable transformants gave a PCR product with this short extension time whereas both of the unstable transformants did give a PCR product. DNA sequence analysis of these two PCR products showed that one had a single nucleotide deletion and the other had an insertion of 134 nt at the expected target site. This insertion consisted of two small fragments of the pTrex2gHyg vector.

A different 6 stable hygromycin resistant RL-P37 transformants were analyzed using the PCR protocol described earlier designed to enable amplification of the region of the pyr2 locus presuming a large DNA fragment was inserted at the target site in the pyr2 locus. All 6 transformants gave a large PCR product (between approximately 5 kb and >12 kb depending on the transformant) with this long extension time protocol. DNA sequence analysis of 5 of these PCR products showed that pTrex2gHyg vector DNA, or fragments thereof, was integrated in all cases.

Taken together, these data show that repair of a double strand break caused by Cas9 predominantly involves integration of large vector fragments in stable transformants. This can be a very efficient method of gene inactivation. This also demonstrates that a DNA fragment or vector bearing a functional gene and having no sequence homology with the target site can integrate in a site-specific manner at the target site following Cas9 cleavage and double strand break formation. In contrast, small deletions or insertions (indels) are associated with inactivation of a gene by Cas9 in unstable transformants. This is the method of choice for gene inactivation if vector integration is undesirable.

Example 7

Expression of Cas9 and sgRNA Using Expression Vector with Telomeres

A version of the Cas9 and guide RNA expression vector pTrex2gHyg MoCAS gPyr2 TS6 was constructed that contained *Trichoderma reesei* telomere sequences (shown in FIG. 6). The DNA sequence shown below (SEQ ID NO:38) was inserted into the vector. The underlined regions contain the repeated telomere sequences, each reading in towards center of this fragment. The central portion is a bacterial kanamycin resistance gene with promoter and terminator that enables selection in *E. coli* to ensure maintenance of the telomere repeats. In *Trichoderma*, a vector with telomeres is expected to linearize with the telomere sequences at each end and should be maintained autonomously at low copy number although occasional integration into the chromosomal DNA can also occur.

(SEQ ID NO: 38)

tcaggaaatagctttaagtagcttattaagtattaaaattatatatat ttttaatataactatatttctttaataaataggtattttaagctttat atataaatataataataaaataatatattatatagctttttattaata aataaaatagctaaaaatataaaaaaaatagctttaaaatacttattt ttaattagaattttatatatttttaatatataagatcttttactttttt tataagcttcctaccttaaattaaattttttactttttttttactatttt actatatcttaaataaaggctttaaaaatataaaaaaaatcttcttat atattataagctataaggattatatatatattttttttttaatttttaa agtaagtattaaagctagaattaaagttttaatttttttaaggctttat ttaaaaaaaggcagtaatagcttataaaagaaatttctttttctttta tactaaaagtactttttttttaataaggttagggttagggtttactca caccgaccatcccaaccacatcttagggttagggttagggttagggtt agggttagggttagggttagggtaagggtttaaacaaagccacgttgt gtctcaaaatctctgatgttacattgcacaagataaaaatatatcatc atgaacaataaaactgtctgcttacataaacagtaatacaaggggtgt tatgagccatattcaacgggaaacgtcttgctcgaggccgcgattaaa ttccaacatggatgctgatttatatgggtataaatgggctcgcgataa tgtcgggcaatcaggtgcgacaatctatcgattgtatgggaagcccga -continued tgcgccagagttgtttctgaaacatggcaaaggtagcgttgccaatga tgttacagatgagatggtcagactaaactggctgacggaatttatgcc tcttccgaccatcaagcattttatccgtactcctgatgatgcatggtt actcaccactgcgatccccgggaaaacagcattccaggtattagaaga atatcctgattcaggtgaaaatattgttgatgcgctggcagtgttcct gcgccggttgcattcgattcctgtttgtaattgtccttttaacagcga tcgcgtatttcgtctcgctcaggcgcaatcacgaatgaataacggttt ggttgatgcgagtgattttgatgacgagcgtaatggctggcctgttga acaagtctggaaagaaatgcataagcttttgccattctcaccggattc agtcgtcactcatggtgatttctcacttgataaccttatttttgacga ggggaaattaataggttgtattgatgttggacgagtcggaatcgcaga ccgataccaggatcttgccatcctatggaactgcctcggtgagttttc tccttcattacagaaacggctttttcaaaaatatggtattgataatcc tgatatgaataaattgcagtttcatttgatgctcgatgagtttttcta atcagaattggttaattggttgtaacactggcagagcattacgctgac ttgacgggacggcggctttgttgaataaatcgaacttttgctgagttg aaggatcagatcacgcatcttcccgacaacgcagaccgttccgtggca aagcaaaagttcaaaatcaccaactggtccacctacaacaaagctctc atcaaccgtggctccctcactttctggctggatgatggggcgattcag gcctggtatgagtcagcaacaccttcttcacgaggcagacctcagcgg tttaaacctaaccctaaccctaaccctaaccctaaccctaaccctaac cctaaccctaaccctaaccctaaccctaaccctaaccctaacctaacc ctaatggggtcgatctgaaccgaggatgagggttctatagactaatct acaggccgtacatggtgtgattgcagatgcgacgggcaaggtgtacag tgtccagaaggaggagagcggcataggtattgtaatagaccagcttta cataataatcgcctgttgctactgactgatgaccttcttccctaacca gtttcctaattaccactgcagtgaggataaccctaactcgctctgggg ttattattatactgattagcaggtggcttatatagtgctgaagtacta taagagtttctgcgggaggaggtggaaggactataaactggacacagt tagggatagagtgatgacaagacctgaatgttatcctccggtgtggta tagcgaattggctgaccttgcagatggtaatggtttaggcagggtttt tgcagagggggacgagaacgcgttctgcgatttaacggctgctgccgc caagctttacggttctctaatgggcggccgc This vector was inserted into *T. reesei* strain RL-P37 by PEG-mediated transformation of protoplasts. Transformants were selected for hygromycin resistance and transferred to fresh agar plates with hygromycin. The majority of transformants showed an unstable hygromycin resistance phenotype. Individual transformed colonies were transferred to minimal medium agar plates containing 2 mg/ml uridine and 1.2 mg/ml 5-fluoroorotic acid to select for those that were able to grow and thus had a Pyr-minus phenotype. Eight out of 142 (6%) of the unstable transformants were Pyr-minus. Analysis by PCR of the pyr2 locus and sequencing of three of these transformants showed that two had small deletions at the target site (1 bp and 27 bp respectively) and one had a 1 bp deletion combined with an insertion of 68 bp derived from the bacterial vector portion of pTrex2gHyg MoCAS gPyr2 TS6. The other 5 transformants did not give a PCR product despite using PCR conditions designed to amplify large DNA fragments [PCR conditions: Step 1: 94° C. for 1 minute; Step 2: 94° C. for 25 seconds; Step 3: 63 C for 30 seconds (temperature reduced by 0.2 C per cycle); Step 4: 70° C. for 8 minutes; Steps 2-4 repeated 24 more times; Step 5: Hold at 4° C. Polymerase: PfuUltra II Fusion HS DNA polymerase (Agilent Technologies)].

These results demonstrate that expression of Cas9 and guide RNA from an autonomously replicating vector enables Cas9 targeting to a specific locus (pyr2 in this case). The resulting gene inactivation can occur without insertion of vector DNA at the target site.

Example 8

Gene Editing by Homologous Integration

*Trichoderma reesei* strain T4(1)7 was used for the following experiments. This is a strain derived from RL-P37 by screening for increased cellulase productivity and having a single point mutation that inactivates the pyr2 gene making the strain a uridine auxotroph.

A synthetic DNA fragment called Gla1rep having the sequence shown below (SEQ ID NO:39) was designed and custom-made.

```
gtgtgtctaatgcctccaccacaggaaccaaaccggctttgacctctg
ggaagaagtcaatgggagctcattctttactgttgccaaccagcaccg
aggtatgaagcaaatcctcgacattcgctgctactgcacatgagcatt
gttactgaccagctctacagcacttgtcgagggcgccactcttgctgc
cactcttggccagtcgggaagcgcttattcatctgttgctccccaggt
tttgtgctttctccaacgattctgggtgtcgtctggtggatacgtcga
ctccaacagtatgtcttttcactgtttatatgagattggccaatactg
atagctcgcctctagtcaacaccaacgagggcaggactggcaaggatg
tcaactccgtcctgacttccatccacaccttcgatcccaaccttggct
gtgacgcaggcaccttccagccatgcagtgacaaagcgctctccaacc
tcaaggttgttgtcgactccttccgctccatctacggcgtgaacaagg
gcattcctgCGgtgctgccgtcgccattggccggtatgcagaggatgt
gtactacaacggcaacccttggtatcttgctacatttgctgctgccga
gcagctgtacgatgccatctacgtctggaagaagacgggctccatcac
ggtgaccgccacctccctggccttcttccaggagcttgttcctggcgt
gacggccgggacctactccagcagctcttcgacctttaccaacatcat
caacgccgtctcgacatacgccgatggcttcctcagcgaggctgccaa
gtacgtccccgccgacggttcgctggccgagcagtttgaccgcaacag
cggcactccgctgtctgcgcttcacctgacgtggtcgtacgcctcgtt
cttgacagccacggcccgtcgggctggcatcgtgccccccctcgtgggc
caacagcagcgctagcacgatc
```

The Gla1rep sequence is 982 bp of the gla1 locus from within the ORF. It spans the TS11 target site (underlined). A single "C" nucleotide within the "CCG" PAM sequence of the wild type Gla1 gene, right upstream of the TS11 target site, has been deleted to create a frame shift in the Gla1 coding sequence and to destroy the PAM adjacent to TS11, thereby preventing cleavage by Cas9. The remaining two nucleotides of the PAM are shown in upper case bold font.

The Gla1rep fragment was amplified by PCR for use in transformation using the primers gla1rep F and gla1rep R (5'-gtgtgtctaatgcctccaccac [SEQ ID NO:32] and 5'-gatcgtgctagcgctgctgttg [SEQ ID NO:33] respectively).

Protoplasts of *T. reesei* strain T4(1)7 were co-transformed by the PEG-mediated method with pTrex2gHyg MoCas gTrGA TS11B (2 ug) plus Gla1 rep (8 ug). Transformants were selected on agar plates with Vogel's minimal medium containing 50 ug/ml hygromycin B, 2 mg/ml uridine and 1.1M sorbitol. Plasmid pTrex2gHyg MoCas gTrGA TS11B is the same as pTrex2gHyg MoCas gTrGA TS11 except that the expression cassette for TS11 guide RNA is in the opposite orientation relative to the rest of the plasmid.

Transformants were picked to fresh agar plates of Vogel's minimal medium with uridine and hygromycin and it was possible to distinguish between stable and unstable hygromycin resistant phenotypes. Transformants were transferred to agar plates of Vogel's minimal medium with uridine and 1% insoluble starch as sole carbon source in order to score for glucoamylase positive or negative phenotypes. Approximately 83% of the stable hygromycin resistant transformants were negative for glucoamylase production whereas 15% of the unstable hygromycin resistant transformants were negative for glucoamylase production. Seven unstable transformants with glucoamylase-minus phenotype were transferred to non-selective agar medium (Vogel's+uridine) and allowed to grow for 1 week. When subsequently picked to plates of Vogel's+uridine+hygromycin they were all hygromycin-sensitive demonstrating loss of the hygromycin resistance gene associated with pTrex2gHyg MoCas gTrGA TS11B.

Genomic DNA was isolated from 5 unstable hygromycin-sensitive and glucoamylase-negative transformants obtained with pTrex2gHyg MoCas gTrGA TS11B plus Gla1rep (transformants #31, 107, 114, 118 and 120) and used as template in PCR (program as described above) using primers glaA and glaD (5'-ccgttagttgaagatccttgccg [SEQ ID NO:26] and 5'-gagagacgcaggatgactcaaag [SEQ ID NO:28] respectively) designed to amplify approx. 3.2 kb spanning TS11 or glaK [SEQ ID NO:31] (see above) and glaH 5'-tgccgtgggtcattggcatattc [SEQ ID NO:29]. The PCR products were sequenced using gla1rep F and gla1rep R (5'-gtgtgtctaatgcctccaccac [SEQ ID NO:32] and 5'-gatcgtgctagcgctgctgttg [SEQ ID NO:33] respectively) as primers to determine the alterations at the target site TS11. One of the transformants showed PCR and sequencing results consistent with homologous recombination of Gla1rep at the gla1 locus that introduced the single bp deletion at the PAM associated with TS11 and inactivated the gla1 gene. Two of the transformants had small indels at the TS11 target site whereas the other two showed insertion of fragments of Gla1rep into the Cas9 cleavage site rather than homologous integration across this site.

The above experiment was repeated in which protoplasts were co-transformed with pTrex2gHyg MoCas gTrGA TS11A (identical to pTrex2gHyg MoCas gTrGA TS11B except that the guide RNA expression cassette was in the opposite orientation within the vector) plus a linear DNA fragment designed to integrate by homologous recombination at the gla1 locus. However, instead of using the 982 bp Gla1rep DNA fragment as donor for homologous recombination at the target site TS11 in the glucoamylase gene a longer, approximately 2 kb, fragment called Gla1repL was used. The central portion of Gla1repL was the same sequence as Gla1rep but the 5' and 3' ends of the fragment were extended to include more of the upstream and downstream portions of the gla1 locus. *Trichoderma reesei* strain RL-P37 was used in this experiment instead of strain T4(1)7 used above. As a control, protoplasts were co-transformed with Gla1repL and pTrex2gHyg MoCas to determine the frequency with which Gla1repL integrates at the gla1 locus in the absence of active Cas9. Following transformation and phenotypic screening transformants could be assigned to the following categories.

| Transforming DNA | No. Hyg$^R$ transformants | No. glucoamylase-minus transformants (% among respective Hyg$^R$ transformants) |
|---|---|---|
| pTrex2gHyg MoCAS + | 26 unstable | 0 |
| Gla1repL | 19 stable | 2 (10%) |
| pTrex2gHyg MoCAS gTrGA | 52 stable | 46 (88%) |
| TS11A + Gla1repL | 16 unstable | 14 (87%) |

Genomic DNA was isolated from 5 stable and 5 unstable hygromycin-sensitive and glucoamylase-negative transformants obtained with pTrex2gHyg MoCas gTrGA TS11A plus Gla1repL (stable transformants #51, 52, 60, 61 and 67; unstable transformants 338, 41, 65, 66 and 68) and used as template in PCR using primers glaA and glaD (see above). The PCR product was expected to be 3.2 kb if no insertion or large deletion had occurred at the target site TS11 in the gla1 gene.

Three of the 5 stable transformants (#52, 60 and 61) gave a PCR product of approximately 3.2 kb whereas the other 2 gave larger products indicative of an insertion of DNA at TS11. The 3 PCR products of approximately 3.2 kb were sequenced using glarepF as a primer. For two transformants (#52 and 61) the sequencing results were consistent with integration of Gla1repL by homologous recombination at the gla1 locus and the other had a mixed signal that could not easily be interpreted.

Only one of the 5 unstable transformants (#66) gave a PCR product of approximately 3.2 kb whereas the other 4 gave larger products indicative of an insertion of DNA at TS11. The one PCR product of approximately 3.2 kb was sequenced using glarepF as a primer and the results were consistent with integration of Gla1repL by homologous recombination at the gla1 locus.

Taken together, these results show that homologous integration of a linear DNA fragment can be stimulated by Cas9 cleavage at a targeted locus. However, small indels or large insertions of DNA by non-homologous end joining (NHEJ) are also common occurrences. Use of a larger homologous linear DNA fragment helps to improve the frequency of homologous integration at the target site versus other events. It is possible to obtain homologous integration at the target site in unstable hygromycin resistant transformants from which the pTrex2g MoCas-based vector can subsequently be removed by allowing growth on medium without hygromycin.

Example 9

Gene Editing in a NHEJ-Deficient Strain of *T. reesei*

A strain (MAD6) derived from a "quad-delete strain" of *Trichoderma reesei* (derived from RL-P37 and having the cellobiohydrolase 1, cellobiohydrolase 2, endoglucanase 1, and endoclucanase 2 genes deleted (Δcbh1, Δcbh2, Δegl1, and Δegl2 strain; see WO 92/06184 and WO 05/001036)) and having deletions in the native endoglucanase-3 and betaglucosidase-1 genes was used for experiments designed to determine the role of non-homologous end joining (NHEJ) DNA insertion at Cas9 target site. The MAD6 strain was also deleted for a native gene, orthologous to human ku80, essential for the major NHEJ pathway for DNA recombination (see US20130149742 A1 "Filamentous fungal host strains and DNA constructs, and methods of use thereof" for a description of how the MAD6 strain was made). The strain was co-transformed with pTrex2gHyg MoCAS gTrGA TS11B plus donor Gla1rep fragment described above. Integration of this fragment by homologous recombination at the gla1 locus would inactivate the gla1 gene and remove the TS11 target site by deleting one bp from the PAM sequence. Transformants were obtained from protoplasts by the PEG-mediated method. Selection for transformants was on Vogel's minimal medium containing 1.1M sorbitol and 100 ug/mL hygromycin B. Out of 91 transformants transferred to fresh agar plates of minimal medium with hygromycin only 4 had a stable hygromycin resistant phenotype (confirmed by their ability to grow when re-plated on medium with hygromycin following a period of growth under non-selective conditions). All transformants were transferred to Vogel's minimal medium with 1% insoluble starch as sole carbon source, and 17 (18%) were shown to be glucoamylase-negative, including the 4 stable transformants. PCR and DNA sequence analysis showed that 12 of the 13 unstable transformants and one of the stable transformants had the single bp deletion at the TS11 PAM expected if donor Gla1rep had integrated by homologous recombination at the gla1 locus. The other unstable transformant had the wild-type gla1 sequence even though it had a glucoamylase-negative phenotype. The other three stable transformants did not give a clear PCR product of the size expected for the gla1 locus and vector or donor Gla1rep insertion may have occurred in these. All of the unstable glucoamylase-negative transformants were grown on medium without hygromycin and transferred back onto medium with hygromycin. None were able to grow indicating that they had lost the pTrex2gHyg MoCAS gTrGA TS11B vector.

These results clearly show that vector or donor DNA fragment insertion at the Cas9 target site is minimized in a strain deficient for NHEJ. As a result, a high frequency of very specific gene editing (deletion of a single bp) is possible through homologous recombination of a donor DNA fragment in unstable transformants with transient expression of Cas9 and guide RNA.

Section B: Direct Introduction of Cas Nickase/Guide RNA

Example 10

Heterologous Expression of CRISPR SpyCas9-D10A Nickase in *E. coli*

*E. coli* codon-optimized *Streptococcus pyogenes* Cas9-D10A (SpyCas9-D10A) nickase gene was synthesized and inserted into the expression vector pET30a at NcoI and HindIII sites by Generay (Shanghai, China), resulting in the plasmid pET30a-SpyCas9-D10A nickase (FIG. 7). As indicated in the plasmid map in FIG. 7, the full coding sequence of the expression cassette contains, in 5' to 3' orientation, a sequence encoding an N-terminal His6 tag/thrombin/S•Tag™/enterokinase region (SEQ ID NO:68, including a start codon for methionine), a sequence encoding an SV40 nuclear localization signal (SEQ ID NO:69), a sequence encoding the SpyCas9-D10A nickase (SEQ ID NO:65), and a sequence encoding the BLR2 nuclear localization signal (SEQ ID NO:70) all in operable linkage. This entire coding sequence is shown in SEQ ID NO: 54. The amino acid sequence of the N-terminal His6 tag/thrombin/S•Tag™/enterokinase region encoded by SEQ ID NO:68 is shown in SEQ ID NO:67 (including the methionine at position 1), the amino acid sequence of the SV40 nuclear localization signal encoded by SEQ ID NO:69 is shown in SEQ ID NO:46, the amino acid sequence of the SpyCas9-D10A nickase encoded by SEQ ID NO:65 is shown in SEQ ID NO:66, and the amino acid sequence of the BLR2 nuclear localization signal encoded by SEQ ID NO:70 is shown in SEQ ID NO:47. The amino acid sequence encoded by SEQ ID NO: 54 is shown in SEQ ID NO:55.

The pET30a-SpyCas9-D10A nickase plasmid was transformed into Rosetta2 (De3)plysS *E. coli* strain (Novagen®, EMD Biosciences, Inc., Merck KGaA, Darmstadt, Germany) and the transformation products were spread on Luria Agar plates supplemented with 34 ppm Chloramphenicol and 50 ppm Kanamycin. Colonies were picked and subjected to fermentation in 25 ml of Invitrogen MagicMedia™ (Thermo Fisher Scientific Inc.) in a 250 ml shake flask for 24 hours at 30° C. at 300 rpm.

The amino acid sequence of the wild-type Cas9 protein from *Streptococcus pyogenes*, from which the SpyCas9-D10A sequence is derived, is set forth as SEQ ID NO:45.

Example 11

Purification of SpyCas9-D10A

For purification of SpyCas9(D10A), a combination of affinity, hydrophobic interaction and size exclusion chromatographic steps were applied. Two liters of crude broth were obtained and centrifuged. Cells were pelleted and resuspended in 400 ml lysis buffer (20 mM HEPES, pH7.5, 500 mM NaCl, 0.1% Triton X-100, 1 mM DTT and 1 mM TCEP, protease inhibitor cocktail purchased from Roche) and lysed via ultra-sonicator (35% power, 20 min, 2 s on/3 s off) (SCIENT2-II D, Ningbo Scientz Biotechnology Co., LTD., Zhejiang, China). The lysate was cleared by centrifugation at 20,000 g for 40 min.

The clarified lysate was incubated with Ni-NTA resin (GE Healthcare) overnight at 4° C., 30 rpm in a Rolling Incubator (Kylin-Bell Lab Instruments Co., Ltd., Haimen, China). After centrifugation, the resin was transferred to a XK26/20 column (GE Healthcare) and connected to AKTA Explorer system (GE Healthcare). After washing extensively with equilibration buffer (20 mM HEPES, pH 7.5, 300 mM NaCl, 0.1% Triton X-100) and wash buffer (25 mM imidazole in equilibration buffer), the target protein was eluted with 50, 250 and 500 mM imidazole in equilibration buffer. The desired protein was found with relatively high purity in 50 and 250 mM imidazole eluates, which were pooled and further processed separately.

To the active fraction collected from the affinity step, ammonium sulfate was added to 0.6 M and loaded onto a 20 ml phenyl-Sepharose HP column (GE Healthcare). The column was eluted with a gradient of 0.6 M to 0.0 M ammonium sulfate in HEPES buffer at pH 7.5. The purity of each fraction was evaluated by SDS-PAGE gel which revealed that the protein of interest mainly present in the flow-through fraction.

Finally, the protein was further purified by size exclusion chromatography on a Superdex 200 16/60 column (GE Healthcare) in 20 mM HEPES pH7.5, 150 mM KCl and 10% glycerol. The protein-containing pure fractions were pooled and concentrated using an Amicon 30 KDa membrane filter (Millipore). The two batches of purified protein (from 50 mM imidazole and 250 mM imidazole elution, respectively) were stored in 20 mM HEPES buffer with 150 mM KCl and 40% glycerol at pH7.5 at −20° C. until use.

Example 12

Nickase In Vitro Assay

Preparation of Substrate DNA Fragment for In Vitro Nickase Cleavage Assays

Genomic DNA was extracted from a *Trichoderma reesei* strain derived from RL-P37 and having the cellobiohydrolase 1, cellobiohydrolase 2, endoglucanase 1, and endoclucanase 2 genes deleted (Δcbh1, Δcbh2, Δegl1, and Δegl2 strain; also called "quad-delete strain"; see WO 92/06184 and WO 05/001036)) using a ZF Fungal/Bacterial DNA miniprep kit from Zymo Research Corporation (Irvine, Calif.). With 1 ng of extracted genomic DNA as template a DNA fragment containing the *Trichoderma reesei* glucoamylase (TrGA) gene (Gene ID: 18483895) and its partial 5'-UTR (SEQ ID NO:56) was amplified by PCR using KOD-Plus PCR kit (Toyobo Co., LTD, Japan) and 0.4 μM of each forward and reverse primers: 5'-gactgtctccaccatgtaattttc-3'(SEQ ID NO:57) and 5'-ggcagactacaagtctactagtactac-3' (SEQ ID NO:58). PCR products were purified and concentrated with a DNA Clean & Concentrator™-5 kit from Zymo Research Corporation, and its DNA concentration was determined by NanoDrop™ Spectrophotometer (Thermo Fisher Scientific Inc.).

SEQ ID NO:56 (below) shows the nucleotide sequences of the substrate DNA fragment. The UTR sequences are shown in lowercase while the TrGA gene is shown in uppercase. Two selected VT domains, TrGA_sgF1 and TrGA_sgR1, are shown in bold and underlined, respectively (note that these sequences overlap).

(SEQ ID NO: 56)

```
gactgtctccaccatgtaattttccctgcgactccatataacgccgg

atcgtgaaattttcttctttcttttccttccttctcaacaaacaacgg

atctgtgctttgcggtcccctgcgttcacgcgtcagggtcgactgctc

tgcagctcgataactccatggagccatcaacttgctatggtgtcaatc

atcctatcgacaggtccaagaacaagccggcctccggctgcctcattc

gctgtcgcaagacggcttgagtgttgtggctggaggattcgggggccc

catattccaacccttttttccaaggccgtcggccggtgaggttgagga

aaaccatgggttgcctacatattatcgatgctggtgtttggtagtagc

aatgtttgcggtggcagtttgagccgagcctcgtcttgggcttctgac

ccaggcaacgccatctgactagctgcgccgaaggaaggatgattcatt

gtacgacgccagtcaatggaatcttcaagtaaaagcccgacgaaccga

ccatgtcagatatcagaattctcctggctggtggggttggttggagac
```

-continued tgcttacggagtcgatgcctcgtgactgtcatggccgcgtccagcctc ctgggactctgtccgatattatgacacgagtaaagcctgcatgatgtc agtttgctgcgtctcatgtcgagaacaacacacctggtgctacatagg caatactacctcgtagcttcaaagttgactgttttgctttgatgtctt tgatcatgcccatccatcccttgtcttgcagtgcatgtggatctctac gtccagacggggagaaagcttgtctgtgataaagtacgatgatgcatt gatgcctgtggctacggcccttttatccccatcgtcatgcatctctat attaatccaggagactctcctcctggcatgggtgagtacaagtgacga ggacatgtagaagcagagccacgcaacgtcttgacatctgtacctatt ttgggccaaaaatcgagacccaccagctcgtcctaccttacatgtgaa gatcttagcccacaatcctactgttttactagtattactgcacagctg tcatcacgagtcctcggttgcttgtgaaacccagctcagctcctgagc acatgcagtaacgccgactcggcgtcatttcgccacacccaatttgga cctgagggatgctggaagctgctgagcagatcccgttaccgattcatg gcactactacatccatacgcagcaaacatgggcttgggcttggcttct caatgcaaaattgcccgcaaaagtcccggcattgtcgatgcagagatg cagatttcagcgggcgattctagggtagggcgactactactactaata ccacctagtcagtatgtatctagcaccggaggctaggcggttagtgga cgggaacctggtcattccatcgcaaccaggatcccgcacttcgttgcg cttctgcccccacggggcgggagttggcagaggcagaatgcggagcag ccccttgtctgccctggccggggcctgttgaagcaagcagacgagagc agagcggttgagaagcggtggttgacgcttgacggtacgaagacgagc gagaatcccgttaagccgaggctgggctcccccccccgtcatcatcat gcccatcctgctcttccagcccactcgtctccctgcctcgtcgcctcc cctccctcccccgattagctgcgcatgttctcctgacagcgtgactaa tgacgcgttgccagcccattcgcctgacgcatcccggcatctgagtct agctcgtcacgctggcaatcttggcccaggcagagcagcaagacggcg ggcatgattgggccgtgccctggcgggcatcagctggccatccgctgc cacccgagaccgcatcaccgacttgtcggatctctccgagcagcagga ggctgatcctggccggcgagacgattgaaaagggctgccgggcccgga gcaggacagcggcgagagcgagcgagagagaggaaaagaagaaggtcg actgtcttattttcagccagccccggctcaacagaagcagaggagaag gcgaacgacgtcaacgacgacgacgacgacgacgaagacggtgaagtc cgttagttgaagatccttgccgtcacaacaccatctcgtggatattgc tttcccctgccgttgcgttgccacctgttccctctttctcttcccccc ttcttcctcattccgagcgctactggttcctactccgcagccttcggt tgtgcctttctctttgtcgaccattgcaccgcccgtcgcggcacttgg gccccggagaattcggccctttcgcagcattttggccctcagttcccc atggggacggtccacacttcctctcttggccctgcagaccttttgtcg tcggtccgagtcggaagaagctcagtcttgagcgcttgagtagcatct acgcgcgaatcactggacaaagtcggcaagacgaagccgtcgtcgcct -continued gctgctgctgctgttactgcgacaggcgctccgactgggggcatcggc ataataaaaagatgcccgccttcgccatggacctggccatgagccact cggcatcggctctctctctcaacgcttcctctcacacatcctccttca ttccgcccatcATGCACGTCCTGTCGACTGCGGTGCTGCTCGGCTCCG

TTGCCGTTCAAAAGGTCCTGGGAAGACCAGGATCAAGCGGTCTGTCCG

ACGTCACCAAGAGGTCTGTTGACGACTTCATCAGCACCGAGACGCCTA

TTGCACTGAACAATCTTCTTTGCAATGTTGGTCCTGATGGATGCCGTG

CATTCGGCACATCAGCTGGTGCGGTGATTGCATCTCCCAGCACAATTG

ACCCGGACTGTAAGTTGGCCTTGATGAACCATATCATATATCGCCGAG

AAGTGGACCGCGTGCTGAGACTGAGACAGACTATTACATGTGGACGCG

AGATAGCGCTCTTGTCTTCAAGAACCTCATCGACCGCTTCACCGAAAC

GTACGATGCGGGCCTGCAGCGCCGCATCGAGCAGTACATTACTGCCCA

GGTCACTCTCCAGGGCCTCTCTAACCCCTCGGGCTCCCTCGCGGACGG

CTCTGGTCTCGGCGAGCCCAAGTTTGAGTTGACCCTGAAGCCTTTCAC

CGGCAACTGGGGTCGACCGCAGCGGGATGGCCCAGCTCTGCGAGCCAT

TGCCTTGATTGGATACTCAAAGTGGCTCATCAACAACAACTATCAGTC

GACTGTGTCCAACGTCATCTGGCCTATTGTGCGCAACGACCTCAACTA

TGTTGCCCAGTACTGGTCAGTGCTTGCTTGCTCTTGAATTACGTCTTT

GCTTGTGTGTCTAATGCCTCCACCACAGGAACCAAACCGGCTTTGACC

TCTGGGAAGAAGTCAATGGGAGCTCATTCTTTACTGTTGCCAACCAGC

ACCGAGGTATGAAGCAAATCCTCGACATTCGCTGCTACTGCACATGAG

CATTGTTACTGACCAGCTCTACAGCACTTGTCGAGGGCGCCACTCTTG

CTGCCACTCTTGGCCAGTCGGGAAGCGCTTATTCATCTGTTGCTCCCC

AGGTTTTGTGCTTTCTCCAACGATTCTGGGTGTCGTCTGGTGGATACG

TCGACTCCAACAGTATGTCTTTTCACTGTTTATATGAGATTGGCCAAT

ACTGATAGCTCGCCTCTAGTCAACACCAACGAGGGCAGGACTGGCAAG

GATGTCAACTCCGTCCTGACTTCCATCCACACCTTCGATCCCAACCTT

GGCTGTGACGCAGGCACCTTCCAGCCATGCAGTGACAAAGCGCTCTCC

AACCTCAAGGTTGTTGTCGACTCCTTCCGCTCCATCTACGGCGTGAAC

AAGGGCATTCCTGCCGGTGCTGCCGTCGCCATTGGCCGGTATGCAGAG

GATGTGTACTACAACGGCAACCCTTGGTATCTTGCTACATTTGCTGCT

GCCGAGCAGCTGTACGATGCCATCTACGTCTGGAAGAAGACGGGCTCC

ATCACGGTGACCGCCACCTCCCTGGCCTTCTTCCAGGAGCTTGTTCCT

GGCGTGACGGCCGGGACCTACTCCAGCAGCTCTTCGACCTTTACCAAC

ATCATCAACGCCGTCTCGACATACGCCGATGGCTTCCTCAGCGAGGCT

GCCAAGTACGTCCCCGCCGACGGTTCGCTGGCCGAGCAGTTTGACCGC

AACAGCGGCACTCCGCTGTCTGCGCTTCACCTGACGTGGTCGTACGCC

TCGTTCTTGACAGCCACGGCCCGTCGGGCTGGCATCGTGCCCCCCTCG

TGGGCCAACAGCAGCGCTAGCACGATCCCCTCGACGTGCTCCGGCGCG

TCCGTGGTCGGATCCTACTCGCGTCCCACCGCCACGTCATTCCCTCCG

-continued

```
TCGCAGACGCCCAAGCCTGGCGTGCCTTCCGGTACTCCCTACACGCCC
CTGCCCTGCGCGACCCCAACCTCCGTGGCCGTCACCTTCCACGAGCTC
GTGTCGACACAGTTTGGCCAGACGGTCAAGGTGGCGGGCAACGCCGCG
GCCCTGGGCAACTGGAGCACGAGCGCCGCCGTGGCTCTGGACGCCGTC
AACTATGCCGATAACCACCCCCTGTGGATTGGGACGGTCAACCTCGAG
GCTGGAGACGTCGTGGAGTACAAGTACATCAATGTGGGCCAAGATGGC
TCCGTGACCTGGGAGAGTGATCCCAACCACACTTACACGGTTCCTGCG
GTGGCTTGTGTGACGCAGGTTGTCAAGGAGGACACctggcagtcgtaa
tgaatcggcaaggggtagtactagtagacttgtagtctgcc
```

In Vitro Transcription

Two VT domains in the TrGA gene, TrGA_sgF1 and TrGA_sgR1 and their specific PAMs, were identified for downstream activity and transformation experiments. Oligonucleotides containing the T7 promoter and single-guide RNA sequences, with either TrGA_sgF1 (SEQ ID NO:59) or TrGA_sgR1 (SEQ ID NO:60) were synthesized and inserted into the pMD18T vector by Generay, resulted in pMD18T (T7-Spy-TrGA_sgF1) (FIG. 8A) or pMD18T (T7-Spy-TrGA_sgR1) (FIG. 8B), respectively. DNA fragments for the in vitro transcription were amplified from either pMD18T (T7-Spy-TrGA_sgF1) or pMD18T (T7-Spy-TrGA_sgR1) by PCR with 0.4 μM of each forward and reverse primers: 5'-tgatgacggtgaaaacctc-3' (SEQ ID NO:71) and 5'-aaaagcaccgactcgg-3' (SEQ ID NO:72). PCR products were purified and concentrated with the DNA Clean & Concentrator™-5 kit from Zymo Research Corporation, and its DNA concentration was determined by the NanoDrop™ Spectrophotometer.

With the above specific PCR product as template, RNA for VT domain TrGA_sgF1 or TrGA_sgR1 was generated by in vitro transcription using MEGAshortscript™ T7 transcription kit from Invitrogen, Thermo Fisher Scientific Inc. according to the manufacturer's instructions. Transcribed RNAs were purified using MEGAclear™ Transcription Clean-Up kit from Invitrogen, Thermo Fisher Scientific Inc. The RNA concentration was measured by NanoDrop™.

SpyCas9 in vitro assays were performed to confirm the function of the synthesized single-guide RNAs. To initiate the assay, 1 μg of purified SpyCas9, 200 ng of substrate DNA fragment and 200 ng of single-guided RNA (or water as control) were mixed together in 15 μl reaction buffer containing 50 mM HEPES pH 7.3, 150 mM KCl, 0.5 mM DTT and 10 mM MgCl2. Assays were carried out at 37° C. for 20 min, followed by the addition of 2 μg of Proteinase K (Sigma, Cat No. P6556). The reaction was continued at 40° C. for 20 min and terminated by an additional incubation at 80° C. for 20 min. And the reaction results were analyzed using 0.8% agarose gel, running at 140 volts for 30 min, and the result is shown in FIG. 9. In FIG. 9, Lane 1 is a DNA ladder (molecular weights are shown on the left), Lane 2 is a control SpyCas9 reaction (no guide RNA), Lanes 3 & 4 show SpyCas9 in the presence of TrGA_sgR1, and Lanes 5 & 6 show SpyCas9 in the presence of TrGA_sgF1. The size of intact DNA substrate (SEQ ID NO:56) is 4.9 Kb (Lane 2), while the sizes of cut products in the presence of either sgRNA are 2.8 Kb and 2.1 Kb. As shown in FIG. 9, in the presence of specific single-guide RNA, SpyCas9 can successfully cut substrate DNA fragment into the desired sizes, confirming the correct function of the synthesized RNAs.

SEQ ID NO:59 (below) shows the oligonucleotide sequences for the transcription of the T7 promoter, CER domain, and the VT domain TrGA_sgF1. The VT domain is shown in upper case, while the T7 promoter and CER domain region are shown in bold and lower case, respectively.

taatacgactcactataGGGAAGACCAGGATCAAGgttttagagctag
aaatagcaagttaaaataaggctagtccgttatcaacttgaaaaagtg
gcaccgagtcggtgc SEQ ID NO:60 (below) shows the oligonucleotide sequences for the transcription of the T7 promoter, CER domain, and the VT domain TrGA_sgR1. The VT domain is shown in upper case, while the T7 promoter and CER domain region are shown in bold and lower case, respectively.

taatacgactcactataGGACAGACCGCTTGATCCgttttagagctag
aaatagcaagttaaaataaggctagtccgttatcaacttgaaaaagtg
gcaccgagtcggtgc In Vitro Nickase Cleavage Assays with Purified SpyCas9 (D10A)

The in vitro nickase cleavage assay is a two-step reaction. For the first step, 1 μg of purified SpyCas9(D10A), 200 ng of substrate DNA fragment and 200 ng of single-guided RNA (or water as control) were mixed together in 15 μl reaction buffer containing 50 mM HEPES pH 7.3, 150 mM KCl, 0.5 mM DTT and 10 mM MgCl2. The reaction was performed as described in SpyCas9 nuclease assay. Following the termination of the first-step reaction, 1 μg of SpyCas9(D10A) and 200 ng of specific single-guide RNA were added. After repeating the first-step reaction, the reaction results were subsequently analyzed using 0.8% agarose gel, running at 140 volts for 30 min, and the result is shown in FIG. 10. In FIG. 10, Lane 1 is the DNA ladder (molecular weights shown on the left), Lane 2 shows a reaction of SpyCas9(D10A) with substrate DNA and TrGA_sgF1 alone, Lane 3 shows a reaction of SpyCas9(D10A) with substrate DNA and TrGA_sgR1 alone, and Lane 4 shows a reaction of SpyCas9(D10A) with substrate DNA and both sgRNAs. The size of intact DNA substrate (SEQ ID NO:56) would be 4.9 Kb, while the sizes of cut products with both sgRNAs would be 2.8 Kb and 2.1 Kb. As shown in FIG. 10, the substrate DNA fragment is only cut in the presence of both RNAs (Lane 4), suggesting that SpyCas9(D10A) is an active nickase.

Example 13

In Vivo Nickase Uptake Experiment

Protoplast Preparation

For protoplast preparation, $5\times10^8$ spores of a quad-delete strain of *T. reesei* (described above) with additional deletions of the endoglucanase-3, endoglucanase-4, endoglucanase-5, endoglucanase-6, mannanase-1, and alpha-amylase genes, but with normal NHEJ mechanism (grown on a PDA plate for 5 days at 30° C.) were inoculated into 50 ml germination medium (recipe described in U.S. Pat. No. 8,679,815) in a 250 ml shake flask with 4 baffles and incubated at 27° C. for 17 hours at 170 rpm. The mycelia were recovered by transferring the liquid volume into 50 ml conical tubes and spinning at 3000 rpm for 10 minutes. The supernatant was decanted and the mycelial pellets were washed twice using 1.2 M $MgSO_4$—10 mM Na-phosphate buffer and resuspended in 15 ml lysing enzyme buffer (dissolve Lysing Enzymes from *Trichoderma harzianum* (Sigma catalog #L1412)) using in 1.2 M $MgSO_4$—10 mM Na-phosphate buffer (pH 5.8), 50 mg/ml). The cell suspension was transferred into a 250 ml shake flask with 4 baffles and shaken at room temperature for at least 2 hours at 200 rpm. The protoplasts were harvested by filtration through Miracloth (Calbiochem Art. No. 475855) folded in a glass funnel into a Greiner tube. 0.6 M Sorbitol—0.1 M Tris-HCl buffer was added carefully on top of the filtered protoplasts. The protoplasts were collected by centrifugation for 15 minutes at 4000 rpm. The middle phase containing the protoplasts was transferred into a new tube and added at least an equal volume of 1.2 M Sorbitol—10 mM Tris-HCl buffer. The protoplasts were collected by centrifugation for 5 minutes at 4000 rpm, and washed two times using 1.2 M sorbitol, 10 mM Tris-HCl buffer. The pellet was resuspended into at least 1 ml 1.2 M Sorbitol—10 mM Tris-HCl pH 7.5-10 mM $CaCl_2$ buffer and the number of protoplasts counted under a microscope. The protoplast suspension was diluted using 4 parts of 1.2 M Sorbitol—10 mM Tris-HCl—10 mM $CaCl_2$ and 1 part of 25% PEG6000—50 mM $CaCl_2$—10 mM Tris-HCl until $5\times10^8$ per ml for the future transformation.

Preparation of Deletion Cassette

A TrGA deletion cassette was constructed and schematically depicted in FIG. 11. It contained a pyr2 expression cassette including pyr2 promotor, pyr2 CDS and pyr2 terminator, a 500 bp repeat sequence for subsequent loop out, flanked by 5' and 3' TrGA-homologous regions.

TrGA knockout transformants can be screened on Vogel's agar plates without glucose and with 1% insoluble starch (Vogel's-starch medium). TrGA knockout transformants grow poorly on this medium compared to strains with an intact TrGA gene. The nucleotide sequence of the TrGA knockout cassette is 4248 base pairs in length: bases 1-1000 correspond to the TrGA 5' homologous region; bases 1001-2730 correspond to the pyr2 expression cassette; bases 2739-3248 correspond to the 500 bp repeat; and bases 3249-4248 correspond to the TrGA 3' homologous region. The nucleotide sequence of the TrGA knockout cassette is provided as SEQ ID NO:61 (shown below):

```
ccctgcctcgtcgcctcccctccctcccccgattagctgcgcatgttc

tcctgacagcgtgactaatgacgcgttgccagcccattcgcctgacgc

atcccggcatctgagtctagctcgtcacgctggcaatcttggcccagg

cagagcagcaagacggcgggcatgattgggccgtgccctggcgggcat

cagctggccatccgctgccacccgagaccgcatcaccgacttgtcgga

tctctccgagcagcaggaggctgatcctggccggcgagacgattgaaa

agggctgccgggcccggagcaggacagcggcgagagcgagcgagagag

aggaaaagaagaaggtcgactgtcttattttcagccagccccggctca

acagaagcagaggagaaggcgaacgacgtcaacgacgacgacgacgac

gacgaagacggtgaagtccgttagttgaagatccttgccgtcacaaca

ccatctcgtggatattgctttcccctgccgttgcgttgccacctgttc
```

-continued

```
cctctttctcttccccccttcttcctcattccgagcgctactggttcc

tactccgcagccttcggttgtgcctttctctttgtcgaccattgcacc

gcccgtcgcggcacttgggccccggagaattcggccctttcgcagcat

tttggccctcagttccccatggggacggtccacacttcctctcttggc

cctgcagaccttttgtcgtcggtccgagtcggaagaagctcagtcttg

agcgcttgagtagcatctacgcgcgaatcactggacaaagtcggcaag

acgaagccgtcgtcgcctgctgctgctgctgttactgcgacaggcgct

ccgactgggggcatcggcataataaaaagatgcccgccttcgccatgg

acctggccatgagccactcggcatcggctctctctctcaacgcttcct

ctcacacatcctccttcattccgcccatcatggtttaaacctcgagtt

tataagtgacaacatgctctcaaagcgctcatggctggcacaagcctg

gaaagaaccaacacaaagcatactgcagcaaatcagctgaattcgtca

ccaattaagtgaacatcaacctgaaggcagagtatgaggccagaagca

catctggatcgcagatcatggattgcccctcttgttgaagatgagaat

ctagaaagatggcggggtatgagataagagcgatgggggggcacatca

tcttccaagacaaacaacctttgcagagtcaggcaatttttcgtataa

gagcaggaggagggagtccagtcatttcatcagcggtaaaatcactct

agacaatcttcaagatgagttctgccttgggtgacttatagccatcat

catacctagacagaagottgtgggatactaagaccaacgtacaagctc

gcactgtacgctttgacttccatgtgaaaactcgatacggcgcgcctc

taaattttatagctcaaccactccaatccaacctctgcatccctctca

ctcgtcctgatctactgttcaaatcagagaataaggacactatccaaa

tccaacagaatggctaccacctcccagctgcctgcctacaagcaggac

ttcctcaaatccgccatcgacggcggcgtcctcaagtttggcagcttc

gagctcaagtccaagcggatatcccccctacttcttcaacgcgggcgaa

ttccacacggcgcgcctcgccggcgccatcgcctccgcctttgcaaag

accatcatcgaggcccaggagaaggccggcctagagttcgacatcgta

tcggcccggcctacaagggcatcccgctgtgctccgccatcaccatca

agctcggcgagctggcgccccagaacctggaccgcgtctcctactcgt

ttgaccgcaaggaggccaaggaccacggcgagggcggcaacatcgtcg

gcgcttcgctcaagggcaagagggtcctgattgtcgacgacgtcatca

ccgccggcaccgccaagagggacgccattgagaagatcaccaaggagg

gcggcatcgtcgccggcatcgtcgtggccctggaccgcatggagaagc

tccccgctgcggatggcgacgactccaagcctggaccgagtgccattg

gcgagctgaggaaggagtacggcatccccatctttgccatcctcactc

tggatgacattatcgatggcatgaagggctttgctacccctgaggata

tcaagaacacggaggattaccgtgccaagtacaaggcgactgactgat

tgaggcgttcaatgtcagaagggagagaaagactgaaaaggtggaaag

aagaggcaaattgttgttattattattattctatctcgaatcttctag

atcttgtcgtaaataaacaagcgtaactagctagcctccgtacaactg

cttgaatttgatacccgtatggagggcagttattttattttgttttc
```

-continued

```
aagattttccattcgccgttgaactcgtctcacatcgcgtgtattgcc

cggttgcccatgtgttctcctactaccccaagtccctcacgggttgtc

tcactttctttctcctttatcctccctatttttttcaagtcagcgac

agagcagtcatatggggatacgtgcaactgggactcacaacaggccat

cttatggcctaatagccggcgttggatccactagtcaattggtttaaa

cagcacatgcagtaacgccgactcggcgtcatttcgccacacccaatt

tggacctgagggatgctggaagctgctgagcagatcccgttaccgatt

catggcactactacatccatacgcagcaaacatgggcttgggcttggc

ttctcaatgcaaaattgcccgcaaaagtcccggcattgtcgatgcaga

gatgcagatttcagcgggcgattctagggtagggcgactactactact

aataccacctagtcagtatgtatctagcaccggaggctaggcggttag

tggacgggaacctggtcattccatcgcaaccaggatcccgcacttcgt

tgcgcttctgcccccacggggcgggagttggcagaggcagaatgcgga

gcagccccttgtctgccctggccggggcctgttgaagcaagcagacga

gagcagagcggttgagaagcggtggttgacgcttgacggtacgaagac

gagcgagaatcccgttaagccgaggctgggctaattaattaatgaatc

ggcaaggggtagtactagtagacttgtagtctgccggattattgattg

gagttggtcagtagaatgaaccacgggaatattcggtcaccgggacat

ttgggatatagcgtttcgagaagctgctggttgcagcacattggagaa

ggatgcccttttacgacttataccgctatgccgggtatattaatttag

ccgttatgaaactcaaagagacgatgataatgatgacgagtaattgtt

cgtttcaatttcgaaagctgactcccacgaagaatatgccaatgaccc

acggcatgaagcctgaactgggcgtgtgtaacactttaatttgcctga

cggcggacaaaacaaaggcggcagcaatgttgagaccgtgtgataaac

caaggttcccgagggagagagagagagagagagagagagagctaggtg

aaagaatgagtccgcctttgagtcatcctgcgtctctctctcccccctc

tctcactctctgtatcccatcaacctcttccctgttccttctcctatc

gcatccatgcgtttgcatcttccatttcattctttccccttgagcccc

atctatgcaaactcatcatccggcgcctcgatggaatccttgaccttg

atgagaatcgccgtcatccaaggctccagcctgctcgtgcggtcgaac

tggaacagcagctcgctaaactcatcctggctgtggttgtcgacggcg

ttgcacaggtcctcgagcagcttgtacttgtattgagaggagaactcg

gggtccttttggcggtaggactcgacggcgcggcgggtgccgaccatg

tcgcccgtggcgaggtggcagatgccggccttgaagcagtaggtcgag

aggctccacttcatggtgccgttgccgatcatggtgttgatgatgcgg

tcgtacgtctcgatggcgccgtagtagtcgccgtcgagggcggcgagg

tcggcgtactgcgtccagagctt
```

Transformation

To knock out TrGA gene in *T. reesei* using a Spycas9 nickase premix and deletion cassette, 25 μg Spycas9 nickase protein in storage buffer (20 mM HEPES pH 7.5, 150 mM KCl, and 40% glycerol) was mixed with 20 μg sgRNA (TrGA_sgR1) dissolved in nuclease-free water in 3 μl NEB buffer 3 (New England Biolabs) gently to obtain a 30 μl premix, and incubated for 30 min at room temperature. 30 μl premix was added to 200 μL protoplasts ($1\times10^8$) with 20 μg (20 μl) deletion cassette and kept on ice for 30 min. After incubation on ice for 30 min, protoplasts were added to cooled molten sorbitol/Vogel agar (1.1 M sorbitol in minimal Vogel's agar with 2% glucose) to be used as the top layer of the minimal Vogel's agar plate (Davis et al., (1970) Methods in Enzymology 17A, pgs. 79-143 and Davis, Rowland, NEUROSPORA, CONTRIBUTIONS OF A MODEL ORGANISM, Oxford University Press, (2000)). The plates were incubated at 30° C. for a week. The detailed steps are described in U.S. Pat. No. 8,679,815 (incorporated herein by reference).

Ninety transformants were selected and inoculated into four 24-well plates with 1 ml fresh Vogel agar per well alongside 3 controls: the quad-delete strain with additional deletions of the endoglucanase-3, endoglucanase-4, endoglucanase-5, endoglucanase-6, mannanase-1 (*T. reesei* strain described above; "cellu" in FIG. 12), the "cellu" strain with an additional deletion of the alpha-amylase gene (AA deletion; ΔAA in FIG. 12), and the "cellu" strain with an additional glucoamylase gene deletion (GA deletion; ΔGA in FIG. 12). After one week, the transformants were transferred into another four 24-well plates with 1 ml fresh Vogel's-starch agar per well. After one week, the morphology of these 90 strains was observed. 47 transformants have the retarded growth as compared with those of the "cellu" strain and the "cellu" strain with the AA deletion (ΔAA), but looked similar to that of the "cellu" strain with the GA deletion (ΔGA) in Vogel's-starch plate (FIG. 12). On Vogel's-starch agar, the sole carbon source was starch in comparison to the regular Vogel's agar with glucose as carbon source. Glucoamylase consecutively hydrolyzes α-1,4 glycosidic bonds from the non-reducing ends of starch, resulting in the production of glucose, which can be utilized by the fungal strain. When glucoamylase is deleted, the retarded growth can be observed due to the limited availability of glucose.

Strain Verification

Forty-seven out of 90 strains showed retarded growth in Vogel's-starch agar. Nice of them (see FIG. 12, from #1 to #9) were selected randomly to perform PCR screening using Fw1 (5'-cactactacatccatacgcagcaaacatgg-3'(SEQ ID NO:62)) and R3 (5'-ggtcaagaagcacatgccagagttcg-3'(SEQ ID NO:63)) as primers. FIG. 13A shows the genomic loci of wild type and TrGA deletion strains as well as the primer annealing sites (the arrows indicate the direction of polymerization when used in PCR reactions).

The 9 strains were pre-screened by PCR with primer pair FW1 and R3. The PCR conditions for amplifying the PCR product were as follows: Step 1: 95° C. for 5 min. Step 2: 95° C. for 30 sec. Step 3: 60° C. for 30 sec. Step 4: 68° C. for 3 min. Steps 2, 3 and 4 were repeated for an additional 29 cycles. Step 5: 68° C. for 10 min. In the ideal condition, two PCR fragments (1.9-kb and 5.2-kb) would be expected from the PCR pre-screening. In this result, the 5.2-kb product could not be observed clearly. However, the 1.9-kb fragment as compared with the 5.1-kb product from spores of cellulighter (C1) and the PCR product from spores of cellulighter plus TrGA deletion cassette (C2) could confirm for certain that the TrGA deletion cassette was integrated at the TrGA locus by homologous recombination (FIG. 13B, top gel).

Two (#1 and #3) out of the 9 stains were selected to do the further PCR confirmation with primer pair FW1/R1, F4/R3, and KOF1/KOR2, respectively. The TrGA deletion cassette integrated at the TrGA locus by homologous recombination was confirmed by PCR with primer pair FW1/R1 and F4/R3 further, when 2.0-kb and 2.2-kb fragments were obtained from the spores of #1 and #3 as compared with the result from C2 (spores of cellulighter plus TrGA deletion cassette) (FIG. 13B, bottom left gel). PCR with another pair of primers, KOF1 and KOR2, also confirmed the result, when no PCR product was got from the spores of #1 and #3 while a product of 2.1 kb was amplified from cellulighter (C1) (FIG. 13B, bottom right gel, first 4 lanes, including molecular weight marker).

The PCR products from the spores of #1 and #3 for the whole region of TrGA locus by using primers TrGAF2 (5' gactgtctccaccatgtaatttttc 3'(SEQ ID NO:64)) and R3 (SEQ ID NO:63) were obtained and their DNA sequence determined. The sequencing result showed that TrGA gene has been replaced by pyr2 expression cassette (see PCR result in FIG. 13B, bottom right gel, last 2 lanes; data not shown for sequencing result).

The results above demonstrate that the SpyCas9 nickase and sgRNA were able to promote homologous recombination in filamentous fungus, allowing for homologous recombination-based gene deletion on the filamentous fungus *T. reesei*. Specifically, 47 out of 90 transformants (~52%) showed the retarded growth phenotype on Vogel's-starch plates, indicating that the TrGA gene has been disrupted. The intended homologous recombination event was verified by PCR product sequencing, confirming that the deletion cassette was successfully incorporated into the TrGA locus in the host cells by homologous recombination and as a result, the TrGA gene was replaced by pyr2 expression cassette. Our data demonstrate that directly introducing a functional SpyCas9 nickase complex into a target fungal cell in addition to the donor DNA (i.e., the DNA that is to be homologously recombined at the genomic locus of interest), the homologous recombination ratio in fungi can be significantly increased.

Section C: Introduction of Cas/Guide RNA and Donor DNA on a Single Expression Vector

Example 14

Deletion of a Single Base from the gla1 Gene by Use of cas9 Expression Plasmid Containing a Directed Homologous Donor Fragment for Gene Editing In this example, a gene disruption was directed by incorporating a homologous gla1 donor fragment containing a single base deletion into the plasmid pTrex2gHyg MoCas gTrGA TS11B (described in example 8). The plasmid pTrexMoCasGATS11-HDR (FIG. 14) was created by inserting the approximately 1 kb synthetic DNA fragment Gla1rep (SEQ ID NO:39, labeled as "Tr-gla 1 kb homologous fragment" in FIG. 14) into the unique EcoRV restriction site of the plasmid pTrex2gHygMoCasgTrGATS11B. The EcoRV site resides in a polylinker sequence between the pSL1180 sequence and the *N. crassa* cpc1 promoter of the hygromycin resistance marker (hph). The primers 1556F (5'-ATGCGCAAATTTAAAGCGCTGATgtgtgtctaatgcctccaccac [SEQ ID NO:73]) and 1557R (5'-ATATGGATCTGCGCGCGATCGATgatcgtgctagcgctgctgttg [SEQ ID NO:74]) were used to amplify Gla1rep and addend homologous tails to overlap both sides of the EcoRV site in pTrex2gHygMoCasgTrGATS11B to facilitate Gibson Assembly of the fragment with the EcoRV-cut pTrex2gHygMoCasgTrGATS11B plasmid (using NEB Gibson Assembly Master Mix, New England Biolabs, Beverly, Mass.).

The pTrexMoCasGATS11-HDR plasmid was used to transform *T. reesei* strain RL-P37, a strain with normal NHEJ mechanism, using protoplasts and PEG-mediated DNA uptake. This strain was auxotrophic for pyr2, incidental for this experiment, but requiring uridine (at 2 g/L) to be included in all growth media.

Transformants were initially grown on selective media agar plates of Vogel's minimal medium+1.2M sorbitol+75 ppm hygromycin. After growth, 80 transformants of both stable and unstable phenotypes were transferred to second agar plates of Vogel's-starch medium. After growth on second plates, the presence or absence of a starch clearing zone was used as a reporter to determine if the gla1 gene was disrupted. Transformants were transferred from the second plates onto non-selective third plates of Vogel's minimal medium. After a few days of growth, transformants were transferred from the third plates of Vogel's minimal medium to selective fourth plates of Vogel's minimal medium+75 ppm hygromycinB. On these fourth plates transformants could be accessed for growth to determine whether transformants maintained the ability to grow on hygromycin-containing media after growth on the non-selective media of the second and third plates.

It was found that only 11 of 80 transformants produced a clearing zone on Vogel's-starch medium, indicating gla1 disruption, and did not grow on the fourth hygromycin selective plates of Vogel's minimal medium+75 ppm hygromycin. These transformants presumably had alterations of the gla1 gene and did not incorporate the hygromycin marker from the plasmid into their genome.

Genomic DNA was isolated from these 11 gla1-transformants, from mycelia of the third Vogel's minimal medium plates. Primers glaK (SEQ ID NO:31) and glaH (SEQ ID NO:29) were used to PCR amplify the gla1 gene from genomic DNA to determine status of the TS11 locus. PCR products were isolated and sequenced using primers

```
1538F
                                    (SEQ ID NO: 75)
5'-CCACCACAGGAACCAAACC,

1539R
                                    (SEQ ID NO: 76)
5'-CTGCGACGGAGGGAATGACG,

1540F
                                    (SEQ ID NO: 77)
5'-GGGCAGGACTGGCAAGGATGT
and

1541R
                                    (SEQ ID NO: 78)
5'-GCCGTCACGCCAGGAACAAG.
```

The sequencing result revealed that 8 of these 11 gla1-transformants contained the single base deletion of the Gla1rep sequence. Two gla1-transformants contained gla1 deletions at the TS11 locus of 9 and 100 bases. One gla1-transformant contained an insertion of 470 bases at TS11.

Incorporation of the donor Gla1rep fragment into the plasmid pTrex2gHyg MoCas TrGA TS11 generated a single plasmid which directed gene editing. A high frequency of the hygromycin-unstable transformants contained the single base deletion in the gla1 gene that was engineered into the donor Gla1rep fragment. Unstable transformants were generated on the first selective agar medium, Vogel's minimal medium+75 ppm hygromycinB, which subsequently lost the transforming cas9 plasmid. Such strains are more advantageous because they do not have the inconvenience of NHEJ incorporation of the gene editing plasmid into the genome.

In another experiment for which data is not shown here, a substitutional mutation of gla1 was successfully introduced into *T. reesei* strain P37 using the same homologous integration method as described herein, with a gla1 homologous DNA fragment containing substitutional nucleotides instead of deletions inserted in pTrex2gHyg MoCas gTrGA TS11B.

These results demonstrate the utility of creating a single cas9 editing plasmid incorporating a homologous fragment along with cas9 and target site guide RNA. A single plasmid vector is created that directs both the specific cas9 targeted cleavage and gene editing homologous recombination at the targeted locus. By screening unstable hygromycin resistance transformants, the incidence of NHEJ insertion of plasmid DNA into the target locus is minimized. Additionally, by screening unstable hygromycin resistant transformants in this example, transformants may be found that have incorporated the homologous donor fragment into the target locus by homologous recombination. Yet, such transformants have conveniently lost the plasmid that directed the targeted recombination.

Although the foregoing compositions and methods have been described in some detail by way of illustration and example for purposes of clarity of understanding, it is readily apparent to those of ordinary skill in the art in light of the teachings herein that certain changes and modifications may be made thereto without departing from the spirit or scope of the appended claims.

Accordingly, the preceding merely illustrates the principles of the present compositions and methods. It will be appreciated that those skilled in the art will be able to devise various arrangements which, although not explicitly described or shown herein, embody the principles of the present compositions and methods and are included within its spirit and scope. Furthermore, all examples and conditional language recited herein are principally intended to aid the reader in understanding the principles of the present compositions and methods and the concepts contributed by the inventors to furthering the art, and are to be construed as being without limitation to such specifically recited examples and conditions. Moreover, all statements herein reciting principles, aspects, and embodiments of the present compositions and methods as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present compositions and methods, therefore, is not intended to be limited to the exemplary embodiments shown and described herein.

Sequences:
Putative *T. reesei* U6 gene

SEQ ID NO: 1

AAAAAACACTAGTAAGTACTTACTTATGTATTATTAACTACTTTAGCT

AACTTCTGCAGTACTACCTAAGAGGCTAGGGGTAGTTTTATAGCAGAC

TTATAGCTATTATTTTTATTTAGTAAAGTGCTTTTAAAGTAAGGTCTT

TTTTATAGCACTTTTTATTTATTATAATATATATTATATAATAATTTT

-continued

AAGCCTGGAATAGTAAAGAGGCTTATATAATAATTTATAGTAATAAAA

GCTTAGCAGCTGTAATATAATTCCTAAAGAAACAGCATGAAATGGTAT

TATGTAAGAGCTATAGTCTAAAGGCACTCTGCTGGATAAAAATAGTGG

CTATAAGTCTGCTGCAAAACTACCCCCAACCTCGTAGGTATATAAGTA

CTGTTTGATGGTAGTCTATCGCCTTCGGGCATTTGGTCAATTTATAAC

GATACAGGTTCGTTTCGGCTTTTCCTCGGAACCCCCAGAGGTCATCAG

TTCGAATCGCTAACAGGTCAACAGAGAAGATTAGCATGGCCCCTGCAC

TAAGGATGACACGCTCACTCAAAGAGAAGCTAAACATTTTTTTTCTCT

TCCAAGTCGTGATGGTTATCTTTTTGCTTAGAGAATCTATTCTTGTGG

ACGATTAGTATTGGTAAATCCCTGCTGCACATTGCGGCGGATGGTCTC

AACGGCATAATACCCCATTCGTGATGCAGCGGTGATCTTCAATATGTA

GTGTAATACGTTGCATACACCACCAGGTTCGGTGCCTCCTGTATGTAC

AGTACTGTAGTTCGACTCCTCCGCGCAGGTGGAAACGATTCCCTAGTG

GGCAGGTATTTTGGCGGGGTCAAGAA sequence of sgRNA (N is sequence complementary to target site)

SEQ ID NO: 2

NNNNNNNNNNNNNNNNNNNNGUUUUAGAGCUAGAAAUAGCAAGUUAAA

AUAAGGCUAGUCCGUUAUCAACUUGAAAAAGUGGCACCGAGUCGGUGG

UGC sgRNA: gAd3A TS1

SEQ ID NO: 3 guccucgagcaaaaggugccGUUUUAGAGCUAGAAAUAGCAAGUUAAA

AUAAGGCUAGUCCGUUAUCAACUUGAAAAAGUGGCACCGAGUCGGUGG

UGC sgRNA: gTrGA TS2

SEQ ID NO: 4 guucagugcaauaggcgucuGUUUUAGAGCUAGAAAUAGCAAGUUAAA

AUAAGGCUAGUCCGUUAUCAACUUGAAAAAGUGGCACCGAGUCGGUGG

UGC sgRNA: gTrGA TS11

SEQ ID NO: 5 gccaauggcgacggcagcacGUUUUAGAGCUAGAAAUAGCAAGUUAAA

AUAAGGCUAGUCCGUUAUCAACUUGAAAAAGUGGCACCGAGUCGGUGG

UGC sgRNA: gPyr2 TS6

SEQ ID NO: 6 gcacagcgggaugcccuuguGUUUUAGAGCUAGAAAUAGCAAGUUAAA

AUAAGGCUAGUCCGUUAUCAACUUGAAAAAGUGGCACCGAGUCGGUGG

UGC

Codon optimized *Streptococcus pyogenes* Cas9-encoding gene; with N- and C-terminal NLS sequences

SEQ ID NO: 7 atggcaccgaagaagaagcgcaaggtgatggacaagaagtacagcatc ggcctcgacatcggcaccaactcggtgggctgggccgtcatcacggac gaatataaggtcccgtcgaagaagttcaaggtcctcggcaatacagac cgccacagcatcaagaaaaacttgatcggcgccctcctgttcgatagc -continued ggcgagaccgcggaggcgaccaggctcaagaggaccgccaggagacgg tacactaggcgcaagaacaggatctgctacctgcaggagatcttcagc aacgagatggcgaaggtggacgactccttcttccaccgcctggaggaa tcattcctggtggaggaggacaagaagcatgagcggcacccaatcttc ggcaacatcgtcgacgaggtggcctaccacgagaagtacccgacaatc taccacctccggaagaaactggtggacagcacagacaaggcggacctc cggctcatctaccttgccctcgcgcatatgatcaagttccgcggccac ttcctcatcgagggcgacctgaacccggacaactccgacgtggacaag ctgttcatccagctcgtgcagacgtacaatcaactgttcgaggagaac cccataaacgctagcggcgtggacgccaaggccatcctctcggccagg ctctcgaaatcaagaaggctggagaaccttatcgcgcagttgccaggc gaaaagaagaacggcctcttcggcaaccttattgcgctcagcctcggc ctgacgccgaacttcaaatcaaacttcgacctcgcggaggacgccaag ctccagctctcaaaggacacctacgacgacgacctcgacaacctcctg gcccagataggagaccagtacgcggacctcttcctcgccgccaagaac ctctccgacgctatcctgctcagcgacatccttcgggtcaacaccgaa attaccaaggcaccgctgtccgccagcatgattaaacgctacgacgag caccatcaggacctcacgctgctcaaggcactcgtccgccagcagctc cccgagaagtacaaggagatcttcttcgaccaatcaaaaaacggctac gcgggatatatcgacggcggtgccagccaggaagagttctacaagttc atcaaaccaatcctggagaagatggacggcaccgaggagttgctggtc aagctcaacagggaggacctcctcaggaagcagaggaccttcgacaac ggctccatcccgcatcagatccacctgggcgaactgcatgccatcctg cggcgccaggaggacttctacccgttcctgaaggataaccgggagaag atcgagaagatcttgacgttccgcatcccatactacgtgggcccgctg gctcgcggcaactcccggttcgcctggatgacccggaagtcggaggag accatcacaccctggaactttgaggaggtggtcgataagggcgctagc gctcagagcttcatcgagcgcatgaccaacttcgataaaaacctgccc aatgaaaaagtcctccccaagcactcgctgctctacgagtacttcacc gtgtacaacgagctcaccaaggtcaaatacgtcaccgagggcatgcgg aagccggcgttcctgagcggcgagcagaagaaggcgatagtggacctc ctcttcaagaccaacaggaaggtgaccgtgaagcaattaaaagaggac tacttcaagaaaatagagtgcttcgactccgtggagatctcgggcgtg gaggatcggttcaacgcctcactcggcacgtatcacgacctcctcaag atcattaaagacaaggacttcctcgacaacgaggagaacgaggacatc ctcgaggacatcgtcctcaccctgaccctgttcgaggaccgcgaaatg atcgaggagaggctgaagacctacgcgcacctgttcgacgacaaggtc atgaaacagctcaagaggcgccgctacactggttggggaaggctgtcc cgcaagctcattaatggcatcagggacaagcagagcggcaagaccatc ctggacttcctcaagtccgacgggttcgccaaccgcaacttcatgcag -continued ctcattcacgacgactcgctcacgttcaaggaagacatccagaaggca caggtgagcgggcagggtgactccctccacgaacacatcgccaacctg gccggctcgccggccattaaaaagggcatcctgcagacggtcaaggtc gtcgacgagctcgtgaaggtgatgggccggcacaagcccgaaaatatc gtcatagagatggccagggagaaccagaccacccaaaaagggcagaag aactcgcgcgagcggatgaaacggatcgaggagggcattaaagagctc gggtcccagatcctgaaggagcaccccgtggaaaatacccagctccag aatgaaaagctctacctctactacctgcagaacggccgcgacatgtac gtggaccaggagctggacattaatcggctatcggactacgacgtcgac cacatcgtgccgcagtcgttcctcaaggacgatagcatcgacaacaag gtgctcacccggtcggataaaaatcggggcaagagcgacaacgtgccc agcgaggaggtcgtgaagaagatgaaaaactactggcgccagctcctc aacgcgaaactgatcacccagcgcaagttcgacaacctgacgaaggcg gaacgcggtggcttgagcgaactcgataaggcgggcttcataaaaagg cagctggtcgagacgcgccagatcacgaagcatgtcgcccagatcctg gacagccgcatgaatactaagtacgatgaaaacgacaagctgatccgg gaggtgaaggtgatcacgctgaagtccaagctcgtgtcggacttccgc aaggacttccagttctacaaggtccgcgagatcaacaactaccaccac gcccacgacgcctacctgaatgcggtggtcgggaccgccctgatcaag aagtacccgaagctggagtcggagttcgtgtacggcgactacaaggtc tacgacgtgcgcaaaatgatcgccaagtccgagcaggagatcggcaag gccacggcaaaatacttcttctactcgaacatcatgaacttcttcaag accgagatcaccctcgcgaacggcgagatccgcaagcgcccgctcatc gaaaccaacggcgagacgggcgagatcgtctgggataagggccgggat ttcgcgacggtccgcaaggtgctctccatgccgcaagtcaatatcgtg aaaaagacggaggtccagacgggcgggttcagcaaggagtccatcctc ccgaagcgcaactccgacaagctcatcgcgaggaagaaggattgggac ccgaaaaaatatggcggcttcgacagcccgaccgtcgcatacagcgtc ctcgtcgtggcgaaggtggagaagggcaagtcaaagaagctcaagtcc gtgaaggagctgctcgggatcacgattatggagcggtcctccttcgag aagaacccgatcgacttcctagaggccaagggatataaggaggtcaag aaggacctgattattaaactgccgaagtactcgctcttcgagctggaa aacggccgcaagaggatgctcgcctccgcaggcgagttgcagaagggc aacgagctcgccctcccgagcaaatacgtcaatttcctgtacctcgct agccactatgaaaagctcaagggcagcccggaggacaacgagcagaag cagctcttcgtggagcagcacaagcattacctggacgagatcatcgag cagatcagcgagttctcgaagcgggtgatcctcgccgacgcgaacctg gacaaggtgctgtcggcatataacaagcaccgcgacaaaccaatacgc gagcaggccgaaaatatcatccacctcttcaccctcaccaacctcggc gctccggcagccttcaagtacttcgacaccacgattgaccggaagcgg tacacgagcacgaaggaggtgctcgatgcgacgctgatccaccagagc -continued atcacagggctctatgaaacacgcatcgacctgagccagctgggcgga gacaagaagaagaagctcaagctctag

*Streptococcus pyogenes* Cas9 encoded by SEQ ID NO: 7; with N- and C-terminal NLS sequences

SEQ ID NO: 8

MAPKKKRKVMDKKYSIGLDIGTNSVGWAVITDEYKVPSKKFKVLGNTD

RHSIKKNLIGALLFDSGETAEATRLKRTARRRYTRRKNRICYLQEIFS

NEMAKVDDSFFHRLEESFLVEEDKKHERHPIFGNIVDEVAYHEKYPTI

YHLRKKLVDSTDKADLRLIYLALAHMIKFRGHFLIEGDLNPDNSDVDK

LFIQLVQTYNQLFEENPINASGVDAKAILSARLSKSRRLENLIAQLPG

EKKNGLFGNLIALSLGLTPNFKSNFDLAEDAKLQLSKDTYDDDLDNLL

AQIGDQYADLFLAAKNLSDAILLSDILRVNTEITKAPLSASMIKRYDE

HHQDLTLLKALVRQQLPEKYKEIFFIDOSKNGYAGYIDGGASQEEFYK

FIKPILEKMDGTEELLVKLNREDLLRKORTFDNGSIPHQIHLGELHAI

LRRQEDFYPFLKDNREKIEKILTFRIPYYVGPLARGNSRFAWMTRKSE

ETITPWNFEEVVDKGASAQSFIERMTNFDKNLPNEKVLPKHSLLYEYF

TVYNELTKVKYVTEGMRKPAFLSGEQKKAIVDLLFKTNRKVTVKQLKE

DYFKKIECFDSVEISGVEDRFNASLGTYHDLLKIIKDKDFLDNEENED

ILEDIVLTLTLFEDREMIEERLKTYAHLFDDKVMKQLKRRRYTGWGRL

SRKLINGIRDKQSGKTILDFLKSDGFANRNFMQLIHDDSLTFKEDIQK

AQVSGQGDSLHEHIANLAGSPAIKKGILQTVKVVDELVKVMGRHKPEN

IVIEMARENQTTQKGQKNSRERMKRIEEGIKELGSQILKEHPVENTQL

QNEKLYLYYLQNGRDMYVDQELDINRLSDYDVDHIVPQSFLKDDSIDN

KVLTRSDKNRGKSDNVPSEEVVKKMKNYWROLLNAKLITQRKFDNLTK

AERGGLSELDKAGFIKRQLVETRQITKHVAQILDSRMNTKYDENDKLI

REVKVITLKSKLVSDFRKDFQFYKVREINNYHHAHDAYLNAVVGTALI

KKYPKLESEFVYGDYKVYDVRKMIAKSEQEIGKATAKYFFYSNIMNFF

KTEITLANGEIRKRPLIETNGETGEIVWDKGRDFATVRKVLSMPQVNI

VKKTEVQTGGFSKESILPKRNSDKLIARKKDWDPKKYGGFDSPTVAYS

VLVVAKVEKGKSKKLKSVKELLGITIMERSSFEKNPIDFLEAKGYKEV

KKDLIIKLPKYSLFELENGRKRMLASAGELQKGNELALPSKYVNFLYL

ASHYEKLKGSPEDNEQKQLFVEQHKHYLDEIIEQISEFSKRVILADAN

LDKVLSAYNKHRDKPIREQAENIIHLFTLTNLGAPAAFKYFDTTIDRK

RYTSTKEVLDATLIHQSITGLYETRIDLSQLGGDKKKKLKL

Synthetic DNA: gAd3A TS1-1 (gAd3A TS1 sgRNA (SEQ ID NO: 3) with *Saccharomyces cerevisiae* snr52 promoter and *S. cerevisiae* sup4 terminator)

SEQ ID NO: 9 gaattcggatccTCTTTGAAAAGATAATGTATGATTATGCTTTCACTC

ATATTTATACAGAAACTTGATGTTTTCTTTCGAGTATATACAAGGTGA

TTACATGTACGTTTGAAGTACAACTCTAGATTTTGTAGTGCCCTCTTG

GGCTAGCGGTAAAGGTGCGCATTTTTTCACACCCTACAATGTTCTGTT

CAAAAGATTTTGGTCAAACGCTGTAGAAGTGAAAGTTGGTGCGCATGT

-continued

TTCGGCGTTCGAAACTTCTCCGCAGTGAAAGATAAATGATCgtcctcg agcaaaaggtgccGTTTTAGAGCTAGAAATAGCAAGTTAAAATAAGGC

TAGTCCGTTATCAACTTGAAAAAGTGGCACCGAGTCGGTGGTGCTTTT

TTTGTTTTTTATGTCTgaattcggatcc

Synthetic DNA: gAd3A TS1-2 (gAd3A TS1 sgRNA (SEQ ID NO: 3) with *T. reesei* U6 promoter and terminator)

SEQ ID NO: 10 gaattcggatccAAAAAACACTAGTAAGTACTTACTTATGTATTATTA

ACTACTTTAGCTAACTTCTGCAGTACTACCTAAGAGGCTAGGGGTAGT

TTTATAGCAGACTTATAGCTATTATTTTTATTTAGTAAAGTGCTTTTA

AAGTAAGGTCTTTTTTATAGCACTTTTTATTTATTATAATATATATTA

TATAATAATTTTAAGCCTGGAATAGTAAAGAGGCTTATATAATAATTT

ATAGTAATAAAAGCTTAGCAGCTGTAATATAATTCCTAAAGAAACAGC

ATGAAATGGTATTATGTAAGAGCTATAGTCTAAAGGCACTCTGCTGGA

TAAAAATAGTGGCTATAAGTCTGCTGCAAAACTACCCCCAACCTCGTA

GGTATATAAGTACTGTTTGATGGTAGTCTATCgtcctcgagcaaaagg tgccGTTTTAGAGCTAGAAATAGCAAGTTAAAATAAGGCTAGTCCGTT

ATCAACTTGAAAAAGTGGCACCGAGTCGGTGGTGCTTTTTTTTCTCTT gaattcggatcc

Synthetic DNA: gAd3A TS1-3 (gAd3A TS1 sgRNA (SEQ ID NO: 3) with *T. reesei* U6 promoter, terminator and intron)

SEQ ID NO: 11 gaattcggatccAAAAAACACTAGTAAGTACTTACTTATGTATTATTA

ACTACTTTAGCTAACTTCTGCAGTACTACCTAAGAGGCTAGGGGTAGT

TTTATAGCAGACTTATAGCTATTATTTTTATTTAGTAAAGTGCTTTTA

AAGTAAGGTCTTTTTTATAGCACTTTTTATTTATTATAATATATATTA

TATAATAATTTTAAGCCTGGAATAGTAAAGAGGCTTATATAATAATTT

ATAGTAATAAAAGCTTAGCAGCTGTAATATAATTCCTAAAGAAACAGC

ATGAAATGGTATTATGTAAGAGCTATAGTCTAAAGGCACTCTGCTGGA

TAAAAATAGTGGCTATAAGTCTGCTGCAAAACTACCCCCAACCTCGTA

GGTATATAAGTACTGTTTGATGGTAGTCTATCgtcctcgagcaaaagg tgccGTTTTAGAGCTAGAGTTCGTTTCGGCTTTTCCTCGGAACCCCCA

GAGGTCATCAGTTCGAATCGCTAACAGAATAGCAAGTTAAAATAAGGC

TAGTCCGTTATCAACTTGAAAAAGTGGCACCGAGTCGGTGGTGCTTTT

TTTTCTCTTgaattcggatcc

Guide RNA expression cassettes with a shorter *T. reesei* U6 promoter region were obtained as synthetic DNA. An example is provided here that includes the sequence for an sgRNA targeting the *T. reesei* gla1 gene at TS11.

SEQ ID NO: 12

AATTCCTAAAGAAACAGCATGAAATGGTATTATGTAAGAGCTATAGTC

TAAAGGCACTCTGCTGGATAAAAATAGTGGCTATAAGTCTGCTGCAAA

ACTACCCCCAACCTCGTAGGTATATAAGTACTGTTTGATGGTAGTCTA

TCgccaatggcgacggcagcacGTTTTAGAGCTAGAGTTCGTTTCGGC

-continued

TTTTCCTCGGAACCCCCAGAGGTCATCAGTTCGAATCGCTAACAGAAT

AGCAAGTTAAAATAAGGCTAGTCCGTTATCAACTTGAAAAAGTGGCAC

CGAGTCGGTGGTGCTTTTTTTTCTCTT

Primer: gRNA fwd afIII

SEQ ID NO: 13 cgtcagcttaagAATTCCTAAAGAAACAGCATGAAATGG

Primer: gRNA rev sfiI

SEQ ID NO: 14 cgtcagggccacgtgggccAAGAGAAAAAAAAGCACCACCGACTCGG

Primer: Ad3 5' fwd

SEQ ID NO: 15 tgaacacagccaccgacatcagc

Primer: Ad3 5' rev

SEQ ID NO: 16 gctggtgagggtttgtgctattg

Primer: Ad3a 5005 rev

SEQ ID NO: 17 gattgcttgggaggaggacat

Primer: Ad3 3' fwd

SEQ ID NO: 18 cgaggccactgatgaagttgttc

Primer: Ad3 3' rev

SEQ ID NO: 19

Cagttttccaaggctgccaacgc

Primer: Ad3a 5003 fwd

SEQ ID NO: 20 ctgatcttgcaccctggaaatc

Ad3mid rev

SEQ ID NO: 21 ctctctatcatttgccaccctcc

Primer: Adfrag fwd

SEQ ID NO: 22 ctccattcaccctcaattctcc

Primer: Adfrag rev

SEQ ID NO: 23 gttcccttggcggtgcttggatc

Primer: Ad3a 2k fwd

SEQ ID NO: 24 caatagcacaaaccctcaccagc

Ad3a 2k rev

SEQ ID NO: 25 gaacaacttcatcagtggcctcg

Primer: glaA

SEQ ID NO: 26 ccgttagttgaagatccttgccg

Primer: glaB

SEQ ID NO: 27 gtcgaggatttgcttcatacctc

Primer: glaD

SEQ ID NO: 28 gagagacgcaggatgactcaaag

Primer: glaH

SEQ ID NO: 29 tgccgtgggtcattggcatattc

Primer: glaJ

SEQ ID NO: 30 tgccgactttgtccagtgattcg

Primer: glaK

SEQ ID NO: 31 ttacatgtggacgcgagatagcg

-continued

Primer: gla1repF

SEQ ID NO: 32 gtgtgtctaatgcctccaccac

Primer: gla1repR

SEQ ID NO: 33 gatcgtgctagcgctgctgttg

Primer: 1553R

SEQ ID NO: 34

CCGTGATGGAGCCCGTCTTCT

Primer: 1555F

SEQ ID NO: 35

CGCGGTGAGTTCAGGCTTTTTC

Primer: pyr2F

SEQ ID NO: 36 gtataagagcaggaggagggag

Primer: pyr2R

SEQ ID NO: 37 gaacgcctcaatcagtcagtcg

Bacterial kanamycin resistance gene (with promoter and terminator) between *Trichoderma reesei* telomere sequences

SEQ ID NO: 38 tcaggaaatagctttaagtagcttattaagtattaaaattatatatat ttttaatataactatatttctttaataaataggtattttaagctttat atataaatataataataaaataatatattatatagctttttattaata aataaaatagctaaaaatataaaaaaaatagctttaaaatacttattt ttaattagaattttatatattttaatatataagatcttttactttttt tataagcttcctaccttaaattaaatttttacttttttttactatttt actatatcttaaataaaggctttaaaaatataaaaaaaatcttcttat atattataagctataaggattatatatatatttttttttaatttttaa agtaagtattaaagctagaattaaagttttaatttttttaaggctttat ttaaaaaaaggcagtaatagcttataaaagaaatttctttttcttta tactaaaagtacttttttttttaataaggttagggttagggtttactca caccgaccatcccaaccacatcttagggttagggttagggttagggtt agggttagggttagggttagggtaagggtttaaacaaagccacgttgt gtctcaaaatctctgatgttacattgcacaagataaaaatatatcatc atgaacaataaaactgtctgcttacataaacagtaatacaaggggtgt tatgagccatattcaacgggaaacgtcttgctcgaggccgcgattaaa ttccaacatggatgctgatttatatgggtataaatgggctcgcgataa tgtcgggcaatcaggtgcgacaatctatcgattgtatgggaagcccga tgcgccagagttgtttctgaaacatggcaaaggtagcgttgccaatga tgttacagatgagatggtcagactaaactggctgacggaatttatgcc tcttccgaccatcaagcattttatccgtactcctgatgatgcatggtt actcaccactgcgatccccgggaaaacagcattccaggtattagaaga atatcctgattcaggtgaaaatattgttgatgcgctggcagtgttcct gcgccggttgcattcgattcctgtttgtaattgtccttttaacagcga tcgcgtatttcgtctcgctcaggcgcaatcacgaatgaataacggttt ggttgatgcgagtgattttgatgacgagcgtaatggctggcctgttga -continued acaagtctggaaagaaatgcataagcttttgccattctcaccggattc agtcgtcactcatggtgatttctcacttgataaccttatttttgacga ggggaaattaataggttgtattgatgttggacgagtcggaatcgcaga ccgataccaggatcttgccatcctatggaactgcctcggtgagttttc tccttcattacagaaacggctttttcaaaaatatggtattgataatcc tgatatgaataaattgcagtttcatttgatgctcgatgagtttttcta atcagaattggttaattggttgtaacactggcagagcattacgctgac ttgacgggacggcggctttgttgaataaatcgaactttgctgagttg aaggatcagatcacgcatcttcccgacaacgcagaccgttccgtggca aagcaaaagttcaaaatcaccaactggtccacctacaacaaagctctc atcaaccgtggctccctcactttctggctggatgatggggcgattcag gcctggtatgagtcagcaacaccttcttcacgaggcagacctcagcgg tttaaacctaaccctaaccctaaccctaaccctaaccctaaccctaac cctaaccctaaccctaaccctaaccctaaccctaaccctaacctaacc ctaatggggtcgatctgaaccgaggatgagggttctatagactaatct acaggccgtacatggtgtgattgcagatgcgacgggcaaggtgtacag tgtccagaaggaggagagcggcataggtattgtaatagaccagcttta cataataatcgcctgttgctactgactgatgaccttcttccctaacca gtttcctaattaccactgcagtgaggataaccctaactcgctctgggg ttattattatactgattagcaggtggcttatatagtgctgaagtacta taagagtttctgcgggaggaggtggaaggactataaactggacacagt tagggatagagtgatgacaagacctgaatgttatcctccggtgtggta tagcgaattggctgaccttgcagatggtaatggtttaggcagggtttt tgcagagggggacgagaacgcgttctgcgatttaacggctgctgccgc caagctttacggttctctaatgggcggccgc A synthetic DNA: Gla1rep

SEQ ID NO: 39 gtgtgtctaatgcctccaccacaggaaccaaaccggctttgacctctg ggaagaagtcaatgggagctcattctttactgttgccaaccagcaccg aggtatgaagcaaatcctcgacattcgctgctactgcacatgagcatt gttactgaccagctctacagcacttgtcgagggcgccactcttgctgc cactcttggccagtcgggaagcgcttattcatctgttgctccccaggt tttgtgctttctccaacgattctgggtgtcgtctggtggatacgtcga ctccaacagtatgtcttttcactgtttatatgagattggccaatactg atagctcgcctctagtcaacaccaacgagggcaggactggcaaggatg tcaactccgtcctgacttccatccacaccttcgatcccaaccttggct gtgacgcaggcaccttccagccatgcagtgacaaagcgctctccaacc tcaaggttgttgtcgactccttccgctccatctacggcgtgaacaagg gcattcctgCGgtgctgccgtcgccattggccggtatgcagaggatgt gtactacaacggcaacccttggtatcttgctacatttgctgctgccga gcagctgtacgatgccatctacgtctggaagaagacgggctccatcac -continued ggtgaccgccacctccctggccttcttccaggagcttgttcctggcgt gacggccgggacctactccagcagctcttcgacctttaccaacatcat caacgccgtctcgacatacgccgatggcttcctcagcgaggctgccaa gtacgtccccgccgacggttcgctggccgagcagtttgaccgcaacag cggcactccgctgtctgcgcttcacctgacgtggtcgtacgcctcgtt cttgacagccacggcccgtcgggctggcatcgtgccccctcgtgggc caacagcagcgctagcacgatc Full U6 gene promoter sequence (not including transcription start site)

SEQ ID NO: 40

AAAAAACACTAGTAAGTACTTACTTATGTATTATTAACTACTTTAGCT

AACTTCTGCAGTACTACCTAAGAGGCTAGGGGTAGTTTTATAGCAGAC

TTATAGCTATTATTTTTATTTAGTAAAGTGCTTTTAAAGTAAGGTCTT

TTTTATAGCACTTTTTATTTATTATAATATATATTATATAATAATTTT

AAGCCTGGAATAGTAAAGAGGCTTATATAATAATTTATAGTAATAAAA

GCTTAGCAGCTGTAATATAATTCCTAAAGAAACAGCATGAAATGGTAT

TATGTAAGAGCTATAGTCTAAAGGCACTCTGCTGGATAAAAATAGTGG

CTATAAGTCTGCTGCAAAACTACCCCCAACCTCGTAGGTATATAAGTA

CTGTTTGATGGTAGTCTATC

Truncated/shorter U6 gene promoter sequence (not including transcription start site)

SEQ ID NO: 41

AATTCCTAAAGAAACAGCATGAAATGGTATTATGTAAGAGCTATAGTC

TAAAGGCACTCTGCTGGATAAAAATAGTGGCTATAAGTCTGCTGCAAA

ACTACCCCCAACCTCGTAGGTATATAAGTACTGTTTGATGGTAGTCTA

TC

U6 gene intron

SEQ ID NO: 42

GTTCGTTTCGGCTTTTCCTCGGAACCCCCAGAGGTCATCAGTTCGAAT

CGCTAACAG

U6 gene transcriptional terminator sequence

SEQ ID NO: 43

TTTTTTTTCTCTT

Filamentous fungal cell Codon optimized *Streptococcus pyogenes* Cas9-encoding gene; no NLS

SEQ ID NO: 44 atggacaagaagtacagcatcggcctcgacatcggcaccaactcggtg ggctgggccgtcatcacggacgaatataaggtcccgtcgaagaagttc aaggtcctcggcaatacagaccgccacagcatcaagaaaaacttgatc ggcgccctcctgttcgatagcggcgagaccgcggaggcgaccaggctc aagaggaccgccaggagacggtacactaggcgcaagaacaggatctgc tacctgcaggagatcttcagcaacgagatggcgaaggtggacgactcc ttcttccaccgcctggaggaatcattcctggtggaggaggacaagaag catgagcggcacccaatcttcggcaacatcgtcgacgaggtggcctac cacgagaagtacccgacaatctaccacctccggaagaaactggtggac agcacagacaaggcggacctccggctcatctaccttgccctcgcgcat atgatcaagttccgcggccacttcctcatcgagggcgacctgaacccg -continued gacaactccgacgtggacaagctgttcatccagctcgtgcagacgtac aatcaactgttcgaggagaaccccataaacgctagcggcgtggacgcc aaggccatcctctcggccaggctctcgaaatcaagaaggctggagaac cttatcgcgcagttgccaggcgaaaagaagaacggcctcttcggcaac cttattgcgctcagcctcggcctgacgccgaacttcaaatcaaacttc gacctcgcggaggacgccaagctccagctctcaaaggacacctacgac gacgacctcgacaacctcctggcccagataggagaccagtacgcggac ctcttcctcgccgccaagaacctctccgacgctatcctgctcagcgac atccttcgggtcaacaccgaaattaccaaggcaccgctgtccgccagc atgattaaacgctacgacgagcaccatcaggacctcacgctgctcaag gcactcgtccgccagcagctccccgagaagtacaaggagatcttcttc gaccaatcaaaaaacggctacgcgggatatatcgacggcggtgccagc caggaagagttctacaagttcatcaaaccaatcctggagaagatggac ggcaccgaggagttgctggtcaagctcaacagggaggacctcctcagg aagcagaggaccttcgacaacggctccatcccgcatcagatccacctg ggcgaactgcatgccatcctgcggcgccaggaggacttctacccgttc ctgaaggataaccgggagaagatcgagaagatcttgacgttccgcatc ccatactacgtgggcccgctggctcgcggcaactcccggttcgcctgg atgacccggaagtcggaggagaccatcacaccctggaactttgaggag gtggtcgataagggcgctagcgctcagagcttcatcgagcgcatgacc aacttcgataaaaacctgcccaatgaaaaagtcctccccaagcactcg ctgctctacgagtacttcaccgtgtacaacgagctcaccaaggtcaaa tacgtcaccgagggcatgcggaagccggcgttcctgagcggcgagcag aagaaggcgatagtggacctcctcttcaagaccaacaggaaggtgacc gtgaagcaattaaaagaggactacttcaagaaaatagagtgcttcgac tccgtggagatctcgggcgtggaggatcggttcaacgcctcactcggc acgtatcacgacctcctcaagatcattaaagacaaggacttcctcgac aacgaggagaacgaggacatcctcgaggacatcgtcctcaccctgacc ctgttcgaggaccgcgaaatgatcgaggagaggctgaagacctacgcg cacctgttcgacgacaaggtcatgaaacagctcaagaggcgccgctac actggttggggaaggctgtcccgcaagctcattaatggcatcagggac aagcagagcggcaagaccatcctggacttcctcaagtccgacgggttc gccaaccgcaacttcatgcagctcattcacgacgactcgctcacgttc aaggaagacatccagaaggcacaggtgagcgggcagggtgactccctc cacgaacacatcgccaacctggccggctcgccggccattaaaaagggc atcctgcagacggtcaaggtcgtcgacgagctcgtgaaggtgatgggc cggcacaagcccgaaaatatcgtcatagagatggccagggagaaccag accacccaaaaagggcagaagaactcgcgcgagcggatgaaacggatc gaggagggcattaaagagctcgggtcccagatcctgaaggagcacccc gtggaaaatacccagctccagaatgaaaagctctacctctactacctg cagaacggccgcgacatgtacgtggaccaggagctggacattaatcgg ctatcggactacgacgtcgaccacatcgtgccgcagtcgttcctcaag gacgatagcatcgacaacaaggtgctcacccggtcggataaaaatcgg ggcaagagcgacaacgtgcccagcgaggaggtcgtgaagaagatgaaa aactactggcgccagctcctcaacgcgaaactgatcacccagcgcaag ttcgacaacctgacgaaggcggaacgcggtggcttgagcgaactcgat aaggcgggcttcataaaaaggcagctggtcgagacgcgccagatcacg aagcatgtcgcccagatcctggacagccgcatgaatactaagtacgat gaaaacgacaagctgatccgggaggtgaaggtgatcacgctgaagtcc aagctcgtgtcggacttccgcaaggacttccagttctacaaggtccgc gagatcaacaactaccaccacgcccacgacgcctacctgaatgcggtg gtcgggaccgccctgatcaagaagtacccgaagctggagtcggagttc gtgtacggcgactacaaggtctacgacgtgcgcaaaatgatcgccaag tccgagcaggagatcggcaaggccacggcaaaatacttcttctactcg aacatcatgaacttcttcaagaccgagatcaccctcgcgaacggcgag atccgcaagcgcccgctcatcgaaaccaacggcgagacgggcgagatc gtctgggataagggccgggatttcgcgacggtccgcaaggtgctctcc atgccgcaagtcaatatcgtgaaaaagacggaggtccagacgggcggg ttcagcaaggagtccatcctcccgaagcgcaactccgacaagctcatc gcgaggaagaaggattgggacccgaaaaaatatggcggcttcgacagc ccgaccgtcgcatacagcgtcctcgtcgtggcgaaggtggagaagggc aagtcaaagaagctcaagtccgtgaaggagctgctcgggatcacgatt atggagcggtcctccttcgagaagaacccgatcgacttcctagaggcc aagggatataaggaggtcaagaaggacctgattattaaactgccgaag tactcgctcttcgagctggaaaacggccgcaagaggatgctcgcctcc gcaggcgagttgcagaagggcaacgagctcgccctcccgagcaaatac gtcaatttcctgtacctcgctagccactatgaaaagctcaagggcagc ccggaggacaacgagcagaagcagctcttcgtggagcagcacaagcat tacctggacgagatcatcgagcagatcagcgagttctcgaagcgggtg atcctcgccgacgcgaacctggacaaggtgctgtcggcatataacaag caccgcgacaaaccaatacgcgagcaggccgaaaatatcatccacctc ttcaccctcaccaacctcggcgctccggcagccttcaagtacttcgac accacgattgaccggaagcggtacacgagcacgaaggaggtgctcgat gcgacgctgatccaccagagcatcacagggctctatgaaacacgcatc gacctgagccagctgggcggagac

*Streptococcus pyogenes* Cas9 encoded by
SEQ ID NO: 44; no NLS

SEQ ID NO: 45

MDKKYSIGLDIGTNSVGWAVITDEYKVPSKKFKVLGNTDRHSIKKNLI

GALLFDSGETAEATRLKRTARRRYTRRKNRICYLQEIFSNEMAKVDDS

FFHRLEESFLVEEDKKHERHPIFGNIVDEVAYHEKYPTIYHLRKKLVD

STDKADLRLIYLALAHMIKFRGHFLIEGDLNPDNSDVDKLFIQLVQTY

-continued

NQLFEENPINASGVDAKAILSARLSKSRRLENLIAQLPGEKKNGLFGN

LIALSLGLTPNFKSNFDLAEDAKLQLSKDTYDDDLDNLLAQIGDQYAD

LFLAAKNLSDAILLSDILRVNTEITKAPLSASMIKRYDEHHQDLTLLK

ALVRQQLPEKYKEIFFDQSKNGYAGYIDGGASQEEFYKFIKPILEKMD

GTEELLVKLNREDLLRKQRTFDNGSIPHQIHLGELHAILRRQEDFYPF

LKDNREKIEKILTFRIPYYVGPLARGNSRFAWMTRKSEETITPWNFEE

VVDKGASAQSFIERMTNFDKNLPNEKVLPKHSLLYEYFTVYNELTKVK

YVTEGMRKPAFLSGEQKKAIVDLLFKTNRKVTVKQLKEDYFKKIECFD

SVEISGVEDRFNASLGTYHDLLKIIKDKDFLDNEENEDILEDIVLTLT

LFEDREMIEERLKTYAHLFDDKVMKQLKRRRYTGWGRLSRKLINGIRD

KQSGKTILDFLKSDGFANRNFMQLIHDDSLTFKEDIQKAQVSGQGDSL

HEHIANLAGSPAIKKGILQTVKVVDELVKVMGRHKPENIVIEMARENQ

TTQKGQKNSRERMKRIEEGIKELGSQILKEHPVENTQLQNEKLYLYYL

QNGRDMYVDQELDINRLSDYDVDHIVPQSFLKDDSIDNKVLTRSDKNR

GKSDNVPSEEVVKKMKNYWRQLLNAKLITQRKFDNLTKAERGGLSELD

KAGFIKRQLVETRQITKHVAQILDSRMNTKYDENDKLIREVKVITLKS

KLVSDFRKDFQFYKVREINNYHHAHDAYLNAVVGTALIKKYPKLESEF

VYGDYKVYDVRKMIAKSEQEIGKATAKYFFYSNIMNFFKTEITLANGE

IRKRPLIETNGETGEIVWDKGRDFATVRKVLSMPQVNIVKKTEVQTGG

FSKESILPKRNSDKLIARKKDWDPKKYGGFDSPTVAYSVLVVAKVEKG

KSKKLKSVKELLGITIMERSSFEKNPIDFLEAKGYKEVKKDLIIKLPK

YSLFELENGRKRMLASAGELQKGNELALPSKYVNFLYLASHYEKLKGS

PEDNEQKQLFVEQHKHYLDEIIEQISEFSKRVILADANLDKVLSAYNK

HRDKPIREQAENIIHLFTLTNLGAPAAFKYFDTTIDRKRYTSTKEVLD

ATLIHQSITGLYETRIDLSQLGGD

SV40 NLS

SEQ ID NO: 46

PKKKRKV

*T. reesei* blr2 (blue light regulator 2) gene NLS

SEQ NO: 47

KKKKLKL

*Streptococcus thermophilus* LMD-9 Cas9

SEQ ID NO: 48

MTKPYSIGLDIGTNSVGWAVTTDNYKVPSKKMKVLGNTSKKYIKKNLL

GVLLFDSGITAEGRRLKRTARRRYTRRRNRILYLQEIFSTEMATLDDA

FFQRLDDSFLVPDDKRDSKYPIFGNLVEEKAYHDEFPTIYHLRKYLAD

STKKADLRLVYLALAHMIKYRGHFLIEGEFNSKNNDIQKNFQDFLDTY

NAIFESDLSLENSKQLEEIVKDKISKLEKKDRILKLFPGEKNSGIFSE

FLKLIVGNQADFRKCFNLDEKASLHFSKESYDEDLETLLGYIGDDYSD

VFLKAKKLYDAILLSGFLTVTDNETEAPLSSAMIKRYNEHKEDLALLK

EYIRNISLKTYNEVFKDDTKNGYAGYIDGKTNQEDFYVYLKKLLAEFE

GADYFLEKIDREDFLRKQRTFDNGSIPYQIHLQEMRAILDKQAKFYPF

LAKNKERIEKILTFRIPYYVGPLARGNSDFAWSIRKRNEKITPWNFED

VIDKESSAEAFINRMTSFDLYLPEEKVLPKHSLLYETFNVYNELTKVR

-continued

FIAESMRDYQFLDSKQKKDIVRLYFKDKRKVTDKDIIEYLHAIYGYDG

IELKGIEKQFNSSLSTYHDLLNIINDKEFLDDSSNEAIIEEIIHTLTI

FEDREMIKQRLSKFENIFDKSVLKKLSRRHYTGWGKLSAKLINGIRDE

KSGNTILDYLIDDGISNRNFMQLIHDDALSFKKKIQKAQIIGDEDKGN

IKEVVKSLPGSPAIKKGILQSIKIVDELVKVMGGRKPESIVVEMAREN

QYTNQGKSNSQQRLKRLEKSLKELGSKILKENIPAKLSKIDNNALQND

RLYLYYLQNGKDMYTGDDLDIDRLSNYDIDHIIPQAFLKDNSIDNKVL

VSSASNRGKSDDVPSLEVVKKRKTFWYQLLKSKLISQRKFDNLTKAER

GGLSPEDKAGFIQRQLVETRQITKHVARLLDEKFNNKKDENNRAVRTV

KIITLKSTLVSQFRKDFELYKVREINDFHHAHDAYLNAVVASALLKKY

PKLEPEFVYGDYPKYNSFRERKSATEKVYFYSNIMNIFKKSISLADGR

VIERPLIEVNEETGESVWNKESDLATVRRVLSYPQVNVVKKVEEQNHG

LDRGKPKGLFNANLSSKPKRNSNENLVGAKEYLDPKKYGGYAGISNSF

TVLVKGTIEKGAKKKITNVLEFQGISILDRINYRKDKLNFLLEKGYKD

IELIIELPKYSLFELSDGSRRMLASILSTNNKRGEIHKGNQIFLSQKF

VKLLYHAKRISNTINENHRKYVENHKKEFEELFYYILEFNENYVGAKK

NGKLLNSAFQSWQNHSIDELCSSFIGPTGSERKGLFELTSRGSAADFE

FLGVKIPRYRDYTPSSLLKDATLIHQSVTGLYETRIDLAKLGEG

*Streptococcus mutans* UA159 Cas9

SEQ ID NO: 49

MKKPYSIGLDIGTNSVGWAVVTDDYKVPAKKMKVLGNTDKSHIEKNLL

GALLFDSGNTAEDRRLKRTARRRYTRRRNRILYLQEIFSEEMGKVDDS

FFHRLEDSFLVTEDKRGERHPIFGNLEEEVKYHENFPTIYHLRQYLAD

NPEKVDLRLVYLALAHIIKFRGHFLIEGKFDTRNNDVQRLFQEFLAVY

DNTFENSSLQEQNVQVEEILTDKISKSAKKDRVLKLFPNEKSNGRFAE

FLKLIVGNQADFKKHFELEEKAPLQFSKDTYEEELEVLLAQIGDNYAE

LFLSAKKLYDSILLSGILTVTDVGTKAPLSASMIQRYNEHQMDLAQLK

QFIRQKLSDKYNEVFSDVSKDGYAGYIDGKINQEAFYKYLKGLLNKIE

GSGYFLDKIEREDFLRKQRTFDNGSIPHQIHLQEMRAIIRRQAEFYPF

LADNQDRIEKLLTFRIPYYVGPLARGKSDFAWLSRKSADKITPWNFDE

IVDKESSAEAFINRMTNYDLYLPNQKVLPKHSLLYEKFTVYNELTKVK

YKTEQGKTAFFDANMKQEIFDGVFKVYRKVTKDKLMDFLEKEFDEFRI

VDLTGLDKENKVFNASYGTYHDLCKILDKDFLDNSKNEKILEDIVLTL

TLFEDREMIRKRLENYSDLLTKEQVKKLERRHYTGWGRLSAELIHGIR

NKESRKTILDYLIDDGNSNRNFMQLINDDALSFKEEIAKAQVIGETDN

LNQVVSDIAGSPAIKKGILQSLKIVDELVKIMGHQPENIVVEMARENQ

FTNQGRRNSQQRLKGLTDSIKEFGSQILKEHPVENSQLQNDRLFLYYL

QNGRDMYTGEELDIDYLSQYDIDHIIPQAFIKDNSIDNRVLTSSKENR

GKSDDVPSKDVVRKMKSYWSKLLSAKLITQRKFDNLTKAERGGLTDDD

KAGFIKRQLVETRUTKHVARILDERFNTETDENNKKIRQVKIVTLKSN

LVSNFRKKEFELYKVREINDYHHAHDAYLNAVIGKALLGVYPQLEPEFV

-continued

YGDYPHFHGHKENKATAKKFFYSNIMNFFKKDDVRTDKNGEIIWKKDE

HISNIKKVLSYPQVNIVKKVEEQTGGFSKESILPKGNSDKLIPRKTKK

FYWDTKKYGGFDSPIVAYSILVIADIEKGKSKKLKTVKALVGVTIMEK

MTFERDPVAFLERKGYRNVQEENIIKLPKYSLFKLENGRKRLLASARE

LQKGNEIVLPNHLGTLLYHAKNIHKVDEPKHLDYVDKHKDEFKELLDV

VSNFSKKYTLAEGNLEKIKELYAQNNGEDLKELASSFINLLTFTAIGA

PATFKFFDKNIDRKRYTSTTEILNATLIHQSITGLYETRIDLNKLGGD

*Campylobacter jejuni* Cas9

SEQ ID NO: 50

MARILAFDIGISSIGWAFSENDELKDCGVRIFTKVENPKTGESLALPR

RLARSARKRLARRKARLNHLKHLIANEFKLNYEDYQSEDESLAKAYKG

SLISPYELRFRALNELLSKQDFARVILHIAKRRGYDDIKNSDDKEKGA

ILKAIKQNEEKLANYQSVGEYLYKEYFQKFKENSKEFTNVRNKKESYE

RCIAQSFLKDELKLIFKKQREFGFSFSKKFEEEVLSVAFYKRALKDFS

HLVGNCSFFTDEKRAPKNSPLAFMFVALTRIINLLNNLKNTEGILYTK

DDLNALLNEVLKNGTLTYKQTKKLLGLSDDYEFKGEKGTYFIEFKKYK

EFIKALGEHNLSQDDLNEIAKDITLIKDEIKLKKALAKYDLNQNQIDS

LSKLEFKDHLNISFKALKLVTPLMLEGKKYDEACNELNLKVAINEDKK

DFLPAFNETYYKDEVTNPVVLRAIKEYRKVLNALLKKYGKVHKINIEL

AREVGKNHSQRAKIEKEQNENYKAKKDAELECEKLGLKINSKNILKLR

LFKEQKEFCAYSGEKIKISDLQDEKMLEIDHIYPYSRSFDDSYMNKVL

VFTKQNQEKLNQTPFEAFGNDSAKWQKIEVLAKNLPTKKQKRILDKNY

KDKEQKNFKDRNLNDTRYIARLVLNYTKDYLDFLPLSDDENTKLNDTQ

KGSKVHVEAKSGMLTSALRHTWGFSAKDRNNHLHHAIDAVIIAYANNS

IVKAFSDFKKEQESNSAELYAKKISELDYKNKRKFFEPFSGFRQKVLD

KIDEIFVSKPERKKPSGALHEETFRKEEEFYQSYGGKEGVLKALELGK

IRKVNGKIVKNGDMFRVDIFKHKKTNKFYAVPIYTMDFALKVLPNKAV

ARSKKGEIKDWILMDENYEFCFSLYKDSLILIQTKDMQEPEFVYYNAF

TSSTVSLIVSKHDNKFETLSKNQKILFKNANEKEVIAKSIGIQNLKVF

EKYIVSALGEVTKAEFRQREDFKK

*Neisseria meningitides* Cas9

SEQ ID NO: 51

MAAFKPNSINYILGLDIGIASVGWAMVEIDEEENPIRLIDLGVRVFER

AEVPKTGDSLAMARRLARSVRRLTRRRAHRLLRTRRLLKREGVLQAAN

FDENGLIKSLPNTPWQLRAAALDRKLTPLEWSAVLLHLIKHRGYLSQR

KNEGETADKELGALLKGVAGNAHALQTGDFRTPAELALNKFEKESGHI

RNQRSDYSHTFSRKDLQAELILLFEKQKEFGNPHVSGGLKEGIETLLM

TQRPALSGDAVQKMLGHCTFEPAEPKAAKNTYTAERFIWLTKLNNLRI

LEQGSERPLTDTERATLMDEPYRKSKLTYAQARKLLGLEDTAFFKGLR

YGKDNAEASTLMEMKAYHAISRALEKEGLKDKKSPLNLSPELQDEIGT

AFSLFKTDEDITGRLKDRIQPEILEALLKHISFDKFVQISLKALRRIV

PLMEQGKRYDEACAEIYGDHYGKKNTEEKIYLPPIPADEIRNPVVLRA

LSQARKVINGVVRRYGSPARIHIETAREVGKSFKDRKEIEKRQEENRK

-continued

DREKAAAKFREYFPNFVGEPKSKDILKLRLYEQQHGKCLYSGKEINLG

RLNEKGYVEIDHALPFSRTWDDSFNNKVLVLGSENQNKGNQTPYEYFN

GKDNSREWQEFKARVETSRFPRSKKQRILLQKFDEDGFKERNLNDTRY

VNRFLCQFVADRMRLTGKGKKRVFASNGQITNLLRGFWGLRKVRAEND

RHHALDAVVVACSTVAMQQKITRFVRYKEMNAFDGKTIDKETGEVLHQ

KTHFPQPWEFFAQEVMIRVFGKPDGKPEFEEADTLEKLRTLLAEKLSS

RPEAVHEYVTPLFVSRAPNRKMSGQGHMETVKSAKRLDEGVSVLRVPL

TQLKLKDLEKMVNREREPKLYEALKARLEAHKDDPAKAFAEPFYKYDK

AGNRTQQVKAVRVEQVQKTGVWVRNHNGIADNATMVRVDVFEKGDKYY

LVPIYSWQVAKGILPDRAVVQGKDEEDWQLIDDSFNFKFSLHPNDLVE

VITKKARMFGYFASCHRGTGNINIRIHDLDHKIGKNGILEGIGVKTAL

SFQKYQIDELGKEIRPCRLKKRPPVR

*Francisella tularensis* subsp. *novicida* Cas9

SEQ ID NO: 52

MNFKILPIAIDLGVKNTGVFSAFYQKGTSLERLDNKNGKVYELSKDSY

TLLMNNRTARRHQRRGIDRKQLVKRLFKLIWTEQLNLEWDKDTQQAIS

FLFNRRGFSFITDGYSPEYLNIVPEQVKAILMDIFDDYNGEDDLDSYL

KLATEQESKISEIYNKLMQKILEFKLMKLCTDIKDDKVSTKTLKEITS

YEFELLADYLANYSESLKTQKFSYTDKQGNLKELSYYHHDKYNIQEFL

KRHATINDRILDTLLTDDLDIWNFNFEKFDFDKNEEKLQNQEDKDHIQ

AHLHHFVFAVNKIKSEMASGGRHRSQYFQEITNVLDENNHQEGYLKNF

CENLHNKKYSNLSVKNLVNLIGNLSNLELKPLRKYFNDKIHAKADHWD

EQKFTETYCHWILGEWRVGVKDQDKKDGAKYSYKDLCNELKQKVTKAG

LVDFLLELDPCRTIPPYLDNNNRKPPKCQSLILNPKFLDNQYPNWQQY

LQELKKLQSIQNYLDSFETDLKVLKSSKDQPYFVEYKSSNQQIASGQR

DYKDLDARILQFIFDRVKASDELLLNEIYFQAKKLKQKASSELEKLES

SKKLDEVIANSQLSQILKSQHTNGIFEQGTFLHLVCKYYKQRQRARDS

RLYIMPEYRYDKKLHKYNNTGRFDDDNQLLTYCNHKPRQKRYQLLNDL

AGVLQVSPNFLKDKIGSDDDLFISKWLVEHIRGFKKACEDSLKIQKDN

RGLLNHKINIARNTKGKCEKEIFNLICKIEGSEDKKGNYKHGLAYELG

VLLFGEPNEASKPEFDRKIKKFNSIYSFAQIQQIAFAERKGNANTCAV

CSADNAHRMQQIKITEPVEDNKDKIILSAKAQRLPAIPTRIVDGAVKK

MATILAKNIVDDNWQNIKQVLSAKHQLHIPIITESNAFEFEPALADVK

GKSLKDRRKKALERISPENIFKDKNNRIKEFAKGISAYSGANLTDGDF

DGAKEELDHIIPRSHKKYGTLNDEANLICVTRGDNKNKGNRIFCLRDL

ADNYKLKQFETTDDLEIEKKIADTIWDANKKDFKFGNYRSFINLTPQE

QKAFRHALFLADENPIKQAVIRAINNRNRTFVNGTQRYFAEVLANNIY

LRAKKENLNTDKISFDYFGIPTIGNGRGIAEIRQLYEKVDSDIQAYAK

GDKPQASYSHLIDAMLAFCIAADEHRNDGSIGLEIDKNYSLYPLDKNT

GEVFTKDIFSQIKITDNEFSDKKLVRKKAIEGFNTHRQMTRDGIYAEN

YLPILIHKELNEVRKGYTWKNSEEIKIFKGKKYDIQQLNNLVYCLKFV

-continued

DKPISIDIQISTLEELRNILTTNNIAATAEYYYINLKTQKLHEYYIEN

YNTALGYKKYSKEMEFLRSLAYRSERVKIKSIDDVKQVLDKDSNFIIG

KITLPFKKEWQRLYREWQNTTIKDDYEFLKSFFNVKSITKLHKKVRKD

FSLPISTNEGKFLVKRKTWDNNFIYQILNDSDSRADGTKPFIRAFDIS

KNEIVEAIIDSFTSKNIFWLPKNIELQKVDNKNIFAIDTSKWFEVETP

SDLRDIGIATIQYKIDNNSRPKVRVKLDYVIDDDSKINYFMNHSLLKS

RYPDKVLEILKQSTIIEFESSGFNKTIKEMLGMKLAGIYNETSNN

*Pasteurella multocida* Cas9

SEQ ID NO: 53

MQTTNLSYILGLDLGIASVGWAVVEINENEDPIGLIDVGVRIFERAEV

PKTGESLALSRRLARSTRRLIRRRAHRLLLAKRFLKREGILSTIDLEK

GLPNQAWELRVAGLERRLSAIEWGAVLLHLIKHRGYLSKRKNESQTNN

KELGALLSGVAQNHQLLQSDDYRTPAELALKKFAKEEGHIRNQRGAYT

HTFNRLDLLAELNLLFAQQHQFGNPHCKEHIQQYMTELLMWQKPALSG

EAILKMLGKCTHEKNEFKAAKHTYSAERFVWLTKLNNLRILEDGAERA

LNEEERQLLINHPYEKSKLTYAQVRKLLGLSEQAIFKHLRYSKENAES

ATFMELKAWHAIRKALENQGLKDTWQDLAKKPDLLDEIGTAFSLYKTD

EDIQQYLTNKVPNSVINALLVSLNFDKFIELSLKSLRKILPLMEQGKR

YDQACREIYGHHYGEANQKTSQLLPAIPAQEIRNPVVLRTLSQARKVI

NAIIRQYGSPARVHIETGRELGKSFKERREIQKQQEDNRTKRESAVQK

FKELFSDFSSEPKSKDILKFRLYEQQHGKCLYSGKEINIHRLNEKGYV

EIDHALPFSRTWDDSFNNKVLVLASENQNKGNQTPYEWLQGKINSERW

KNFVALVLGSQCSAAKKQRLLTQVIDDNKFIDRNLNDTRYIARFLSNY

IQENLLLVGKNKKNVFTPNGQITALLRSRWGLIKARENNNRHHALDAI

VVACATPSMQQKITRFIRFKEVHPYKIENRYEMVDQESGEIISPHFPE

PWAYFRQEVNIRVFDNHPDTVLKEMLPDRPQANHQFVQPLFVSRAPTR

KMSGQGHMETIKSAKRLAEGISVLRIPLTQLKPNLLENMVNKEREPAL

YAGLKARLAEFNQDPAKAFATPFYKQGGQQVKAIRVEQVQKSGVLVRE

NNGVADNASIVRTDVFIKNNKFFLVPIYTWQVAKGILPNKAIVAHKNE

DEWEEMDEGAKFKFSLFPNDLVELKTKKEYFFGYYIGLDRATGNISLK

EHDGEISKGKDGVYRVGVKLALSFEKYQVDELGKNRQICRPQQRQPVR

The nucleotide sequence of the synthesized Cas9-D10A Nickase gene in plasmid pET30a-Cas9-D10A nickase. the oligonucleotide encoding the N-terminal His6 tag is in underlined and italicized, the oligonucleotide encoding the SV40 nuclear localization signal is shown in italic and grey highlight and the oligonucleotide encoding the BLR nuclear localization signal is shown in underlined and grey highlight.

SEQ ID NO: 54 atg*caccatcatcatcatcat*tcttctggtctggtgccacgcggttc tggtatgaaagaaaccgctgctgctaaattcgaacgccagcacatgga cagcccagatctgggtaccgacgacgacgacaaggccatggccccaaa aaagaaacgcaaggttatggataaaaaatacagcattggtctggccat cggaaccaacagcgttgggtgggcagtaataacagatgaatacaaagt -continued gccgtcaaaaaaatttaaggttctggggaatacagatcgccacagcat aaaaaagaatctgattggggcattgctgtttgattcgggtgagacagc tgaggccacgcgtctgaaacgtacagcaagaagacgttacacacgtcg taaaaatcgtatttgctacttacaggaaatttttttctaacgaaatggc caaggtagatgatagtttcttccatcgtctcgaagaatcttttctggt tgaggaagataaaaaacacgaacgtcaccctatctttggcaatatcgt ggatgaagtggcctatcatgaaaaataccctacgatttatcatcttcg caagaagttggttgatagtacggacaaagcggatctgcgtttaatcta tcttgcgttagcgcacatgatcaaatttcgtggtcatttcttaattga aggtgatctgaatcctgataactctgatgtggacaaattgtttataca attagtgcaaacctataatcagctgttcgaggaaaaccccattaatgc ctctggagttgatgccaaagcgattttaagcgcgagactttctaagtc ccggcgtctggagaatctgatcgcccagttaccaggggaaaagaaaaa tggtctgtttggtaatctgattgccctcagtctggggcttaccccgaa cttcaaatccaattttgacctggctgaggacgcaaagctgcagctgag caaagatacttatgatgatgacctcgacaatctgctcgcccagattgg tgaccaatatgcggatctgtttctggcagcgaagaatctttcggatgc tatcttgctgtcggatattctgcgtgttaataccgaaatcaccaaagc gcctctgtctgcaagtatgatcaagagatacgacgagcaccaccagga cctgactcttcttaaggcactggtacgccaacagcttccggagaaata caaagaaatattcttcgaccagtccaagaatggttacgcgggctacat cgatggtggtgcatcacaggaagagttctataaatttattaaaccaat ccttgagaaaatggatggcacggaagagttacttgttaaacttaaccg cgaagacttgcttagaaagcaacgtacattcgacaacggctccatccc acaccagattcatttaggtgaacttcacgccatcttgcgcagacaaga agatttctatcccttcttaaaagacaatcgggagaaaatcgagaagat cctgacgttccgcattccctattatgtcggtcccctggcacgtggtaa ttctcggtttgcctggatgacgcgcaaaagtgaggaaaccatcacccc ttggaactttgaagaagtcgtggataaaggtgctagcgcgcagtcttt tatagaaagaatgacgaacttcgataaaaacttgcccaacgaaaaagt cctgcccaagcactctcttttatatgagtactttactgtgtacaacga actgactaaagtgaaatacgttacggaaggtatgcgcaaacctgcctt tcttagtggcgagcagaaaaaagcaattgtcgatcttctctttaaaac gaatcgcaaggtaactgtaaaacagctgaaggaagattatttcaaaaa gatcgaatgctttgattctgtcgagatctcgggtgtcgaagatcgttt caacgcttccttagggacctatcatgatttgctgaagataataaaaga caaagactttctcgacaatgaagaaaatgaagatattctggaggatat tgttttgaccttgaccttattcgaagatagagagatgatcgaggagcg cttaaaaacctatgcccacctgtttgatgacaaagtcatgaagcaatt aaagcgccgcagatatacggggtggggccgcttgagccgcaagttgat taacggtattagagacaagcagagcggaaaaactatcctggatttcct -continued caaatctgacggatttgcgaaccgcaattttatgcagcttatacatga
tgattcgcttacattcaaagaggatattcagaaggctcaggtgtctgg
gcaaggtgattcactccacgaacatatagcaaatttggccggctctcc
tgcgattaagaaggggatcctgcaaacagttaaagttgtggatgaact
tgtaaaagtaatgggccgccacaagccggagaatatcgtgatagaaat
ggcgcgcgagaatcaaacgacacaaaaaggtcaaaagaactcaagaga
gagaatgaagcgcattgaggaggggataaaggaacttggatctcaaat
tctgaaagaacatccagttgaaaacactcagctgcaaaatgaaaaatt
gtacctgtactacctgcagaatggaagagacatgtacgtggatcagga
attggatatcaatagactctcggactatgacgtagatcacattgtccc
tcagagcttcctcaaggatgattctatagataataaagtacttacgag
atcggacaaaaatcgcggtaaatcggataacgtcccatcggaggaagt
cgttaaaaagatgaaaaactattggcgtcaactgctgaacgccaagct
gatcacacagcgtaagtttgataatctgactaaagccgaacgcggtgg
tcttagtgaactcgataaagcaggatttataaaacggcagttagtaga
aacgcgccaaattacgaaacacgtggctcagatcctcgattctagaat
gaatacaaagtacgatgaaaacgataaactgatccgtgaagtaaaagt
cattaccttaaaatctaaacttgtgtccgatttccgcaaagattttca
gttttacaaggtccgggaaatcaataactatcaccatgcacatgatgc
atatttaaatgcggttgtaggcacggcccttattaagaaataccctaa
actcgaaagtgagtttgtttatggggattataaagtgtatgacgttcg
caaaatgatcgcgaaatcagaacaggaaatcggtaaggctaccgctaa
atactttttttattccaacattatgaatttttttaagaccgaaataac
tctcgcgaatggtgaaatccgtaaacggcctcttatagaaaccaatgg
tgaaacgggagaaatcgtttgggataaaggtcgtgactttgccaccgt
tcgtaaagtcctctcaatgccgcaagttaacattgtcaagaagacgga
agttcaaacaggggggattctccaaagaatctatcctgccgaagcgtaa
cagtgataaacttattgccagaaaaaaagattgggatccaaaaaaata
cggaggctttgattcccctaccgtcgcgtatagtgtgctggtggttgc
taaagtcgagaaagggaaaagcaagaaattgaaatcagttaaagaact
gctgggtattacaattatggaaagatcgtcctttgagaaaaatccgat
cgactttttagaggccaaggggtataaggaagtgaaaaaagatctcat
catcaaattaccgaagtatagtctttttgagctggaaaacggcagaaa
aagaatgctggcctccgcgggcgagttacagaagggaaatgagctggc
gctgccttccaaatatgttaattttctgtaccttgccagtcattatga
gaaactgaagggcagccccgaagataacgaacagaaacaattattcgt
ggaacagcataagcactatttagatgaaattatagagcaaattagtga
attttctaagcgcgttatcctcgcggatgctaatttagacaaagtact
gtcagcttataataaacatcgggataagccgattagagaacaggccga
aaatatcattcatttgtttaccttaaccaaccttggagcaccagctgc -continued cttcaaatatttcgataccacaattgatcgtaaacggtatacaagtac
aaaagaagtcttggacgcaaccctcattcatcaatctattactggatt
atatgagacacgcattgatctttcacagctgggcggagacaagaaaaa
aaaactgaaactg The amino acid sequence of the Cas9-D10A nickase protein expressed from plasmid pET30a-Cas9-D10A nickase(encoded by SEQ ID NO: 54). the N-terminal His6 tag is shown in underline and italics, the mutated amino acid is in bold underline (D10A), the SV40 nuclear localization signal is shown in italic and grey and the BLR nuclear localization signal is shown in underlined and grey.

SEQ ID NO: 55 m*hhhhhh*ssglvprgsgmketaaakferqhmdspdlgtddddkama*pk*
*kkrky*mdkkysiglaigtnsvgwavitdeykvpskkfkvlgntdrhsi
kknligallfdsgetaeatrlkrtarrrytrrknricylqeifsnema
kvddsffhrleesflveedkkherhpifgnivdevayhekyptiyhlr
kklvdstdkadlrliylalahmikfrghfliegdlnpdnsdvdklfiq
lvqtynqlfeenpinasgvdakailsarlsksrrlenliaqlpgekkn
glfgnlialslgltpnfksnfdlaedaklqlskdtydddldnllaqig
dqyadlflaaknlsdaillsdilrvnteitkaplsasmikrydehhqd
ltllkalvrqqlpekykeiffdqskngyagyidggasqeefykfikpi
lekmdgteellvklnredllrkqrtfdngsiphqihlgelhailrrqe
dfypflkdnrekiekiltfripyyvgplargnsrfawmtrkseetitp
wnfeevvdkgasaqsfiermtnfdknlpnekvlpkhsllyeyftvyne
ltkvkyvtegmrkpaflsgeqkkaivdllfktnrkvtvkqlkedyfkk
iecfdsveisgvedrfnaslgtyhdllkiikdkdfldneenediledi
vltltlfedremieerlktyahlfddkvmkqlkrrrytgwgrlsrkli
ngirdkqsgktildflksdgfanrnfmqlihddsltfkediqkaqvsg
qgdslhehianlagspaikkgilqtvkvvdelvkvmgrhkpeniviem
arenqttqkgqknsrermkrieegikelgsqilkehpventqlqnekl
ylyylqngrdmyvdqeldinrlsdydvdhivpqsflkddsidnkvltr
sdknrgksdnvpseewkkmknywrqllnaklitqrkfdnltkaergg l
seldkagfikrqlvetrqitkhvaqildsrmntkydendklirevkvi
tlksklvsdfrkdfqfykvreinnyhhandaylnavvgtalikkypkl
esefvygdykvydvrkmiakseqeigkatakyffysnimnffkteitl
angeirkrplietngetgeivwdkgrdfatvrkvlsmpqvnivkktev
qtggfskesilpkrnsdkliarkkdwdpkkyggfdsptvaysvlvvak
vekgkskklksvkellgitimerssfeknpidfleakgykevkkdlii
klpkyslfelengrkrmlasagelqkgnelalpskyvnflylashyek
lkgspedneqkqlfveqhkhyldeiiegisefskrviladanldkvls
aynkhrdkpireqaeniihlftltnlgapaafkyfdttidrkrytstk
evldatlihqsitglyetridlsqlggdkkkklkl The nucleotide sequences of the substrate DNA fragment. The UTR sequences were shown in lowercase while the TrGA gene was shown in -continued uppercase. Two selected VT domains, TrGA_sgF1 and TrGA_sgR1, were shown in bold and underlined, respectively.

SEQ ID NO: 56 gactgtctccaccatgtaatttttccctgcgactccatataacgccgg atcgtgaaatttcttctttcttttccttccttctcaacaaacaacgg atctgtgctttgcggtcccctgcgttcacgcgtcagggtcgactgctc tgcagctcgataactccatggagccatcaacttgctatggtgtcaatc atcctatcgacaggtccaagaacaagccggcctccggctgcctcattc gctgtcgcaagacggcttgagtgttgtggctggaggattcgggggccc catattccaaccctttttccaaggccgtcggccggtgaggttgagga aaaccatgggttgcctacatattatcgatgctggtgtttggtagtagc aatgtttgcggtggcagtttgagccgagcctcgtcttgggcttctgac ccaggcaacgccatctgactagctgcgccgaaggaaggatgattcatt gtacgacgccagtcaatggaatcttcaagtaaaagcccgacgaaccga ccatgtcagatatcagaattctcctggctggtggggttggttggagac tgcttacggagtcgatgcctcgtgactgtcatggccgcgtccagcctc ctgggactctgtccgatattatgacacgagtaaagcctgcatgatgtc agtttgctgcgtctcatgtcgagaacaacacacctggtgctacatagg caatactacctcgtagcttcaaagttgactgttttgctttgatgtctt tgatcatgcccatccatcccttgtcttgcagtgcatgtggatctctac gtccagacggggagaaagcttgtctgtgataaagtacgatgatgcatt gatgcctgtggctacggcccttttatccccatcgtcatgcatctctat attaatccaggagactctcctcctggcatgggtgagtacaagtgacga ggacatgtagaagcagagccacgcaacgtcttgacatctgtacctatt ttgggccaaaaatcgagacccaccagctcgtcctaccttacatgtgaa gatcttagcccacaatcctactgttttactagtattactgcacagctg tcatcacgagtcctcggttgcttgtgaaacccagctcagctcctgagc acatgcagtaacgccgactcggcgtcatttcgccacacccaatttgga cctgagggatgctggaagctgctgagcagatcccgttaccgattcatg gcactactacatccatacgcagcaaacatgggcttgggcttggcttct caatgcaaaattgcccgcaaaagtcccggcattgtcgatgcagagatg cagatttcagcgggcgattctagggtagggcgactactactactaata ccacctagtcagtatgtatctagcaccggaggctaggcggttagtgga cgggaacctggtcattccatcgcaaccaggatcccgcacttcgttgcg cttctgcccccacggggcgggagttggcagaggcagaatgcggagcag ccccttgtctgccctggccggggcctgttgaagcaagcagacgagagc agagcggttgagaagcggtggttgacgcttgacggtacgaagacgagc gagaatcccgttaagccgaggctgggctcccccccccgtcatcatcat gcccatcctgctcttccagcccactcgtctccctgcctcgtcgcctcc cctccctcccccgattagctgcgcatgttctcctgacagcgtgactaa tgacgcgttgccagcccattcgcctgacgcatcccggcatctgagtct agctcgtcacgctggcaatcttggcccaggcagagcagcaagacggcg -continued ggcatgattgggccgtgccctggcgggcatcagctggccatccgctgc cacccgagaccgcatcaccgacttgtcggatctctccgagcagcagga ggctgatcctggccggcgagacgattgaaaagggctgccgggcccgga gcaggacagcggcgagagcgagcgagagagaggaaaagaagaaggtcg actgtcttattttcagccagccccggctcaacagaagcagaggagaag gcgaacgacgtcaacgacgacgacgacgacgacgaagacggtgaagtc cgttagttgaagatccttgccgtcacaacaccatctcgtggatattgc tttcccctgccgttgcgttgccacctgttccctctttctcttcccccc ttcttcctcattccgagcgctactggttcctactccgcagccttcggt tgtgcctttctctttgtcgaccattgcaccgcccgtcgcggcacttgg gccccggagaattcggccctttcgcagcattttggccctcagttcccc atggggacggtccacacttcctctcttggccctgcagaccttttgtcg tcggtccgagtcggaagaagctcagtcttgagcgcttgagtagcatct acgcgcgaatcactggacaaagtcggcaagacgaagccgtcgtcgcct gctgctgctgctgttactgcgacaggcgctccgactgggggcatcggc ataataaaaagatgcccgccttcgccatggacctggccatgagccact cggcatcggctctctctctcaacgcttcctctcacacatcctccttca ttccgcccatcATGCACGTCCTGTCGACTGCGGTGCTGCTCGGCTCCG

TTGCCGTTCAAAAGGTCCTGGGAAGACCAGGATCAAGCGGTCTGTCCG

ACGTCACCAAGAGGTCTGTTGACGACTTCATCAGCACCGAGACGCCTA

TTGCACTGAACAATCTTCTTTGCAATGTTGGTCCTGATGGATGCCGTG

CATTCGGCACATCAGCTGGTGCGGTGATTGCATCTCCCAGCACAATTG

ACCCGGACTGTAAGTTGGCCTTGATGAACCATATCATATATCGCCGAG

AAGTGGACCGCGTGCTGAGACTGAGACAGACTATTACATGTGGACGCG

AGATAGCGCTCTTGTCTTCAAGAACCTCATCGACCGCTTCACCGAAAC

GTACGATGCGGGCCTGCAGCGCCGCATCGAGCAGTACATTACTGCCCA

GGTCACTCTCCAGGGCCTCTCTAACCCCTCGGGCTCCCTCGCGGACGG

CTCTGGTCTCGGCGAGCCCAAGTTTGAGTTGACCCTGAAGCCTTTCAC

CGGCAACTGGGGTCGACCGCAGCGGGATGGCCCAGCTCTGCGAGCCAT

TGCCTTGATTGGATACTCAAAGTGGCTCATCAACAACAACTATCAGTC

GACTGTGTCCAACGTCATCTGGCCTATTGTGCGCAACGACCTCAACTA

TGTTGCCCAGTACTGGTCAGTGCTTGCTTGCTCTTGAATTACGTCTTT

GCTTGTGTGTCTAATGCCTCCACCACAGGAACCAAACCGGCTTTGACC

TCTGGGAAGAAGTCAATGGGAGCTCATTCTTTACTGTTGCCAACCAGC

ACCGAGGTATGAAGCAAATCCTCGACATTCGCTGCTACTGCACATGAG

CATTGTTACTGACCAGCTCTACAGCACTTGTCGAGGGCGCCACTCTTG

CTGCCACTCTTGGCCAGTCGGGAAGCGCTTATTCATCTGTTGCTCCCC

AGGTTTTGTGCTTTCTCCAACGATTCTGGGTGTCGTCTGGTGGATACG

TCGACTCCAACAGTATGTCTTTTCACTGTTTATATGAGATTGGCCAAT

ACTGATAGCTCGCCTCTAGTCAACACCAACGAGGGCAGGACTGGCAAG

-continued

GATGTCAACTCCGTCCTGACTTCCATCCACACCTTCGATCCCAACCTT

GGCTGTGACGCAGGCACCTTCCAGCCATGCAGTGACAAAGCGCTCTCC

AACCTCAAGGTTGTTGTCGACTCCTTCCGCTCCATCTACGGCGTGAAC

AAGGGCATTCCTGCCGGTGCTGCCGTCGCCATTGGCCGGTATGCAGAG

GATGTGTACTACAACGGCAACCCTTGGTATCTTGCTACATTTGCTGCT

GCCGAGCAGCTGTACGATGCCATCTACGTCTGGAAGAAGACGGGCTCC

ATCACGGTGACCGCCACCTCCCTGGCCTTCTTCCAGGAGCTTGTTCCT

GGCGTGACGGCCGGGACCTACTCCAGCAGCTCTTCGACCTTTACCAAC

ATCATCAACGCCGTCTCGACATACGCCGATGGCTTCCTCAGCGAGGCT

GCCAAGTACGTCCCCGCCGACGGTTCGCTGGCCGAGCAGTTTGACCGC

AACAGCGGCACTCCGCTGTCTGCGCTTCACCTGACGTGGTCGTACGCC

TCGTTCTTGACAGCCACGGCCCGTCGGGCTGGCATCGTGCCCCCCTCG

TGGGCCAACAGCAGCGCTAGCACGATCCCCTCGACGTGCTCCGGCGCG

TCCGTGGTCGGATCCTACTCGCGTCCCACCGCCACGTCATTCCCTCCG

TCGCAGACGCCCAAGCCTGGCGTGCCTTCCGGTACTCCCTACACGCCC

CTGCCCTGCGCGACCCCAACCTCCGTGGCCGTCACCTTCCACGAGCTC

GTGTCGACACAGTTTGGCCAGACGGTCAAGGTGGCGGGCAACGCCGCG

GCCCTGGGCAACTGGAGCACGAGCGCCGCCGTGGCTCTGGACGCCGTC

AACTATGCCGATAACCACCCCCTGTGGATTGGGACGGTCAACCTCGAG

GCTGGAGACGTCGTGGAGTACAAGTACATCAATGTGGGCCAAGATGGC

TCCGTGACCTGGGAGAGTGATCCCAACCACACTTACACGGTTCCTGCG

GTGGCTTGTGTGACGCAGGTTGTCAAGGAGGACACctggcagtcgtaa tgaatcggcaaggggtagtactagtagacttgtagtctgcc forward primer for SEQ ID NO: 56:

SEQ ID NO: 57

5'-gactgtctccaccatgtaattttc-3'

TrGA primer KOR2; reverse primer for SEQ ID NO: 56:

SEQ ID NO: 58

5'-ggcagactacaagtctactagtactac-3'

The oligonucleotide sequences for the transcription of the T7 promoter, CER domain, and the VT domain TrGA_sgF1. The VT domain is shown in uppercase, while the T7 promoter and CER domain region are shown in bold and lowercase, respectively.

SEQ ID NO: 59 taatacgactcactataGGGAAGACCAGGATCAAGgttttagagctag aaatagcaagttaaaataaggctagtccgttatcaacttgaaaaagtg gcaccgagtcggtgc The oligonucleotide sequences for the transcription of the T7 promoter, CER domain, and the VT domain TrGA_sgR1. The VT domain is shown in uppercase, while the T7 promoter and CER domain region are shown in bold and lowercase, respectively.

SEQ ID NO: 60 taatacgactcactataGGACAGACCGCTTGATCCgttttagagctag aaatagcaagttaaaataaggctagtccgttatcaacttgaaaaagtg gcaccgagtcggtgc -continued The nucleotide sequence of the TrGA knockout cassette:

SEQ ID NO: 61 ccctgcctcgtcgcctcccctccctcccccgattagctgcgcatgttc tcctgacagcgtgactaatgacgcgttgccagcccattcgcctgacgc atcccggcatctgagtctagctcgtcacgctggcaatcttggcccagg cagagcagcaagacggcgggcatgattgggccgtgccctggcgggcat cagctggccatccgctgccacccgagaccgcatcaccgacttgtcgga tctctccgagcagcaggaggctgatcctggccggcgagacgattgaaa agggctgccgggcccggagcaggacagcggcgagagcgagcgagagag aggaaaagaagaaggtcgactgtcttattttcagccagccccggctca acagaagcagaggagaaggcgaacgacgtcaacgacgacgacgacgac gacgaagacggtgaagtccgttagttgaagatccttgccgtcacaaca ccatctcgtggatattgctttcccctgccgttgcgttgccacctgttc cctctttctcttccccccttcttcctcattccgagcgctactggttcc tactccgcagccttcggttgtgcctttctctttgtcgaccattgcacc gcccgtcgcggcacttgggccccggagaattcggccctttcgcagcat tttggccctcagttccccatggggacggtccacacttcctctcttggc cctgcagaccttttgtcgtcggtccgagtcggaagaagctcagtcttg agcgcttgagtagcatctacgcgcgaatcactggacaaagtcggcaag acgaagccgtcgtcgcctgctgctgctgctgttactgcgacaggcgct ccgactgggggcatcggcataataaaaagatgcccgccttcgccatgg acctggccatgagccactcggcatcggctctctctctcaacgcttcct ctcacacatcctccttcattccgcccatcatggtttaaacctcgagtt tataagtgacaacatgctctcaaagcgctcatggctggcacaagcctg gaaagaaccaacacaaagcatactgcagcaaatcagctgaattcgtca ccaattaagtgaacatcaacctgaaggcagagtatgaggccagaagca catctggatcgcagatcatggattgcccctcttgttgaagatgagaat ctagaaagatggcggggtatgagataagagcgatggggggggcacatca tcttccaagacaaacaacctttgcagagtcaggcaatttttcgtataa gagcaggaggagggagtccagtcatttcatcagcggtaaaatcactct agacaatcttcaagatgagttctgccttgggtgacttatagccatcat catacctagacagaagcttgtgggatactaagaccaacgtacaagctc gcactgtacgctttgacttccatgtgaaaactcgatacggcgcgcctc taaattttatagctcaaccactccaatccaacctctgcatccctctca ctcgtcctgatctactgttcaaatcagagaataaggacactatccaaa tccaacagaatggctaccacctcccagctgcctgcctacaagcaggac ttcctcaaatccgccatcgacggcggcgtcctcaagtttggcagcttc gagctcaagtccaagcggatatcccccctacttcttcaacgcgggcgaa ttccacacggcgcgcctcgccggcgccatcgcctccgcctttgcaaag accatcatcgaggcccaggagaaggccggcctagagttcgacatcgto ttcggccoggcctacaagggcatcccgctgtgctccgccatcaccatc -continued aagctcggcgagctggcgccccagaacctggaccgcgtctcctactcg tttgaccgcaaggaggccaaggaccacggcgagggcggcaacatcgtc ggcgcttcgctcaagggcaagagggtcctgattgtcgacgacgtcatc accgccggcaccgccaagagggacgccattgagaagatcaccaaggag ggcggcatcgtcgccggcatcgtcgtggccctggaccgcatggagaag ctccccgctgcggatggcgacgactccaagcctggaccgagtgccatt ggcgagctgaggaaggagtacggcatccccatctttgccatcctcact ctggatgacattatcgatggcatgaagggctttgctacccctgaggat atcaagaacacggaggattaccgtgccaagtacaaggcgactgactga ttgaggcgttcaatgtcagaagggagagaaagactgaaaaggtggaaa gaagaggcaaattgttgttattattattattctatctcgaatcttcta gatcttgtcgtaaataaacaagcgtaactagctagcctccgtacaact gcttgaatttgatacccgtatggagggcagttattttattttgtttt caagattttccattcgccgttgaactcgtctcacatcgcgtgtattgc ccggttgcccatgtgttctcctactaccccaagtccctcacgggttgt ctcactttctttctcctttatcctccctatttttttcaagtcagcga cagagcagtcatatggggatacgtgcaactgggactcacaacaggcca tcttatggcctaatagccggcgttggatccactagtcaattggtttaa acagcacatgcagtaacgccgactcggcgtcatttcgccacacccaat ttggacctgagggatgctggaagctgctgagcagatcccgttaccgat tcatggcactactacatccatacgcagcaaacatgggcttgggcttgg cttctcaatgcaaaattgcccgcaaaagtcccggcattgtcgatgcag agatgcagatttcagcgggcgattctagggtagggcgactactactac taataccacctagtcagtatgtatctagcaccggaggctaggcggtta gtggacgggaacctggtcattccatcgcaaccaggatcccgcacttcg ttgcgcttctgcccccacggggcgggagttggcagaggcagaatgcgg agcagccccttgtctgccctggccggggcctgttgaagcaagcagacg agagcagagcggttgagaagcggtggttgacgcttgacggtacgaaga cgagcgagaatcccgttaagccgaggctgggctaattaattaatgaat cggcaaggggtagtactagtagacttgtagtctgccggattattgatt ggagttggtcagtagaatgaaccacgggaatattcggtcaccgggaca tttgggatatagcgtttcgagaagctgctggttgcagcacattggaga aggatgcccttttacgacttataccgctatgccgggtatattaattta gccgttatgaaactcaaagagacgatgataatgatgacgagtaattgt tcgtttcaatttcgaaagctgactcccacgaagaatatgccaatgacc cacggcatgaagcctgaactgggcgtgtgtaacactttaatttgcctg acggcggacaaaacaaaggcggcagcaatgttgagaccgtgtgataaa ccaaggttcccgagggagagagagagagagagagagagagagctaggt gaaagaatgagtccgcctttgagtcatcctgcgtctctctctcccccct ctctcactctctgtatcccatcaacctcttccctgttccttctcctat cgcatccatgcgtttgcatcttccatttcattctttccccttgagccc catctatgcaaactcatcatccggcgcctcgatggaatccttgacctt gatgagaatcgccgtcatccaaggctccagcctgctcgtgcggtcgaa ctggaacagcagctcgctaaactcatcctggctgtggttgtcgacggc gttgcacaggtcctcgagcagcttgtacttgtattgagaggagaactc ggggtccttttggcggtaggactcgacggcgcggcgggtgccgaccat gtcgcccgtggcgaggtggcagatgccggccttgaagcagtaggtcga gaggctccacttcatggtgccgttgccgatcatggtgttgatgatgcg gtcgtacgtctcgatggcgccgtagtagtcgccgtcgagggcggcgag gtcggcgtactgcgtccagagctt Fw1
SEQ ID NO: 62
(5'-cactactacatccatacgcagcaaacatgg-3')

and

R3
SEQ ID NO: 63
(5'-ggtcaagaagcacatgccagagttcg-3')

TrGAF2
SEQ ID NO: 64
(5' gactgtctccaccatgtaatttttc 3')

*E. coli* codon-optimized Cas9-D10A nickase gene (no stop codon)
SEQ ID NO: 65 atggataaaaaatacagcattggtctggccatcggaaccaacagcgtt gggtgggcagtaataacagatgaatacaaagtgccgtcaaaaaaattt aaggttctggggaatacagatcgccacagcataaaaaagaatctgatt ggggcattgctgtttgattcgggtgagacagctgaggccacgcgtctg aaacgtacagcaagaagacgttacacacgtcgtaaaaatcgtatttgc tacttacaggaaatttttttctaacgaaatggccaaggtagatgatagt ttcttccatcgtctcgaagaatcttttctggttgaggaagataaaaaa cacgaacgtcaccctatctttggcaatatcgtggatgaagtggcctat catgaaaaatacctacgatttatcatcttcgcaagaagttggttgat agtacggacaaagcggatctgcgtttaatctatcttgcgttagcgcac atgatcaaatttcgtggtcatttcttaattgaaggtgatctgaatcct gataactctgatgtggacaaattgtttatacaattagtgcaaacctat aatcagctgttcgaggaaaaccccattaatgcctctggagttgatgcc aaagcgattttaagcgcgagactttctaagtcccggcgtctggagaat ctgatcgcccagttaccaggggaaaagaaaaatggtctgtttggtaat ctgattgccctcagtctggggcttaccccgaacttcaaatccaatttt gacctggctgaggacgcaaagctgcagctgagcaaagatacttatgat gatgacctcgacaatctgctcgcccagattggtgaccaatatgcggat ctgtttctggcagcgaagaatctttcggatgctatcttgctgtcggat attctgcgtgttaataccgaaatcaccaaagcgcctctgtctgcaagt atgatcaagagatacgacgagcaccaccaggacctgactcttcttaag gcactggtacgccaacagcttccggagaaatacaaagaaatattcttc gaccagtccaagaatggttacgcgggctacatcgatggtggtgcatca -continued caggaagagttctataaatttattaaaccaatccttgagaaaatggat ggcacggaagagttacttgttaaacttaaccgcgaagacttgcttaga aagcaacgtacattcgacaacggctccatcccacaccagattcattta ggtgaacttcacgccatcttgcgcagacaagaagatttctatcccttc ttaaaagacaatcgggagaaaatcgagaagatcctgacgttccgcatt ccctattatgtcggtcccctggcacgtggtaattctcggtttgcctgg atgacgcgcaaaagtgaggaaaccatcaccccttggaactttgaagaa gtcgtggataaaggtgctagcgcgcagtcttttatagaaagaatgacg aacttcgataaaaacttgcccaacgaaaaagtcctgcccaagcactct cttttatatgagtactttactgtgtacaacgaactgactaaagtgaaa tacgttacggaaggtatgcgcaaacctgcctttcttagtggcgagcag aaaaaagcaattgtcgatcttctctttaaaacgaatcgcaaggtaact gtaaaacagctgaaggaagattatttcaaaaagatcgaatgctttgat tctgtcgagatctcgggtgtcgaagatcgtttcaacgcttccttaggg acctatcatgatttgctgaagatataaaagacaaagactttctcgac aatgaagaaaatgaagatattctggaggatattgttttgaccttgacc ttattcgaagatagagagatgatcgaggagcgcttaaaaacctatgcc cacctgtttgatgacaaagtcatgaagcaattaaagcgccgcagatat acggggtggggccgcttgagccgcaagttgattaacggtattagagac aagcagagcggaaaaactatcctggatttcctcaaatctgacggattt gcgaaccgcaattttatgcagcttatacatgatgattcgcttacattc aaagaggatattcagaaggctcaggtgtctgggcaaggtgattcactc cacgaacatatagcaaatttggccggctctcctgcgattaagaagggg atcctgcaaacagttaaagttgtggatgaacttgtaaaagtaatgggc cgccacaagccggagaatatcgtgatagaaatggcgcgcgagaatcaa acgacacaaaaaggtcaaaagaactcaagagagagaatgaagcgcatt gaggaggggataaaggaacttggatctcaaattctgaaagaacatcca gttgaaaacactcagctgcaaaatgaaaaattgtacctgtactacctg cagaatggaagagacatgtacgtggatcaggaattggatatcaataga ctctcggactatgacgtagatcacattgtccctcagagcttcctcaag gatgattctatagataataaagtacttacgagatcggacaaaaatcgc ggtaaatcggataacgtcccatcggaggaagtcgttaaaaagatgaaa aactattggcgtcaactgctgaacgccaagctgatcacacagcgtaag tttgataatctgactaaagccgaacgcggtggtcttagtgaactcgat aaagcaggatttataaaacggcagttagtagaaacgcgccaaattacg aaacacgtggctcagatcctcgattctagaatgaatacaaagtacgat gaaaacgataaactgatccgtgaagtaaaagtcattaccttaaaatct aaacttgtgtccgatttccgcaaagattttcagttttacaaggtccgg gaaatcaataactatcaccatgcacatgatgcatatttaaatgcggtt gtaggcacggcccttattaagaaataccctaaactcgaaagtgagttt gtttatggggattataaagtgtatgacgttcgcaaaatgatcgcgaaa -continued tcagaacaggaaatcggtaaggctaccgctaaatacttttttttattcc aacattatgaatttttttaagaccgaaataactctcgcgaatggtgaa atccgtaaacggcctcttatagaaaccaatggtgaaacgggagaaatc gtttgggataaaggtcgtgactttgccaccgttcgtaaagtcctctca atgccgcaagttaacattgtcaagaagacggaagttcaaacaggggga ttctccaaagaatctatcctgccgaagcgtaacagtgataaacttatt gccagaaaaaaagattgggatccaaaaaaatacggaggctttgattcc cctaccgtcgcgtatagtgtgctggtggttgctaaagtcgagaaaggg aaaagcaagaaattgaaatcagttaaagaactgctgggtattacaatt atggaaagatcgtcctttgagaaaaatccgatcgactttttagaggcc aaggggtataaggaagtgaaaaaagatctcatcatcaaattaccgaag tatagtctttttgagctggaaaacggcagaaaaagaatgctggcctcc gcgggcgagttacagaagggaaatgagctggcgctgccttccaaatat gttaattttctgtaccttgccagtcattatgagaaactgaagggcagc cccgaagataacgaacagaaacaattattcgtggaacagcataagcac tatttagatgaaattatagagcaaattagtgaattttctaagcgcgtt atcctcgcggatgctaatttagacaaagtactgtcagcttataataaa catcgggataagccgattagagaacaggccgaaaatatcattcatttg tttaccttaaccaaccttggagcaccagctgccttcaaatatttcgat accacaattgatcgtaaacggtatacaagtacaaaagaagtcttggac gcaaccctcattcatcaatctattactggattatatgagacacgcatt gatctttcacagctgggcggagac Amino acid sequence of the Cas9-D10A nickase from *Streptococcus pyogenes*; encoded by SEQ ID NO: 65

SEQ ID NO: 66 mdkkysiglaigtnsvgwavitdeykvpskkfkvlgntdrhsikknli gallfdsgetaeatrlkrtarrrytrrknricylqeifsnemakvdds ffhrleesflveedkkherhpifgnivdevayhekyptiyhlrkklvd stdkadlrliylalahmikfrghfliegdlnpdnsdvdklfiqlvqty nqlfeenpinasgydakailsarlsksrrlenliaqlpgekknglfgn lialslgltpnfksnfdlaedaklqlskdtydddldnllaqigdqyad lflaaknlsdaillsdilrvnteitkaplsasmikrydehhqdltllk alvrqqlpekykeiffdqsknggyagyidggasqeefykfikpilekmd gteellyklnredllrkqrtfdngsiphqihlgelhailrrqedfypf lkdnrekiekiltfripyyvgplargnsrfawmtrkseetitpwnfee vvdkgasaqsfiermtnfdknlpnekvlpkhsllyeyftvyneltkvk yvtegmrkpaflsgeqkkaivdllfktnrkvtvkqlkedyfkkiecfd sveisgvedrfnaslgtyhdllkiikdkdfldneenediledivltlt lfedremieerlktyahlfddkvmkqlkrrrytgwgrlsrklingird kqsgktildflksdgfanrnfmqlihddsltfkediqkaqvsgqgdsl hehianlagspaikkgilqtvkvvdelvkvmgrhkpeniviemarenq -continued ttqkgqknsrermkrieegikelgsqilkehpventqlqneklylyyl qngrdmyvdqeldinrlsdydvdhivpqsflkddsidnkvltrsdknr gksdnvpseevykkmknywrqllnaklitqrkfdnltkaergglseld kagfikrqlvetrqitkhvaqildsrmntkydendklirevkvitlks klvsdfrkdfqfykvreinnyhhandaylnavvgtalikkypklesef vygdykvydvrkmiakseqeigkatakyffysnimnffkteitlange irkrplietngetgeivwdkgrdfatvrkvlsmpqvnivkktevqtgg fskesilpkrnsdkliarkkdwdpkkyggfdsptvaysvlvvakvekg kskklksvkellgitimerssfeknpidfleakgykevkkdliiklpk yslfelengrkrmlasagelqkgnelalpskyvnflylashyeklkgs pedneqkqlfveqhkhyldeiieqisefskrviladanldkvlsaynk hrdkpireqaeniihlftltnlgapaafkyfdttidrkrytstkevld atlihqsitglyetridlsqlggd N-terminal His6 tag/thrombin/S·Tag™/enterokinase region amino acid sequence (with start methionine)

SEQ ID NO: 67 mhhhhhhssglvprgsgmketaaakferqhmdspdlgtddddkama

N-terminal His6 tag/thrombin/S·Tag™/enterokinase region polynucleotide sequence (with start codon); encodes SEQ ID NO: 67

SEQ ID NO: 68 atgcaccatcatcatcatcattcttctggtctggtgccacgcggttct ggtatgaaagaaaccgctgctgctaaattcgaacgccagcacatggac agcccagatctgggtaccgacgacgacgacaaggccatggcc SV40 NLS coding sequence (encodes SEQ ID NO: 46)

SEQ ID NO: 69 ccaaaaaagaaacgcaaggtt

-continued

BLR nuclear localization signal coding sequence (encodes SEQ ID NO: 47)

SEQ ID NO: 70

Aagaagaaaaaactgaaactg

SEQ ID NO: 71 tgatgacggtgaaaacctc

SEQ ID NO: 72 aaaagcaccgactcgg

Gla1rep Primer 1556F

SEQ ID NO: 73

ATGCGCAAATTTAAAGCGCTGATgtgtgtctaatgcctccaccac

Gla1rep Primer 1557R

SEQ ID NO: 74

ATATGGATCTGCGCGCGATCGATgatcgtgctagcgctgctgttg

Sequencing primer 1538F

SEQ ID NO: 75

CCACCACAGGAACCAAACC

Sequencing primer 1539R

SEQ ID NO: 76

CTGCGACGGAGGGAATGACG

Sequencing primer 1540F

SEQ ID NO: 77

GGGCAGGACTGGCAAGGATGT

Sequencing primer 1541R

SEQ ID NO: 78

GCCGTCACGCCAGGAACAAG

TrGA Primer KOF1

SEQ ID NO: 79 gaacaatcttctttgcaatgttggtc

Pyr2 Primer R1

SEQ ID NO: 80 gaggaagtcctgcttgtaggcaggc

Pyr2 Primer F4

SEQ ID NO: 81 cgacagagcagtcatatggggatacg

---

That which is claimed:

1. A method for homologous recombination of a donor DNA with a genomic locus in a filamentous fungal cell, the method comprising:

a) introducing into a population of filamentous fungal cells a Cas9 endonuclease, a guide RNA, and a donor DNA comprising a domain with homology to the genomic locus of the fungal cell, wherein the Cas9 endonuclease and guide RNA form a complex that enables the Cas9 endonuclease to act at a target site in or near the genomic locus of the fungal cells, wherein non-homologous end joining (NHEJ) at the target site in the fungal cells is inactivated, non-functional, or reduced, wherein the Cas9 endonuclease acts at said target site resulting in a population in which homologous recombination of the donor DNA with the genomic locus has occurred; and, b) identifying at least one fungal cell from the population of (a) in which homologous recombination of the donor DNA with the genomic locus has occurred, wherein the Cas9 endonuclease, the guide RNA, or both are introduced transiently into the population of fungal cells, and wherein the introducing step comprises introducing into the fungal cells a DNA construct comprising a sequence encoding a selectable marker and the donor DNA, and wherein the identifying step comprises culturing the population of cells from step (a) under conditions to screen for unstable transformants that have lost the selectable marker yet retained the donor DNA.

2. The method of claim 1, wherein said non-homologous end joining (NHEJ) is non-functional, or reduced by one or more non-functional or reduced activity components.

3. The method of claim 2, wherein the one or more non-functional or reduced-activity components are selected from the group consisting of ku80, ku70, mre11, xrs2, lig4, xrs, and combinations thereof.

4. The method of claim 3, wherein the one or more non-functional or reduced-activity components is ku80.

5. The method of claim 1, wherein the donor DNA comprises a polynucleotide sequence of interest, and wherein homologous recombination at the genomic locus results in the insertion of the polynucleotide sequence of interest in the genomic locus.

6. The method of claim 1, wherein the introducing step comprises introducing a DNA construct comprising an expression cassette for the Cas9 endonuclease into the fungal cells.

7. The method of claim 1, wherein the introducing step comprises introducing a DNA construct comprising an expression cassette for the guide RNA into the fungal cells.

8. The method of claim 1, wherein the introducing step comprises introducing into the fungal cells a DNA construct comprising: a sequence encoding the Cas9 endonuclease, a sequence encoding the guide RNA, a sequence encoding a selectable marker, and the donor DNA.

9. The method of claim 6, wherein the expression cassette for the Cas9 endonuclease comprises a Cas9 coding sequence that is optimized for expression in the filamentous fungal cell.

10. The method of claim 1, wherein the introducing step comprises directly introducing the Cas9 endonuclease into the fungal cells.

11. The method of claim 1, wherein the introducing step comprises directly introducing the guide RNA into the fungal cells.

12. The method of claim 1, wherein the Cas9 endonuclease is operably linked to a nuclear localization signal.

13. The method of claim 1, wherein the filamentous fungal cell is a Eumycotina or Pezizomycotina fungal cell.

14. The method of claim 1, wherein the filamentous fungal cell is selected from the group consisting of *Trichoderma, Penicillium, Aspergillus, Humicola, Chrysosporium, Fusarium, Myceliophthora, Neurospora, Hypocrea*, and *Emericella*.

15. The method of claim 1, wherein the target site is located within a region of a gene of interest selected from the group consisting of an open reading frame, a promoter, a regulatory sequence, a terminator sequence, a regulatory element sequence, a splice site, a coding sequence, a polyubiquitination site, an intron site, and an intron enhancing motif.

16. The method of claim 1, wherein the homologous recombination results in a modification of the DNA sequence at or near the target site, wherein the modification is selected from the group consisting of a deletion of one or more nucleotides, an insertion of one or more nucleotides, insertion of an expression cassette encoding a protein of interest, a substitution of one or more nucleotides, and any combination thereof.

* * * * *

SEQUENCE LISTING

<160> NUMBER OF SEQ ID NOS: 81

<210> SEQ ID NO 1
<211> LENGTH: 842
<212> TYPE: DNA
<213> ORGANISM: T. reesei

<400> SEQUENCE: 1
aaaaaacact agtaagtact tacttatgta ttattaacta ctttagctaa cttctgcagt 60
actacctaag aggctagggg tagttttata gcagacttat agctattatt tttatttagt 120
aaagtgcttt taaagtaagg tctttttat agcactttt atttattata atatatatta 180
tataataatt ttaagcctgg aatagtaaag aggcttatat aataatttat agtaataaaa 240
gcttagcagc tgtaatataa ttcctaaaga aacagcatga aatggtatta tgtaagagct 300
atagtctaaa ggcactctgc tggataaaaa tagtggctat aagtctgctg caaaactacc 360
cccaacctcg taggtatata agtactgttt gatggtagtc tatcgccttc gggcatttgg 420
tcaatttata acgatacagg ttcgtttcgg cttttcctcg gaacccccag aggtcatcag 480
ttcgaatcgc taacaggtca acagagaaga ttagcatggc ccctgcacta aggatgacac 540
gctcactcaa agagaagcta aacatttttt ttctcttcca agtcgtgatg gttatctttt 600
tgcttagaga atctattctt gtggacgatt agtattggta aatccctgct gcacattgcg 660
gcggatggtc tcaacggcat aataccccat tcgtgatgca gcggtgatct tcaatatgta 720
gtgtaatacg ttgcatacac caccaggttc ggtgcctcct gtatgtacag tactgtagtt 780
cgactcctcc gcgcaggtgg aaacgattcc ctagtgggca ggtattttgg cggggtcaag 840
aa 842

<210> SEQ ID NO 2
<211> LENGTH: 99
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(20)
<223> OTHER INFORMATION: n is a, c, g, or u

<400> SEQUENCE: 2
nnnnnnnnnn nnnnnnnnnn guuuuagagc uagaaauagc aaguuaaaau aaggcuaguc 60
cguuaucaac uugaaaaagu ggcaccgagu cgguggugc 99

<210> SEQ ID NO 3
<211> LENGTH: 99
<212> TYPE: RNA
<213> ORGANISM: Artificial Sequence
<220> FEATURE:
<223> OTHER INFORMATION: Synthetic sequence

<400> SEQUENCE: 3
guccucgagc aaaaggugcc guuuuagagc uagaaauagc aaguuaaaau aaggcuaguc 60
cguuaucaac uugaaaaagu ggcaccgagu cgguggugc 99

<210> SEQ ID NO 4
<211> LENGTH: 99
<212> TYPE: RNA
<213> ORGANISM: Artificial Sequence
<220> FEATURE:
<223> OTHER INFORMATION: Synthetic sequence

<400> SEQUENCE: 4
guucagugca auaggcgucu guuuuagagc uagaaauagc aaguuaaaau aaggcuaguc 60
cguuaucaac uugaaaaagu ggcaccgagu cgguggugc 99

<210> SEQ ID NO 5
<211> LENGTH: 99
<212> TYPE: RNA
<213> ORGANISM: Artificial Sequence
<220> FEATURE:
<223> OTHER INFORMATION: Synthetic sequence

<400> SEQUENCE: 5
gccaauggcg acggcagcac guuuuagagc uagaaauagc aaguuaaaau aaggcuaguc 60
cguuaucaac uugaaaaagu ggcaccgagu cgguggugc 99

<210> SEQ ID NO 6
<211> LENGTH: 99
<212> TYPE: RNA
<213> ORGANISM: Artificial Sequence
<220> FEATURE:
<223> OTHER INFORMATION: Synthetic sequence

<400> SEQUENCE: 6
gcacagcggg augcccuugu guuuuagagc uagaaauagc aaguuaaaau aaggcuaguc 60
cguuaucaac uugaaaaagu ggcaccgagu cgguggugc 99

<210> SEQ ID NO 7
<211> LENGTH: 4155
<212> TYPE: DNA
<213> ORGANISM: Artificial Sequence
<220> FEATURE:
<223> OTHER INFORMATION: codon optimized seqs

<400> SEQUENCE: 7
atggcaccga agaagaagcg caaggtgatg gacaagaagt acagcatcgg cctcgacatc 60
ggcaccaact cggtgggctg ggccgtcatc acggacgaat ataaggtccc gtcgaagaag 120
ttcaaggtcc tcggcaatac agaccgccac agcatcaaga aaaacttgat cggcgccctc 180
ctgttcgata gcggcgagac cgcggaggcg accaggctca agaggaccgc caggagacgg 240
tacactaggc gcaagaacag gatctgctac ctgcaggaga tcttcagcaa cgagatggcg 300
aaggtggacg actccttctt ccaccgcctg gaggaatcat tcctggtgga ggaggacaag 360
aagcatgagc ggcacccaat cttcggcaac atcgtcgacg aggtggccta ccacgagaag 420
tacccgacaa tctaccacct ccggaagaaa ctggtggaca gcacagacaa ggcggacctc 480
cggctcatct accttgccct cgcgcatatg atcaagttcc gcggccactt cctcatcgag 540
ggcgacctga acccggacaa ctccgacgtg gacaagctgt tcatccagct cgtgcagacg 600
tacaatcaac tgttcgagga gaaccccata aacgctagcg gcgtggacgc caaggccatc 660
ctctcggcca ggctctcgaa atcaagaagg ctggagaacc ttatcgcgca gttgccaggc 720
gaaaagaaga acggcctctt cggcaacctt attgcgctca gcctcggcct gacgccgaac 780
ttcaaatcaa acttcgacct cgcggaggac gccaagctcc agctctcaaa ggacacctac 840
gacgacgacc tcgacaacct cctggcccag ataggagacc agtacgcgga cctcttcctc 900
gccgccaaga acctctccga cgctatcctg ctcagcgaca tccttcgggt caacaccgaa 960
attaccaagg caccgctgtc cgccagcatg attaaacgct acgacgagca ccatcaggac 1020
ctcacgctgc tcaaggcact cgtccgccag cagctccccg agaagtacaa ggagatcttc 1080
ttcgaccaat caaaaaacgg ctacgcggga tatatcgacg gcggtgccag ccaggaagag 1140
ttctacaagt tcatcaaacc aatcctggag aagatggacg gcaccgagga gttgctggtc 1200
aagctcaaca gggaggacct cctcaggaag cagaggacct tcgacaacgg ctccatcccg 1260
catcagatcc acctgggcga actgcatgcc atcctgcggc gccaggagga cttctacccg 1320
ttcctgaagg ataaccggga gaagatcgag aagatcttga cgttccgcat cccatactac 1380
gtgggcccgc tggctcgcgg caactcccgg ttcgcctgga tgacccggaa gtcggaggag 1440
accatcacac cctggaactt tgaggaggtg gtcgataagg gcgctagcgc tcagagcttc 1500
atcgagcgca tgaccaactt cgataaaaac ctgcccaatg aaaaagtcct ccccaagcac 1560
tcgctgctct acgagtactt caccgtgtac aacgagctca ccaaggtcaa atacgtcacc 1620
gagggcatgc ggaagccggc gttcctgagc ggcgagcaga agaaggcgat agtggacctc 1680
ctcttcaaga ccaacaggaa ggtgaccgtg aagcaattaa aagaggacta cttcaagaaa 1740
atagagtgct tcgactccgt ggagatctcg ggcgtggagg atcggttcaa cgcctcactc 1800
ggcacgtatc acgacctcct caagatcatt aaagacaagg acttcctcga caacgaggag 1860
aacgaggaca tcctcgagga catcgtcctc accctgaccc tgttcgagga ccgcgaaatg 1920

-continued

```
atcgaggaga ggctgaagac ctacgcgcac ctgttcgacg acaaggtcat gaaacagctc   1980
aagaggcgcc gctacactgg ttggggaagg ctgtcccgca agctcattaa tggcatcagg   2040
gacaagcaga gcggcaagac catcctggac ttcctcaagt ccgacgggtt cgccaaccgc   2100
aacttcatgc agctcattca cgacgactcg ctcacgttca aggaagacat ccagaaggca   2160
caggtgagcg ggcagggtga ctccctccac gaacacatcg ccaacctggc cggctcgccg   2220
gccattaaaa agggcatcct gcagacggtc aaggtcgtcg acgagctcgt gaaggtgatg   2280
ggccggcaca agcccgaaaa tatcgtcata gagatggcca gggagaacca gaccacccaa   2340
aaagggcaga agaactcgcg cgagcggatg aaacggatcg aggagggcat taaagagctc   2400
gggtcccaga tcctgaagga gcaccccgtg gaaaataccc agctccagaa tgaaaagctc   2460
tacctctact acctgcagaa cggccgcgac atgtacgtgg accaggagct ggacattaat   2520
cggctatcgg actacgacgt cgaccacatc gtgccgcagt cgttcctcaa ggacgatagc   2580
atcgacaaca aggtgctcac ccggtcggat aaaaatcggg gcaagagcga caacgtgccc   2640
agcgaggagg tcgtgaagaa gatgaaaaac tactggcgcc agctcctcaa cgcgaaactg   2700
atcacccagc gcaagttcga caacctgacg aaggcggaac gcggtggctt gagcgaactc   2760
gataaggcgg gcttcataaa aaggcagctg gtcgagacgc gccagatcac gaagcatgtc   2820
gcccagatcc tggacagccg catgaatact aagtacgatg aaaacgacaa gctgatccgg   2880
gaggtgaagg tgatcacgct gaagtccaag ctcgtgtcgg acttccgcaa ggacttccag   2940
ttctacaagg tccgcgagat caacaactac caccacgccc acgacgccta cctgaatgcg   3000
gtggtcggga ccgccctgat caagaagtac ccgaagctgg agtcggagtt cgtgtacggc   3060
gactacaagg tctacgacgt gcgcaaaatg atcgccaagt ccgagcagga gatcggcaag   3120
gccacggcaa aatacttctt ctactcgaac atcatgaact tcttcaagac cgagatcacc   3180
ctcgcgaacg gcgagatccg caagcgcccg ctcatcgaaa ccaacggcga gacgggcgag   3240
atcgtctggg ataagggccg ggatttcgcg acggtccgca aggtgctctc catgccgcaa   3300
gtcaatatcg tgaaaaagac ggaggtccag acgggcgggt tcagcaagga gtccatcctc   3360
ccgaagcgca actccgacaa gctcatcgcg aggaagaagg attgggaccc gaaaaaatat   3420
ggcggcttcg acagcccgac cgtcgcatac agcgtcctcg tcgtggcgaa ggtggagaag   3480
ggcaagtcaa agaagctcaa gtccgtgaag gagctgctcg ggatcacgat tatggagcgg   3540
tcctccttcg agaagaaccc gatcgacttc ctagaggcca agggatataa ggaggtcaag   3600
aaggacctga ttattaaact gccgaagtac tcgctcttcg agctggaaaa cggccgcaag   3660
aggatgctcg cctccgcagg cgagttgcag aagggcaacg agctcgccct cccgagcaaa   3720
tacgtcaatt tcctgtacct cgctagccac tatgaaaagc tcaagggcag cccggaggac   3780
aacgagcaga agcagctctt cgtggagcag cacaagcatt acctggacga gatcatcgag   3840
cagatcagcg agttctcgaa gcgggtgatc ctcgccgacg cgaacctgga caaggtgctg   3900
tcggcatata acaagcaccg cgacaaacca atacgcgagc aggccgaaaa tatcatccac   3960
ctcttcaccc tcaccaacct cggcgctccg gcagccttca agtacttcga caccacgatt   4020
gaccggaagc ggtacacgag cacgaaggag gtgctcgatg cgacgctgat ccaccagagc   4080
atcacagggc tctatgaaac acgcatcgac ctgagccagc tgggcggaga caagaagaag   4140
aagctcaagc tctag                                                    4155
```

<210> SEQ ID NO 8

```
<211> LENGTH: 1384
<212> TYPE: PRT
<213> ORGANISM: Artificial Sequence
<220> FEATURE:
<223> OTHER INFORMATION: protein expressed from synthetic construct

<400> SEQUENCE: 8

Met Ala Pro Lys Lys Lys Arg Lys Val Met Asp Lys Lys Tyr Ser Ile
1               5                   10                  15

Gly Leu Asp Ile Gly Thr Asn Ser Val Gly Trp Ala Val Ile Thr Asp
            20                  25                  30

Glu Tyr Lys Val Pro Ser Lys Lys Phe Lys Val Leu Gly Asn Thr Asp
        35                  40                  45

Arg His Ser Ile Lys Lys Asn Leu Ile Gly Ala Leu Leu Phe Asp Ser
    50                  55                  60

Gly Glu Thr Ala Glu Ala Thr Arg Leu Lys Arg Thr Ala Arg Arg Arg
65                  70                  75                  80

Tyr Thr Arg Arg Lys Asn Arg Ile Cys Tyr Leu Gln Glu Ile Phe Ser
                85                  90                  95

Asn Glu Met Ala Lys Val Asp Asp Ser Phe Phe His Arg Leu Glu Glu
            100                 105                 110

Ser Phe Leu Val Glu Glu Asp Lys Lys His Glu Arg His Pro Ile Phe
        115                 120                 125

Gly Asn Ile Val Asp Glu Val Ala Tyr His Glu Lys Tyr Pro Thr Ile
    130                 135                 140

Tyr His Leu Arg Lys Lys Leu Val Asp Ser Thr Asp Lys Ala Asp Leu
145                 150                 155                 160

Arg Leu Ile Tyr Leu Ala Leu Ala His Met Ile Lys Phe Arg Gly His
                165                 170                 175

Phe Leu Ile Glu Gly Asp Leu Asn Pro Asp Asn Ser Asp Val Asp Lys
            180                 185                 190

Leu Phe Ile Gln Leu Val Gln Thr Tyr Asn Gln Leu Phe Glu Glu Asn
        195                 200                 205

Pro Ile Asn Ala Ser Gly Val Asp Ala Lys Ala Ile Leu Ser Ala Arg
    210                 215                 220

Leu Ser Lys Ser Arg Arg Leu Glu Asn Leu Ile Ala Gln Leu Pro Gly
225                 230                 235                 240

Glu Lys Lys Asn Gly Leu Phe Gly Asn Leu Ile Ala Leu Ser Leu Gly
                245                 250                 255

Leu Thr Pro Asn Phe Lys Ser Asn Phe Asp Leu Ala Glu Asp Ala Lys
            260                 265                 270

Leu Gln Leu Ser Lys Asp Thr Tyr Asp Asp Asp Leu Asp Asn Leu Leu
        275                 280                 285

Ala Gln Ile Gly Asp Gln Tyr Ala Asp Leu Phe Leu Ala Ala Lys Asn
    290                 295                 300

Leu Ser Asp Ala Ile Leu Leu Ser Asp Ile Leu Arg Val Asn Thr Glu
305                 310                 315                 320

Ile Thr Lys Ala Pro Leu Ser Ala Ser Met Ile Lys Arg Tyr Asp Glu
                325                 330                 335

His His Gln Asp Leu Thr Leu Leu Lys Ala Leu Val Arg Gln Gln Leu
            340                 345                 350

Pro Glu Lys Tyr Lys Glu Ile Phe Phe Asp Gln Ser Lys Asn Gly Tyr
        355                 360                 365

Ala Gly Tyr Ile Asp Gly Gly Ala Ser Gln Glu Glu Phe Tyr Lys Phe
    370                 375                 380
```

```
Ile Lys Pro Ile Leu Glu Lys Met Asp Gly Thr Glu Glu Leu Leu Val
385                 390                 395                 400

Lys Leu Asn Arg Glu Asp Leu Leu Arg Lys Gln Arg Thr Phe Asp Asn
                405                 410                 415

Gly Ser Ile Pro His Gln Ile His Leu Gly Glu Leu His Ala Ile Leu
            420                 425                 430

Arg Arg Gln Glu Asp Phe Tyr Pro Phe Leu Lys Asp Asn Arg Glu Lys
        435                 440                 445

Ile Glu Lys Ile Leu Thr Phe Arg Ile Pro Tyr Tyr Val Gly Pro Leu
    450                 455                 460

Ala Arg Gly Asn Ser Arg Phe Ala Trp Met Thr Arg Lys Ser Glu Glu
465                 470                 475                 480

Thr Ile Thr Pro Trp Asn Phe Glu Glu Val Val Asp Lys Gly Ala Ser
                485                 490                 495

Ala Gln Ser Phe Ile Glu Arg Met Thr Asn Phe Asp Lys Asn Leu Pro
            500                 505                 510

Asn Glu Lys Val Leu Pro Lys His Ser Leu Leu Tyr Glu Tyr Phe Thr
        515                 520                 525

Val Tyr Asn Glu Leu Thr Lys Val Lys Tyr Val Thr Glu Gly Met Arg
    530                 535                 540

Lys Pro Ala Phe Leu Ser Gly Glu Gln Lys Lys Ala Ile Val Asp Leu
545                 550                 555                 560

Leu Phe Lys Thr Asn Arg Lys Val Thr Val Lys Gln Leu Lys Glu Asp
                565                 570                 575

Tyr Phe Lys Lys Ile Glu Cys Phe Asp Ser Val Glu Ile Ser Gly Val
            580                 585                 590

Glu Asp Arg Phe Asn Ala Ser Leu Gly Thr Tyr His Asp Leu Leu Lys
        595                 600                 605

Ile Ile Lys Asp Lys Asp Phe Leu Asp Asn Glu Glu Asn Glu Asp Ile
    610                 615                 620

Leu Glu Asp Ile Val Leu Thr Leu Thr Leu Phe Glu Asp Arg Glu Met
625                 630                 635                 640

Ile Glu Glu Arg Leu Lys Thr Tyr Ala His Leu Phe Asp Asp Lys Val
                645                 650                 655

Met Lys Gln Leu Lys Arg Arg Arg Tyr Thr Gly Trp Gly Arg Leu Ser
            660                 665                 670

Arg Lys Leu Ile Asn Gly Ile Arg Asp Lys Gln Ser Gly Lys Thr Ile
        675                 680                 685

Leu Asp Phe Leu Lys Ser Asp Gly Phe Ala Asn Arg Asn Phe Met Gln
    690                 695                 700

Leu Ile His Asp Asp Ser Leu Thr Phe Lys Glu Asp Ile Gln Lys Ala
705                 710                 715                 720

Gln Val Ser Gly Gln Gly Asp Ser Leu His Glu His Ile Ala Asn Leu
                725                 730                 735

Ala Gly Ser Pro Ala Ile Lys Lys Gly Ile Leu Gln Thr Val Lys Val
            740                 745                 750

Val Asp Glu Leu Val Lys Val Met Gly Arg His Lys Pro Glu Asn Ile
        755                 760                 765

Val Ile Glu Met Ala Arg Glu Asn Gln Thr Thr Gln Lys Gly Gln Lys
    770                 775                 780

Asn Ser Arg Glu Arg Met Lys Arg Ile Glu Glu Gly Ile Lys Glu Leu
785                 790                 795                 800
```

-continued

```
Gly Ser Gln Ile Leu Lys Glu His Pro Val Glu Asn Thr Gln Leu Gln
                805                 810                 815

Asn Glu Lys Leu Tyr Leu Tyr Tyr Leu Gln Asn Gly Arg Asp Met Tyr
            820                 825                 830

Val Asp Gln Glu Leu Asp Ile Asn Arg Leu Ser Asp Tyr Asp Val Asp
        835                 840                 845

His Ile Val Pro Gln Ser Phe Leu Lys Asp Asp Ser Ile Asp Asn Lys
    850                 855                 860

Val Leu Thr Arg Ser Asp Lys Asn Arg Gly Lys Ser Asp Asn Val Pro
865                 870                 875                 880

Ser Glu Glu Val Val Lys Lys Met Lys Asn Tyr Trp Arg Gln Leu Leu
                885                 890                 895

Asn Ala Lys Leu Ile Thr Gln Arg Lys Phe Asp Asn Leu Thr Lys Ala
            900                 905                 910

Glu Arg Gly Gly Leu Ser Glu Leu Asp Lys Ala Gly Phe Ile Lys Arg
        915                 920                 925

Gln Leu Val Glu Thr Arg Gln Ile Thr Lys His Val Ala Gln Ile Leu
    930                 935                 940

Asp Ser Arg Met Asn Thr Lys Tyr Asp Glu Asn Asp Lys Leu Ile Arg
945                 950                 955                 960

Glu Val Lys Val Ile Thr Leu Lys Ser Lys Leu Val Ser Asp Phe Arg
                965                 970                 975

Lys Asp Phe Gln Phe Tyr Lys Val Arg Glu Ile Asn Asn Tyr His His
            980                 985                 990

Ala His Asp Ala Tyr Leu Asn Ala  Val Val Gly Thr Ala  Leu Ile Lys
        995                 1000                1005

Lys Tyr  Pro Lys Leu Glu Ser  Glu Phe Val Tyr Gly  Asp Tyr Lys
    1010                1015                1020

Val Tyr  Asp Val Arg Lys Met  Ile Ala Lys Ser Glu  Gln Glu Ile
    1025                1030                1035

Gly Lys  Ala Thr Ala Lys Tyr  Phe Phe Tyr Ser Asn  Ile Met Asn
    1040                1045                1050

Phe Phe  Lys Thr Glu Ile Thr  Leu Ala Asn Gly Glu  Ile Arg Lys
    1055                1060                1065

Arg Pro  Leu Ile Glu Thr Asn  Gly Glu Thr Gly Glu  Ile Val Trp
    1070                1075                1080

Asp Lys  Gly Arg Asp Phe Ala  Thr Val Arg Lys Val  Leu Ser Met
    1085                1090                1095

Pro Gln  Val Asn Ile Val Lys  Lys Thr Glu Val Gln  Thr Gly Gly
    1100                1105                1110

Phe Ser  Lys Glu Ser Ile Leu  Pro Lys Arg Asn Ser  Asp Lys Leu
    1115                1120                1125

Ile Ala  Arg Lys Lys Asp Trp  Asp Pro Lys Lys Tyr  Gly Gly Phe
    1130                1135                1140

Asp Ser  Pro Thr Val Ala Tyr  Ser Val Leu Val Val  Ala Lys Val
    1145                1150                1155

Glu Lys  Gly Lys Ser Lys Lys  Leu Lys Ser Val Lys  Glu Leu Leu
    1160                1165                1170

Gly Ile  Thr Ile Met Glu Arg  Ser Ser Phe Glu Lys  Asn Pro Ile
    1175                1180                1185

Asp Phe  Leu Glu Ala Lys Gly  Tyr Lys Glu Val Lys  Lys Asp Leu
    1190                1195                1200
```

-continued

```
Ile Ile  Lys Leu Pro Lys Tyr  Ser Leu Phe Glu Leu  Glu Asn Gly
    1205                 1210                 1215

Arg Lys  Arg Met Leu Ala Ser  Ala Gly Glu Leu Gln  Lys Gly Asn
    1220                 1225                 1230

Glu Leu  Ala Leu Pro Ser Lys  Tyr Val Asn Phe Leu  Tyr Leu Ala
    1235                 1240                 1245

Ser His  Tyr Glu Lys Leu Lys  Gly Ser Pro Glu Asp  Asn Glu Gln
    1250                 1255                 1260

Lys Gln  Leu Phe Val Glu Gln  His Lys His Tyr Leu  Asp Glu Ile
    1265                 1270                 1275

Ile Glu  Gln Ile Ser Glu Phe  Ser Lys Arg Val Ile  Leu Ala Asp
    1280                 1285                 1290

Ala Asn  Leu Asp Lys Val Leu  Ser Ala Tyr Asn Lys  His Arg Asp
    1295                 1300                 1305

Lys Pro  Ile Arg Glu Gln Ala  Glu Asn Ile Ile His  Leu Phe Thr
    1310                 1315                 1320

Leu Thr  Asn Leu Gly Ala Pro  Ala Ala Phe Lys Tyr  Phe Asp Thr
    1325                 1330                 1335

Thr Ile  Asp Arg Lys Arg Tyr  Thr Ser Thr Lys Glu  Val Leu Asp
    1340                 1345                 1350

Ala Thr  Leu Ile His Gln Ser  Ile Thr Gly Leu Tyr  Glu Thr Arg
    1355                 1360                 1365

Ile Asp  Leu Ser Gln Leu Gly  Gly Asp Lys Lys Lys  Lys Leu Lys
    1370                 1375                 1380

Leu


<210> SEQ ID NO 9
<211> LENGTH: 412
<212> TYPE: DNA
<213> ORGANISM: Artificial Sequence
<220> FEATURE:
<223> OTHER INFORMATION: Synthetic sequence

<400> SEQUENCE: 9

gaattcggat cctctttgaa aagataatgt atgattatgc tttcactcat atttatacag     60

aaacttgatg ttttctttcg agtatataca aggtgattac atgtacgttt gaagtacaac    120

tctagatttt gtagtgccct cttgggctag cggtaaaggt gcgcattttt tcacacccta    180

caatgttctg ttcaaaagat tttggtcaaa cgctgtagaa gtgaaagttg gtgcgcatgt    240

ttcggcgttc gaaacttctc cgcagtgaaa gataaatgat cgtcctcgag caaaaggtgc    300

cgttttagag ctagaaatag caagttaaaa taaggctagt ccgttatcaa cttgaaaaag    360

tggcaccgag tcggtggtgc ttttttttgtt ttttatgtct gaattcggat cc           412


<210> SEQ ID NO 10
<211> LENGTH: 540
<212> TYPE: DNA
<213> ORGANISM: Artificial Sequence
<220> FEATURE:
<223> OTHER INFORMATION: Synthetic sequence

<400> SEQUENCE: 10

gaattcggat ccaaaaaaca ctagtaagta cttacttatg tattattaac tactttagct     60

aacttctgca gtactaccta agaggctagg ggtagtttta tagcagactt atagctatta    120

tttttattta gtaaagtgct tttaaagtaa ggtctttttt atagcacttt ttatttatta    180
```

-continued taatatatat tatataataa ttttaagcct ggaatagtaa agaggcttat ataataattt 240
atagtaataa aagcttagca gctgtaatat aattcctaaa gaaacagcat gaaatggtat 300
tatgtaagag ctatagtcta aaggcactct gctggataaa aatagtggct ataagtctgc 360
tgcaaaacta cccccaacct cgtaggtata taagtactgt ttgatggtag tctatcgtcc 420
tcgagcaaaa ggtgccgttt tagagctaga aatagcaagt taaaataagg ctagtccgtt 480
atcaacttga aaaagtggca ccgagtcggt ggtgcttttt tttctcttga attcggatcc 540

<210> SEQ ID NO 11
<211> LENGTH: 597
<212> TYPE: DNA
<213> ORGANISM: Artificial Sequence
<220> FEATURE:
<223> OTHER INFORMATION: Synthetic sequence

<400> SEQUENCE: 11
gaattcggat ccaaaaaaca ctagtaagta cttacttatg tattattaac tactttagct 60
aacttctgca gtactaccta agaggctagg ggtagtttta tagcagactt atagctatta 120
tttttattta gtaaagtgct tttaaagtaa ggtctttttt atagcacttt ttatttatta 180
taatatatat tatataataa ttttaagcct ggaatagtaa agaggcttat ataataattt 240
atagtaataa aagcttagca gctgtaatat aattcctaaa gaaacagcat gaaatggtat 300
tatgtaagag ctatagtcta aaggcactct gctggataaa aatagtggct ataagtctgc 360
tgcaaaacta cccccaacct cgtaggtata taagtactgt ttgatggtag tctatcgtcc 420
tcgagcaaaa ggtgccgttt tagagctaga gttcgtttcg gcttttcctc ggaacccca 480 gaggtcatca gttcgaatcg ctaacagaat agcaagttaa aataaggcta gtccgttatc 540
aacttgaaaa agtggcaccg agtcggtggt gctttttttt ctcttgaatt cggatcc 597

<210> SEQ ID NO 12
<211> LENGTH: 315
<212> TYPE: DNA
<213> ORGANISM: Artificial Sequence
<220> FEATURE:
<223> OTHER INFORMATION: Synthetic sequence

<400> SEQUENCE: 12
aattcctaaa gaaacagcat gaaatggtat tatgtaagag ctatagtcta aaggcactct 60
gctggataaa aatagtggct ataagtctgc tgcaaaacta cccccaacct cgtaggtata 120
taagtactgt ttgatggtag tctatcgcca atggcgacgg cagcacgttt tagagctaga 180
gttcgtttcg gcttttcctc ggaacccca gaggtcatca gttcgaatcg ctaacagaat 240
agcaagttaa aataaggcta gtccgttatc aacttgaaaa agtggcaccg agtcggtggt 300
gctttttttt ctctt 315

<210> SEQ ID NO 13
<211> LENGTH: 39
<212> TYPE: DNA
<213> ORGANISM: Artificial Sequence
<220> FEATURE:
<223> OTHER INFORMATION: Primer

<400> SEQUENCE: 13
cgtcagctta agaattccta aagaaacagc atgaaatgg 39

<210> SEQ ID NO 14
<211> LENGTH: 47

-continued

<212> TYPE: DNA
<213> ORGANISM: Artificial Sequence
<220> FEATURE:
<223> OTHER INFORMATION: Primer

<400> SEQUENCE: 14
cgtcagggcc acgtgggcca agagaaaaaa aagcaccacc gactcgg 47

<210> SEQ ID NO 15
<211> LENGTH: 23
<212> TYPE: DNA
<213> ORGANISM: Artificial Sequence
<220> FEATURE:
<223> OTHER INFORMATION: Primer

<400> SEQUENCE: 15
tgaacacagc caccgacatc agc 23

<210> SEQ ID NO 16
<211> LENGTH: 23
<212> TYPE: DNA
<213> ORGANISM: Artificial Sequence
<220> FEATURE:
<223> OTHER INFORMATION: Primer

<400> SEQUENCE: 16
gctggtgagg gtttgtgcta ttg 23

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
gattgcttgg gaggaggaca t 21

<210> SEQ ID NO 18
<211> LENGTH: 23
<212> TYPE: DNA
<213> ORGANISM: Artificial Sequence
<220> FEATURE:
<223> OTHER INFORMATION: Primer

<400> SEQUENCE: 18
cgaggccact gatgaagttg ttc 23

<210> SEQ ID NO 19
<211> LENGTH: 23
<212> TYPE: DNA
<213> ORGANISM: Artificial Sequence
<220> FEATURE:
<223> OTHER INFORMATION: Primer

<400> SEQUENCE: 19
cagttttcca aggctgccaa cgc 23

<210> SEQ ID NO 20
<211> LENGTH: 22
<212> TYPE: DNA
<213> ORGANISM: Artificial Sequence
<220> FEATURE:
<223> OTHER INFORMATION: Primer

<400> SEQUENCE: 20
ctgatcttgc accctggaaa tc 22

<210> SEQ ID NO 21
<211> LENGTH: 23
<212> TYPE: DNA
<213> ORGANISM: Artificial Sequence
<220> FEATURE:
<223> OTHER INFORMATION: Primer

<400> SEQUENCE: 21
ctctctatca tttgccaccc tcc 23

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
ctccattcac cctcaattct cc 22

<210> SEQ ID NO 23
<211> LENGTH: 23
<212> TYPE: DNA
<213> ORGANISM: Artificial Sequence
<220> FEATURE:
<223> OTHER INFORMATION: Primer

<400> SEQUENCE: 23
gttcccttgg cggtgcttgg atc 23

<210> SEQ ID NO 24
<211> LENGTH: 23
<212> TYPE: DNA
<213> ORGANISM: Artificial Sequence
<220> FEATURE:
<223> OTHER INFORMATION: Primer

<400> SEQUENCE: 24
caatagcaca aaccctcacc agc 23

<210> SEQ ID NO 25
<211> LENGTH: 23
<212> TYPE: DNA
<213> ORGANISM: Artificial Sequence
<220> FEATURE:
<223> OTHER INFORMATION: Primer

<400> SEQUENCE: 25
gaacaacttc atcagtggcc tcg 23

<210> SEQ ID NO 26
<211> LENGTH: 23
<212> TYPE: DNA
<213> ORGANISM: Artificial Sequence
<220> FEATURE:
<223> OTHER INFORMATION: Primer

<400> SEQUENCE: 26
ccgttagttg aagatccttg ccg 23

<210> SEQ ID NO 27

<211> LENGTH: 23
<212> TYPE: DNA
<213> ORGANISM: Artificial Sequence
<220> FEATURE:
<223> OTHER INFORMATION: Primer

<400> SEQUENCE: 27
gtcgaggatt tgcttcatac ctc 23

<210> SEQ ID NO 28
<211> LENGTH: 23
<212> TYPE: DNA
<213> ORGANISM: Artificial Sequence
<220> FEATURE:
<223> OTHER INFORMATION: Primer

<400> SEQUENCE: 28
gagagacgca ggatgactca aag 23

<210> SEQ ID NO 29
<211> LENGTH: 23
<212> TYPE: DNA
<213> ORGANISM: Artificial Sequence
<220> FEATURE:
<223> OTHER INFORMATION: Primer

<400> SEQUENCE: 29
tgccgtgggt cattggcata ttc 23

<210> SEQ ID NO 30
<211> LENGTH: 23
<212> TYPE: DNA
<213> ORGANISM: Artificial Sequence
<220> FEATURE:
<223> OTHER INFORMATION: Primer

<400> SEQUENCE: 30
tgccgacttt gtccagtgat tcg 23

<210> SEQ ID NO 31
<211> LENGTH: 23
<212> TYPE: DNA
<213> ORGANISM: Artificial Sequence
<220> FEATURE:
<223> OTHER INFORMATION: Primer

<400> SEQUENCE: 31
ttacatgtgg acgcgagata gcg 23

<210> SEQ ID NO 32
<211> LENGTH: 22
<212> TYPE: DNA
<213> ORGANISM: Artificial Sequence
<220> FEATURE:
<223> OTHER INFORMATION: Primer

<400> SEQUENCE: 32
gtgtgtctaa tgcctccacc ac 22

<210> SEQ ID NO 33
<211> LENGTH: 22
<212> TYPE: DNA
<213> ORGANISM: Artificial Sequence
<220> FEATURE:
<223> OTHER INFORMATION: Primer

<400> SEQUENCE: 33
gatcgtgcta gcgctgctgt tg 22

<210> SEQ ID NO 34
<211> LENGTH: 21
<212> TYPE: DNA
<213> ORGANISM: Artificial Sequence
<220> FEATURE:
<223> OTHER INFORMATION: Primer

<400> SEQUENCE: 34
ccgtgatgga gcccgtcttc t 21

<210> SEQ ID NO 35
<211> LENGTH: 22
<212> TYPE: DNA
<213> ORGANISM: Artificial Sequence
<220> FEATURE:
<223> OTHER INFORMATION: Primer

<400> SEQUENCE: 35
cgcggtgagt tcaggctttt tc 22

<210> SEQ ID NO 36
<211> LENGTH: 22
<212> TYPE: DNA
<213> ORGANISM: Artificial Sequence
<220> FEATURE:
<223> OTHER INFORMATION: Primer

<400> SEQUENCE: 36
gtataagagc aggaggaggg ag 22

<210> SEQ ID NO 37
<211> LENGTH: 22
<212> TYPE: DNA
<213> ORGANISM: Artificial Sequence
<220> FEATURE:
<223> OTHER INFORMATION: Primer

<400> SEQUENCE: 37
gaacgcctca atcagtcagt cg 22

<210> SEQ ID NO 38
<211> LENGTH: 2431
<212> TYPE: DNA
<213> ORGANISM: Artificial Sequence
<220> FEATURE:
<223> OTHER INFORMATION: Synthetic sequence

<400> SEQUENCE: 38
tcaggaaata gctttaagta gcttattaag tattaaaatt atatatattt ttaatataac 60
tatatttctt taataaatag gtattttaag ctttatatat aaatataata ataaaataat 120
atattatata gctttttatt aataaataaa atagctaaaa atataaaaaa aatagcttta 180
aaatacttat ttttaattag aattttatat atttttaata tataagatct tttacttttt 240
tataagcttc ctaccttaaa ttaaattttt actttttttt actattttac tatatcttaa 300
ataaaggctt taaaaatata aaaaaaatct tcttatatat tataagctat aaggattata 360
tatatatttt tttttaattt ttaaagtaag tattaaagct agaattaaag ttttaatttt 420
ttaaggcttt atttaaaaaa aggcagtaat agcttataaa agaaatttct ttttctttta 480

-continued

```
tactaaaagt actttttttt taataaggtt agggttaggg tttactcaca ccgaccatcc    540
caaccacatc ttagggttag ggttagggtt agggttaggg ttagggttag ggttagggta    600
agggtttaaa caaagccacg ttgtgtctca aaatctctga tgttacattg cacaagataa    660
aaatatatca tcatgaacaa taaaactgtc tgcttacata aacagtaata caaggggtgt    720
tatgagccat attcaacggg aaacgtcttg ctcgaggccg cgattaaatt ccaacatgga    780
tgctgattta tatgggtata aatgggctcg cgataatgtc gggcaatcag gtgcgacaat    840
ctatcgattg tatgggaagc ccgatgcgcc agagttgttt ctgaaacatg gcaaaggtag    900
cgttgccaat gatgttacag atgagatggt cagactaaac tggctgacgg aatttatgcc    960
tcttccgacc atcaagcatt ttatccgtac tcctgatgat gcatggttac tcaccactgc   1020
gatccccggg aaaacagcat tccaggtatt agaagaatat cctgattcag gtgaaaatat   1080
tgttgatgcg ctggcagtgt tcctgcgccg gttgcattcg attcctgttt gtaattgtcc   1140
ttttaacagc gatcgcgtat ttcgtctcgc tcaggcgcaa tcacgaatga ataacggttt   1200
ggttgatgcg agtgattttg atgacgagcg taatggctgg cctgttgaac aagtctggaa   1260
agaaatgcat aagcttttgc cattctcacc ggattcagtc gtcactcatg gtgatttctc   1320
acttgataac cttatttttg acgaggggaa attaataggt tgtattgatg ttggacgagt   1380
cggaatcgca gaccgatacc aggatcttgc catcctatgg aactgcctcg gtgagttttc   1440
tccttcatta cagaaacggc tttttcaaaa atatggtatt gataatcctg atatgaataa   1500
attgcagttt catttgatgc tcgatgagtt tttctaatca gaattggtta attggttgta   1560
acactggcag agcattacgc tgacttgacg ggacggcggc tttgttgaat aaatcgaact   1620
tttgctgagt tgaaggatca gatcacgcat cttcccgaca acgcagaccg ttccgtggca   1680
aagcaaaagt tcaaaatcac caactggtcc acctacaaca aagctctcat caaccgtggc   1740
tccctcactt tctggctgga tgatggggcg attcaggcct ggtatgagtc agcaacacct   1800
tcttcacgag gcagacctca gcggtttaaa cctaacccta accctaaccc taaccctaac   1860
cctaacccta accctaaccc taaccctaac cctaacccta accctaaccc taacctaacc   1920
ctaatggggt cgatctgaac cgaggatgag ggttctatag actaatctac aggccgtaca   1980
tggtgtgatt gcagatgcga cgggcaaggt gtacagtgtc cagaaggagg agagcggcat   2040
aggtattgta atagaccagc tttacataat aatcgcctgt tgctactgac tgatgacctt   2100
cttccctaac cagtttccta attaccactg cagtgaggat aaccctaact cgctctgggg   2160
ttattattat actgattagc aggtggctta tatagtgctg aagtactata agagtttctg   2220
cgggaggagg tggaaggact ataaactgga cacagttagg gatagagtga tgacaagacc   2280
tgaatgttat cctccggtgt ggtatagcga attggctgac cttgcagatg gtaatggttt   2340
aggcagggtt tttgcagagg gggacgagaa cgcgttctgc gatttaacgg ctgctgccgc   2400
caagctttac ggttctctaa tgggcggccg c                                  2431
```

<210> SEQ ID NO 39
<211> LENGTH: 982
<212> TYPE: DNA
<213> ORGANISM: Artificial Sequence
<220> FEATURE:
<223> OTHER INFORMATION: Synthetic sequence

<400> SEQUENCE: 39

```
gtgtgtctaa tgcctccacc acaggaacca aaccggcttt gacctctggg aagaagtcaa     60
tgggagctca ttctttactg ttgccaacca gcaccgaggt atgaagcaaa tcctcgacat    120
```

tcgctgctac tgcacatgag cattgttact gaccagctct acagcacttg tcgagggcgc 180
cactcttgct gccactcttg gccagtcggg aagcgcttat tcatctgttg ctccccaggt 240
tttgtgcttt ctccaacgat tctgggtgtc gtctggtgga tacgtcgact ccaacagtat 300
gtcttttcac tgtttatatg agattggcca atactgatag ctcgcctcta gtcaacacca 360
acgagggcag gactggcaag gatgtcaact ccgtcctgac ttccatccac accttcgatc 420
ccaaccttgg ctgtgacgca ggcaccttcc agccatgcag tgacaaagcg ctctccaacc 480
tcaaggttgt tgtcgactcc ttccgctcca tctacggcgt gaacaagggc attcctgcgg 540
tgctgccgtc gccattggcc ggtatgcaga ggatgtgtac tacaacggca acccttggta 600
tcttgctaca tttgctgctg ccgagcagct gtacgatgcc atctacgtct ggaagaagac 660
gggctccatc acggtgaccg ccacctccct ggccttcttc caggagcttg ttcctggcgt 720
gacggccggg acctactcca gcagctcttc gacctttacc aacatcatca acgccgtctc 780
gacatacgcc gatggcttcc tcagcgaggc tgccaagtac gtccccgccg acggttcgct 840
ggccgagcag tttgaccgca acagcggcac tccgctgtct gcgcttcacc tgacgtggtc 900
gtacgcctcg ttcttgacag ccacggcccg tcgggctggc atcgtgcccc cctcgtgggc 960
caacagcagc gctagcacga tc 982

<210> SEQ ID NO 40
<211> LENGTH: 404
<212> TYPE: DNA
<213> ORGANISM: T. reesei

<400> SEQUENCE: 40
aaaaaacact agtaagtact tacttatgta ttattaacta ctttagctaa cttctgcagt 60
actacctaag aggctagggg tagttttata gcagacttat agctattatt tttatttagt 120
aaagtgcttt taaagtaagg tctttttat agcacttttt atttattata atatatatta 180
tataataatt ttaagcctgg aatagtaaag aggcttatat aataatttat agtaataaaa 240
gcttagcagc tgtaatataa ttcctaaaga aacagcatga aatggtatta tgtaagagct 300
atagtctaaa ggcactctgc tggataaaaa tagtggctat aagtctgctg caaaactacc 360
cccaacctcg taggtatata agtactgttt gatggtagtc tatc 404

<210> SEQ ID NO 41
<211> LENGTH: 146
<212> TYPE: DNA
<213> ORGANISM: T. reesei

<400> SEQUENCE: 41
aattcctaaa gaaacagcat gaaatggtat tatgtaagag ctatagtcta aaggcactct 60
gctggataaa aatagtggct ataagtctgc tgcaaaacta cccccaacct cgtaggtata 120
taagtactgt ttgatggtag tctatc 146

<210> SEQ ID NO 42
<211> LENGTH: 57
<212> TYPE: DNA
<213> ORGANISM: T. reesei

<400> SEQUENCE: 42
gttcgtttcg gcttttcctc ggaaccccca gaggtcatca gttcgaatcg ctaacag 57

<210> SEQ ID NO 43

<211> LENGTH: 13
<212> TYPE: DNA
<213> ORGANISM: T. reesei

<400> SEQUENCE: 43 tttttttct ctt 13

<210> SEQ ID NO 44
<211> LENGTH: 4104
<212> TYPE: DNA
<213> ORGANISM: Artificial Sequence
<220> FEATURE:
<223> OTHER INFORMATION: codon optimized seqs

<400> SEQUENCE: 44
atggacaaga agtacagcat cggcctcgac atcggcacca actcggtggg ctgggccgtc 60
atcacggacg aatataaggt cccgtcgaag aagttcaagg tcctcggcaa tacagaccgc 120
cacagcatca agaaaaactt gatcggcgcc ctcctgttcg atagcggcga gaccgcggag 180
gcgaccaggc tcaagaggac cgccaggaga cggtacacta ggcgcaagaa caggatctgc 240
tacctgcagg agatcttcag caacgagatg gcgaaggtgg acgactcctt cttccaccgc 300
ctggaggaat cattcctggt ggaggaggac aagaagcatg agcggcaccc aatcttcggc 360
aacatcgtcg acgaggtggc ctaccacgag aagtacccga caatctacca cctccggaag 420
aaactggtgg acagcacaga caaggcggac ctccggctca tctaccttgc cctcgcgcat 480
atgatcaagt tccgcggcca cttcctcatc gagggcgacc tgaacccgga caactccgac 540
gtggacaagc tgttcatcca gctcgtgcag acgtacaatc aactgttcga ggagaacccc 600
ataaacgcta gcggcgtgga cgccaaggcc atcctctcgg ccaggctctc gaaatcaaga 660
aggctggaga accttatcgc gcagttgcca ggcgaaaaga agaacggcct cttcggcaac 720
cttattgcgc tcagcctcgg cctgacgccg aacttcaaat caaacttcga cctcgcggag 780
gacgccaagc tccagctctc aaaggacacc tacgacgacg acctcgacaa cctcctggcc 840
cagataggag accagtacgc ggacctcttc ctcgccgcca agaacctctc cgacgctatc 900
ctgctcagcg acatccttcg ggtcaacacc gaaattacca aggcaccgct gtccgccagc 960
atgattaaac gctacgacga gcaccatcag gacctcacgc tgctcaaggc actcgtccgc 1020
cagcagctcc ccgagaagta caaggagatc ttcttcgacc aatcaaaaaa cggctacgcg 1080
ggatatatcg acggcggtgc cagccaggaa gagttctaca agttcatcaa accaatcctg 1140
gagaagatgg acggcaccga ggagttgctg gtcaagctca acagggagga cctcctcagg 1200
aagcagagga ccttcgacaa cggctccatc ccgcatcaga tccacctggg cgaactgcat 1260
gccatcctgc ggcgccagga ggacttctac ccgttcctga aggataaccg ggagaagatc 1320
gagaagatct tgacgttccg catcccatac tacgtgggcc cgctggctcg cggcaactcc 1380
cggttcgcct ggatgacccg gaagtcggag gagaccatca caccctggaa ctttgaggag 1440
gtggtcgata agggcgctag cgctcagagc ttcatcgagc gcatgaccaa cttcgataaa 1500
aacctgccca atgaaaaagt cctccccaag cactcgctgc tctacgagta cttcaccgtg 1560
tacaacgagc tcaccaaggt caaatacgtc accgagggca tgcggaagcc ggcgttcctg 1620
agcggcgagc agaagaaggc gatagtggac ctcctcttca agaccaacag gaaggtgacc 1680
gtgaagcaat taaaagagga ctacttcaag aaaatagagt gcttcgactc cgtggagatc 1740
tcgggcgtgg aggatcggtt caacgcctca ctcggcacgt atcacgacct cctcaagatc 1800
attaaagaca aggacttcct cgacaacgag gagaacgagg acatcctcga ggacatcgtc 1860

```
ctcaccctga ccctgttcga ggaccgcgaa atgatcgagg agaggctgaa gacctacgcg   1920
cacctgttcg acgacaaggt catgaaacag ctcaagaggc gccgctacac tggttgggga   1980
aggctgtccc gcaagctcat taatggcatc agggacaagc agagcggcaa gaccatcctg   2040
gacttcctca agtccgacgg gttcgccaac cgcaacttca tgcagctcat tcacgacgac   2100
tcgctcacgt tcaaggaaga catccagaag gcacaggtga gcgggcaggg tgactccctc   2160
cacgaacaca tcgccaacct ggccggctcg ccggccatta aaaagggcat cctgcagacg   2220
gtcaaggtcg tcgacgagct cgtgaaggtg atgggccggc acaagcccga aaatatcgtc   2280
atagagatgg ccagggagaa ccagaccacc caaaaagggc agaagaactc gcgcgagcgg   2340
atgaaacgga tcgaggaggg cattaaagag ctcgggtccc agatcctgaa ggagcacccc   2400
gtggaaaata cccagctcca gaatgaaaag ctctacctct actacctgca gaacggccgc   2460
gacatgtacg tggaccagga gctggacatt aatcggctat cggactacga cgtcgaccac   2520
atcgtgccgc agtcgttcct caaggacgat agcatcgaca acaaggtgct cacccggtcg   2580
gataaaaatc ggggcaagag cgacaacgtg cccagcgagg aggtcgtgaa gaagatgaaa   2640
aactactggc gccagctcct caacgcgaaa ctgatcaccc agcgcaagtt cgacaacctg   2700
acgaaggcgg aacgcggtgg cttgagcgaa ctcgataagg cgggcttcat aaaaaggcag   2760
ctggtcgaga cgcgccagat cacgaagcat gtcgcccaga tcctggacag ccgcatgaat   2820
actaagtacg atgaaaacga caagctgatc cgggaggtga aggtgatcac gctgaagtcc   2880
aagctcgtgt cggacttccg caaggacttc cagttctaca aggtccgcga gatcaacaac   2940
taccaccacg cccacgacgc ctacctgaat gcggtggtcg ggaccgccct gatcaagaag   3000
tacccgaagc tggagtcgga gttcgtgtac ggcgactaca aggtctacga cgtgcgcaaa   3060
atgatcgcca agtccgagca ggagatcggc aaggccacgg caaaatactt cttctactcg   3120
aacatcatga acttcttcaa gaccgagatc accctcgcga acggcgagat ccgcaagcgc   3180
ccgctcatcg aaaccaacgg cgagacgggc gagatcgtct gggataaggg ccgggatttc   3240
gcgacggtcc gcaaggtgct ctccatgccg caagtcaata tcgtgaaaaa gacggaggtc   3300
cagacgggcg ggttcagcaa ggagtccatc ctcccgaagc gcaactccga caagctcatc   3360
gcgaggaaga aggattggga cccgaaaaaa tatggcggct tcgacagccc gaccgtcgca   3420
tacagcgtcc tcgtcgtggc gaaggtggag aagggcaagt caaagaagct caagtccgtg   3480
aaggagctgc tcgggatcac gattatggag cggtcctcct tcgagaagaa cccgatcgac   3540
ttcctagagg ccaagggata taaggaggtc aagaaggacc tgattattaa actgccgaag   3600
tactcgctct tcgagctgga aaacggccgc aagaggatgc tcgcctccgc aggcgagttg   3660
cagaagggca acgagctcgc cctcccgagc aaatacgtca atttcctgta cctcgctagc   3720
cactatgaaa agctcaaggg cagcccggag gacaacgagc agaagcagct cttcgtggag   3780
cagcacaagc attacctgga cgagatcatc gagcagatca gcgagttctc gaagcgggtg   3840
atcctcgccg acgcgaacct ggacaaggtg ctgtcggcat ataacaagca ccgcgacaaa   3900
ccaatacgcg agcaggccga aaatatcatc cacctcttca ccctcaccaa cctcggcgct   3960
ccggcagcct tcaagtactt cgacaccacg attgaccgga agcggtacac gagcacgaag   4020
gaggtgctcg atgcgacgct gatccaccag agcatcacag ggctctatga aacacgcatc   4080
gacctgagcc agctgggcgg agac                                          4104
```

<210> SEQ ID NO 45

-continued

<211> LENGTH: 1368
<212> TYPE: PRT
<213> ORGANISM: Artificial Sequence
<220> FEATURE:
<223> OTHER INFORMATION: protein expressed from synthetic construct

<400> SEQUENCE: 45

Met Asp Lys Lys Tyr Ser Ile Gly Leu Asp Ile Gly Thr Asn Ser Val
1 5 10 15

Gly Trp Ala Val Ile Thr Asp Glu Tyr Lys Val Pro Ser Lys Lys Phe
20 25 30

Lys Val Leu Gly Asn Thr Asp Arg His Ser Ile Lys Lys Asn Leu Ile
35 40 45

Gly Ala Leu Leu Phe Asp Ser Gly Glu Thr Ala Glu Ala Thr Arg Leu
50 55 60

Lys Arg Thr Ala Arg Arg Arg Tyr Thr Arg Arg Lys Asn Arg Ile Cys
65 70 75 80

Tyr Leu Gln Glu Ile Phe Ser Asn Glu Met Ala Lys Val Asp Asp Ser
85 90 95

Phe Phe His Arg Leu Glu Glu Ser Phe Leu Val Glu Glu Asp Lys Lys
100 105 110

His Glu Arg His Pro Ile Phe Gly Asn Ile Val Asp Glu Val Ala Tyr
115 120 125

His Glu Lys Tyr Pro Thr Ile Tyr His Leu Arg Lys Lys Leu Val Asp
130 135 140

Ser Thr Asp Lys Ala Asp Leu Arg Leu Ile Tyr Leu Ala Leu Ala His
145 150 155 160

Met Ile Lys Phe Arg Gly His Phe Leu Ile Glu Gly Asp Leu Asn Pro
165 170 175

Asp Asn Ser Asp Val Asp Lys Leu Phe Ile Gln Leu Val Gln Thr Tyr
180 185 190

Asn Gln Leu Phe Glu Glu Asn Pro Ile Asn Ala Ser Gly Val Asp Ala
195 200 205

Lys Ala Ile Leu Ser Ala Arg Leu Ser Lys Ser Arg Arg Leu Glu Asn
210 215 220

Leu Ile Ala Gln Leu Pro Gly Glu Lys Lys Asn Gly Leu Phe Gly Asn
225 230 235 240

Leu Ile Ala Leu Ser Leu Gly Leu Thr Pro Asn Phe Lys Ser Asn Phe
245 250 255

Asp Leu Ala Glu Asp Ala Lys Leu Gln Leu Ser Lys Asp Thr Tyr Asp
260 265 270

Asp Asp Leu Asp Asn Leu Leu Ala Gln Ile Gly Asp Gln Tyr Ala Asp
275 280 285

Leu Phe Leu Ala Ala Lys Asn Leu Ser Asp Ala Ile Leu Leu Ser Asp
290 295 300

Ile Leu Arg Val Asn Thr Glu Ile Thr Lys Ala Pro Leu Ser Ala Ser
305 310 315 320

Met Ile Lys Arg Tyr Asp Glu His His Gln Asp Leu Thr Leu Leu Lys
325 330 335

Ala Leu Val Arg Gln Gln Leu Pro Glu Lys Tyr Lys Glu Ile Phe Phe
340 345 350

Asp Gln Ser Lys Asn Gly Tyr Ala Gly Tyr Ile Asp Gly Gly Ala Ser
355 360 365

Gln Glu Glu Phe Tyr Lys Phe Ile Lys Pro Ile Leu Glu Lys Met Asp
370 375 380

```
Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800
```

-continued

```
Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200
```

```
Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365


<210> SEQ ID NO 46
<211> LENGTH: 7
<212> TYPE: PRT
<213> ORGANISM: SV40

<400> SEQUENCE: 46

Pro Lys Lys Lys Arg Lys Val
1               5


<210> SEQ ID NO 47
<211> LENGTH: 7
<212> TYPE: PRT
<213> ORGANISM: T. reesei

<400> SEQUENCE: 47

Lys Lys Lys Lys Leu Lys Leu
1               5


<210> SEQ ID NO 48
<211> LENGTH: 1388
<212> TYPE: PRT
<213> ORGANISM: Streptococcus thermophilus

<400> SEQUENCE: 48

Met Thr Lys Pro Tyr Ser Ile Gly Leu Asp Ile Gly Thr Asn Ser Val
1               5                   10                  15

Gly Trp Ala Val Thr Thr Asp Asn Tyr Lys Val Pro Ser Lys Lys Met
            20                  25                  30

Lys Val Leu Gly Asn Thr Ser Lys Lys Tyr Ile Lys Lys Asn Leu Leu
        35                  40                  45

Gly Val Leu Leu Phe Asp Ser Gly Ile Thr Ala Glu Gly Arg Arg Leu
    50                  55                  60

Lys Arg Thr Ala Arg Arg Arg Tyr Thr Arg Arg Arg Asn Arg Ile Leu
65                  70                  75                  80
```

-continued

```
Tyr Leu Gln Glu Ile Phe Ser Thr Glu Met Ala Thr Leu Asp Asp Ala
                85                  90                  95

Phe Phe Gln Arg Leu Asp Asp Ser Phe Leu Val Pro Asp Asp Lys Arg
            100                 105                 110

Asp Ser Lys Tyr Pro Ile Phe Gly Asn Leu Val Glu Glu Lys Ala Tyr
        115                 120                 125

His Asp Glu Phe Pro Thr Ile Tyr His Leu Arg Lys Tyr Leu Ala Asp
    130                 135                 140

Ser Thr Lys Lys Ala Asp Leu Arg Leu Val Tyr Leu Ala Leu Ala His
145                 150                 155                 160

Met Ile Lys Tyr Arg Gly His Phe Leu Ile Glu Gly Glu Phe Asn Ser
                165                 170                 175

Lys Asn Asn Asp Ile Gln Lys Asn Phe Gln Asp Phe Leu Asp Thr Tyr
            180                 185                 190

Asn Ala Ile Phe Glu Ser Asp Leu Ser Leu Glu Asn Ser Lys Gln Leu
        195                 200                 205

Glu Glu Ile Val Lys Asp Lys Ile Ser Lys Leu Glu Lys Lys Asp Arg
    210                 215                 220

Ile Leu Lys Leu Phe Pro Gly Glu Lys Asn Ser Gly Ile Phe Ser Glu
225                 230                 235                 240

Phe Leu Lys Leu Ile Val Gly Asn Gln Ala Asp Phe Arg Lys Cys Phe
                245                 250                 255

Asn Leu Asp Glu Lys Ala Ser Leu His Phe Ser Lys Glu Ser Tyr Asp
            260                 265                 270

Glu Asp Leu Glu Thr Leu Leu Gly Tyr Ile Gly Asp Asp Tyr Ser Asp
        275                 280                 285

Val Phe Leu Lys Ala Lys Lys Leu Tyr Asp Ala Ile Leu Leu Ser Gly
    290                 295                 300

Phe Leu Thr Val Thr Asp Asn Glu Thr Glu Ala Pro Leu Ser Ser Ala
305                 310                 315                 320

Met Ile Lys Arg Tyr Asn Glu His Lys Glu Asp Leu Ala Leu Leu Lys
                325                 330                 335

Glu Tyr Ile Arg Asn Ile Ser Leu Lys Thr Tyr Asn Glu Val Phe Lys
            340                 345                 350

Asp Asp Thr Lys Asn Gly Tyr Ala Gly Tyr Ile Asp Gly Lys Thr Asn
        355                 360                 365

Gln Glu Asp Phe Tyr Val Tyr Leu Lys Lys Leu Leu Ala Glu Phe Glu
    370                 375                 380

Gly Ala Asp Tyr Phe Leu Glu Lys Ile Asp Arg Glu Asp Phe Leu Arg
385                 390                 395                 400

Lys Gln Arg Thr Phe Asp Asn Gly Ser Ile Pro Tyr Gln Ile His Leu
                405                 410                 415

Gln Glu Met Arg Ala Ile Leu Asp Lys Gln Ala Lys Phe Tyr Pro Phe
            420                 425                 430

Leu Ala Lys Asn Lys Glu Arg Ile Glu Lys Ile Leu Thr Phe Arg Ile
        435                 440                 445

Pro Tyr Tyr Val Gly Pro Leu Ala Arg Gly Asn Ser Asp Phe Ala Trp
    450                 455                 460

Ser Ile Arg Lys Arg Asn Glu Lys Ile Thr Pro Trp Asn Phe Glu Asp
465                 470                 475                 480

Val Ile Asp Lys Glu Ser Ser Ala Glu Ala Phe Ile Asn Arg Met Thr
                485                 490                 495
```

```
Ser Phe Asp Leu Tyr Leu Pro Glu Glu Lys Val Leu Pro Lys His Ser
            500                 505                 510

Leu Leu Tyr Glu Thr Phe Asn Val Tyr Asn Glu Leu Thr Lys Val Arg
        515                 520                 525

Phe Ile Ala Glu Ser Met Arg Asp Tyr Gln Phe Leu Asp Ser Lys Gln
    530                 535                 540

Lys Lys Asp Ile Val Arg Leu Tyr Phe Lys Asp Lys Arg Lys Val Thr
545                 550                 555                 560

Asp Lys Asp Ile Ile Glu Tyr Leu His Ala Ile Tyr Gly Tyr Asp Gly
                565                 570                 575

Ile Glu Leu Lys Gly Ile Glu Lys Gln Phe Asn Ser Ser Leu Ser Thr
            580                 585                 590

Tyr His Asp Leu Leu Asn Ile Ile Asn Asp Lys Glu Phe Leu Asp Asp
        595                 600                 605

Ser Ser Asn Glu Ala Ile Ile Glu Glu Ile Ile His Thr Leu Thr Ile
    610                 615                 620

Phe Glu Asp Arg Glu Met Ile Lys Gln Arg Leu Ser Lys Phe Glu Asn
625                 630                 635                 640

Ile Phe Asp Lys Ser Val Leu Lys Lys Leu Ser Arg Arg His Tyr Thr
                645                 650                 655

Gly Trp Gly Lys Leu Ser Ala Lys Leu Ile Asn Gly Ile Arg Asp Glu
            660                 665                 670

Lys Ser Gly Asn Thr Ile Leu Asp Tyr Leu Ile Asp Asp Gly Ile Ser
        675                 680                 685

Asn Arg Asn Phe Met Gln Leu Ile His Asp Asp Ala Leu Ser Phe Lys
    690                 695                 700

Lys Lys Ile Gln Lys Ala Gln Ile Ile Gly Asp Glu Asp Lys Gly Asn
705                 710                 715                 720

Ile Lys Glu Val Val Lys Ser Leu Pro Gly Ser Pro Ala Ile Lys Lys
                725                 730                 735

Gly Ile Leu Gln Ser Ile Lys Ile Val Asp Glu Leu Val Lys Val Met
            740                 745                 750

Gly Gly Arg Lys Pro Glu Ser Ile Val Val Glu Met Ala Arg Glu Asn
        755                 760                 765

Gln Tyr Thr Asn Gln Gly Lys Ser Asn Ser Gln Gln Arg Leu Lys Arg
    770                 775                 780

Leu Glu Lys Ser Leu Lys Glu Leu Gly Ser Lys Ile Leu Lys Glu Asn
785                 790                 795                 800

Ile Pro Ala Lys Leu Ser Lys Ile Asp Asn Asn Ala Leu Gln Asn Asp
                805                 810                 815

Arg Leu Tyr Leu Tyr Tyr Leu Gln Asn Gly Lys Asp Met Tyr Thr Gly
            820                 825                 830

Asp Asp Leu Asp Ile Asp Arg Leu Ser Asn Tyr Asp Ile Asp His Ile
        835                 840                 845

Ile Pro Gln Ala Phe Leu Lys Asp Asn Ser Ile Asp Asn Lys Val Leu
    850                 855                 860

Val Ser Ser Ala Ser Asn Arg Gly Lys Ser Asp Asp Val Pro Ser Leu
865                 870                 875                 880

Glu Val Val Lys Lys Arg Lys Thr Phe Trp Tyr Gln Leu Leu Lys Ser
                885                 890                 895

Lys Leu Ile Ser Gln Arg Lys Phe Asp Asn Leu Thr Lys Ala Glu Arg
            900                 905                 910
```

-continued

```
Gly Gly Leu Ser Pro Glu Asp Lys Ala Gly Phe Ile Gln Arg Gln Leu
        915                 920                 925

Val Glu Thr Arg Gln Ile Thr Lys His Val Ala Arg Leu Leu Asp Glu
    930                 935                 940

Lys Phe Asn Asn Lys Lys Asp Glu Asn Asn Arg Ala Val Arg Thr Val
945                 950                 955                 960

Lys Ile Ile Thr Leu Lys Ser Thr Leu Val Ser Gln Phe Arg Lys Asp
                965                 970                 975

Phe Glu Leu Tyr Lys Val Arg Glu Ile Asn Asp Phe His His Ala His
            980                 985                 990

Asp Ala Tyr Leu Asn Ala Val Val  Ala Ser Ala Leu Leu  Lys Lys Tyr
        995                 1000                 1005

Pro Lys  Leu Glu Pro Glu Phe  Val Tyr Gly Asp Tyr  Pro Lys Tyr
    1010                 1015                 1020

Asn Ser  Phe Arg Glu Arg Lys  Ser Ala Thr Glu Lys  Val Tyr Phe
    1025                 1030                 1035

Tyr Ser  Asn Ile Met Asn Ile  Phe Lys Lys Ser Ile  Ser Leu Ala
    1040                 1045                 1050

Asp Gly  Arg Val Ile Glu Arg  Pro Leu Ile Glu Val  Asn Glu Glu
    1055                 1060                 1065

Thr Gly  Glu Ser Val Trp Asn  Lys Glu Ser Asp Leu  Ala Thr Val
    1070                 1075                 1080

Arg Arg  Val Leu Ser Tyr Pro  Gln Val Asn Val Val  Lys Lys Val
    1085                 1090                 1095

Glu Glu  Gln Asn His Gly Leu  Asp Arg Gly Lys Pro  Lys Gly Leu
    1100                 1105                 1110

Phe Asn  Ala Asn Leu Ser Ser  Lys Pro Lys Pro Asn  Ser Asn Glu
    1115                 1120                 1125

Asn Leu  Val Gly Ala Lys Glu  Tyr Leu Asp Pro Lys  Lys Tyr Gly
    1130                 1135                 1140

Gly Tyr  Ala Gly Ile Ser Asn  Ser Phe Thr Val Leu  Val Lys Gly
    1145                 1150                 1155

Thr Ile  Glu Lys Gly Ala Lys  Lys Lys Ile Thr Asn  Val Leu Glu
    1160                 1165                 1170

Phe Gln  Gly Ile Ser Ile Leu  Asp Arg Ile Asn Tyr  Arg Lys Asp
    1175                 1180                 1185

Lys Leu  Asn Phe Leu Leu Glu  Lys Gly Tyr Lys Asp  Ile Glu Leu
    1190                 1195                 1200

Ile Ile  Glu Leu Pro Lys Tyr  Ser Leu Phe Glu Leu  Ser Asp Gly
    1205                 1210                 1215

Ser Arg  Arg Met Leu Ala Ser  Ile Leu Ser Thr Asn  Asn Lys Arg
    1220                 1225                 1230

Gly Glu  Ile His Lys Gly Asn  Gln Ile Phe Leu Ser  Gln Lys Phe
    1235                 1240                 1245

Val Lys  Leu Leu Tyr His Ala  Lys Arg Ile Ser Asn  Thr Ile Asn
    1250                 1255                 1260

Glu Asn  His Arg Lys Tyr Val  Glu Asn His Lys Lys  Glu Phe Glu
    1265                 1270                 1275

Glu Leu  Phe Tyr Tyr Ile Leu  Glu Phe Asn Glu Asn  Tyr Val Gly
    1280                 1285                 1290

Ala Lys  Lys Asn Gly Lys Leu  Leu Asn Ser Ala Phe  Gln Ser Trp
    1295                 1300                 1305
```

```
Gln Asn  His Ser Ile Asp Glu  Leu Cys Ser Ser Phe  Ile Gly Pro
    1310                 1315                 1320

Thr Gly  Ser Glu Arg Lys Gly  Leu Phe Glu Leu Thr  Ser Arg Gly
    1325                 1330                 1335

Ser Ala  Ala Asp Phe Glu Phe  Leu Gly Val Lys Ile  Pro Arg Tyr
    1340                 1345                 1350

Arg Asp  Tyr Thr Pro Ser Ser  Leu Leu Lys Asp Ala  Thr Leu Ile
    1355                 1360                 1365

His Gln  Ser Val Thr Gly Leu  Tyr Glu Thr Arg Ile  Asp Leu Ala
    1370                 1375                 1380

Lys Leu  Gly Glu Gly
    1385


<210> SEQ ID NO 49
<211> LENGTH: 1345
<212> TYPE: PRT
<213> ORGANISM: Streptococcus mutans

<400> SEQUENCE: 49

Met Lys Lys Pro Tyr Ser Ile Gly Leu Asp Ile Gly Thr Asn Ser Val
1               5                   10                  15

Gly Trp Ala Val Val Thr Asp Asp Tyr Lys Val Pro Ala Lys Lys Met
            20                  25                  30

Lys Val Leu Gly Asn Thr Asp Lys Ser His Ile Glu Lys Asn Leu Leu
        35                  40                  45

Gly Ala Leu Leu Phe Asp Ser Gly Asn Thr Ala Glu Asp Arg Arg Leu
    50                  55                  60

Lys Arg Thr Ala Arg Arg Arg Tyr Thr Arg Arg Arg Asn Arg Ile Leu
65                  70                  75                  80

Tyr Leu Gln Glu Ile Phe Ser Glu Glu Met Gly Lys Val Asp Asp Ser
                85                  90                  95

Phe Phe His Arg Leu Glu Asp Ser Phe Leu Val Thr Glu Asp Lys Arg
            100                 105                 110

Gly Glu Arg His Pro Ile Phe Gly Asn Leu Glu Glu Glu Val Lys Tyr
        115                 120                 125

His Glu Asn Phe Pro Thr Ile Tyr His Leu Arg Gln Tyr Leu Ala Asp
    130                 135                 140

Asn Pro Glu Lys Val Asp Leu Arg Leu Val Tyr Leu Ala Leu Ala His
145                 150                 155                 160

Ile Ile Lys Phe Arg Gly His Phe Leu Ile Glu Gly Lys Phe Asp Thr
                165                 170                 175

Arg Asn Asn Asp Val Gln Arg Leu Phe Gln Glu Phe Leu Ala Val Tyr
            180                 185                 190

Asp Asn Thr Phe Glu Asn Ser Ser Leu Gln Glu Gln Asn Val Gln Val
        195                 200                 205

Glu Glu Ile Leu Thr Asp Lys Ile Ser Lys Ser Ala Lys Lys Asp Arg
    210                 215                 220

Val Leu Lys Leu Phe Pro Asn Glu Lys Ser Asn Gly Arg Phe Ala Glu
225                 230                 235                 240

Phe Leu Lys Leu Ile Val Gly Asn Gln Ala Asp Phe Lys Lys His Phe
                245                 250                 255

Glu Leu Glu Glu Lys Ala Pro Leu Gln Phe Ser Lys Asp Thr Tyr Glu
            260                 265                 270
```

```
Glu Glu Leu Glu Val Leu Leu Ala Gln Ile Gly Asp Asn Tyr Ala Glu
        275                 280                 285

Leu Phe Leu Ser Ala Lys Lys Leu Tyr Asp Ser Ile Leu Leu Ser Gly
    290                 295                 300

Ile Leu Thr Val Thr Asp Val Gly Thr Lys Ala Pro Leu Ser Ala Ser
305                 310                 315                 320

Met Ile Gln Arg Tyr Asn Glu His Gln Met Asp Leu Ala Gln Leu Lys
                325                 330                 335

Gln Phe Ile Arg Gln Lys Leu Ser Asp Lys Tyr Asn Glu Val Phe Ser
            340                 345                 350

Asp Val Ser Lys Asp Gly Tyr Ala Gly Tyr Ile Asp Gly Lys Thr Asn
        355                 360                 365

Gln Glu Ala Phe Tyr Lys Tyr Leu Lys Gly Leu Leu Asn Lys Ile Glu
    370                 375                 380

Gly Ser Gly Tyr Phe Leu Asp Lys Ile Glu Arg Glu Asp Phe Leu Arg
385                 390                 395                 400

Lys Gln Arg Thr Phe Asp Asn Gly Ser Ile Pro His Gln Ile His Leu
                405                 410                 415

Gln Glu Met Arg Ala Ile Ile Arg Arg Gln Ala Glu Phe Tyr Pro Phe
            420                 425                 430

Leu Ala Asp Asn Gln Asp Arg Ile Glu Lys Leu Leu Thr Phe Arg Ile
        435                 440                 445

Pro Tyr Tyr Val Gly Pro Leu Ala Arg Gly Lys Ser Asp Phe Ala Trp
    450                 455                 460

Leu Ser Arg Lys Ser Ala Asp Lys Ile Thr Pro Trp Asn Phe Asp Glu
465                 470                 475                 480

Ile Val Asp Lys Glu Ser Ser Ala Glu Ala Phe Ile Asn Arg Met Thr
                485                 490                 495

Asn Tyr Asp Leu Tyr Leu Pro Asn Gln Lys Val Leu Pro Lys His Ser
            500                 505                 510

Leu Leu Tyr Glu Lys Phe Thr Val Tyr Asn Glu Leu Thr Lys Val Lys
        515                 520                 525

Tyr Lys Thr Glu Gln Gly Lys Thr Ala Phe Phe Asp Ala Asn Met Lys
    530                 535                 540

Gln Glu Ile Phe Asp Gly Val Phe Lys Val Tyr Arg Lys Val Thr Lys
545                 550                 555                 560

Asp Lys Leu Met Asp Phe Leu Glu Lys Glu Phe Asp Glu Phe Arg Ile
                565                 570                 575

Val Asp Leu Thr Gly Leu Asp Lys Glu Asn Lys Val Phe Asn Ala Ser
            580                 585                 590

Tyr Gly Thr Tyr His Asp Leu Cys Lys Ile Leu Asp Lys Asp Phe Leu
        595                 600                 605

Asp Asn Ser Lys Asn Glu Lys Ile Leu Glu Asp Ile Val Leu Thr Leu
    610                 615                 620

Thr Leu Phe Glu Asp Arg Glu Met Ile Arg Lys Arg Leu Glu Asn Tyr
625                 630                 635                 640

Ser Asp Leu Leu Thr Lys Glu Gln Val Lys Lys Leu Glu Arg Arg His
                645                 650                 655

Tyr Thr Gly Trp Gly Arg Leu Ser Ala Glu Leu Ile His Gly Ile Arg
            660                 665                 670

Asn Lys Glu Ser Arg Lys Thr Ile Leu Asp Tyr Leu Ile Asp Asp Gly
        675                 680                 685
```

-continued

```
Asn Ser Asn Arg Asn Phe Met Gln Leu Ile Asn Asp Asp Ala Leu Ser
    690                 695                 700

Phe Lys Glu Glu Ile Ala Lys Ala Gln Val Ile Gly Glu Thr Asp Asn
705                 710                 715                 720

Leu Asn Gln Val Val Ser Asp Ile Ala Gly Ser Pro Ala Ile Lys Lys
                725                 730                 735

Gly Ile Leu Gln Ser Leu Lys Ile Val Asp Glu Leu Val Lys Ile Met
            740                 745                 750

Gly His Gln Pro Glu Asn Ile Val Val Glu Met Ala Arg Glu Asn Gln
        755                 760                 765

Phe Thr Asn Gln Gly Arg Arg Asn Ser Gln Gln Arg Leu Lys Gly Leu
    770                 775                 780

Thr Asp Ser Ile Lys Glu Phe Gly Ser Gln Ile Leu Lys Glu His Pro
785                 790                 795                 800

Val Glu Asn Ser Gln Leu Gln Asn Asp Arg Leu Phe Leu Tyr Tyr Leu
                805                 810                 815

Gln Asn Gly Arg Asp Met Tyr Thr Gly Glu Glu Leu Asp Ile Asp Tyr
            820                 825                 830

Leu Ser Gln Tyr Asp Ile Asp His Ile Ile Pro Gln Ala Phe Ile Lys
        835                 840                 845

Asp Asn Ser Ile Asp Asn Arg Val Leu Thr Ser Ser Lys Glu Asn Arg
    850                 855                 860

Gly Lys Ser Asp Asp Val Pro Ser Lys Asp Val Val Arg Lys Met Lys
865                 870                 875                 880

Ser Tyr Trp Ser Lys Leu Leu Ser Ala Lys Leu Ile Thr Gln Arg Lys
                885                 890                 895

Phe Asp Asn Leu Thr Lys Ala Glu Arg Gly Gly Leu Thr Asp Asp Asp
            900                 905                 910

Lys Ala Gly Phe Ile Lys Arg Gln Leu Val Glu Thr Arg Gln Ile Thr
        915                 920                 925

Lys His Val Ala Arg Ile Leu Asp Glu Arg Phe Asn Thr Glu Thr Asp
    930                 935                 940

Glu Asn Asn Lys Lys Ile Arg Gln Val Lys Ile Val Thr Leu Lys Ser
945                 950                 955                 960

Asn Leu Val Ser Asn Phe Arg Lys Glu Phe Glu Leu Tyr Lys Val Arg
                965                 970                 975

Glu Ile Asn Asp Tyr His His Ala His Asp Ala Tyr Leu Asn Ala Val
            980                 985                 990

Ile Gly Lys Ala Leu Leu Gly Val  Tyr Pro Gln Leu Glu  Pro Glu Phe
        995                 1000                1005

Val Tyr  Gly Asp Tyr Pro His  Phe His Gly His Lys  Glu Asn Lys
    1010                1015                1020

Ala Thr  Ala Lys Lys Phe Phe  Tyr Ser Asn Ile Met  Asn Phe Phe
    1025                1030                1035

Lys Lys  Asp Asp Val Arg Thr  Asp Lys Asn Gly Glu  Ile Ile Trp
    1040                1045                1050

Lys Lys  Asp Glu His Ile Ser  Asn Ile Lys Lys Val  Leu Ser Tyr
    1055                1060                1065

Pro Gln  Val Asn Ile Val Lys  Lys Val Glu Glu Gln  Thr Gly Gly
    1070                1075                1080

Phe Ser  Lys Glu Ser Ile Leu  Pro Lys Gly Asn Ser  Asp Lys Leu
    1085                1090                1095
```

```
Ile Pro  Arg Lys Thr Lys Lys  Phe Tyr Trp Asp Thr  Lys Lys Tyr
    1100                 1105                 1110

Gly Gly  Phe Asp Ser Pro Ile  Val Ala Tyr Ser Ile  Leu Val Ile
    1115                 1120                 1125

Ala Asp  Ile Glu Lys Gly Lys  Ser Lys Lys Leu Lys  Thr Val Lys
    1130                 1135                 1140

Ala Leu  Val Gly Val Thr Ile  Met Glu Lys Met Thr  Phe Glu Arg
    1145                 1150                 1155

Asp Pro  Val Ala Phe Leu Glu  Arg Lys Gly Tyr Arg  Asn Val Gln
    1160                 1165                 1170

Glu Glu  Asn Ile Ile Lys Leu  Pro Lys Tyr Ser Leu  Phe Lys Leu
    1175                 1180                 1185

Glu Asn  Gly Arg Lys Arg Leu  Leu Ala Ser Ala Arg  Glu Leu Gln
    1190                 1195                 1200

Lys Gly  Asn Glu Ile Val Leu  Pro Asn His Leu Gly  Thr Leu Leu
    1205                 1210                 1215

Tyr His  Ala Lys Asn Ile His  Lys Val Asp Glu Pro  Lys His Leu
    1220                 1225                 1230

Asp Tyr  Val Asp Lys His Lys  Asp Glu Phe Lys Glu  Leu Leu Asp
    1235                 1240                 1245

Val Val  Ser Asn Phe Ser Lys  Lys Tyr Thr Leu Ala  Glu Gly Asn
    1250                 1255                 1260

Leu Glu  Lys Ile Lys Glu Leu  Tyr Ala Gln Asn Asn  Gly Glu Asp
    1265                 1270                 1275

Leu Lys  Glu Leu Ala Ser Ser  Phe Ile Asn Leu Leu  Thr Phe Thr
    1280                 1285                 1290

Ala Ile  Gly Ala Pro Ala Thr  Phe Lys Phe Phe Asp  Lys Asn Ile
    1295                 1300                 1305

Asp Arg  Lys Arg Tyr Thr Ser  Thr Thr Glu Ile Leu  Asn Ala Thr
    1310                 1315                 1320

Leu Ile  His Gln Ser Ile Thr  Gly Leu Tyr Glu Thr  Arg Ile Asp
    1325                 1330                 1335

Leu Asn  Lys Leu Gly Gly Asp
    1340                 1345


<210> SEQ ID NO 50
<211> LENGTH: 984
<212> TYPE: PRT
<213> ORGANISM: Campylobacter jejuni

<400> SEQUENCE: 50

Met Ala Arg Ile Leu Ala Phe Asp Ile Gly Ile Ser Ser Ile Gly Trp
1               5                   10                  15

Ala Phe Ser Glu Asn Asp Glu Leu Lys Asp Cys Gly Val Arg Ile Phe
            20                  25                  30

Thr Lys Val Glu Asn Pro Lys Thr Gly Glu Ser Leu Ala Leu Pro Arg
        35                  40                  45

Arg Leu Ala Arg Ser Ala Arg Lys Arg Leu Ala Arg Arg Lys Ala Arg
    50                  55                  60

Leu Asn His Leu Lys His Leu Ile Ala Asn Glu Phe Lys Leu Asn Tyr
65                  70                  75                  80

Glu Asp Tyr Gln Ser Phe Asp Glu Ser Leu Ala Lys Ala Tyr Lys Gly
                85                  90                  95
```

```
Ser Leu Ile Ser Pro Tyr Glu Leu Arg Phe Arg Ala Leu Asn Glu Leu
            100                 105                 110

Leu Ser Lys Gln Asp Phe Ala Arg Val Ile Leu His Ile Ala Lys Arg
        115                 120                 125

Arg Gly Tyr Asp Asp Ile Lys Asn Ser Asp Asp Lys Glu Lys Gly Ala
    130                 135                 140

Ile Leu Lys Ala Ile Lys Gln Asn Glu Glu Lys Leu Ala Asn Tyr Gln
145                 150                 155                 160

Ser Val Gly Glu Tyr Leu Tyr Lys Glu Tyr Phe Gln Lys Phe Lys Glu
                165                 170                 175

Asn Ser Lys Glu Phe Thr Asn Val Arg Asn Lys Lys Glu Ser Tyr Glu
            180                 185                 190

Arg Cys Ile Ala Gln Ser Phe Leu Lys Asp Glu Leu Lys Leu Ile Phe
        195                 200                 205

Lys Lys Gln Arg Glu Phe Gly Phe Ser Phe Ser Lys Lys Phe Glu Glu
    210                 215                 220

Glu Val Leu Ser Val Ala Phe Tyr Lys Arg Ala Leu Lys Asp Phe Ser
225                 230                 235                 240

His Leu Val Gly Asn Cys Ser Phe Phe Thr Asp Glu Lys Arg Ala Pro
                245                 250                 255

Lys Asn Ser Pro Leu Ala Phe Met Phe Val Ala Leu Thr Arg Ile Ile
            260                 265                 270

Asn Leu Leu Asn Asn Leu Lys Asn Thr Glu Gly Ile Leu Tyr Thr Lys
        275                 280                 285

Asp Asp Leu Asn Ala Leu Leu Asn Glu Val Leu Lys Asn Gly Thr Leu
    290                 295                 300

Thr Tyr Lys Gln Thr Lys Lys Leu Leu Gly Leu Ser Asp Asp Tyr Glu
305                 310                 315                 320

Phe Lys Gly Glu Lys Gly Thr Tyr Phe Ile Glu Phe Lys Lys Tyr Lys
                325                 330                 335

Glu Phe Ile Lys Ala Leu Gly Glu His Asn Leu Ser Gln Asp Asp Leu
            340                 345                 350

Asn Glu Ile Ala Lys Asp Ile Thr Leu Ile Lys Asp Glu Ile Lys Leu
        355                 360                 365

Lys Lys Ala Leu Ala Lys Tyr Asp Leu Asn Gln Asn Gln Ile Asp Ser
    370                 375                 380

Leu Ser Lys Leu Glu Phe Lys Asp His Leu Asn Ile Ser Phe Lys Ala
385                 390                 395                 400

Leu Lys Leu Val Thr Pro Leu Met Leu Glu Gly Lys Lys Tyr Asp Glu
                405                 410                 415

Ala Cys Asn Glu Leu Asn Leu Lys Val Ala Ile Asn Glu Asp Lys Lys
            420                 425                 430

Asp Phe Leu Pro Ala Phe Asn Glu Thr Tyr Tyr Lys Asp Glu Val Thr
        435                 440                 445

Asn Pro Val Val Leu Arg Ala Ile Lys Glu Tyr Arg Lys Val Leu Asn
    450                 455                 460

Ala Leu Leu Lys Lys Tyr Gly Lys Val His Lys Ile Asn Ile Glu Leu
465                 470                 475                 480

Ala Arg Glu Val Gly Lys Asn His Ser Gln Arg Ala Lys Ile Glu Lys
                485                 490                 495

Glu Gln Asn Glu Asn Tyr Lys Ala Lys Lys Asp Ala Glu Leu Glu Cys
            500                 505                 510
```

-continued

```
Glu Lys Leu Gly Leu Lys Ile Asn Ser Lys Asn Ile Leu Lys Leu Arg
        515                 520                 525

Leu Phe Lys Glu Gln Lys Glu Phe Cys Ala Tyr Ser Gly Glu Lys Ile
    530                 535                 540

Lys Ile Ser Asp Leu Gln Asp Glu Lys Met Leu Glu Ile Asp His Ile
545                 550                 555                 560

Tyr Pro Tyr Ser Arg Ser Phe Asp Asp Ser Tyr Met Asn Lys Val Leu
                565                 570                 575

Val Phe Thr Lys Gln Asn Gln Glu Lys Leu Asn Gln Thr Pro Phe Glu
            580                 585                 590

Ala Phe Gly Asn Asp Ser Ala Lys Trp Gln Lys Ile Glu Val Leu Ala
        595                 600                 605

Lys Asn Leu Pro Thr Lys Lys Gln Lys Arg Ile Leu Asp Lys Asn Tyr
    610                 615                 620

Lys Asp Lys Glu Gln Lys Asn Phe Lys Asp Arg Asn Leu Asn Asp Thr
625                 630                 635                 640

Arg Tyr Ile Ala Arg Leu Val Leu Asn Tyr Thr Lys Asp Tyr Leu Asp
                645                 650                 655

Phe Leu Pro Leu Ser Asp Asp Glu Asn Thr Lys Leu Asn Asp Thr Gln
            660                 665                 670

Lys Gly Ser Lys Val His Val Glu Ala Lys Ser Gly Met Leu Thr Ser
        675                 680                 685

Ala Leu Arg His Thr Trp Gly Phe Ser Ala Lys Asp Arg Asn Asn His
    690                 695                 700

Leu His His Ala Ile Asp Ala Val Ile Ile Ala Tyr Ala Asn Asn Ser
705                 710                 715                 720

Ile Val Lys Ala Phe Ser Asp Phe Lys Lys Glu Gln Glu Ser Asn Ser
                725                 730                 735

Ala Glu Leu Tyr Ala Lys Lys Ile Ser Glu Leu Asp Tyr Lys Asn Lys
            740                 745                 750

Arg Lys Phe Phe Glu Pro Phe Ser Gly Phe Arg Gln Lys Val Leu Asp
        755                 760                 765

Lys Ile Asp Glu Ile Phe Val Ser Lys Pro Glu Arg Lys Lys Pro Ser
    770                 775                 780

Gly Ala Leu His Glu Glu Thr Phe Arg Lys Glu Glu Glu Phe Tyr Gln
785                 790                 795                 800

Ser Tyr Gly Gly Lys Glu Gly Val Leu Lys Ala Leu Glu Leu Gly Lys
                805                 810                 815

Ile Arg Lys Val Asn Gly Lys Ile Val Lys Asn Gly Asp Met Phe Arg
            820                 825                 830

Val Asp Ile Phe Lys His Lys Lys Thr Asn Lys Phe Tyr Ala Val Pro
        835                 840                 845

Ile Tyr Thr Met Asp Phe Ala Leu Lys Val Leu Pro Asn Lys Ala Val
    850                 855                 860

Ala Arg Ser Lys Lys Gly Glu Ile Lys Asp Trp Ile Leu Met Asp Glu
865                 870                 875                 880

Asn Tyr Glu Phe Cys Phe Ser Leu Tyr Lys Asp Ser Leu Ile Leu Ile
                885                 890                 895

Gln Thr Lys Asp Met Gln Glu Pro Glu Phe Val Tyr Tyr Asn Ala Phe
            900                 905                 910

Thr Ser Ser Thr Val Ser Leu Ile Val Ser Lys His Asp Asn Lys Phe
        915                 920                 925
```

Glu Thr Leu Ser Lys Asn Gln Lys Ile Leu Phe Lys Asn Ala Asn Glu
    930                 935                 940

Lys Glu Val Ile Ala Lys Ser Ile Gly Ile Gln Asn Leu Lys Val Phe
945                 950                 955                 960

Glu Lys Tyr Ile Val Ser Ala Leu Gly Glu Val Thr Lys Ala Glu Phe
                965                 970                 975

Arg Gln Arg Glu Asp Phe Lys Lys
            980

<210> SEQ ID NO 51
<211> LENGTH: 1082
<212> TYPE: PRT
<213> ORGANISM: Neisseria meningitides

<400> SEQUENCE: 51

Met Ala Ala Phe Lys Pro Asn Ser Ile Asn Tyr Ile Leu Gly Leu Asp
1               5                   10                  15

Ile Gly Ile Ala Ser Val Gly Trp Ala Met Val Glu Ile Asp Glu Glu
            20                  25                  30

Glu Asn Pro Ile Arg Leu Ile Asp Leu Gly Val Arg Val Phe Glu Arg
        35                  40                  45

Ala Glu Val Pro Lys Thr Gly Asp Ser Leu Ala Met Ala Arg Arg Leu
    50                  55                  60

Ala Arg Ser Val Arg Arg Leu Thr Arg Arg Arg Ala His Arg Leu Leu
65                  70                  75                  80

Arg Thr Arg Arg Leu Leu Lys Arg Glu Gly Val Leu Gln Ala Ala Asn
                85                  90                  95

Phe Asp Glu Asn Gly Leu Ile Lys Ser Leu Pro Asn Thr Pro Trp Gln
            100                 105                 110

Leu Arg Ala Ala Ala Leu Asp Arg Lys Leu Thr Pro Leu Glu Trp Ser
        115                 120                 125

Ala Val Leu Leu His Leu Ile Lys His Arg Gly Tyr Leu Ser Gln Arg
    130                 135                 140

Lys Asn Glu Gly Glu Thr Ala Asp Lys Glu Leu Gly Ala Leu Leu Lys
145                 150                 155                 160

Gly Val Ala Gly Asn Ala His Ala Leu Gln Thr Gly Asp Phe Arg Thr
                165                 170                 175

Pro Ala Glu Leu Ala Leu Asn Lys Phe Glu Lys Glu Ser Gly His Ile
            180                 185                 190

Arg Asn Gln Arg Ser Asp Tyr Ser His Thr Phe Ser Arg Lys Asp Leu
        195                 200                 205

Gln Ala Glu Leu Ile Leu Leu Phe Glu Lys Gln Lys Glu Phe Gly Asn
    210                 215                 220

Pro His Val Ser Gly Gly Leu Lys Glu Gly Ile Glu Thr Leu Leu Met
225                 230                 235                 240

Thr Gln Arg Pro Ala Leu Ser Gly Asp Ala Val Gln Lys Met Leu Gly
                245                 250                 255

His Cys Thr Phe Glu Pro Ala Glu Pro Lys Ala Ala Lys Asn Thr Tyr
            260                 265                 270

Thr Ala Glu Arg Phe Ile Trp Leu Thr Lys Leu Asn Asn Leu Arg Ile
        275                 280                 285

Leu Glu Gln Gly Ser Glu Arg Pro Leu Thr Asp Thr Glu Arg Ala Thr
    290                 295                 300

```
Leu Met Asp Glu Pro Tyr Arg Lys Ser Lys Leu Thr Tyr Ala Gln Ala
305                 310                 315                 320

Arg Lys Leu Leu Gly Leu Glu Asp Thr Ala Phe Phe Lys Gly Leu Arg
                325                 330                 335

Tyr Gly Lys Asp Asn Ala Glu Ala Ser Thr Leu Met Glu Met Lys Ala
            340                 345                 350

Tyr His Ala Ile Ser Arg Ala Leu Glu Lys Glu Gly Leu Lys Asp Lys
        355                 360                 365

Lys Ser Pro Leu Asn Leu Ser Pro Glu Leu Gln Asp Glu Ile Gly Thr
    370                 375                 380

Ala Phe Ser Leu Phe Lys Thr Asp Glu Asp Ile Thr Gly Arg Leu Lys
385                 390                 395                 400

Asp Arg Ile Gln Pro Glu Ile Leu Glu Ala Leu Leu Lys His Ile Ser
                405                 410                 415

Phe Asp Lys Phe Val Gln Ile Ser Leu Lys Ala Leu Arg Arg Ile Val
            420                 425                 430

Pro Leu Met Glu Gln Gly Lys Arg Tyr Asp Glu Ala Cys Ala Glu Ile
        435                 440                 445

Tyr Gly Asp His Tyr Gly Lys Lys Asn Thr Glu Glu Lys Ile Tyr Leu
    450                 455                 460

Pro Pro Ile Pro Ala Asp Glu Ile Arg Asn Pro Val Val Leu Arg Ala
465                 470                 475                 480

Leu Ser Gln Ala Arg Lys Val Ile Asn Gly Val Val Arg Arg Tyr Gly
                485                 490                 495

Ser Pro Ala Arg Ile His Ile Glu Thr Ala Arg Glu Val Gly Lys Ser
            500                 505                 510

Phe Lys Asp Arg Lys Glu Ile Glu Lys Arg Gln Glu Glu Asn Arg Lys
        515                 520                 525

Asp Arg Glu Lys Ala Ala Ala Lys Phe Arg Glu Tyr Phe Pro Asn Phe
    530                 535                 540

Val Gly Glu Pro Lys Ser Lys Asp Ile Leu Lys Leu Arg Leu Tyr Glu
545                 550                 555                 560

Gln Gln His Gly Lys Cys Leu Tyr Ser Gly Lys Glu Ile Asn Leu Gly
                565                 570                 575

Arg Leu Asn Glu Lys Gly Tyr Val Glu Ile Asp His Ala Leu Pro Phe
            580                 585                 590

Ser Arg Thr Trp Asp Asp Ser Phe Asn Asn Lys Val Leu Val Leu Gly
        595                 600                 605

Ser Glu Asn Gln Asn Lys Gly Asn Gln Thr Pro Tyr Glu Tyr Phe Asn
    610                 615                 620

Gly Lys Asp Asn Ser Arg Glu Trp Gln Glu Phe Lys Ala Arg Val Glu
625                 630                 635                 640

Thr Ser Arg Phe Pro Arg Ser Lys Lys Gln Arg Ile Leu Leu Gln Lys
                645                 650                 655

Phe Asp Glu Asp Gly Phe Lys Glu Arg Asn Leu Asn Asp Thr Arg Tyr
            660                 665                 670

Val Asn Arg Phe Leu Cys Gln Phe Val Ala Asp Arg Met Arg Leu Thr
        675                 680                 685

Gly Lys Gly Lys Lys Arg Val Phe Ala Ser Asn Gly Gln Ile Thr Asn
    690                 695                 700

Leu Leu Arg Gly Phe Trp Gly Leu Arg Lys Val Arg Ala Glu Asn Asp
705                 710                 715                 720
```

Arg His His Ala Leu Asp Ala Val Val Val Ala Cys Ser Thr Val Ala
725 730 735

Met Gln Gln Lys Ile Thr Arg Phe Val Arg Tyr Lys Glu Met Asn Ala
740 745 750

Phe Asp Gly Lys Thr Ile Asp Lys Glu Thr Gly Glu Val Leu His Gln
755 760 765

Lys Thr His Phe Pro Gln Pro Trp Glu Phe Phe Ala Gln Glu Val Met
770 775 780

Ile Arg Val Phe Gly Lys Pro Asp Gly Lys Pro Glu Phe Glu Glu Ala
785 790 795 800

Asp Thr Leu Glu Lys Leu Arg Thr Leu Leu Ala Glu Lys Leu Ser Ser
805 810 815

Arg Pro Glu Ala Val His Glu Tyr Val Thr Pro Leu Phe Val Ser Arg
820 825 830

Ala Pro Asn Arg Lys Met Ser Gly Gln Gly His Met Glu Thr Val Lys
835 840 845

Ser Ala Lys Arg Leu Asp Glu Gly Val Ser Val Leu Arg Val Pro Leu
850 855 860

Thr Gln Leu Lys Leu Lys Asp Leu Glu Lys Met Val Asn Arg Glu Arg
865 870 875 880

Glu Pro Lys Leu Tyr Glu Ala Leu Lys Ala Arg Leu Glu Ala His Lys
885 890 895

Asp Asp Pro Ala Lys Ala Phe Ala Glu Pro Phe Tyr Lys Tyr Asp Lys
900 905 910

Ala Gly Asn Arg Thr Gln Gln Val Lys Ala Val Arg Val Glu Gln Val
915 920 925

Gln Lys Thr Gly Val Trp Val Arg Asn His Asn Gly Ile Ala Asp Asn
930 935 940

Ala Thr Met Val Arg Val Asp Val Phe Glu Lys Gly Asp Lys Tyr Tyr
945 950 955 960

Leu Val Pro Ile Tyr Ser Trp Gln Val Ala Lys Gly Ile Leu Pro Asp
965 970 975

Arg Ala Val Val Gln Gly Lys Asp Glu Glu Asp Trp Gln Leu Ile Asp
980 985 990

Asp Ser Phe Asn Phe Lys Phe Ser Leu His Pro Asn Asp Leu Val Glu
995 1000 1005

Val Ile Thr Lys Lys Ala Arg Met Phe Gly Tyr Phe Ala Ser Cys
1010 1015 1020

His Arg Gly Thr Gly Asn Ile Asn Ile Arg Ile His Asp Leu Asp
1025 1030 1035

His Lys Ile Gly Lys Asn Gly Ile Leu Glu Gly Ile Gly Val Lys
1040 1045 1050

Thr Ala Leu Ser Phe Gln Lys Tyr Gln Ile Asp Glu Leu Gly Lys
1055 1060 1065

Glu Ile Arg Pro Cys Arg Leu Lys Lys Arg Pro Pro Val Arg
1070 1075 1080

<210> SEQ ID NO 52
<211> LENGTH: 1629
<212> TYPE: PRT
<213> ORGANISM: Francisella tularensis

<400> SEQUENCE: 52

Met Asn Phe Lys Ile Leu Pro Ile Ala Ile Asp Leu Gly Val Lys Asn
1 5 10 15

-continued

```
Thr Gly Val Phe Ser Ala Phe Tyr Gln Lys Gly Thr Ser Leu Glu Arg
            20                  25                  30

Leu Asp Asn Lys Asn Gly Lys Val Tyr Glu Leu Ser Lys Asp Ser Tyr
        35                  40                  45

Thr Leu Leu Met Asn Asn Arg Thr Ala Arg Arg His Gln Arg Arg Gly
    50                  55                  60

Ile Asp Arg Lys Gln Leu Val Lys Arg Leu Phe Lys Leu Ile Trp Thr
65                  70                  75                  80

Glu Gln Leu Asn Leu Glu Trp Asp Lys Asp Thr Gln Gln Ala Ile Ser
                85                  90                  95

Phe Leu Phe Asn Arg Arg Gly Phe Ser Phe Ile Thr Asp Gly Tyr Ser
            100                 105                 110

Pro Glu Tyr Leu Asn Ile Val Pro Glu Gln Val Lys Ala Ile Leu Met
        115                 120                 125

Asp Ile Phe Asp Asp Tyr Asn Gly Glu Asp Asp Leu Asp Ser Tyr Leu
    130                 135                 140

Lys Leu Ala Thr Glu Gln Glu Ser Lys Ile Ser Glu Ile Tyr Asn Lys
145                 150                 155                 160

Leu Met Gln Lys Ile Leu Glu Phe Lys Leu Met Lys Leu Cys Thr Asp
                165                 170                 175

Ile Lys Asp Asp Lys Val Ser Thr Lys Thr Leu Lys Glu Ile Thr Ser
            180                 185                 190

Tyr Glu Phe Glu Leu Leu Ala Asp Tyr Leu Ala Asn Tyr Ser Glu Ser
        195                 200                 205

Leu Lys Thr Gln Lys Phe Ser Tyr Thr Asp Lys Gln Gly Asn Leu Lys
    210                 215                 220

Glu Leu Ser Tyr Tyr His His Asp Lys Tyr Asn Ile Gln Glu Phe Leu
225                 230                 235                 240

Lys Arg His Ala Thr Ile Asn Asp Arg Ile Leu Asp Thr Leu Leu Thr
                245                 250                 255

Asp Asp Leu Asp Ile Trp Asn Phe Asn Phe Glu Lys Phe Asp Phe Asp
            260                 265                 270

Lys Asn Glu Glu Lys Leu Gln Asn Gln Glu Asp Lys Asp His Ile Gln
        275                 280                 285

Ala His Leu His His Phe Val Phe Ala Val Asn Lys Ile Lys Ser Glu
    290                 295                 300

Met Ala Ser Gly Gly Arg His Arg Ser Gln Tyr Phe Gln Glu Ile Thr
305                 310                 315                 320

Asn Val Leu Asp Glu Asn Asn His Gln Glu Gly Tyr Leu Lys Asn Phe
                325                 330                 335

Cys Glu Asn Leu His Asn Lys Lys Tyr Ser Asn Leu Ser Val Lys Asn
            340                 345                 350

Leu Val Asn Leu Ile Gly Asn Leu Ser Asn Leu Glu Leu Lys Pro Leu
        355                 360                 365

Arg Lys Tyr Phe Asn Asp Lys Ile His Ala Lys Ala Asp His Trp Asp
    370                 375                 380

Glu Gln Lys Phe Thr Glu Thr Tyr Cys His Trp Ile Leu Gly Glu Trp
385                 390                 395                 400

Arg Val Gly Val Lys Asp Gln Asp Lys Lys Asp Gly Ala Lys Tyr Ser
                405                 410                 415

Tyr Lys Asp Leu Cys Asn Glu Leu Lys Gln Lys Val Thr Lys Ala Gly
            420                 425                 430
```

-continued

```
Leu Val Asp Phe Leu Leu Glu Leu Asp Pro Cys Arg Thr Ile Pro Pro
        435                 440                 445

Tyr Leu Asp Asn Asn Asn Arg Lys Pro Pro Lys Cys Gln Ser Leu Ile
    450                 455                 460

Leu Asn Pro Lys Phe Leu Asp Asn Gln Tyr Pro Asn Trp Gln Gln Tyr
465                 470                 475                 480

Leu Gln Glu Leu Lys Lys Leu Gln Ser Ile Gln Asn Tyr Leu Asp Ser
                485                 490                 495

Phe Glu Thr Asp Leu Lys Val Leu Lys Ser Ser Lys Asp Gln Pro Tyr
            500                 505                 510

Phe Val Glu Tyr Lys Ser Ser Asn Gln Gln Ile Ala Ser Gly Gln Arg
        515                 520                 525

Asp Tyr Lys Asp Leu Asp Ala Arg Ile Leu Gln Phe Ile Phe Asp Arg
    530                 535                 540

Val Lys Ala Ser Asp Glu Leu Leu Leu Asn Glu Ile Tyr Phe Gln Ala
545                 550                 555                 560

Lys Lys Leu Lys Gln Lys Ala Ser Ser Glu Leu Glu Lys Leu Glu Ser
                565                 570                 575

Ser Lys Lys Leu Asp Glu Val Ile Ala Asn Ser Gln Leu Ser Gln Ile
            580                 585                 590

Leu Lys Ser Gln His Thr Asn Gly Ile Phe Glu Gln Gly Thr Phe Leu
        595                 600                 605

His Leu Val Cys Lys Tyr Tyr Lys Gln Arg Gln Arg Ala Arg Asp Ser
    610                 615                 620

Arg Leu Tyr Ile Met Pro Glu Tyr Arg Tyr Asp Lys Lys Leu His Lys
625                 630                 635                 640

Tyr Asn Asn Thr Gly Arg Phe Asp Asp Asp Asn Gln Leu Leu Thr Tyr
                645                 650                 655

Cys Asn His Lys Pro Arg Gln Lys Arg Tyr Gln Leu Leu Asn Asp Leu
            660                 665                 670

Ala Gly Val Leu Gln Val Ser Pro Asn Phe Leu Lys Asp Lys Ile Gly
        675                 680                 685

Ser Asp Asp Asp Leu Phe Ile Ser Lys Trp Leu Val Glu His Ile Arg
    690                 695                 700

Gly Phe Lys Lys Ala Cys Glu Asp Ser Leu Lys Ile Gln Lys Asp Asn
705                 710                 715                 720

Arg Gly Leu Leu Asn His Lys Ile Asn Ile Ala Arg Asn Thr Lys Gly
                725                 730                 735

Lys Cys Glu Lys Glu Ile Phe Asn Leu Ile Cys Lys Ile Glu Gly Ser
            740                 745                 750

Glu Asp Lys Lys Gly Asn Tyr Lys His Gly Leu Ala Tyr Glu Leu Gly
        755                 760                 765

Val Leu Leu Phe Gly Glu Pro Asn Glu Ala Ser Lys Pro Glu Phe Asp
    770                 775                 780

Arg Lys Ile Lys Lys Phe Asn Ser Ile Tyr Ser Phe Ala Gln Ile Gln
785                 790                 795                 800

Gln Ile Ala Phe Ala Glu Arg Lys Gly Asn Ala Asn Thr Cys Ala Val
                805                 810                 815

Cys Ser Ala Asp Asn Ala His Arg Met Gln Gln Ile Lys Ile Thr Glu
            820                 825                 830

Pro Val Glu Asp Asn Lys Asp Lys Ile Ile Leu Ser Ala Lys Ala Gln
        835                 840                 845
```

```
Arg Leu Pro Ala Ile Pro Thr Arg Ile Val Asp Gly Ala Val Lys Lys
    850                 855                 860

Met Ala Thr Ile Leu Ala Lys Asn Ile Val Asp Asp Asn Trp Gln Asn
865                 870                 875                 880

Ile Lys Gln Val Leu Ser Ala Lys His Gln Leu His Ile Pro Ile Ile
                885                 890                 895

Thr Glu Ser Asn Ala Phe Glu Phe Glu Pro Ala Leu Ala Asp Val Lys
            900                 905                 910

Gly Lys Ser Leu Lys Asp Arg Arg Lys Lys Ala Leu Glu Arg Ile Ser
        915                 920                 925

Pro Glu Asn Ile Phe Lys Asp Lys Asn Asn Arg Ile Lys Glu Phe Ala
    930                 935                 940

Lys Gly Ile Ser Ala Tyr Ser Gly Ala Asn Leu Thr Asp Gly Asp Phe
945                 950                 955                 960

Asp Gly Ala Lys Glu Glu Leu Asp His Ile Ile Pro Arg Ser His Lys
                965                 970                 975

Lys Tyr Gly Thr Leu Asn Asp Glu Ala Asn Leu Ile Cys Val Thr Arg
            980                 985                 990

Gly Asp Asn Lys Asn Lys Gly Asn  Arg Ile Phe Cys Leu  Arg Asp Leu
        995                 1000                1005

Ala Asp  Asn Tyr Lys Leu Lys  Gln Phe Glu Thr Thr  Asp Asp Leu
    1010                1015                1020

Glu Ile  Glu Lys Lys Ile Ala  Asp Thr Ile Trp Asp  Ala Asn Lys
    1025                1030                1035

Lys Asp  Phe Lys Phe Gly Asn  Tyr Arg Ser Phe Ile  Asn Leu Thr
    1040                1045                1050

Pro Gln  Glu Gln Lys Ala Phe  Arg His Ala Leu Phe  Leu Ala Asp
    1055                1060                1065

Glu Asn  Pro Ile Lys Gln Ala  Val Ile Arg Ala Ile  Asn Asn Arg
    1070                1075                1080

Asn Arg  Thr Phe Val Asn Gly  Thr Gln Arg Tyr Phe  Ala Glu Val
    1085                1090                1095

Leu Ala  Asn Asn Ile Tyr Leu  Arg Ala Lys Lys Glu  Asn Leu Asn
    1100                1105                1110

Thr Asp  Lys Ile Ser Phe Asp  Tyr Phe Gly Ile Pro  Thr Ile Gly
    1115                1120                1125

Asn Gly  Arg Gly Ile Ala Glu  Ile Arg Gln Leu Tyr  Glu Lys Val
    1130                1135                1140

Asp Ser  Asp Ile Gln Ala Tyr  Ala Lys Gly Asp Lys  Pro Gln Ala
    1145                1150                1155

Ser Tyr  Ser His Leu Ile Asp  Ala Met Leu Ala Phe  Cys Ile Ala
    1160                1165                1170

Ala Asp  Glu His Arg Asn Asp  Gly Ser Ile Gly Leu  Glu Ile Asp
    1175                1180                1185

Lys Asn  Tyr Ser Leu Tyr Pro  Leu Asp Lys Asn Thr  Gly Glu Val
    1190                1195                1200

Phe Thr  Lys Asp Ile Phe Ser  Gln Ile Lys Ile Thr  Asp Asn Glu
    1205                1210                1215

Phe Ser  Asp Lys Lys Leu Val  Arg Lys Lys Ala Ile  Glu Gly Phe
    1220                1225                1230

Asn Thr  His Arg Gln Met Thr  Arg Asp Gly Ile Tyr  Ala Glu Asn
    1235                1240                1245
```

-continued

```
Tyr Leu  Pro Ile Leu Ile His  Lys Glu Leu Asn Glu  Val Arg Lys
    1250                 1255                 1260

Gly Tyr  Thr Trp Lys Asn Ser  Glu Glu Ile Lys Ile  Phe Lys Gly
    1265                 1270                 1275

Lys Lys  Tyr Asp Ile Gln Gln  Leu Asn Asn Leu Val  Tyr Cys Leu
    1280                 1285                 1290

Lys Phe  Val Asp Lys Pro Ile  Ser Ile Asp Ile Gln  Ile Ser Thr
    1295                 1300                 1305

Leu Glu  Glu Leu Arg Asn Ile  Leu Thr Thr Asn Asn  Ile Ala Ala
    1310                 1315                 1320

Thr Ala  Glu Tyr Tyr Tyr Ile  Asn Leu Lys Thr Gln  Lys Leu His
    1325                 1330                 1335

Glu Tyr  Tyr Ile Glu Asn Tyr  Asn Thr Ala Leu Gly  Tyr Lys Lys
    1340                 1345                 1350

Tyr Ser  Lys Glu Met Glu Phe  Leu Arg Ser Leu Ala  Tyr Arg Ser
    1355                 1360                 1365

Glu Arg  Val Lys Ile Lys Ser  Ile Asp Asp Val Lys  Gln Val Leu
    1370                 1375                 1380

Asp Lys  Asp Ser Asn Phe Ile  Ile Gly Lys Ile Thr  Leu Pro Phe
    1385                 1390                 1395

Lys Lys  Glu Trp Gln Arg Leu  Tyr Arg Glu Trp Gln  Asn Thr Thr
    1400                 1405                 1410

Ile Lys  Asp Asp Tyr Glu Phe  Leu Lys Ser Phe Phe  Asn Val Lys
    1415                 1420                 1425

Ser Ile  Thr Lys Leu His Lys  Lys Val Arg Lys Asp  Phe Ser Leu
    1430                 1435                 1440

Pro Ile  Ser Thr Asn Glu Gly  Lys Phe Leu Val Lys  Arg Lys Thr
    1445                 1450                 1455

Trp Asp  Asn Asn Phe Ile Tyr  Gln Ile Leu Asn Asp  Ser Asp Ser
    1460                 1465                 1470

Arg Ala  Asp Gly Thr Lys Pro  Phe Ile Pro Ala Phe  Asp Ile Ser
    1475                 1480                 1485

Lys Asn  Glu Ile Val Glu Ala  Ile Ile Asp Ser Phe  Thr Ser Lys
    1490                 1495                 1500

Asn Ile  Phe Trp Leu Pro Lys  Asn Ile Glu Leu Gln  Lys Val Asp
    1505                 1510                 1515

Asn Lys  Asn Ile Phe Ala Ile  Asp Thr Ser Lys Trp  Phe Glu Val
    1520                 1525                 1530

Glu Thr  Pro Ser Asp Leu Arg  Asp Ile Gly Ile Ala  Thr Ile Gln
    1535                 1540                 1545

Tyr Lys  Ile Asp Asn Asn Ser  Arg Pro Lys Val Arg  Val Lys Leu
    1550                 1555                 1560

Asp Tyr  Val Ile Asp Asp Asp  Ser Lys Ile Asn Tyr  Phe Met Asn
    1565                 1570                 1575

His Ser  Leu Leu Lys Ser Arg  Tyr Pro Asp Lys Val  Leu Glu Ile
    1580                 1585                 1590

Leu Lys  Gln Ser Thr Ile Ile  Glu Phe Glu Ser Ser  Gly Phe Asn
    1595                 1600                 1605

Lys Thr  Ile Lys Glu Met Leu  Gly Met Lys Leu Ala  Gly Ile Tyr
    1610                 1615                 1620

Asn Glu  Thr Ser Asn Asn
    1625
```

```
<210> SEQ ID NO 53
<211> LENGTH: 1056
<212> TYPE: PRT
<213> ORGANISM: Pasteurella multocida

<400> SEQUENCE: 53

Met Gln Thr Thr Asn Leu Ser Tyr Ile Leu Gly Leu Asp Leu Gly Ile
1               5                   10                  15

Ala Ser Val Gly Trp Ala Val Val Glu Ile Asn Glu Asn Glu Asp Pro
            20                  25                  30

Ile Gly Leu Ile Asp Val Gly Val Arg Ile Phe Glu Arg Ala Glu Val
        35                  40                  45

Pro Lys Thr Gly Glu Ser Leu Ala Leu Ser Arg Arg Leu Ala Arg Ser
    50                  55                  60

Thr Arg Arg Leu Ile Arg Arg Arg Ala His Arg Leu Leu Leu Ala Lys
65                  70                  75                  80

Arg Phe Leu Lys Arg Glu Gly Ile Leu Ser Thr Ile Asp Leu Glu Lys
                85                  90                  95

Gly Leu Pro Asn Gln Ala Trp Glu Leu Arg Val Ala Gly Leu Glu Arg
            100                 105                 110

Arg Leu Ser Ala Ile Glu Trp Gly Ala Val Leu Leu His Leu Ile Lys
        115                 120                 125

His Arg Gly Tyr Leu Ser Lys Arg Lys Asn Glu Ser Gln Thr Asn Asn
    130                 135                 140

Lys Glu Leu Gly Ala Leu Leu Ser Gly Val Ala Gln Asn His Gln Leu
145                 150                 155                 160

Leu Gln Ser Asp Asp Tyr Arg Thr Pro Ala Glu Leu Ala Leu Lys Lys
                165                 170                 175

Phe Ala Lys Glu Glu Gly His Ile Arg Asn Gln Arg Gly Ala Tyr Thr
            180                 185                 190

His Thr Phe Asn Arg Leu Asp Leu Leu Ala Glu Leu Asn Leu Leu Phe
        195                 200                 205

Ala Gln Gln His Gln Phe Gly Asn Pro His Cys Lys Glu His Ile Gln
    210                 215                 220

Gln Tyr Met Thr Glu Leu Leu Met Trp Gln Lys Pro Ala Leu Ser Gly
225                 230                 235                 240

Glu Ala Ile Leu Lys Met Leu Gly Lys Cys Thr His Glu Lys Asn Glu
                245                 250                 255

Phe Lys Ala Ala Lys His Thr Tyr Ser Ala Glu Arg Phe Val Trp Leu
            260                 265                 270

Thr Lys Leu Asn Asn Leu Arg Ile Leu Glu Asp Gly Ala Glu Arg Ala
        275                 280                 285

Leu Asn Glu Glu Glu Arg Gln Leu Leu Ile Asn His Pro Tyr Glu Lys
    290                 295                 300

Ser Lys Leu Thr Tyr Ala Gln Val Arg Lys Leu Leu Gly Leu Ser Glu
305                 310                 315                 320

Gln Ala Ile Phe Lys His Leu Arg Tyr Ser Lys Glu Asn Ala Glu Ser
                325                 330                 335

Ala Thr Phe Met Glu Leu Lys Ala Trp His Ala Ile Arg Lys Ala Leu
            340                 345                 350

Glu Asn Gln Gly Leu Lys Asp Thr Trp Gln Asp Leu Ala Lys Lys Pro
        355                 360                 365

Asp Leu Leu Asp Glu Ile Gly Thr Ala Phe Ser Leu Tyr Lys Thr Asp
    370                 375                 380
```

```
Glu Asp Ile Gln Gln Tyr Leu Thr Asn Lys Val Pro Asn Ser Val Ile
385                 390                 395                 400

Asn Ala Leu Leu Val Ser Leu Asn Phe Asp Lys Phe Ile Glu Leu Ser
            405                 410                 415

Leu Lys Ser Leu Arg Lys Ile Leu Pro Leu Met Glu Gln Gly Lys Arg
        420                 425                 430

Tyr Asp Gln Ala Cys Arg Glu Ile Tyr Gly His His Tyr Gly Glu Ala
            435                 440                 445

Asn Gln Lys Thr Ser Gln Leu Leu Pro Ala Ile Pro Ala Gln Glu Ile
        450                 455                 460

Arg Asn Pro Val Val Leu Arg Thr Leu Ser Gln Ala Arg Lys Val Ile
465                 470                 475                 480

Asn Ala Ile Ile Arg Gln Tyr Gly Ser Pro Ala Arg Val His Ile Glu
            485                 490                 495

Thr Gly Arg Glu Leu Gly Lys Ser Phe Lys Glu Arg Arg Glu Ile Gln
            500                 505                 510

Lys Gln Gln Glu Asp Asn Arg Thr Lys Arg Glu Ser Ala Val Gln Lys
        515                 520                 525

Phe Lys Glu Leu Phe Ser Asp Phe Ser Ser Glu Pro Lys Ser Lys Asp
        530                 535                 540

Ile Leu Lys Phe Arg Leu Tyr Glu Gln Gln His Gly Lys Cys Leu Tyr
545                 550                 555                 560

Ser Gly Lys Glu Ile Asn Ile His Arg Leu Asn Glu Lys Gly Tyr Val
            565                 570                 575

Glu Ile Asp His Ala Leu Pro Phe Ser Arg Thr Trp Asp Asp Ser Phe
            580                 585                 590

Asn Asn Lys Val Leu Val Leu Ala Ser Glu Asn Gln Asn Lys Gly Asn
        595                 600                 605

Gln Thr Pro Tyr Glu Trp Leu Gln Gly Lys Ile Asn Ser Glu Arg Trp
        610                 615                 620

Lys Asn Phe Val Ala Leu Val Leu Gly Ser Gln Cys Ser Ala Ala Lys
625                 630                 635                 640

Lys Gln Arg Leu Leu Thr Gln Val Ile Asp Asp Asn Lys Phe Ile Asp
            645                 650                 655

Arg Asn Leu Asn Asp Thr Arg Tyr Ile Ala Arg Phe Leu Ser Asn Tyr
            660                 665                 670

Ile Gln Glu Asn Leu Leu Leu Val Gly Lys Asn Lys Lys Asn Val Phe
        675                 680                 685

Thr Pro Asn Gly Gln Ile Thr Ala Leu Leu Arg Ser Arg Trp Gly Leu
        690                 695                 700

Ile Lys Ala Arg Glu Asn Asn Asn Arg His His Ala Leu Asp Ala Ile
705                 710                 715                 720

Val Val Ala Cys Ala Thr Pro Ser Met Gln Gln Lys Ile Thr Arg Phe
            725                 730                 735

Ile Arg Phe Lys Glu Val His Pro Tyr Lys Ile Glu Asn Arg Tyr Glu
            740                 745                 750

Met Val Asp Gln Glu Ser Gly Glu Ile Ile Ser Pro His Phe Pro Glu
        755                 760                 765

Pro Trp Ala Tyr Phe Arg Gln Glu Val Asn Ile Arg Val Phe Asp Asn
        770                 775                 780

His Pro Asp Thr Val Leu Lys Glu Met Leu Pro Asp Arg Pro Gln Ala
785                 790                 795                 800
```

```
Asn His Gln Phe Val Gln Pro Leu Phe Val Ser Arg Ala Pro Thr Arg
                805                 810                 815

Lys Met Ser Gly Gln Gly His Met Glu Thr Ile Lys Ser Ala Lys Arg
            820                 825                 830

Leu Ala Glu Gly Ile Ser Val Leu Arg Ile Pro Leu Thr Gln Leu Lys
        835                 840                 845

Pro Asn Leu Leu Glu Asn Met Val Asn Lys Glu Arg Glu Pro Ala Leu
    850                 855                 860

Tyr Ala Gly Leu Lys Ala Arg Leu Ala Glu Phe Asn Gln Asp Pro Ala
865                 870                 875                 880

Lys Ala Phe Ala Thr Pro Phe Tyr Lys Gln Gly Gly Gln Gln Val Lys
                885                 890                 895

Ala Ile Arg Val Glu Gln Val Gln Lys Ser Gly Val Leu Val Arg Glu
            900                 905                 910

Asn Asn Gly Val Ala Asp Asn Ala Ser Ile Val Arg Thr Asp Val Phe
        915                 920                 925

Ile Lys Asn Asn Lys Phe Phe Leu Val Pro Ile Tyr Thr Trp Gln Val
    930                 935                 940

Ala Lys Gly Ile Leu Pro Asn Lys Ala Ile Val Ala His Lys Asn Glu
945                 950                 955                 960

Asp Glu Trp Glu Glu Met Asp Glu Gly Ala Lys Phe Lys Phe Ser Leu
                965                 970                 975

Phe Pro Asn Asp Leu Val Glu Leu Lys Thr Lys Lys Glu Tyr Phe Phe
            980                 985                 990

Gly Tyr Tyr Ile Gly Leu Asp Arg  Ala Thr Gly Asn Ile  Ser Leu Lys
        995                 1000                1005

Glu His  Asp Gly Glu Ile Ser  Lys Gly Lys Asp Gly  Val Tyr Arg
    1010                1015                1020

Val Gly  Val Lys Leu Ala Leu  Ser Phe Glu Lys Tyr  Gln Val Asp
    1025                1030                1035

Glu Leu  Gly Lys Asn Arg Gln  Ile Cys Arg Pro Gln  Gln Arg Gln
    1040                1045                1050

Pro Val  Arg
    1055
```

<210> SEQ ID NO 54
<211> LENGTH: 4284
<212> TYPE: DNA
<213> ORGANISM: Artificial Sequence
<220> FEATURE:
<223> OTHER INFORMATION: Synthetic construct

<400> SEQUENCE: 54

```
atgcaccatc atcatcatca ttcttctggt ctggtgccac gcggttctgg tatgaaagaa      60

accgctgctg ctaaattcga acgccagcac atggacagcc cagatctggg taccgacgac     120

gacgacaagg ccatggcccc aaaaaagaaa cgcaaggtta tggataaaaa atacagcatt     180

ggtctggcca tcggaaccaa cagcgttggg tgggcagtaa taacagatga atacaaagtg     240

ccgtcaaaaa aatttaaggt tctgggggaat acagatcgcc acagcataaa aaagaatctg     300

attggggcat tgctgtttga ttcgggtgag acagctgagg ccacgcgtct gaaacgtaca     360

gcaagaagac gttacacacg tcgtaaaaat cgtatttgct acttacagga aattttttct     420

aacgaaatgg ccaaggtaga tgatagtttc ttccatcgtc tcgaagaatc ttttctggtt     480

gaggaagata aaaaacacga acgtcaccct atctttggca atatcgtgga tgaagtggcc     540
```

-continued

```
tatcatgaaa aataccctac gatttatcat cttcgcaaga agttggttga tagtacggac    600
aaagcggatc tgcgtttaat ctatcttgcg ttagcgcaca tgatcaaatt tcgtggtcat    660
ttcttaattg aaggtgatct gaatcctgat aactctgatg tggacaaatt gtttatacaa    720
ttagtgcaaa cctataatca gctgttcgag gaaaacccca ttaatgcctc tggagttgat    780
gccaaagcga ttttaagcgc gagactttct aagtcccggc gtctggagaa tctgatcgcc    840
cagttaccag ggaaaaagaa aaatggtctg tttggtaatc tgattgccct cagtctgggg    900
cttaccccga acttcaaatc caattttgac ctggctgagg acgcaaagct gcagctgagc    960
aaagatactt atgatgatga cctcgacaat ctgctcgccc agattggtga ccaatatgcg   1020
gatctgtttc tggcagcgaa gaatctttcg gatgctatct tgctgtcgga tattctgcgt   1080
gttaataccg aaatcaccaa agcgcctctg tctgcaagta tgatcaagag atacgacgag   1140
caccaccagg acctgactct tcttaaggca ctggtacgcc aacagcttcc ggagaaatac   1200
aaagaaatat tcttcgacca gtccaagaat ggttacgcgg gctacatcga tggtggtgca   1260
tcacaggaag agttctataa atttattaaa ccaatccttg agaaaatgga tggcacggaa   1320
gagttacttg ttaaacttaa ccgcgaagac ttgcttagaa agcaacgtac attcgacaac   1380
ggctccatcc cacaccagat tcatttaggt gaacttcacg ccatcttgcg cagacaagaa   1440
gatttctatc ccttcttaaa agacaatcgg gagaaaatcg agaagatcct gacgttccgc   1500
attccctatt atgtcggtcc cctggcacgt ggtaattctc ggtttgcctg gatgacgcgc   1560
aaaagtgagg aaaccatcac cccttggaac tttgaagaag tcgtggataa aggtgctagc   1620
gcgcagtctt ttatagaaag aatgacgaac ttcgataaaa acttgcccaa cgaaaaagtc   1680
ctgcccaagc actctctttt atatgagtac tttactgtgt acaacgaact gactaaagtg   1740
aaatacgtta cggaaggtat gcgcaaacct gcctttctta gtggcgagca gaaaaaagca   1800
attgtcgatc ttctctttaa aacgaatcgc aaggtaactg taaaacagct gaaggaagat   1860
tatttcaaaa agatcgaatg ctttgattct gtcgagatct cgggtgtcga agatcgtttc   1920
aacgcttcct tagggaccta tcatgatttg ctgaagataa taaaagacaa agactttctc   1980
gacaatgaag aaaatgaaga tattctggag gatattgttt tgaccttgac cttattcgaa   2040
gatagagaga tgatcgagga gcgcttaaaa acctatgccc acctgtttga tgacaaagtc   2100
atgaagcaat taaagcgccg cagatatacg gggtggggcc gcttgagccg caagttgatt   2160
aacggtatta gagacaagca gagcggaaaa actatcctgg atttcctcaa atctgacgga   2220
tttgcgaacc gcaattttat gcagcttata catgatgatt cgcttacatt caaagaggat   2280
attcagaagg ctcaggtgtc tgggcaaggt gattcactcc acgaacatat agcaaatttg   2340
gccggctctc ctgcgattaa gaaggggatc ctgcaaacag ttaaagttgt ggatgaactt   2400
gtaaaagtaa tgggccgcca caagccggag aatatcgtga tagaaatggc gcgcgagaat   2460
caaacgacac aaaaaggtca aaagaactca agagagagaa tgaagcgcat tgaggagggg   2520
ataaaggaac ttggatctca aattctgaaa gaacatccag ttgaaaacac tcagctgcaa   2580
aatgaaaaat tgtacctgta ctacctgcag aatggaagag acatgtacgt ggatcaggaa   2640
ttggatatca atagactctc ggactatgac gtagatcaca ttgtccctca gagcttcctc   2700
aaggatgatt ctatagataa taaagtactt acgagatcgg acaaaaatcg cggtaaatcg   2760
gataacgtcc catcggagga agtcgttaaa aagatgaaaa actattggcg tcaactgctg   2820
aacgccaagc tgatcacaca gcgtaagttt gataatctga ctaaagccga acgcggtggt   2880
```

-continued

```
cttagtgaac tcgataaagc aggatttata aaacggcagt tagtagaaac gcgccaaatt   2940

acgaaacacg tggctcagat cctcgattct agaatgaata caaagtacga tgaaaacgat   3000

aaactgatcc gtgaagtaaa agtcattacc ttaaaatcta aacttgtgtc cgatttccgc   3060

aaagattttc agttttacaa ggtccgggaa atcaataact atcaccatgc acatgatgca   3120

tatttaaatg cggttgtagg cacggccctt attaagaaat accctaaact cgaaagtgag   3180

tttgtttatg ggattataa agtgtatgac gttcgcaaaa tgatcgcgaa atcagaacag   3240

gaaatcggta aggctaccgc taaatacttt ttttattcca acattatgaa ttttttaag   3300

accgaaataa ctctcgcgaa tggtgaaatc cgtaaacggc ctcttataga aaccaatggt   3360

gaaacgggag aaatcgtttg ggataaaggt cgtgactttg ccaccgttcg taaagtcctc   3420

tcaatgccgc aagttaacat tgtcaagaag acggaagttc aaacaggggg attctccaaa   3480

gaatctatcc tgccgaagcg taacagtgat aaacttattg ccagaaaaaa agattgggat   3540

ccaaaaaaat acggaggctt tgattcccct accgtcgcgt atagtgtgct ggtggttgct   3600

aaagtcgaga aagggaaaag caagaaattg aaatcagtta aagaactgct gggtattaca   3660

attatggaaa gatcgtcctt tgagaaaaat ccgatcgact tttagaggc caaggggtat   3720

aaggaagtga aaaaagatct catcatcaaa ttaccgaagt atagtctttt tgagctggaa   3780

aacggcagaa aaagaatgct ggcctccgcg ggcgagttac agaagggaaa tgagctggcg   3840

ctgccttcca aatatgttaa ttttctgtac cttgccagtc attatgagaa actgaagggc   3900

agccccgaag ataacgaaca gaaacaatta ttcgtggaac agcataagca ctatttagat   3960

gaaattatag agcaaattag tgaattttct aagcgcgtta tcctcgcgga tgctaattta   4020

gacaaagtac tgtcagctta taataaacat cgggataagc cgattagaga acaggccgaa   4080

aatatcattc atttgtttac cttaaccaac cttggagcac cagctgcctt caaatatttc   4140

gataccacaa ttgatcgtaa acggtataca agtacaaaag aagtcttgga cgcaaccctc   4200

attcatcaat ctattactgg attatatgag acacgcattg atctttcaca gctgggcgga   4260

gacaagaaga aaaaactgaa actg                                          4284
```

<210> SEQ ID NO 55
<211> LENGTH: 1428
<212> TYPE: PRT
<213> ORGANISM: Artificial Sequence
<220> FEATURE:
<223> OTHER INFORMATION: protein expressed from synthetic construct

<400> SEQUENCE: 55

```
Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Asp Lys Ala Met Ala Pro Lys
        35                  40                  45

Lys Lys Arg Lys Val Met Asp Lys Lys Tyr Ser Ile Gly Leu Ala Ile
    50                  55                  60

Gly Thr Asn Ser Val Gly Trp Ala Val Ile Thr Asp Glu Tyr Lys Val
65                  70                  75                  80

Pro Ser Lys Lys Phe Lys Val Leu Gly Asn Thr Asp Arg His Ser Ile
                85                  90                  95

Lys Lys Asn Leu Ile Gly Ala Leu Leu Phe Asp Ser Gly Glu Thr Ala
            100                 105                 110
```

-continued

```
Glu Ala Thr Arg Leu Lys Arg Thr Ala Arg Arg Arg Tyr Thr Arg Arg
        115                 120                 125

Lys Asn Arg Ile Cys Tyr Leu Gln Glu Ile Phe Ser Asn Glu Met Ala
    130                 135                 140

Lys Val Asp Asp Ser Phe Phe His Arg Leu Glu Glu Ser Phe Leu Val
145                 150                 155                 160

Glu Glu Asp Lys Lys His Glu Arg His Pro Ile Phe Gly Asn Ile Val
                165                 170                 175

Asp Glu Val Ala Tyr His Glu Lys Tyr Pro Thr Ile Tyr His Leu Arg
            180                 185                 190

Lys Lys Leu Val Asp Ser Thr Asp Lys Ala Asp Leu Arg Leu Ile Tyr
        195                 200                 205

Leu Ala Leu Ala His Met Ile Lys Phe Arg Gly His Phe Leu Ile Glu
    210                 215                 220

Gly Asp Leu Asn Pro Asp Asn Ser Asp Val Asp Lys Leu Phe Ile Gln
225                 230                 235                 240

Leu Val Gln Thr Tyr Asn Gln Leu Phe Glu Glu Asn Pro Ile Asn Ala
                245                 250                 255

Ser Gly Val Asp Ala Lys Ala Ile Leu Ser Ala Arg Leu Ser Lys Ser
            260                 265                 270

Arg Arg Leu Glu Asn Leu Ile Ala Gln Leu Pro Gly Glu Lys Lys Asn
        275                 280                 285

Gly Leu Phe Gly Asn Leu Ile Ala Leu Ser Leu Gly Leu Thr Pro Asn
    290                 295                 300

Phe Lys Ser Asn Phe Asp Leu Ala Glu Asp Ala Lys Leu Gln Leu Ser
305                 310                 315                 320

Lys Asp Thr Tyr Asp Asp Asp Leu Asp Asn Leu Leu Ala Gln Ile Gly
                325                 330                 335

Asp Gln Tyr Ala Asp Leu Phe Leu Ala Ala Lys Asn Leu Ser Asp Ala
            340                 345                 350

Ile Leu Leu Ser Asp Ile Leu Arg Val Asn Thr Glu Ile Thr Lys Ala
        355                 360                 365

Pro Leu Ser Ala Ser Met Ile Lys Arg Tyr Asp Glu His His Gln Asp
    370                 375                 380

Leu Thr Leu Leu Lys Ala Leu Val Arg Gln Gln Leu Pro Glu Lys Tyr
385                 390                 395                 400

Lys Glu Ile Phe Phe Asp Gln Ser Lys Asn Gly Tyr Ala Gly Tyr Ile
                405                 410                 415

Asp Gly Gly Ala Ser Gln Glu Glu Phe Tyr Lys Phe Ile Lys Pro Ile
            420                 425                 430

Leu Glu Lys Met Asp Gly Thr Glu Glu Leu Leu Val Lys Leu Asn Arg
        435                 440                 445

Glu Asp Leu Leu Arg Lys Gln Arg Thr Phe Asp Asn Gly Ser Ile Pro
    450                 455                 460

His Gln Ile His Leu Gly Glu Leu His Ala Ile Leu Arg Arg Gln Glu
465                 470                 475                 480

Asp Phe Tyr Pro Phe Leu Lys Asp Asn Arg Glu Lys Ile Glu Lys Ile
                485                 490                 495

Leu Thr Phe Arg Ile Pro Tyr Tyr Val Gly Pro Leu Ala Arg Gly Asn
            500                 505                 510

Ser Arg Phe Ala Trp Met Thr Arg Lys Ser Glu Glu Thr Ile Thr Pro
        515                 520                 525
```

-continued

```
Trp Asn Phe Glu Glu Val Val Asp Lys Gly Ala Ser Ala Gln Ser Phe
    530                 535                 540

Ile Glu Arg Met Thr Asn Phe Asp Lys Asn Leu Pro Asn Glu Lys Val
545                 550                 555                 560

Leu Pro Lys His Ser Leu Leu Tyr Glu Tyr Phe Thr Val Tyr Asn Glu
                565                 570                 575

Leu Thr Lys Val Lys Tyr Val Thr Glu Gly Met Arg Lys Pro Ala Phe
            580                 585                 590

Leu Ser Gly Glu Gln Lys Lys Ala Ile Val Asp Leu Leu Phe Lys Thr
        595                 600                 605

Asn Arg Lys Val Thr Val Lys Gln Leu Lys Glu Asp Tyr Phe Lys Lys
    610                 615                 620

Ile Glu Cys Phe Asp Ser Val Glu Ile Ser Gly Val Glu Asp Arg Phe
625                 630                 635                 640

Asn Ala Ser Leu Gly Thr Tyr His Asp Leu Leu Lys Ile Ile Lys Asp
                645                 650                 655

Lys Asp Phe Leu Asp Asn Glu Glu Asn Glu Asp Ile Leu Glu Asp Ile
            660                 665                 670

Val Leu Thr Leu Thr Leu Phe Glu Asp Arg Glu Met Ile Glu Glu Arg
        675                 680                 685

Leu Lys Thr Tyr Ala His Leu Phe Asp Asp Lys Val Met Lys Gln Leu
    690                 695                 700

Lys Arg Arg Arg Tyr Thr Gly Trp Gly Arg Leu Ser Arg Lys Leu Ile
705                 710                 715                 720

Asn Gly Ile Arg Asp Lys Gln Ser Gly Lys Thr Ile Leu Asp Phe Leu
                725                 730                 735

Lys Ser Asp Gly Phe Ala Asn Arg Asn Phe Met Gln Leu Ile His Asp
            740                 745                 750

Asp Ser Leu Thr Phe Lys Glu Asp Ile Gln Lys Ala Gln Val Ser Gly
        755                 760                 765

Gln Gly Asp Ser Leu His Glu His Ile Ala Asn Leu Ala Gly Ser Pro
    770                 775                 780

Ala Ile Lys Lys Gly Ile Leu Gln Thr Val Lys Val Val Asp Glu Leu
785                 790                 795                 800

Val Lys Val Met Gly Arg His Lys Pro Glu Asn Ile Val Ile Glu Met
                805                 810                 815

Ala Arg Glu Asn Gln Thr Thr Gln Lys Gly Gln Lys Asn Ser Arg Glu
            820                 825                 830

Arg Met Lys Arg Ile Glu Glu Gly Ile Lys Glu Leu Gly Ser Gln Ile
        835                 840                 845

Leu Lys Glu His Pro Val Glu Asn Thr Gln Leu Gln Asn Glu Lys Leu
    850                 855                 860

Tyr Leu Tyr Tyr Leu Gln Asn Gly Arg Asp Met Tyr Val Asp Gln Glu
865                 870                 875                 880

Leu Asp Ile Asn Arg Leu Ser Asp Tyr Asp Val Asp His Ile Val Pro
                885                 890                 895

Gln Ser Phe Leu Lys Asp Asp Ser Ile Asp Asn Lys Val Leu Thr Arg
            900                 905                 910

Ser Asp Lys Asn Arg Gly Lys Ser Asp Asn Val Pro Ser Glu Glu Val
        915                 920                 925

Val Lys Lys Met Lys Asn Tyr Trp Arg Gln Leu Leu Asn Ala Lys Leu
    930                 935                 940
```

-continued

```
Ile Thr Gln Arg Lys Phe Asp Asn Leu Thr Lys Ala Glu Arg Gly Gly
945                 950                 955                 960

Leu Ser Glu Leu Asp Lys Ala Gly Phe Ile Lys Arg Gln Leu Val Glu
                965                 970                 975

Thr Arg Gln Ile Thr Lys His Val Ala Gln Ile Leu Asp Ser Arg Met
            980                 985                 990

Asn Thr Lys Tyr Asp Glu Asn Asp  Lys Leu Ile Arg Glu  Val Lys Val
        995                 1000                 1005

Ile Thr  Leu Lys Ser Lys Leu  Val Ser Asp Phe Arg  Lys Asp Phe
    1010                 1015                 1020

Gln Phe  Tyr Lys Val Arg Glu  Ile Asn Asn Tyr His  His Ala His
    1025                 1030                 1035

Asp Ala  Tyr Leu Asn Ala Val  Val Gly Thr Ala Leu  Ile Lys Lys
    1040                 1045                 1050

Tyr Pro  Lys Leu Glu Ser Glu  Phe Val Tyr Gly Asp  Tyr Lys Val
    1055                 1060                 1065

Tyr Asp  Val Arg Lys Met Ile  Ala Lys Ser Glu Gln  Glu Ile Gly
    1070                 1075                 1080

Lys Ala  Thr Ala Lys Tyr Phe  Phe Tyr Ser Asn Ile  Met Asn Phe
    1085                 1090                 1095

Phe Lys  Thr Glu Ile Thr Leu  Ala Asn Gly Glu Ile  Arg Lys Arg
    1100                 1105                 1110

Pro Leu  Ile Glu Thr Asn Gly  Glu Thr Gly Glu Ile  Val Trp Asp
    1115                 1120                 1125

Lys Gly  Arg Asp Phe Ala Thr  Val Arg Lys Val Leu  Ser Met Pro
    1130                 1135                 1140

Gln Val  Asn Ile Val Lys Lys  Thr Glu Val Gln Thr  Gly Gly Phe
    1145                 1150                 1155

Ser Lys  Glu Ser Ile Leu Pro  Lys Arg Asn Ser Asp  Lys Leu Ile
    1160                 1165                 1170

Ala Arg  Lys Lys Asp Trp Asp  Pro Lys Lys Tyr Gly  Gly Phe Asp
    1175                 1180                 1185

Ser Pro  Thr Val Ala Tyr Ser  Val Leu Val Val Ala  Lys Val Glu
    1190                 1195                 1200

Lys Gly  Lys Ser Lys Lys Leu  Lys Ser Val Lys Glu  Leu Leu Gly
    1205                 1210                 1215

Ile Thr  Ile Met Glu Arg Ser  Ser Phe Glu Lys Asn  Pro Ile Asp
    1220                 1225                 1230

Phe Leu  Glu Ala Lys Gly Tyr  Lys Glu Val Lys Lys  Asp Leu Ile
    1235                 1240                 1245

Ile Lys  Leu Pro Lys Tyr Ser  Leu Phe Glu Leu Glu  Asn Gly Arg
    1250                 1255                 1260

Lys Arg  Met Leu Ala Ser Ala  Gly Glu Leu Gln Lys  Gly Asn Glu
    1265                 1270                 1275

Leu Ala  Leu Pro Ser Lys Tyr  Val Asn Phe Leu Tyr  Leu Ala Ser
    1280                 1285                 1290

His Tyr  Glu Lys Leu Lys Gly  Ser Pro Glu Asp Asn  Glu Gln Lys
    1295                 1300                 1305

Gln Leu  Phe Val Glu Gln His  Lys His Tyr Leu Asp  Glu Ile Ile
    1310                 1315                 1320

Glu Gln  Ile Ser Glu Phe Ser  Lys Arg Val Ile Leu  Ala Asp Ala
    1325                 1330                 1335
```

```
Asn Leu  Asp Lys Val Leu Ser  Ala Tyr Asn Lys His  Arg Asp Lys
    1340                 1345                 1350

Pro Ile  Arg Glu Gln Ala Glu  Asn Ile Ile His Leu  Phe Thr Leu
    1355                 1360                 1365

Thr Asn  Leu Gly Ala Pro Ala  Ala Phe Lys Tyr Phe  Asp Thr Thr
    1370                 1375                 1380

Ile Asp  Arg Lys Arg Tyr Thr  Ser Thr Lys Glu Val  Leu Asp Ala
    1385                 1390                 1395

Thr Leu  Ile His Gln Ser Ile  Thr Gly Leu Tyr Glu  Thr Arg Ile
    1400                 1405                 1410

Asp Leu  Ser Gln Leu Gly Gly  Asp Lys Lys Lys Lys  Leu Lys Leu
    1415                 1420                 1425


<210> SEQ ID NO 56
<211> LENGTH: 4889
<212> TYPE: DNA
<213> ORGANISM: Artificial Sequence
<220> FEATURE:
<223> OTHER INFORMATION: Synthetic sequence

<400> SEQUENCE: 56

gactgtctcc accatgtaat ttttccctgc gactccatat aacgccggat cgtgaaattt     60

tcttctttct tttccttcct tctcaacaaa caacggatct gtgctttgcg gtcccctgcg    120

ttcacgcgtc agggtcgact gctctgcagc tcgataactc catggagcca tcaacttgct    180

atggtgtcaa tcatcctatc gacaggtcca agaacaagcc ggcctccggc tgcctcattc    240

gctgtcgcaa gacggcttga gtgttgtggc tggaggattc gggggcccca tattccaacc    300

ctttttttcca aggccgtcgg ccggtgaggt tgaggaaaac catgggttgc ctacatatta    360

tcgatgctgg tgtttggtag tagcaatgtt tgcggtggca gtttgagccg agcctcgtct    420

tgggcttctg acccaggcaa cgccatctga ctagctgcgc cgaaggaagg atgattcatt    480

gtacgacgcc agtcaatgga atcttcaagt aaaagcccga cgaaccgacc atgtcagata    540

tcagaattct cctggctggt ggggttggtt ggagactgct tacggagtcg atgcctcgtg    600

actgtcatgg ccgcgtccag cctcctggga ctctgtccga tattatgaca cgagtaaagc    660

ctgcatgatg tcagtttgct gcgtctcatg tcgagaacaa cacacctggt gctacatagg    720

caatactacc tcgtagcttc aaagttgact gttttgcttt gatgtctttg atcatgccca    780

tccatccctt gtcttgcagt gcatgtggat ctctacgtcc agacggggag aaagcttgtc    840

tgtgataaag tacgatgatg cattgatgcc tgtggctacg gcccttttat ccccatcgtc    900

atgcatctct atattaatcc aggagactct cctcctggca tgggtgagta caagtgacga    960

ggacatgtag aagcagagcc acgcaacgtc ttgacatctg tacctatttt gggccaaaaa   1020

tcgagaccca ccagctcgtc ctaccttaca tgtgaagatc ttagcccaca atcctactgt   1080

tttactagta ttactgcaca gctgtcatca cgagtcctcg gttgcttgtg aaacccagct   1140

cagctcctga gcacatgcag taacgccgac tcggcgtcat ttcgccacac ccaatttgga   1200

cctgagggat gctggaagct gctgagcaga tcccgttacc gattcatggc actactacat   1260

ccatacgcag caaacatggg cttgggcttg gcttctcaat gcaaaattgc ccgcaaaagt   1320

cccggcattg tcgatgcaga gatgcagatt tcagcgggcg attctagggt agggcgacta   1380

ctactactaa taccacctag tcagtatgta tctagcaccg gaggctaggc ggttagtgga   1440

cgggaacctg gtcattccat cgcaaccagg atcccgcact tcgttgcgct tctgccccca   1500
```

-continued

```
cggggcggga gttggcagag gcagaatgcg gagcagcccc ttgtctgccc tggccggggc   1560
ctgttgaagc aagcagacga gagcagagcg gttgagaagc ggtggttgac gcttgacggt   1620
acgaagacga gcgagaatcc cgttaagccg aggctgggct cccccccccg tcatcatcat   1680
gcccatcctg ctcttccagc ccactcgtct ccctgcctcg tcgcctcccc tccctccccc   1740
gattagctgc gcatgttctc ctgacagcgt gactaatgac gcgttgccag cccattcgcc   1800
tgacgcatcc cggcatctga gtctagctcg tcacgctggc aatcttggcc caggcagagc   1860
agcaagacgg cgggcatgat tgggccgtgc cctggcgggc atcagctggc catccgctgc   1920
cacccgagac cgcatcaccg acttgtcgga tctctccgag cagcaggagg ctgatcctgg   1980
ccggcgagac gattgaaaag ggctgccggg cccggagcag gacagcggcg agagcgagcg   2040
agagagagga aaagaagaag gtcgactgtc ttattttcag ccagccccgg ctcaacagaa   2100
gcagaggaga aggcgaacga cgtcaacgac gacgacgacg acgacgaaga cggtgaagtc   2160
cgttagttga agatccttgc cgtcacaaca ccatctcgtg gatattgctt tcccctgccg   2220
ttgcgttgcc acctgttccc tctttctctt cccccctcct tcctcattcc gagcgctact   2280
ggttcctact ccgcagcctt cggttgtgcc tttctctttg tcgaccattg caccgcccgt   2340
cgcggcactt gggccccgga gaattcggcc ctttcgcagc attttggccc tcagttcccc   2400
atggggacgg tccacacttc ctctcttggc cctgcagacc ttttgtcgtc ggtccgagtc   2460
ggaagaagct cagtcttgag cgcttgagta gcatctacgc gcgaatcact ggacaaagtc   2520
ggcaagacga agccgtcgtc gcctgctgct gctgctgtta ctgcgacagg cgctccgact   2580
gggggcatcg gcataataaa aagatgcccg ccttcgccat ggacctggcc atgagccact   2640
cggcatcggc tctctctctc aacgcttcct ctcacacatc ctccttcatt ccgcccatca   2700
tgcacgtcct gtcgactgcg gtgctgctcg gctccgttgc cgttcaaaag gtcctgggaa   2760
gaccaggatc aagcggtctg tccgacgtca ccaagaggtc tgttgacgac ttcatcagca   2820
ccgagacgcc tattgcactg aacaatcttc tttgcaatgt tggtcctgat ggatgccgtg   2880
cattcggcac atcagctggt gcggtgattg catctcccag cacaattgac ccggactgta   2940
agttggcctt gatgaaccat atcatatatc gccgagaagt ggaccgcgtg ctgagactga   3000
gacagactat tacatgtgga cgcgagatag cgctcttgtc ttcaagaacc tcatcgaccg   3060
cttcaccgaa acgtacgatg cgggcctgca gcgccgcatc gagcagtaca ttactgccca   3120
ggtcactctc cagggcctct ctaacccctc gggctccctc gcggacggct ctggtctcgg   3180
cgagcccaag tttgagttga ccctgaagcc tttcaccggc aactggggtc gaccgcagcg   3240
ggatggccca gctctgcgag ccattgcctt gattggatac tcaaagtggc tcatcaacaa   3300
caactatcag tcgactgtgt ccaacgtcat ctggcctatt gtgcgcaacg acctcaacta   3360
tgttgcccag tactggtcag tgcttgcttg ctcttgaatt acgtctttgc ttgtgtgtct   3420
aatgcctcca ccacaggaac caaaccggct ttgacctctg ggaagaagtc aatgggagct   3480
cattctttac tgttgccaac cagcaccgag gtatgaagca aatcctcgac attcgctgct   3540
actgcacatg agcattgtta ctgaccagct ctacagcact tgtcgagggc gccactcttg   3600
ctgccactct tggccagtcg ggaagcgctt attcatctgt tgctccccag gttttgtgct   3660
ttctccaacg attctgggtg tcgtctggtg gatacgtcga ctccaacagt atgtcttttc   3720
actgtttata tgagattggc caatactgat agctcgcctc tagtcaacac caacgagggc   3780
aggactggca aggatgtcaa ctccgtcctg acttccatcc acaccttcga tcccaacctt   3840
ggctgtgacg caggcacctt ccagccatgc agtgacaaag cgctctccaa cctcaaggtt   3900
```

gttgtcgact ccttccgctc catctacggc gtgaacaagg gcattcctgc cggtgctgcc 3960
gtcgccattg gccggtatgc agaggatgtg tactacaacg gcaacccttg gtatcttgct 4020
acatttgctg ctgccgagca gctgtacgat gccatctacg tctggaagaa gacgggctcc 4080
atcacggtga ccgccacctc cctggccttc ttccaggagc ttgttcctgg cgtgacggcc 4140
gggacctact ccagcagctc ttcgaccttt accaacatca tcaacgccgt ctcgacatac 4200
gccgatggct tcctcagcga ggctgccaag tacgtccccg ccgacggttc gctggccgag 4260
cagtttgacc gcaacagcgg cactccgctg tctgcgcttc acctgacgtg gtcgtacgcc 4320
tcgttcttga cagccacggc ccgtcgggct ggcatcgtgc ccccctcgtg ggccaacagc 4380
agcgctagca cgatcccctc gacgtgctcc ggcgcgtccg tggtcggatc ctactcgcgt 4440
cccaccgcca cgtcattccc tccgtcgcag acgcccaagc ctggcgtgcc ttccggtact 4500
ccctacacgc ccctgccctg cgcgacccca acctccgtgg ccgtcacctt ccacgagctc 4560
gtgtcgacac agtttggcca gacggtcaag gtggcgggca acgccgcggc cctgggcaac 4620
tggagcacga gcgccgccgt ggctctggac gccgtcaact atgccgataa ccacccccctg 4680 tggattggga cggtcaacct cgaggctgga gacgtcgtgg agtacaagta catcaatgtg 4740
ggccaagatg gctccgtgac ctgggagagt gatcccaacc acacttacac ggttcctgcg 4800
gtggcttgtg tgacgcaggt tgtcaaggag gacacctggc agtcgtaatg aatcggcaag 4860
gggtagtact agtagacttg tagtctgcc 4889

<210> SEQ ID NO 57
<211> LENGTH: 25
<212> TYPE: DNA
<213> ORGANISM: Artificial Sequence
<220> FEATURE:
<223> OTHER INFORMATION: Primer

<400> SEQUENCE: 57
gactgtctcc accatgtaat ttttc 25

<210> SEQ ID NO 58
<211> LENGTH: 27
<212> TYPE: DNA
<213> ORGANISM: Artificial Sequence
<220> FEATURE:
<223> OTHER INFORMATION: Primer

<400> SEQUENCE: 58
ggcagactac aagtctacta gtactac 27

<210> SEQ ID NO 59
<211> LENGTH: 111
<212> TYPE: DNA
<213> ORGANISM: Artificial Sequence
<220> FEATURE:
<223> OTHER INFORMATION: Synthetic sequence

<400> SEQUENCE: 59
taatacgact cactataggg aagaccagga tcaaggtttt agagctagaa atagcaagtt 60
aaaataaggc tagtccgtta tcaacttgaa aaagtggcac cgagtcggtg c 111

<210> SEQ ID NO 60
<211> LENGTH: 111
<212> TYPE: DNA
<213> ORGANISM: Artificial Sequence
<220> FEATURE:

<223> OTHER INFORMATION: Synthetic sequence

<400> SEQUENCE: 60

```
taatacgact cactatagga cagaccgctt gatccgtttt agagctagaa atagcaagtt     60

aaaataaggc tagtccgtta tcaacttgaa aaagtggcac cgagtcggtg c             111
```

<210> SEQ ID NO 61
<211> LENGTH: 4248
<212> TYPE: DNA
<213> ORGANISM: Artificial Sequence
<220> FEATURE:
<223> OTHER INFORMATION: Synthetic sequence

<400> SEQUENCE: 61

```
ccctgcctcg tcgcctcccc tccctccccc gattagctgc gcatgttctc ctgacagcgt     60

gactaatgac gcgttgccag cccattcgcc tgacgcatcc cggcatctga gtctagctcg    120

tcacgctggc aatcttggcc caggcagagc agcaagacgg cgggcatgat tgggccgtgc    180

cctggcgggc atcagctggc catccgctgc cacccgagac cgcatcaccg acttgtcgga    240

tctctccgag cagcaggagg ctgatcctgg ccggcgagac gattgaaaag ggctgccggg    300

cccggagcag gacagcggcg agagcgagcg agagagagga aaagaagaag gtcgactgtc    360

ttattttcag ccagccccgg ctcaacagaa gcagaggaga aggcgaacga cgtcaacgac    420

gacgacgacg acgacgaaga cggtgaagtc cgttagttga agatccttgc cgtcacaaca    480

ccatctcgtg gatattgctt tcccctgccg ttgcgttgcc acctgttccc tctttctctt    540

ccccccttct tcctcattcc gagcgctact ggttcctact ccgcagcctt cggttgtgcc    600

tttctctttg tcgaccattg caccgcccgt cgcggcactt gggccccgga gaattcggcc    660

ctttcgcagc attttggccc tcagttcccc atggggacgg tccacacttc ctctcttggc    720

cctgcagacc ttttgtcgtc ggtccgagtc ggaagaagct cagtcttgag cgcttgagta    780

gcatctacgc gcgaatcact ggacaaagtc ggcaagacga agccgtcgtc gcctgctgct    840

gctgctgtta ctgcgacagg cgctccgact gggggcatcg gcataataaa aagatgcccg    900

ccttcgccat ggacctggcc atgagccact cggcatcggc tctctctctc aacgcttcct    960

ctcacacatc ctccttcatt ccgcccatca tggtttaaac ctcgagttta taagtgacaa   1020

catgctctca aagcgctcat ggctggcaca agcctggaaa gaaccaacac aaagcatact   1080

gcagcaaatc agctgaattc gtcaccaatt aagtgaacat caacctgaag gcagagtatg   1140

aggccagaag cacatctgga tcgcagatca tggattgccc ctcttgttga agatgagaat   1200

ctagaaagat ggcggggtat gagataagag cgatgggggg gcacatcatc ttccaagaca   1260

aacaaccttt gcagagtcag gcaatttttc gtataagagc aggaggaggg agtccagtca   1320

tttcatcagc ggtaaaatca ctctagacaa tcttcaagat gagttctgcc ttgggtgact   1380

tatagccatc atcataccta gacagaagct tgtgggatac taagaccaac gtacaagctc   1440

gcactgtacg ctttgacttc catgtgaaaa ctcgatacgg cgcgcctcta aattttatag   1500

ctcaaccact ccaatccaac ctctgcatcc ctctcactcg tcctgatcta ctgttcaaat   1560

cagagaataa ggacactatc caaatccaac agaatggcta ccacctccca gctgcctgcc   1620

tacaagcagg acttcctcaa atccgccatc gacggcggcg tcctcaagtt tggcagcttc   1680

gagctcaagt ccaagcggat atccccctac ttcttcaacg cgggcgaatt ccacacggcg   1740

cgcctcgccg gcgccatcgc ctccgccttt gcaaagacca tcatcgaggc ccaggagaag   1800

gccggcctag agttcgacat cgtcttcggc ccggcctaca agggcatccc gctgtgctcc   1860
```

gccatcacca tcaagctcgg cgagctggcg ccccagaacc tggaccgcgt ctcctactcg 1920
tttgaccgca aggaggccaa ggaccacggc gagggcggca acatcgtcgg cgcttcgctc 1980
aagggcaaga gggtcctgat tgtcgacgac gtcatcaccg ccggcaccgc caagagggac 2040
gccattgaga agatcaccaa ggagggcggc atcgtcgccg gcatcgtcgt ggccctggac 2100
cgcatggaga agctccccgc tgcggatggc gacgactcca agcctggacc gagtgccatt 2160
ggcgagctga ggaaggagta cggcatcccc atctttgcca tcctcactct ggatgacatt 2220
atcgatggca tgaagggctt tgctacccct gaggatatca agaacacgga ggattaccgt 2280
gccaagtaca aggcgactga ctgattgagg cgttcaatgt cagaagggag agaaagactg 2340
aaaaggtgga aagaagaggc aaattgttgt tattattatt attctatctc gaatcttcta 2400
gatcttgtcg taaataaaca agcgtaacta gctagcctcc gtacaactgc ttgaatttga 2460
tacccgtatg gagggcagtt attttatttt gtttttcaag attttccatt cgccgttgaa 2520
ctcgtctcac atcgcgtgta ttgcccggtt gcccatgtgt tctcctacta ccccaagtcc 2580
ctcacgggtt gtctcacttt ctttctcctt tatcctccct attttttttc aagtcagcga 2640
cagagcagtc atatggggat acgtgcaact gggactcaca acaggccatc ttatggccta 2700
atagccggcg ttggatccac tagtcaattg gtttaaacag cacatgcagt aacgccgact 2760
cggcgtcatt tcgccacacc caatttggac ctgagggatg ctggaagctg ctgagcagat 2820
cccgttaccg attcatggca ctactacatc catacgcagc aaacatgggc ttgggcttgg 2880
cttctcaatg caaaattgcc cgcaaaagtc ccggcattgt cgatgcagag atgcagattt 2940
cagcgggcga ttctagggta gggcgactac tactactaat accacctagt cagtatgtat 3000
ctagcaccgg aggctaggcg gttagtggac gggaacctgg tcattccatc gcaaccagga 3060
tcccgcactt cgttgcgctt ctgcccccac ggggcgggag ttggcagagg cagaatgcgg 3120
agcagcccct tgtctgccct ggccggggcc tgttgaagca agcagacgag agcagagcgg 3180
ttgagaagcg gtggttgacg cttgacggta cgaagacgag cgagaatccc gttaagccga 3240
ggctgggcta attaattaat gaatcggcaa ggggtagtac tagtagactt gtagtctgcc 3300
ggattattga ttggagttgg tcagtagaat gaaccacggg aatattcggt caccgggaca 3360
tttgggatat agcgtttcga gaagctgctg gttgcagcac attggagaag gatgcccttt 3420
tacgacttat accgctatgc cgggtatatt aatttagccg ttatgaaact caaagagacg 3480
atgataatga tgacgagtaa ttgttcgttt caatttcgaa agctgactcc cacgaagaat 3540
atgccaatga cccacggcat gaagcctgaa ctgggcgtgt gtaacacttt aatttgcctg 3600
acggcggaca aaacaaaggc ggcagcaatg ttgagaccgt gtgataaacc aaggttcccg 3660
agggagagag agagagagag agagagagag ctaggtgaaa gaatgagtcc gcctttgagt 3720
catcctgcgt ctctctctcc ccctctctca ctctctgtat cccatcaacc tcttccctgt 3780
tccttctcct atcgcatcca tgcgtttgca tcttccattt cattctttcc ccttgagccc 3840
catctatgca aactcatcat ccggcgcctc gatggaatcc ttgaccttga tgagaatcgc 3900
cgtcatccaa ggctccagcc tgctcgtgcg gtcgaactgg aacagcagct cgctaaactc 3960
atcctggctg tggttgtcga cggcgttgca caggtcctcg agcagcttgt acttgtattg 4020
agaggagaac tcggggtcct tttggcggta ggactcgacg gcgcggcggg tgccgaccat 4080
gtcgcccgtg gcgaggtggc agatgccggc cttgaagcag taggtcgaga ggctccactt 4140
catggtgccg ttgccgatca tggtgttgat gatgcggtcg tacgtctcga tggcgccgta 4200
gtagtcgccg tcgagggcgg cgaggtcggc gtactgcgtc cagagctt 4248

<210> SEQ ID NO 62
<211> LENGTH: 30
<212> TYPE: DNA
<213> ORGANISM: Artificial Sequence
<220> FEATURE:
<223> OTHER INFORMATION: Primer

<400> SEQUENCE: 62
cactactaca tccatacgca gcaaacatgg 30

<210> SEQ ID NO 63
<211> LENGTH: 26
<212> TYPE: DNA
<213> ORGANISM: Artificial Sequence
<220> FEATURE:
<223> OTHER INFORMATION: Primer

<400> SEQUENCE: 63
ggtcaagaag cacatgccag agttcg 26

<210> SEQ ID NO 64
<211> LENGTH: 25
<212> TYPE: DNA
<213> ORGANISM: Artificial Sequence
<220> FEATURE:
<223> OTHER INFORMATION: Primer

<400> SEQUENCE: 64
gactgtctcc accatgtaat ttttc 25

<210> SEQ ID NO 65
<211> LENGTH: 4104
<212> TYPE: DNA
<213> ORGANISM: Artificial Sequence
<220> FEATURE:
<223> OTHER INFORMATION: codon optimized seqs

<400> SEQUENCE: 65
atggataaaa aatacagcat tggtctggcc atcggaacca acagcgttgg gtgggcagta 60
ataacagatg aatacaaagt gccgtcaaaa aaatttaagg ttctggggaa tacagatcgc 120
cacagcataa aaaagaatct gattggggca ttgctgtttg attcgggtga gacagctgag 180
gccacgcgtc tgaaacgtac agcaagaaga cgttacacac gtcgtaaaaa tcgtatttgc 240
tacttacagg aaatttttc taacgaaatg gccaaggtag atgatagttt cttccatcgt 300
ctcgaagaat cttttctggt tgaggaagat aaaaaacacg aacgtcaccc tatctttggc 360
aatatcgtgg atgaagtggc ctatcatgaa aaatacccta cgatttatca tcttcgcaag 420
aagttggttg atagtacgga caaagcggat ctgcgtttaa tctatcttgc gttagcgcac 480
atgatcaaat ttcgtggtca tttcttaatt gaaggtgatc tgaatcctga taactctgat 540
gtggacaaat tgtttataca attagtgcaa acctataatc agctgttcga ggaaaacccc 600
attaatgcct ctggagttga tgccaaagcg attttaagcg cgagactttc taagtcccgg 660
cgtctggaga atctgatcgc ccagttacca ggggaaaaga aaaatggtct gtttggtaat 720
ctgattgccc tcagtctggg gcttaccccg aacttcaaat ccaattttga cctggctgag 780
gacgcaaagc tgcagctgag caaagatact tatgatgatg acctcgacaa tctgctcgcc 840

-continued

```
cagattggtg accaatatgc ggatctgttt ctggcagcga agaatctttc ggatgctatc    900
ttgctgtcgg atattctgcg tgttaatacc gaaatcacca aagcgcctct gtctgcaagt    960
atgatcaaga gatacgacga gcaccaccag gacctgactc ttcttaaggc actggtacgc   1020
caacagcttc cggagaaata caaagaaata ttcttcgacc agtccaagaa tggttacgcg   1080
ggctacatcg atggtggtgc atcacaggaa gagttctata aatttattaa accaatcctt   1140
gagaaaatgg atggcacgga agagttactt gttaaactta accgcgaaga cttgcttaga   1200
aagcaacgta cattcgacaa cggctccatc ccacaccaga ttcatttagg tgaacttcac   1260
gccatcttgc gcagacaaga agatttctat cccttcttaa aagacaatcg ggagaaaatc   1320
gagaagatcc tgacgttccg cattccctat tatgtcggtc ccctggcacg tggtaattct   1380
cggtttgcct ggatgacgcg caaaagtgag gaaaccatca ccccttggaa ctttgaagaa   1440
gtcgtggata aaggtgctag cgcgcagtct tttatagaaa gaatgacgaa cttcgataaa   1500
aacttgccca acgaaaaagt cctgcccaag cactctcttt tatatgagta ctttactgtg   1560
tacaacgaac tgactaaagt gaaatacgtt acggaaggta tgcgcaaacc tgcctttctt   1620
agtggcgagc agaaaaaagc aattgtcgat cttctcttta aaacgaatcg caaggtaact   1680
gtaaaacagc tgaaggaaga ttatttcaaa aagatcgaat gctttgattc tgtcgagatc   1740
tcgggtgtcg aagatcgttt caacgcttcc ttagggacct atcatgattt gctgaagata   1800
ataaaagaca aagactttct cgacaatgaa gaaaatgaag atattctgga ggatattgtt   1860
ttgaccttga ccttattcga agatagagag atgatcgagg agcgcttaaa aacctatgcc   1920
cacctgtttg atgacaaagt catgaagcaa ttaaagcgcc gcagatatac ggggtggggc   1980
cgcttgagcc gcaagttgat taacggtatt agagacaagc agagcggaaa aactatcctg   2040
gatttcctca aatctgacgg atttgcgaac cgcaatttta tgcagcttat acatgatgat   2100
tcgcttacat tcaaagagga tattcagaag gctcaggtgt ctgggcaagg tgattcactc   2160
cacgaacata tagcaaattt ggccggctct cctgcgatta agaaggggat cctgcaaaca   2220
gttaaagttg tggatgaact tgtaaaagta atgggccgcc acaagccgga gaatatcgtg   2280
atagaaatgg cgcgcgagaa tcaaacgaca caaaaaggtc aaaagaactc aagagagaga   2340
atgaagcgca ttgaggaggg gataaaggaa cttggatctc aaattctgaa agaacatcca   2400
gttgaaaaca ctcagctgca aaatgaaaaa ttgtacctgt actacctgca gaatggaaga   2460
gacatgtacg tggatcagga attggatatc aatagactct cggactatga cgtagatcac   2520
attgtccctc agagcttcct caaggatgat tctatagata ataaagtact tacgagatcg   2580
gacaaaaatc gcggtaaatc ggataacgtc ccatcggagg aagtcgttaa aaagatgaaa   2640
aactattggc gtcaactgct gaacgccaag ctgatcacac agcgtaagtt tgataatctg   2700
actaaagccg aacgcggtgg tcttagtgaa ctcgataaag caggatttat aaaacggcag   2760
ttagtagaaa cgcgccaaat tacgaaacac gtggctcaga tcctcgattc tagaatgaat   2820
acaaagtacg atgaaaacga taaactgatc cgtgaagtaa aagtcattac cttaaaatct   2880
aaacttgtgt ccgatttccg caaagatttt cagttttaca aggtccggga aatcaataac   2940
tatcaccatg cacatgatgc atatttaaat gcggttgtag gcacggccct tattaagaaa   3000
taccctaaac tcgaaagtga gtttgtttat ggggattata aagtgtatga cgttcgcaaa   3060
atgatcgcga aatcagaaca ggaaatcggt aaggctaccg ctaaatactt tttttattcc   3120
aacattatga attttttaa gaccgaaata actctcgcga atggtgaaat ccgtaaacgg    3180
cctcttatag aaaccaatgg tgaaacggga gaaatcgttt gggataaagg tcgtgacttt   3240
```

```
gccaccgttc gtaaagtcct ctcaatgccg caagttaaca ttgtcaagaa gacggaagtt   3300

caaacagggg gattctccaa agaatctatc ctgccgaagc gtaacagtga taaacttatt   3360

gccagaaaaa aagattggga tccaaaaaaa tacggaggct ttgattcccc taccgtcgcg   3420

tatagtgtgc tggtggttgc taaagtcgag aaagggaaaa gcaagaaatt gaaatcagtt   3480

aaagaactgc tgggtattac aattatggaa agatcgtcct ttgagaaaaa tccgatcgac   3540

tttttagagg ccaaggggta taaggaagtg aaaaaagatc tcatcatcaa attaccgaag   3600

tatagtcttt ttgagctgga aaacggcaga aaaagaatgc tggcctccgc gggcgagtta   3660

cagaagggaa atgagctggc gctgccttcc aaatatgtta attttctgta ccttgccagt   3720

cattatgaga aactgaaggg cagccccgaa gataacgaac agaaacaatt attcgtggaa   3780

cagcataagc actatttaga tgaaattata gagcaaatta gtgaattttc taagcgcgtt   3840

atcctcgcgg atgctaattt agacaaagta ctgtcagctt ataataaaca tcgggataag   3900

ccgattagag aacaggccga aaatatcatt catttgttta ccttaaccaa ccttggagca   3960

ccagctgcct tcaaatattt cgataccaca attgatcgta aacggtatac aagtacaaaa   4020

gaagtcttgg acgcaaccct cattcatcaa tctattactg gattatatga gacacgcatt   4080

gatctttcac agctgggcgg agac                                           4104
```

<210> SEQ ID NO 66
<211> LENGTH: 1368
<212> TYPE: PRT
<213> ORGANISM: Artificial Sequence
<220> FEATURE:
<223> OTHER INFORMATION: protein expressed from synthetic construct

<400> SEQUENCE: 66

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205
```

-continued

```
Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620
```

-continued

```
Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035
```

```
Tyr Ser  Asn Ile Met Asn Phe  Phe Lys Thr Glu Ile  Thr Leu Ala
    1040                 1045                 1050

Asn Gly  Glu Ile Arg Lys Arg  Pro Leu Ile Glu Thr  Asn Gly Glu
    1055                 1060                 1065

Thr Gly  Glu Ile Val Trp Asp  Lys Gly Arg Asp Phe  Ala Thr Val
    1070                 1075                 1080

Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365
```

<210> SEQ ID NO 67
<211> LENGTH: 46
<212> TYPE: PRT
<213> ORGANISM: Artificial Sequence
<220> FEATURE:
<223> OTHER INFORMATION: Synthetic sequence

<400> SEQUENCE: 67

```
Met His His His His His His Ser Ser Gly Leu Val Pro Arg Gly Ser
1               5                   10                  15
```

```
Gly Met Lys Glu Thr Ala Ala Ala Lys Phe Glu Arg Gln His Met Asp
            20                  25                  30

Ser Pro Asp Leu Gly Thr Asp Asp Asp Asp Lys Ala Met Ala
        35                  40                  45


<210> SEQ ID NO 68
<211> LENGTH: 138
<212> TYPE: DNA
<213> ORGANISM: Artificial Sequence
<220> FEATURE:
<223> OTHER INFORMATION: Synthetic sequence

<400> SEQUENCE: 68

atgcaccatc atcatcatca ttcttctggt ctggtgccac gcggttctgg tatgaaagaa     60

accgctgctg ctaaattcga acgccagcac atggacagcc cagatctggg taccgacgac    120

gacgacaagg ccatggcc                                                  138


<210> SEQ ID NO 69
<211> LENGTH: 21
<212> TYPE: DNA
<213> ORGANISM: SV40

<400> SEQUENCE: 69

ccaaaaaaga aacgcaaggt t                                               21


<210> SEQ ID NO 70
<211> LENGTH: 21
<212> TYPE: DNA
<213> ORGANISM: T. reesei

<400> SEQUENCE: 70

aagaagaaaa aactgaaact g                                               21


<210> SEQ ID NO 71
<211> LENGTH: 19
<212> TYPE: DNA
<213> ORGANISM: Artificial Sequence
<220> FEATURE:
<223> OTHER INFORMATION: Primer

<400> SEQUENCE: 71

tgatgacggt gaaaacctc                                                  19


<210> SEQ ID NO 72
<211> LENGTH: 16
<212> TYPE: DNA
<213> ORGANISM: Artificial Sequence
<220> FEATURE:
<223> OTHER INFORMATION: Primer

<400> SEQUENCE: 72

aaaagcaccg actcgg                                                     16


<210> SEQ ID NO 73
<211> LENGTH: 45
<212> TYPE: DNA
<213> ORGANISM: T. reesei

<400> SEQUENCE: 73

atgcgcaaat ttaaagcgct gatgtgtgtc taatgcctcc accac                     45


<210> SEQ ID NO 74
```

<211> LENGTH: 45
<212> TYPE: DNA
<213> ORGANISM: T. reesei

<400> SEQUENCE: 74
atatggatct gcgcgcgatc gatgatcgtg ctagcgctgc tgttg 45

<210> SEQ ID NO 75
<211> LENGTH: 19
<212> TYPE: DNA
<213> ORGANISM: Artificial Sequence
<220> FEATURE:
<223> OTHER INFORMATION: Primer

<400> SEQUENCE: 75
ccaccacagg aaccaaacc 19

<210> SEQ ID NO 76
<211> LENGTH: 20
<212> TYPE: DNA
<213> ORGANISM: Artificial Sequence
<220> FEATURE:
<223> OTHER INFORMATION: Primer

<400> SEQUENCE: 76
ctgcgacgga gggaatgacg 20

<210> SEQ ID NO 77
<211> LENGTH: 21
<212> TYPE: DNA
<213> ORGANISM: Artificial Sequence
<220> FEATURE:
<223> OTHER INFORMATION: Primer

<400> SEQUENCE: 77
gggcaggact ggcaaggatg t 21

<210> SEQ ID NO 78
<211> LENGTH: 20
<212> TYPE: DNA
<213> ORGANISM: Artificial Sequence
<220> FEATURE:
<223> OTHER INFORMATION: Primer

<400> SEQUENCE: 78
gccgtcacgc caggaacaag 20

<210> SEQ ID NO 79
<211> LENGTH: 26
<212> TYPE: DNA
<213> ORGANISM: Artificial Sequence
<220> FEATURE:
<223> OTHER INFORMATION: Primer

<400> SEQUENCE: 79
gaacaatctt ctttgcaatg ttggtc 26

<210> SEQ ID NO 80
<211> LENGTH: 25
<212> TYPE: DNA
<213> ORGANISM: Artificial Sequence
<220> FEATURE:
<223> OTHER INFORMATION: Primer -continued

<400> SEQUENCE: 80

```
gaggaagtcc tgcttgtagg caggc                                            25
```

<210> SEQ ID NO 81
<211> LENGTH: 26
<212> TYPE: DNA
<213> ORGANISM: Artificial Sequence
<220> FEATURE:
<223> OTHER INFORMATION: Primer

<400> SEQUENCE: 81

```
cgacagagca gtcatatggg gatacg                                           26
```